United States Patent
Linden et al.

(10) Patent No.: US 12,201,829 B2
(45) Date of Patent: Jan. 21, 2025

(54) STIMULATION APPARATUS

(71) Applicant: Nalu Medical, Inc., Carlsbad, CA (US)

(72) Inventors: Christopher Linden, Vista, CA (US); Andre Castillo, Encinitas, CA (US); Logan Palmer, Santa Monica, CA (US); Ji-Jon Sit, Singapore (SG); Daniel M. Pivonka, Del Mar, CA (US); Lakshmi Narayan Mishra, Carlsbad, CA (US); James C. Makous, Carlsbad, CA (US); Lee Fason Hartley, Carlsbad, CA (US); James C. Lee, Carlsbad, CA (US); J. Christopher Flaherty, Auburndale, FL (US)

(73) Assignee: Nalu Medical, Inc., Carlsbad, CA (US)

(*) Notice: Subject to any disclaimer, the term of this patent is extended or adjusted under 35 U.S.C. 154(b) by 0 days.

(21) Appl. No.: 17/379,928

(22) Filed: Jul. 19, 2021

(65) Prior Publication Data

US 2022/0176108 A1 Jun. 9, 2022

Related U.S. Application Data

(63) Continuation of application No. 16/672,921, filed on Nov. 4, 2019, now Pat. No. 11,097,096, which is a (Continued)

(51) Int. Cl.
*A61N 1/05* (2006.01)
*A61N 1/32* (2006.01)
(Continued)

(52) U.S. Cl.
CPC ............ *A61N 1/0558* (2013.01); *A61N 1/05* (2013.01); *A61N 1/0556* (2013.01);
(Continued)

(58) Field of Classification Search
CPC ............ A61N 1/36007; A61N 1/3605; A61N 1/36062; A61N 1/36071; A61N 1/36114;
(Continued)

(56) References Cited

U.S. PATENT DOCUMENTS

| 3,835,833 | A | 9/1974 | Limoge |
| 3,902,501 | A | 9/1975 | Citron et al. |

(Continued)

FOREIGN PATENT DOCUMENTS

| EP | 1342454 A1 | 9/2003 |
| EP | 1609501 A1 | 12/2005 |

(Continued)

OTHER PUBLICATIONS

EP18797777.2 European Search Report dated Jan. 14, 2021.
(Continued)

*Primary Examiner* — Paula J Stice
(74) *Attorney, Agent, or Firm* — Cooley LLP

(57) ABSTRACT

A medical apparatus for a patient comprises an external system and an implantable system. The external system is configured to transmit one or more transmission signals, each transmission signal comprising at least power or data. The implantable system is configured to receive the one or more transmission signals from the external system, and to deliver stimulation energy to the patient. Methods of delivering stimulation energy are also provided.

27 Claims, 67 Drawing Sheets

Related U.S. Application Data continuation of application No. PCT/US2018/031904, filed on May 9, 2018.

(60) Provisional application No. 62/652,449, filed on Apr. 4, 2018, provisional application No. 62/555,557, filed on Sep. 7, 2017, provisional application No. 62/503,772, filed on May 9, 2017.

(51) Int. Cl.
*A61N 1/36* (2006.01)
*A61N 1/372* (2006.01)
*A61N 1/378* (2006.01)

(52) U.S. Cl.
CPC .......... *A61N 1/0573* (2013.01); *A61N 1/325* (2013.01); *A61N 1/36* (2013.01); *A61N 1/36007* (2013.01); *A61N 1/3605* (2013.01); *A61N 1/36062* (2017.08); *A61N 1/36071* (2013.01); *A61N 1/36075* (2013.01); *A61N 1/36114* (2013.01); *A61N 1/36117* (2013.01); *A61N 1/36135* (2013.01); *A61N 1/37229* (2013.01); *A61N 1/3787* (2013.01); *A61N 1/0551* (2013.01)

(58) Field of Classification Search
CPC ............ A61N 1/36135; A61N 1/37229; A61N 1/3787; A61N 1/0551; A61N 1/36125; A61N 1/36128; A61N 1/36132; A61N 1/3613

See application file for complete search history.

(56) References Cited

U.S. PATENT DOCUMENTS

| | | |
|---|---|---|
| 3,939,843 A | 2/1976 | Smyth et al. |
| 4,033,357 A | 7/1977 | Helland et al. |
| 4,071,033 A | 1/1978 | Nawracaj et al. |
| 4,140,133 A | 2/1979 | Kastrubin et al. |
| 4,236,529 A | 12/1980 | Little |
| 4,262,678 A | 4/1981 | Stokes |
| 4,269,198 A | 5/1981 | Stokes |
| 4,301,815 A | 11/1981 | Doring |
| 4,324,251 A | 4/1982 | Mann |
| 4,407,303 A | 10/1983 | Akerstroem |
| 4,409,994 A | 10/1983 | Doring |
| 4,469,104 A | 9/1984 | Peers-Trevarton |
| 4,506,679 A | 3/1985 | Mann |
| 4,578,598 A | 3/1986 | Faulhaber |
| 4,582,069 A | 4/1986 | Mcarthur |
| 4,592,356 A | 6/1986 | Gutierrez |
| 4,627,438 A | 12/1986 | Liss et al. |
| 4,658,835 A | 4/1987 | Pohndorf |
| 4,716,888 A | 1/1988 | Wesner |
| 4,721,118 A | 1/1988 | Harris |
| 4,796,643 A | 1/1989 | Nakazawa et al. |
| 4,841,971 A | 6/1989 | Hess |
| 4,883,070 A | 11/1989 | Hanson |
| 4,898,173 A | 2/1990 | Daglow et al. |
| 4,922,908 A | 5/1990 | Morawetz et al. |
| 4,945,922 A | 8/1990 | Van Krieken |
| 4,957,118 A | 9/1990 | Erlebacher |
| 5,031,618 A | 7/1991 | Mullett |
| 5,107,856 A | 4/1992 | Kristiansen |
| 5,131,389 A | 7/1992 | Giordani |
| 5,143,067 A | 9/1992 | Rise et al. |
| 5,193,539 A | 3/1993 | Schulman et al. |
| 5,201,312 A | 4/1993 | Schenck et al. |
| 5,257,634 A | 11/1993 | Kroll |
| 5,273,053 A | 12/1993 | Pohndorf |
| 5,282,845 A | 2/1994 | Bush et al. |
| 5,300,107 A | 4/1994 | Stokes et al. |
| 5,540,736 A | 7/1996 | Haimovich et al. |
| 5,545,206 A | 8/1996 | Carson |
| 5,662,697 A | 9/1997 | Li et al. |
| 5,735,887 A | 4/1998 | Barreras, Sr. et al. |
| 5,807,397 A | 9/1998 | Barreras |
| 5,814,089 A | 9/1998 | Stokes et al. |
| 5,827,311 A | 10/1998 | Berelsman et al. |
| 5,833,603 A | 11/1998 | Kovacs et al. |
| 5,868,741 A | 2/1999 | Chia et al. |
| 5,908,433 A | 6/1999 | Eager et al. |
| 5,957,965 A | 9/1999 | Moumane et al. |
| 6,021,354 A | 2/2000 | Warman et al. |
| 6,058,331 A | 5/2000 | King |
| 6,141,591 A | 10/2000 | Lenarz et al. |
| 6,169,925 B1 | 1/2001 | Villaseca et al. |
| 6,181,973 B1 | 1/2001 | Ceron et al. |
| 6,188,932 B1 | 2/2001 | Lindegren |
| 6,240,322 B1 | 5/2001 | Peterfeso et al. |
| 6,275,737 B1 | 8/2001 | Mann |
| 6,304,786 B1 | 10/2001 | Heil, Jr. et al. |
| 6,324,430 B1 | 11/2001 | Zarinetchi et al. |
| 6,324,434 B2 | 11/2001 | Coe et al. |
| 6,405,091 B1 | 6/2002 | Vachon et al. |
| 6,482,152 B2 | 11/2002 | Kim et al. |
| 6,510,347 B2 | 1/2003 | Borkan |
| 6,516,227 B1 | 2/2003 | Meadows et al. |
| 6,517,477 B1 | 2/2003 | Wendlandt |
| 6,522,926 B1 | 2/2003 | Kieval et al. |
| 6,561,975 B1 | 5/2003 | Pool et al. |
| 6,809,701 B2 | 10/2004 | Amundson |
| 6,850,803 B1 | 2/2005 | Jimenez et al. |
| 6,884,122 B2 | 4/2005 | Robinson et al. |
| 6,895,280 B2 | 5/2005 | Meadows et al. |
| 6,904,322 B2 | 6/2005 | Katsnelson |
| 6,909,917 B2 | 6/2005 | Woods et al. |
| 6,950,706 B2 | 9/2005 | Rodriguez et al. |
| 6,999,819 B2 | 2/2006 | Swoyer et al. |
| 7,092,763 B1 | 8/2006 | Griffith et al. |
| 7,096,070 B1 | 8/2006 | Jenkins et al. |
| 7,239,921 B2 | 7/2007 | Canfield et al. |
| 7,346,391 B1 | 3/2008 | Osorio et al. |
| 7,409,245 B1 | 8/2008 | Larson et al. |
| 7,616,990 B2 | 11/2009 | Chavan et al. |
| 7,711,419 B2 | 5/2010 | Armstrong et al. |
| 7,717,848 B2 | 5/2010 | Heruth et al. |
| 7,734,340 B2 | 6/2010 | De Ridder |
| 7,734,354 B1 | 6/2010 | Cox |
| 7,737,905 B1 | 6/2010 | Meloling |
| 7,742,818 B2 | 6/2010 | Dinsmoor et al. |
| 7,801,615 B2 | 9/2010 | Meadows et al. |
| 7,899,550 B1 | 3/2011 | Doan et al. |
| 7,912,555 B2 | 3/2011 | Swoyer et al. |
| 7,925,357 B2 | 4/2011 | Phillips et al. |
| 7,991,479 B2 | 8/2011 | Phillips et al. |
| 8,000,805 B2 | 8/2011 | Swoyer et al. |
| 8,036,756 B2 | 10/2011 | Swoyer et al. |
| 8,086,317 B2 | 12/2011 | Finch et al. |
| 8,170,675 B2 | 5/2012 | Alataris et al. |
| 8,224,453 B2 | 7/2012 | De Ridder |
| 8,252,011 B1 | 8/2012 | Forrester et al. |
| 8,280,517 B2 | 10/2012 | Skelton et al. |
| 8,301,268 B1 | 10/2012 | Jones |
| 8,359,102 B2 | 1/2013 | Alataris et al. |
| 8,364,273 B2 | 1/2013 | De Ridder |
| 8,369,959 B2 | 2/2013 | Meskens |
| 8,388,555 B2 | 3/2013 | Panken et al. |
| 8,401,655 B2 | 3/2013 | De Ridder |
| 8,401,666 B2 | 3/2013 | Skelton et al. |
| 8,423,147 B2 | 4/2013 | Alataris et al. |
| 8,433,415 B2 | 4/2013 | Leiter et al. |
| 8,437,853 B2 | 5/2013 | Inman et al. |
| 8,452,421 B2 | 5/2013 | Thenuwara et al. |
| 8,469,971 B2 | 6/2013 | Barker |
| 8,504,138 B1 | 8/2013 | Pivonka et al. |
| 8,504,150 B2 | 8/2013 | Skelton |
| 8,538,523 B2 | 9/2013 | Sommer et al. |
| 8,538,541 B2 | 9/2013 | Milojevic et al. |
| 8,564,472 B2 | 10/2013 | Okamura et al. |
| 8,579,834 B2 | 11/2013 | Davis et al. |
| 8,612,015 B2 | 12/2013 | Knifong, Sr. |
| 8,620,435 B2 | 12/2013 | Rooney et al. |

(56) References Cited

U.S. PATENT DOCUMENTS

| | | |
|---|---|---|
| 8,626,297 B2 | 1/2014 | Jaax et al. |
| 8,626,314 B2 | 1/2014 | Swoyer et al. |
| 8,634,928 B1 | 1/2014 | O'Driscoll et al. |
| 8,649,842 B2 | 2/2014 | Atalar et al. |
| 8,655,451 B2 | 2/2014 | Klosterman et al. |
| 8,706,240 B2 | 4/2014 | Bradley et al. |
| 8,712,533 B2 | 4/2014 | Alataris et al. |
| 8,718,781 B2 | 5/2014 | Alataris et al. |
| 8,758,274 B2 | 6/2014 | Sahasrabudhe et al. |
| 8,768,472 B2 | 7/2014 | Fang et al. |
| 8,774,927 B2 | 7/2014 | Deridder |
| 8,792,988 B2 | 7/2014 | Alataris et al. |
| 8,798,773 B2 | 8/2014 | Mashiach |
| 8,834,392 B2 | 9/2014 | Panken et al. |
| 8,868,192 B2 | 10/2014 | Alataris et al. |
| 8,874,217 B2 | 10/2014 | Alataris et al. |
| 8,874,222 B2 | 10/2014 | Alataris et al. |
| 8,880,177 B2 | 11/2014 | Alataris et al. |
| 8,880,191 B2 | 11/2014 | Pyles et al. |
| 8,886,326 B2 | 11/2014 | Alataris et al. |
| 8,886,327 B2 | 11/2014 | Alataris et al. |
| 8,886,328 B2 | 11/2014 | Alataris et al. |
| 8,897,870 B2 | 11/2014 | De Ridder |
| 8,903,502 B2 | 12/2014 | Perryman et al. |
| 8,934,981 B2 | 1/2015 | De Ridder |
| 8,954,165 B2 | 2/2015 | Sharma et al. |
| 8,972,502 B2 | 3/2015 | Beslic et al. |
| 9,020,590 B1 | 4/2015 | Honeycutt et al. |
| 9,031,664 B2 | 5/2015 | Trier |
| 9,044,612 B2 | 6/2015 | Mashiach et al. |
| 9,061,151 B2 | 6/2015 | Mashiach et al. |
| 9,106,203 B2 | 8/2015 | Kesler et al. |
| 9,138,582 B2 | 9/2015 | Doan et al. |
| 9,144,681 B2 | 9/2015 | Decre et al. |
| 9,149,210 B2 | 10/2015 | Sahasrabudhe et al. |
| 9,173,811 B2 | 11/2015 | Greiner et al. |
| 9,220,897 B2 | 12/2015 | Perryman et al. |
| 9,254,393 B2 | 2/2016 | Perryman et al. |
| 9,272,081 B2 | 3/2016 | Cameron et al. |
| 9,308,377 B1 | 4/2016 | Schaefer |
| 9,327,125 B2 | 5/2016 | Alataris et al. |
| 9,327,126 B2 | 5/2016 | Alataris et al. |
| 9,327,127 B2 | 5/2016 | Alataris et al. |
| 9,333,357 B2 | 5/2016 | Alataris et al. |
| 9,333,358 B2 | 5/2016 | Alataris et al. |
| 9,339,655 B2 | 5/2016 | Carbunaru |
| 9,403,020 B2 | 8/2016 | Wingeier |
| 9,433,750 B2 | 9/2016 | Pivonka et al. |
| 9,440,084 B2 | 9/2016 | Davis et al. |
| 9,452,288 B2 | 9/2016 | Whitehurst et al. |
| 9,462,398 B2 | 10/2016 | Deridder |
| 9,463,318 B2 | 10/2016 | Mashiach et al. |
| 9,480,842 B2 | 11/2016 | Alataris et al. |
| 9,555,248 B2 | 1/2017 | De Ridder |
| 9,555,257 B2 | 1/2017 | Mashiach et al. |
| 9,585,642 B2 | 3/2017 | Dinsmoor et al. |
| 9,622,700 B2 | 4/2017 | Sahasrabudhe et al. |
| 9,623,245 B2 | 4/2017 | King et al. |
| 9,623,253 B2 | 4/2017 | Perryman et al. |
| 9,643,010 B2 | 5/2017 | Ranu |
| 9,656,077 B2 | 5/2017 | De Ridder |
| 9,656,085 B2 | 5/2017 | Moffitt et al. |
| 9,656,089 B2 | 5/2017 | Yip et al. |
| 9,707,406 B1 | 7/2017 | Dellamano et al. |
| 9,717,921 B2 | 8/2017 | Perryman et al. |
| 9,731,140 B1 | 8/2017 | Perryman et al. |
| 9,764,135 B2 | 9/2017 | De Ridder |
| 9,770,592 B2 | 9/2017 | Lin et al. |
| 9,789,314 B2 | 10/2017 | Perryman et al. |
| 9,789,321 B2 | 10/2017 | Dixit et al. |
| 9,826,963 B2 | 11/2017 | Scott et al. |
| 9,833,629 B2 | 12/2017 | Dellamano et al. |
| 9,913,975 B2 | 3/2018 | Carbunaru et al. |
| 9,919,159 B2 | 3/2018 | Skelton et al. |
| 9,993,646 B2 | 6/2018 | Parramon et al. |
| 10,004,635 B2 | 6/2018 | Kahook |
| 10,016,603 B2 | 7/2018 | Sachs et al. |
| 10,016,608 B2 | 7/2018 | Peterson et al. |
| 10,016,615 B2 | 7/2018 | Simon et al. |
| 10,016,627 B2 | 7/2018 | Viitala et al. |
| 10,022,549 B2 | 7/2018 | Dellamano et al. |
| 10,022,552 B2 | 7/2018 | Stahler et al. |
| 10,035,017 B2 | 7/2018 | Thakkar et al. |
| 10,035,020 B2 | 7/2018 | Wang et al. |
| 10,052,481 B2 | 8/2018 | McClure et al. |
| 10,076,668 B2 | 9/2018 | De Ridder |
| 10,086,201 B2 | 10/2018 | Chang et al. |
| 10,092,758 B2 | 10/2018 | De Ridder |
| 10,143,788 B2 | 12/2018 | Rudser et al. |
| 10,149,976 B1 | 12/2018 | Andresen et al. |
| 10,207,118 B2 | 2/2019 | Skelton |
| 10,238,872 B2 | 3/2019 | Pivonka et al. |
| 10,238,874 B2 | 3/2019 | Perryman et al. |
| 10,245,436 B2 | 4/2019 | Perryman et al. |
| 10,272,239 B1 | 4/2019 | Andresen et al. |
| 10,315,039 B2 | 6/2019 | Perryman et al. |
| 10,320,232 B2 | 6/2019 | Pivonka et al. |
| 10,328,265 B2 | 6/2019 | Moffitt et al. |
| 10,335,596 B2 | 7/2019 | Yakovlev et al. |
| 10,411,760 B2 | 9/2019 | Yakovlev et al. |
| 10,420,947 B2 | 9/2019 | Perryman et al. |
| 10,471,262 B2 | 11/2019 | Perryman et al. |
| 10,644,539 B2 | 5/2020 | Pivonka et al. |
| 10,682,521 B2 | 6/2020 | Jiang et al. |
| 10,849,643 B2 | 12/2020 | Castillo et al. |
| 10,898,719 B2 | 1/2021 | Pivonka et al. |
| 10,967,183 B2 | 4/2021 | Yakovlev et al. |
| 11,018,721 B2 | 5/2021 | Yakovlev et al. |
| 11,090,491 B2 | 8/2021 | Mishra et al. |
| 11,097,096 B2 | 8/2021 | Linden et al. |
| 11,133,709 B2 | 9/2021 | Pivonka et al. |
| 11,160,980 B2 | 11/2021 | Mishra et al. |
| 11,260,236 B2 | 3/2022 | Mathur et al. |
| 11,318,315 B2 | 5/2022 | Hartley et al. |
| 11,331,493 B2 | 5/2022 | Pivonka et al. |
| 11,451,265 B2 | 9/2022 | Yakovlev et al. |
| 11,511,121 B2 | 11/2022 | Sit et al. |
| 11,633,151 B2 | 4/2023 | Pivonka et al. |
| 11,766,561 B2 | 9/2023 | Mishra et al. |
| 11,826,569 B2 | 11/2023 | Mishra et al. |
| 11,938,327 B2 | 3/2024 | Hartley et al. |
| 2002/0014039 A1 | 2/2002 | Merlet |
| 2002/0111659 A1 | 8/2002 | David |
| 2002/0140399 A1 | 10/2002 | Echarri et al. |
| 2003/0055406 A1 | 3/2003 | Lebel et al. |
| 2003/0085684 A1 | 5/2003 | Tsukamoto et al. |
| 2003/0135253 A1 | 7/2003 | Kokones et al. |
| 2004/0059392 A1 | 3/2004 | Parramon et al. |
| 2004/0093039 A1 | 5/2004 | Schumert |
| 2004/0106954 A1 | 6/2004 | Whitehurst et al. |
| 2004/0119552 A1 | 6/2004 | Wray |
| 2004/0215287 A1 | 10/2004 | Swoyer et al. |
| 2004/0215306 A1 | 10/2004 | Heil et al. |
| 2005/0043765 A1 | 2/2005 | Williams et al. |
| 2005/0075696 A1 | 4/2005 | Forsberg et al. |
| 2005/0075699 A1 | 4/2005 | Olson et al. |
| 2005/0151696 A1 | 7/2005 | Govari et al. |
| 2005/0187594 A1 | 8/2005 | Hatlestad |
| 2005/0222656 A1 | 10/2005 | Wahlstrand et al. |
| 2005/0245989 A1 | 11/2005 | Davis |
| 2005/0278000 A1 | 12/2005 | Strother et al. |
| 2005/0288596 A1 | 12/2005 | Eigler et al. |
| 2006/0004429 A1 | 1/2006 | Mrva et al. |
| 2006/0074450 A1 | 4/2006 | Boveja et al. |
| 2006/0074458 A1 | 4/2006 | Imran |
| 2006/0095078 A1 | 5/2006 | Tronnes |
| 2006/0122653 A1 | 6/2006 | Bradley et al. |
| 2006/0149330 A1 | 7/2006 | Mann et al. |
| 2006/0190021 A1 | 8/2006 | Hausman et al. |
| 2006/0217782 A1 | 9/2006 | Boveja et al. |
| 2006/0224225 A1 | 10/2006 | Ransbury et al. |
| 2006/0247738 A1 | 11/2006 | Shmeling |
| 2006/0265057 A1 | 11/2006 | Greenberg et al. |
| 2007/0021802 A1 | 1/2007 | Heruth et al. |

(56) References Cited

U.S. PATENT DOCUMENTS

| | | |
|---|---|---|
| 2007/0032734 A1 | 2/2007 | Najafi et al. |
| 2007/0038250 A1 | 2/2007 | He et al. |
| 2007/0049986 A1 | 3/2007 | Imran |
| 2007/0049989 A1 | 3/2007 | Rossing et al. |
| 2007/0100411 A1 | 5/2007 | Bonde |
| 2007/0123946 A1 | 5/2007 | Masoud |
| 2007/0123952 A1 | 5/2007 | Strother et al. |
| 2007/0129767 A1 | 6/2007 | Wahlstrand |
| 2007/0142874 A1 | 6/2007 | John |
| 2007/0156205 A1 | 7/2007 | Larson et al. |
| 2007/0213773 A1 | 9/2007 | Hill |
| 2007/0255368 A1 | 11/2007 | Bonde et al. |
| 2007/0270928 A1 | 11/2007 | Erlebacher |
| 2007/0288076 A1 | 12/2007 | Bulkes et al. |
| 2008/0045989 A1 | 2/2008 | Welborn |
| 2008/0055178 A1 | 3/2008 | Kim et al. |
| 2008/0082147 A1 | 4/2008 | Dai et al. |
| 2008/0103569 A1 | 5/2008 | Gerber |
| 2008/0103570 A1 | 5/2008 | Gerber |
| 2008/0103578 A1 | 5/2008 | Gerber |
| 2008/0132981 A1 | 6/2008 | Gerber |
| 2008/0143619 A1 | 6/2008 | Wotherspoon |
| 2008/0146871 A1 | 6/2008 | Arneson et al. |
| 2008/0161803 A1 | 7/2008 | Oral et al. |
| 2008/0183227 A1 | 7/2008 | Sutton |
| 2008/0195128 A1 | 8/2008 | Orbay et al. |
| 2008/0214992 A1 | 9/2008 | Haarala |
| 2008/0269591 A1 | 10/2008 | Halperin et al. |
| 2008/0300654 A1 | 12/2008 | Lambert et al. |
| 2008/0300656 A1 | 12/2008 | Donders et al. |
| 2008/0300660 A1 | 12/2008 | John |
| 2008/0319492 A1 | 12/2008 | Katsnelson |
| 2009/0082835 A1 | 3/2009 | Jaax et al. |
| 2009/0088817 A1 | 4/2009 | Starkebaum et al. |
| 2009/0088819 A1 | 4/2009 | Starkebaum et al. |
| 2009/0105782 A1 | 4/2009 | Mickle |
| 2009/0112282 A1 | 4/2009 | Kast et al. |
| 2009/0171408 A1 | 7/2009 | Solem |
| 2009/0171420 A1 | 7/2009 | Brown et al. |
| 2009/0187230 A1 | 7/2009 | Dilorenzo |
| 2009/0204170 A1 | 8/2009 | Hastings et al. |
| 2009/0216296 A1 | 8/2009 | Meskens |
| 2009/0224361 A1 | 9/2009 | Liu et al. |
| 2009/0275956 A1 | 11/2009 | Burnes et al. |
| 2009/0276015 A1 | 11/2009 | Rondoni et al. |
| 2009/0281597 A1 | 11/2009 | Parramon et al. |
| 2009/0319005 A1 | 12/2009 | Lineaweaver |
| 2010/0010383 A1 | 1/2010 | Skelton et al. |
| 2010/0010392 A1 | 1/2010 | Skelton et al. |
| 2010/0036454 A1 | 2/2010 | Bennett et al. |
| 2010/0045114 A1 | 2/2010 | Sample et al. |
| 2010/0069996 A1 | 3/2010 | Strahl |
| 2010/0076525 A1 | 3/2010 | Skelton et al. |
| 2010/0082087 A1 | 4/2010 | Silipo et al. |
| 2010/0114189 A1 | 5/2010 | Donofrio et al. |
| 2010/0125312 A1 | 5/2010 | Stevenson et al. |
| 2010/0137948 A1 | 6/2010 | Aghassian |
| 2010/0161002 A1 | 6/2010 | Aghassian et al. |
| 2010/0168817 A1 | 7/2010 | Yamamoto et al. |
| 2010/0201368 A1 | 8/2010 | Doerr et al. |
| 2010/0225174 A1 | 9/2010 | Jiang |
| 2010/0249888 A1 | 9/2010 | Glenn et al. |
| 2010/0274314 A1 | 10/2010 | Alataris et al. |
| 2010/0274316 A1 | 10/2010 | Alataris et al. |
| 2010/0274318 A1 | 10/2010 | Walker et al. |
| 2010/0298635 A1 | 11/2010 | Hata et al. |
| 2010/0305663 A1* | 12/2010 | Aghassian .......... A61N 1/37223 607/61 |
| 2011/0004278 A1 | 1/2011 | Aghassian |
| 2011/0034886 A1 | 2/2011 | Elbe et al. |
| 2011/0054583 A1 | 3/2011 | Litt |
| 2011/0060395 A1 | 3/2011 | Cantlon |
| 2011/0093032 A1 | 4/2011 | Boggs, II et al. |
| 2011/0106214 A1 | 5/2011 | Carbunaru et al. |
| 2011/0112610 A1 | 5/2011 | Rahman et al. |
| 2011/0137378 A1 | 6/2011 | Klosterman |
| 2011/0172562 A1 | 7/2011 | Sahasrabudhe et al. |
| 2011/0172737 A1 | 7/2011 | Davis et al. |
| 2011/0172743 A1 | 7/2011 | Davis et al. |
| 2011/0184337 A1 | 7/2011 | Evans et al. |
| 2011/0184488 A1 | 7/2011 | De Ridder |
| 2011/0190849 A1 | 8/2011 | Faltys |
| 2011/0218593 A1 | 9/2011 | Rubinstein et al. |
| 2011/0224665 A1 | 9/2011 | Crosby et al. |
| 2011/0234155 A1 | 9/2011 | Chen |
| 2011/0257707 A1 | 10/2011 | Kothandaraman |
| 2011/0264163 A1 | 10/2011 | Tracey et al. |
| 2011/0276110 A1 | 11/2011 | Whitehurst |
| 2011/0301670 A1 | 12/2011 | Gross et al. |
| 2011/0301687 A1 | 12/2011 | Van Waalwijk Van Doorn |
| 2011/0307032 A1 | 12/2011 | Goetz et al. |
| 2012/0004708 A1 | 1/2012 | Chen et al. |
| 2012/0004709 A1 | 1/2012 | Chen et al. |
| 2012/0012630 A1 | 1/2012 | Lui et al. |
| 2012/0016439 A1 | 1/2012 | Alataris et al. |
| 2012/0035692 A1 | 2/2012 | Cantlon |
| 2012/0041508 A1 | 2/2012 | Rousso et al. |
| 2012/0093245 A1 | 4/2012 | Makdissi |
| 2012/0179071 A1* | 7/2012 | Skelton ................. G16Z 99/00 600/595 |
| 2012/0185027 A1 | 7/2012 | Pianca |
| 2012/0197352 A1 | 8/2012 | Carbunaru et al. |
| 2012/0221074 A1 | 8/2012 | Funderburk et al. |
| 2012/0283800 A1 | 11/2012 | Perryman et al. |
| 2012/0296329 A1 | 11/2012 | Ng |
| 2012/0296444 A1 | 11/2012 | Greenberg et al. |
| 2013/0004925 A1 | 1/2013 | Labbe et al. |
| 2013/0012866 A1 | 1/2013 | Deem et al. |
| 2013/0023943 A1 | 1/2013 | Parramon et al. |
| 2013/0053767 A1 | 2/2013 | Pivonka |
| 2013/0079861 A1 | 3/2013 | Reinert |
| 2013/0096650 A1* | 4/2013 | Aghassian .......... A61N 1/3787 607/61 |
| 2013/0110194 A1 | 5/2013 | Wei |
| 2013/0150925 A1 | 6/2013 | Vamos et al. |
| 2013/0193914 A1 | 8/2013 | Gaddam et al. |
| 2013/0197609 A1 | 8/2013 | Moore et al. |
| 2013/0204321 A1 | 8/2013 | Alataris et al. |
| 2013/0211469 A1 | 8/2013 | Lamont |
| 2013/0215979 A1 | 8/2013 | Yakovlev et al. |
| 2013/0261703 A1 | 10/2013 | Chow |
| 2013/0265144 A1 | 10/2013 | Banna |
| 2013/0289637 A1 | 10/2013 | Amely-Velez et al. |
| 2013/0310706 A1 | 11/2013 | Stone et al. |
| 2013/0310901 A1 | 11/2013 | Perryman et al. |
| 2013/0317564 A1 | 11/2013 | Lin et al. |
| 2013/0331638 A1 | 12/2013 | Cameron et al. |
| 2013/0345202 A1 | 12/2013 | Amselem |
| 2014/0025140 A1 | 1/2014 | Lui et al. |
| 2014/0046413 A1 | 2/2014 | Kane et al. |
| 2014/0058467 A1 | 2/2014 | Hamann et al. |
| 2014/0094876 A1* | 4/2014 | Wingeier ............ A61B 5/0031 607/62 |
| 2014/0100636 A1 | 4/2014 | Mashiach et al. |
| 2014/0107709 A1 | 4/2014 | Schmitz et al. |
| 2014/0119552 A1 | 5/2014 | Beaucoup |
| 2014/0142507 A1 | 5/2014 | Armes |
| 2014/0155973 A1 | 6/2014 | Grigsby |
| 2014/0163338 A1 | 6/2014 | Roesick |
| 2014/0163580 A1 | 6/2014 | Tischendorf et al. |
| 2014/0163638 A1* | 6/2014 | Marnfeldt .......... A61N 1/36128 607/46 |
| 2014/0163646 A1 | 6/2014 | Tischendorf et al. |
| 2014/0172047 A1 | 6/2014 | Spitaels et al. |
| 2014/0180365 A1 | 6/2014 | Perryman et al. |
| 2014/0194771 A1 | 7/2014 | Parker et al. |
| 2014/0203823 A1 | 7/2014 | Joshi |
| 2014/0222106 A1 | 8/2014 | Sharma et al. |
| 2014/0257428 A1 | 9/2014 | Zhu |
| 2014/0266774 A1 | 9/2014 | Greene |
| 2014/0275847 A1 | 9/2014 | Perryman et al. |
| 2014/0277281 A1 | 9/2014 | Grandhe |
| 2014/0277282 A1 | 9/2014 | Jaax |
| 2014/0288393 A1 | 9/2014 | Grevious et al. |

(56) References Cited

U.S. PATENT DOCUMENTS

| | | |
|---|---|---|
| 2014/0288616 A1 | 9/2014 | Rawat et al. |
| 2014/0304773 A1 | 10/2014 | Woods et al. |
| 2014/0330348 A1 | 11/2014 | Shelton et al. |
| 2014/0336727 A1 | 11/2014 | Perryman et al. |
| 2014/0346078 A1 | 11/2014 | Chang |
| 2014/0358197 A1* | 12/2014 | Mashiach ............ A61N 1/3606 607/60 |
| 2014/0364919 A1 | 12/2014 | Doan |
| 2014/0371515 A1 | 12/2014 | John |
| 2015/0012057 A1* | 1/2015 | Carlson ............... A61N 1/3606 607/45 |
| 2015/0018699 A1 | 1/2015 | Zeng et al. |
| 2015/0018728 A1 | 1/2015 | Gross et al. |
| 2015/0028798 A1 | 1/2015 | Dearden et al. |
| 2015/0035378 A1 | 2/2015 | Calhoun et al. |
| 2015/0080982 A1 | 3/2015 | Van Funderburk |
| 2015/0100109 A1* | 4/2015 | Feldman ............... A61N 1/3787 607/60 |
| 2015/0100110 A1 | 4/2015 | Towe et al. |
| 2015/0119673 A1 | 4/2015 | Pellinen et al. |
| 2015/0164401 A1 | 6/2015 | Toth et al. |
| 2015/0224326 A1 | 8/2015 | Toth et al. |
| 2015/0265842 A1 | 9/2015 | Ridler et al. |
| 2015/0290379 A1 | 10/2015 | Rudser et al. |
| 2015/0321000 A1 | 11/2015 | Rosenbluth et al. |
| 2015/0321002 A1 | 11/2015 | Khalil et al. |
| 2015/0335285 A1 | 11/2015 | Poon et al. |
| 2016/0015411 A1 | 1/2016 | Keller |
| 2016/0015980 A1 | 1/2016 | Biele et al. |
| 2016/0023006 A1 | 1/2016 | Ridler et al. |
| 2016/0023022 A1 | 1/2016 | Zarins et al. |
| 2016/0030666 A1 | 2/2016 | Lozano et al. |
| 2016/0036261 A1 | 2/2016 | Lenive |
| 2016/0087687 A1 | 3/2016 | Kesler |
| 2016/0106994 A1 | 4/2016 | Crosby et al. |
| 2016/0113671 A1 | 4/2016 | Berger et al. |
| 2016/0121102 A1 | 5/2016 | Tockman et al. |
| 2016/0121124 A1 | 5/2016 | Johanek et al. |
| 2016/0135917 A1 | 5/2016 | Mickle et al. |
| 2016/0136438 A1 | 5/2016 | Perryman et al. |
| 2016/0136443 A1 | 5/2016 | Grandhe et al. |
| 2016/0144184 A1 | 5/2016 | Marnfeldt |
| 2016/0166835 A1 | 6/2016 | De Ridder |
| 2016/0199657 A1 | 7/2016 | Jiang et al. |
| 2016/0199658 A1 | 7/2016 | Nassif et al. |
| 2016/0218433 A1 | 7/2016 | Nghiem et al. |
| 2016/0331956 A1 | 11/2016 | Yakovlev et al. |
| 2016/0346546 A1 | 12/2016 | Zhu |
| 2016/0361545 A1* | 12/2016 | Kaula ................ A61N 1/36057 |
| 2016/0375237 A1 | 12/2016 | Hahn et al. |
| 2017/0001003 A1 | 1/2017 | Pivonka et al. |
| 2017/0028199 A1 | 2/2017 | Roehrlein et al. |
| 2017/0050021 A1 | 2/2017 | Cosman, Sr. |
| 2017/0054324 A1 | 2/2017 | Pivonka et al. |
| 2017/0054332 A1 | 2/2017 | Pivonka et al. |
| 2017/0087353 A1 | 3/2017 | Thota et al. |
| 2017/0095667 A1 | 4/2017 | Yakovlev et al. |
| 2017/0113046 A1 | 4/2017 | Fried et al. |
| 2017/0165491 A9 | 6/2017 | De Ridder |
| 2017/0189683 A1 | 7/2017 | Perryman et al. |
| 2017/0197082 A1 | 7/2017 | Pang et al. |
| 2017/0216602 A1 | 8/2017 | Waataja et al. |
| 2017/0239483 A1 | 8/2017 | Mathur et al. |
| 2017/0252552 A1 | 9/2017 | Cook et al. |
| 2017/0368339 A1 | 12/2017 | De Ridder |
| 2018/0028824 A1 | 2/2018 | Pivonka et al. |
| 2018/0056080 A1 | 3/2018 | Reinke et al. |
| 2018/0064944 A1 | 3/2018 | Grill et al. |
| 2018/0070841 A1 | 3/2018 | Honore et al. |
| 2018/0071512 A1 | 3/2018 | Feldman et al. |
| 2018/0071536 A1 | 3/2018 | Skelton et al. |
| 2018/0083668 A1 | 3/2018 | Yakovlev et al. |
| 2018/0085593 A1 | 3/2018 | Fayram et al. |
| 2018/0090971 A1 | 3/2018 | Graham |
| 2018/0169423 A1 | 6/2018 | Perryman et al. |
| 2018/0200520 A1 | 7/2018 | Tranchina et al. |
| 2018/0236237 A1 | 8/2018 | Kent et al. |
| 2018/0243563 A1 | 8/2018 | Vallejo et al. |
| 2018/0256906 A1 | 9/2018 | Pivonka et al. |
| 2018/0289965 A1 | 10/2018 | Nelson et al. |
| 2018/0326220 A1 | 11/2018 | Kaula et al. |
| 2018/0333578 A1 | 11/2018 | Mock et al. |
| 2018/0345019 A1 | 12/2018 | Greenberg et al. |
| 2018/0368875 A1 | 12/2018 | Castillo et al. |
| 2019/0001139 A1 | 1/2019 | Mishra et al. |
| 2019/0008556 A1 | 1/2019 | Perryman et al. |
| 2019/0009097 A1 | 1/2019 | Hartley et al. |
| 2019/0143124 A1 | 5/2019 | Perryman et al. |
| 2019/0151659 A1 | 5/2019 | Mishra et al. |
| 2019/0247198 A1 | 8/2019 | Zellmer et al. |
| 2019/0262610 A1 | 8/2019 | Kent et al. |
| 2019/0269913 A1 | 9/2019 | Pivonka et al. |
| 2019/0374776 A1 | 12/2019 | Mishra et al. |
| 2019/0388692 A1 | 12/2019 | Dinsmoor et al. |
| 2020/0101291 A1 | 4/2020 | Yakovlev et al. |
| 2020/0139138 A1 | 5/2020 | Sit et al. |
| 2020/0204209 A1 | 6/2020 | Yakovlev et al. |
| 2020/0222000 A1 | 7/2020 | Poon et al. |
| 2020/0306528 A1 | 10/2020 | Linden et al. |
| 2020/0398058 A1 | 12/2020 | Pivonka et al. |
| 2021/0099015 A1 | 4/2021 | Pivonka et al. |
| 2021/0196957 A1 | 7/2021 | Yakovlev et al. |
| 2021/0330981 A1 | 10/2021 | Mishra et al. |
| 2021/0399765 A1 | 12/2021 | Yakovlev et al. |
| 2022/0016103 A1 | 1/2022 | Baltcheva et al. |
| 2022/0016430 A1 | 1/2022 | Hartley et al. |
| 2022/0072300 A1 | 3/2022 | Yakovlev et al. |
| 2022/0080189 A1 | 3/2022 | Mishra et al. |
| 2022/0118251 A1 | 4/2022 | Buddha et al. |
| 2022/0126103 A1 | 4/2022 | Pivonka et al. |
| 2022/0134108 A1 | 5/2022 | Dinsmoor et al. |
| 2022/0176120 A1 | 6/2022 | Kulkarni et al. |
| 2022/0176133 A1 | 6/2022 | Buddha et al. |
| 2022/0218994 A1 | 7/2022 | Mishra et al. |
| 2022/0263346 A1 | 8/2022 | Pivonka et al. |
| 2023/0029600 A1 | 2/2023 | Pivonka et al. |
| 2023/0129373 A1 | 4/2023 | Sit et al. |
| 2023/0146724 A1 | 5/2023 | Debock et al. |
| 2024/0041399 A1 | 2/2024 | Pivonka |
| 2024/0050747 A1 | 2/2024 | Mishra et al. |
| 2024/0050758 A1 | 2/2024 | Castillo et al. |
| 2024/0139517 A1 | 5/2024 | Mishra |

FOREIGN PATENT DOCUMENTS

| | | |
|---|---|---|
| EP | 2155330 B1 | 10/2014 |
| WO | WO-9500203 A1 | 1/1995 |
| WO | WO-2005105201 A2 | 11/2005 |
| WO | WO-2007051146 A1 | 5/2007 |
| WO | WO-2007068284 A1 | 6/2007 |
| WO | WO-2008066556 A1 | 6/2008 |
| WO | WO-2009045297 A1 | 4/2009 |
| WO | WO-2010051062 A1 | 5/2010 |
| WO | WO-2010062517 A1 | 6/2010 |
| WO | WO-2013035092 A2 | 3/2013 |
| WO | WO-2014071079 A1 | 5/2014 |
| WO | WO-2014089299 A2 | 6/2014 |
| WO | WO-2014153124 A1 | 9/2014 |
| WO | WO-2014153219 A1 | 9/2014 |
| WO | WO-2014153228 A1 | 9/2014 |
| WO | WO-2014205129 A1 | 12/2014 |
| WO | WO-2015081231 A1 | 6/2015 |
| WO | WO-2015139053 A1 | 9/2015 |
| WO | WO-2015179177 A1 | 11/2015 |
| WO | WO-2015196164 | 12/2015 |
| WO | WO-2015196164 A3 | 12/2015 |
| WO | WO-2016028608 A1 | 2/2016 |
| WO | WO-2016113832 A1 | 7/2016 |
| WO | WO-2016127130 A1 | 8/2016 |
| WO | WO-2016191055 A1 | 12/2016 |
| WO | WO-2016205373 A1 | 12/2016 |
| WO | WO-2017044904 A1 | 3/2017 |
| WO | WO-2017142948 A1 | 8/2017 |
| WO | WO-2017165410 A1 | 9/2017 |

(56) References Cited

FOREIGN PATENT DOCUMENTS

| WO | WO-2017205675 A1 | 11/2017 |
|---|---|---|
| WO | WO-2018017463 A1 | 1/2018 |
| WO | WO-2018023057 A1 | 2/2018 |
| WO | WO-2018126062 A1 | 7/2018 |
| WO | WO-2018144631 A1 | 8/2018 |
| WO | WO-2018156953 A1 | 8/2018 |
| WO | WO-2018170141 A1 | 9/2018 |
| WO | WO-2018208992 A1 | 11/2018 |
| WO | WO-2021003439 A1 | 1/2021 |
| WO | WO-2021067873 A1 | 4/2021 |
| WO | WO-2021133947 A1 | 7/2021 |
| WO | WO-2021262762 A1 | 12/2021 |
| WO | WO-2022047077 A1 | 3/2022 |
| WO | WO-2022103774 A1 | 5/2022 |
| WO | WO-2022197748 A1 | 9/2022 |

OTHER PUBLICATIONS

PCT/US18/31904 International Search Report dated Jul. 26, 2018.
U.S. Appl. No. 16/672,921 Notice of Allowance dated Apr. 23, 2021.
U.S. Appl. No. 16/672,921 Office Action dated Feb. 16, 2021.
U.S. Appl. No. 16/672,921 Office Action dated Mar. 22, 2021.
Extended European Search Report for European Application No. EP23186171.7 dated Jan. 5, 2024, 7 pages.
Extended European Search Report mailed on Jan. 3, 2024, for EP Application No. 20871125.9, 15 pages.
Final Office Action for U.S. Appl. No. 16/111,868 mailed on Mar. 11, 2021, 24 pages.
Final Office Action mailed on Aug. 18, 2023, for U.S. Appl. No. 17/240,629, filed Apr. 26, 2021, 11 pages.
Final Office Action mailed on Nov. 1, 2023, for U.S. Appl. No. 17/726,378, filed Apr. 21, 2022, 15 pages.
International Search Report and Written Opinion mailed on May 18, 2022, for PCT Application No. PCT/US2022/020452, filed Mar. 15, 2022, 8 pages.
Non-Final Office Action for U.S. Appl. No. 14/975,358 dated Aug. 8, 2019. 12 pages.
Non-Final Office Action for U.S. Appl. No. 16/111,868 mailed on Jul. 8, 2021, 30 pages.
Non-Final Office Action for U.S. Appl. No. 17/726,378 dated Apr. 14, 2023, 15 pages.
Non-Final Office Action for U.S. Appl. No. 18/046,042 dated Aug. 23, 2023, 13 pages.
Non-Final Office Action mailed on Mar. 22, 2023, for U.S. Appl. No. 17/489,580, filed Sep. 29, 2021, 16 pages.
Notice of Allowance for U.S. Appl. No. 16/222,959 dated May 22, 2023, 11 pages.
Notice of Allowance for U.S. Appl. No. 17/489,580 dated Nov. 22, 2023, 9 pages.
Partial Supplementary European Search Report mailed on Sep. 18, 2023, for EP Application No. 20871125.9, 14 pages.
Crosby D N, et al., "Burst and Tonic Spinal Cord Stimulation Differentially Activate GABAergic Mechanisms to Attenuate Pain in a Rat Model of Cervical Radiculopathy", IEEE Transactions on Biomedical Engineering, Jun. 2015, vol. 62 No. 6, pp. 1604-1613.
Extended European Search Report for European Application No. EP21827905.7 dated Jun. 18, 2024, 5 pages.
Extended European Search Report mailed on Jun. 27, 2024, for EP Application No. 24157465.6, 7 pages.
Final Office Action for U.S. Appl. No. 18/046,042 dated Apr. 15, 2024, 14 pages.
He S, et al., The Electrically Evoked Compound Action Potential: From Laboratory to Clinic, Frontiers in Neuroscience, vol. 11, Jun. 2017, pp. 1-20.
Non-Final Office Action for U.S. Appl. No. 17/384,020 dated Jan. 23, 2024, 28 pages.
Non-Final Office Action for U.S. Appl. No. 17/412,044 dated Feb. 2, 2024, 12 pages.
Non-Final Office Action mailed on Feb. 1, 2024, for U.S. Appl. No. 17/081,351, filed Oct. 27, 2020, 13 pages.
Non-Final Office Action mailed on May 20, 2024, for U.S. Appl. No. 17/726,378, filed Apr. 21, 2022, 11 pages.
U.S. Appl. No. 63/082,856, inventors Lakshmi; Narayan Mishra et al., filed on Sep. 24, 2020. 131 pages.
Wheatley D, et al., "Electrically Evoked Compound Action Potential (ECAP) Stimulus-Artefact (SA) Blanking Low-Power Low-Noise CMOS Amplifier", 50th Midwest Symposium on Circuits and Systems, 2007, pp. 41-44.
U.S. Serial No. 16/120, 139 Office Action dated Mar. 26, 2020. 27 pages.
U.S. Serial No. 16/120, 139 Notice of Allowance dated Jul. 28, 2020. 10 pages.
Buhlmann, J. et al., "Modeling of a segmented electrode for desynchronizing deep brain stimulation" Frontiers in Neuroengineering (2011) vol. 4, Article 15, pp. 1-8.
Butson, C. et al., "Current steering to Control the vol. of Tissue Activated During Deep Brain Stimulation" Brain Stimul. (2008) (1): 7-15.
Cardador, L., "Review of Existing, Mounted Targeting Devices for Distal Locking of Intramedullary Nails, " Practice of Intramedullary Locked Nails, Jan. 1, 2006, pp. 265-270.
EP14813206 Examination Report dated Apr. 23, 2020. 2 pages.
EP15809379.9 European Search Report dated Mar. 9, 2018. 7 pages.
European Search Report and Written Opinion in EP Application No. 16845235.7, mailed Apr. 24, 2019, 8 pages.
European Search Report and Written Opinion in EP Application No. 13852295.8, mailed May 12, 2016, 10 pages.
European Search Report and Written Opinion in EP Application No. 14813206.1, mailed Dec. 6, 2016, 7 pages.
European Search Report and Written Opinion in EP Application No. 15761577.4, mailed Oct. 12, 2017, 8 pages.
European Search Report and Written Opinion in EP Application No. 16747389.1, mailed Jul. 5, 2018, 8 pages.
European Search Report and Written Opinion in EP Application No. 17753756.0, mailed Nov. 11, 2019, 9 pages.
European Search Report and Written Opinion in EP Application No. 17770982.1, mailed Sep. 26, 2019, 7 pages.
European Search Report and Written Opinion in EP Application No. 17803620.8, mailed Oct. 30, 2019, 8 pages.
European Search Report and Written Opinion in EP Application No. 17831624.6, mailed Feb. 20, 2020, 9 pages.
European Search Report and Written Opinion in EP Application No. 17887576.1, mailed Oct. 9, 2020, 8 pages.
European Search Report and Written Opinion in EP Application No. 18756643.5, mailed Dec. 3, 2020, 10 pages.
European Search Report and Written Opinion in EP Application No. 20160001.2, mailed Jul. 31, 2020, 7 pages.
European Search Report and Written Opinion in EP Application No. 20212248.7, mailed Apr. 12, 2021, 9 pages.
Final Office Action mailed on Nov. 21, 2022, for U.S. Appl. No. 16/222,959, 21 pages.
International Preliminary Report on Patentability for PCT/US2021/038545, Dec. 13, 2022, 6 pages.
International Preliminary Report on Patentability for International Application No. PCT/US2021/047815, mailed Mar. 9, 2023, 6 pages.
International Search Report and Written Opinion for PCT/US2014/043023; Oct. 6, 2014, 13 pages.
International Search Report and Written Opinion for PCT/US2015/020808, Jun. 24, 2015, 8 pages.
International Search Report and Written Opinion for PCT/US2015/036821, Dec. 18, 2015, 13 pages.
International Search Report and Written Opinion for PCT/US2016/016888, Apr. 14, 2016, 8 pages.
International Search Report and Written Opinion for PCT/US2016/051177, Nov. 10, 2016, 18 pages.
International Search Report and Written Opinion for PCT/US2017/017978, May 5, 2017, 7 pages.
International Search Report and Written Opinion for PCT/US2017/023400, May 23, 2017, 8 pages.

(56) References Cited

OTHER PUBLICATIONS

International Search Report and Written Opinion for PCT/US2017/042351, Sep. 26, 2017, 9 pages.
International Search Report and Written Opinion for PCT/US2017/068803, Mar. 6, 2018, 9 pages.
International Search Report and Written Opinion for PCT/US2018/019522, Jun. 15, 2018, 12 pages.
International Search Report and Written Opinion for PCT/US2020/040766, Oct. 6, 2020, 7 pages.
International Search Report and Written Opinion for PCT/US2020/054150, Jan. 6, 2021, 11 pages.
International Search Report and Written Opinion for PCT/US2020/066901, Mar. 15, 2021, 7 pages.
International Search Report and Written Opinion for PCT/US2021/038545, Mar. 15, 2021, 7 pages.
Lee et al, Predicted effects of pulse width programming in spinal cord stimulation: a mathematical modeling study. Med Biol Eng Comput 49:765-774 (2011). https://doi.org/1 0.1007 /s11517-011-0780-9.
Lenssen, Anneke et al, "Bimodal listeners are not sensitive to interaural time differences in unmodulated low-frequency stimuli," The Journal of the Acoustical Society of America, American Institute of Physics for the Acoustical Society of America, New York, NY, vol. 129, No. 6, Jun. 1, 2011, pp. 3457-3460.
Nag et al., "Flexible charge balanced stimulator with 5.6 fC accuracy for 140 nC injections" IEEE Trans Biomed Circuits Syst. (Jun. 2013) 7(3):266-275.doi: 10.1109/TBCAS.2012.2205574.
Non-Final Office Action mailed on Feb. 24, 2023, for U.S. Appl. No. 17/240,629, filed Apr. 26, 2021, 12 pages.
Office Action dated Oct. 20, 2017 for U.S. Appl. No. 15/264,864, 14 pages.
PCT/US2017/034553 International Search Report and Written Opinion dated Oct. 10, 2017, 9 pages.
Quayle Action mailed on Apr. 12, 2023, for U.S. Appl. No. 17/487,535, filed Sep. 28, 2021, 7 pages.
U.S. Appl. No. 63/042,293, inventors Mishra; Lakshmi Narayan et al., filed on Jun. 22, 2020, 101 pages.
U.S. Appl. No. 14/975,358 Office Action dated Dec. 5, 2019. 9 pages.
U.S. Appl. No. 14/975,358 Office Action dated Jul. 27, 2020. 12 pages.
U.S. Appl. No. 14/975,358 Office Action dated May 15, 2018. 9 pages.
U.S. Appl. No. 14/975,358 Office Action dated Nov. 2, 2020. 18 pages.
U.S. Appl. No. 14/975,358 Office Action dated Nov. 20, 2018. 9 pages.
U.S. Appl. No. 15/264,864 Notice of Allowance dated Nov. 8, 2018, 7 pages.
U.S. Appl. No. 15/264,864 Office Action dated Aug. 1, 2018, 12 pages.
U.S. Appl. No. 15/385,729 Office Action dated Oct. 12, 2018. 16 pages.
U.S. Appl. No. 15/385,729 Notice of Allowance dated Feb. 12, 2019. 7 pages.
U.S. Appl. No. 15/664,231 Office Action dated Aug. 6, 2020. 15 pages.
U.S. Appl. No. 15/664,231 Office Action dated Jan. 24, 2020. 16 pages.
U.S. Appl. No. 15/664,231 Office Action dated Jul. 10, 2020. 15 pages.
U.S. Appl. No. 15/664,231 Office Action dated Mar. 8, 2021. 25 pages.
U.S. Appl. No. 16/104,829 Notice of Allowance dated Jul. 6, 2021. 5 pages.
U.S. Appl. No. 16/104,829 Office Action dated Jan. 8, 2021. 20 pages.
U.S. Appl. No. 16/104,829 Office Action dated May 21, 2020. 15 Pages.
U.S. Appl. No. 16/408,989 Notice of Allowance dated Dec. 2, 2020. 7 pages.
U.S. Appl. No. 16/408,989 Office Action dated Sep. 16, 2020. 8 pages.
Yakovlev, Anatoly et al., "Implantable Biomedical Devices: Wireless powering and communication," IEEE Communications Magazinem, IEEE Service Center, vol. 50, No. 4, Apr. 1, 2012, pp. 152-159.

* cited by examiner

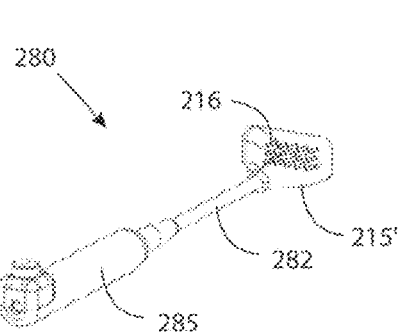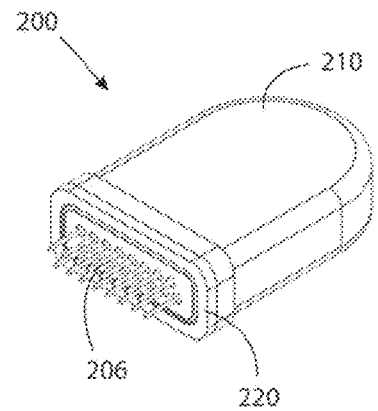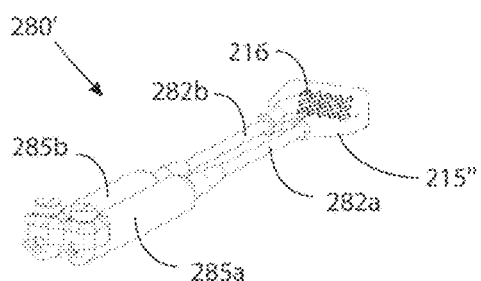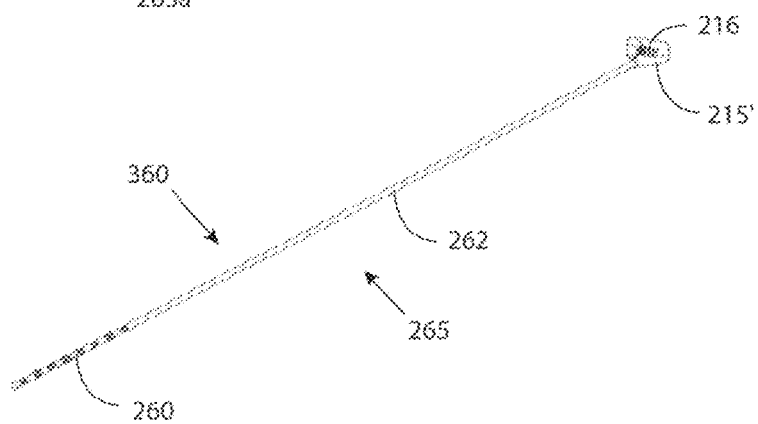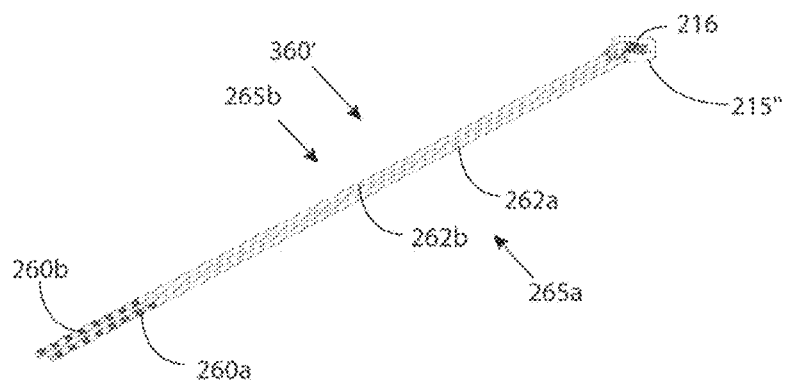

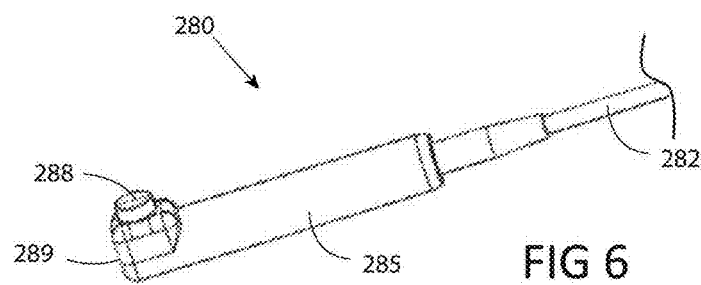
FIG 6
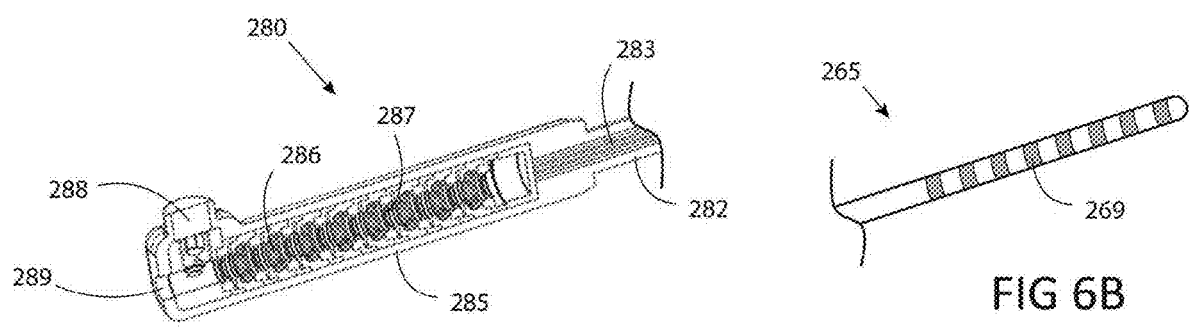
FIG 6A
FIG 6B
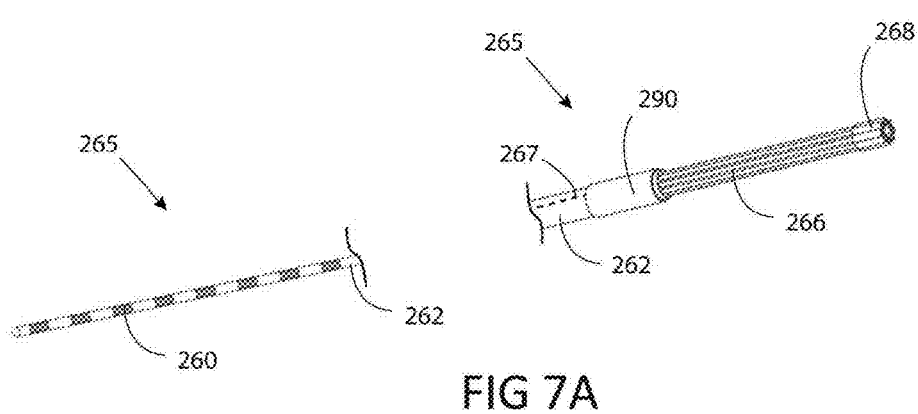
FIG 7A
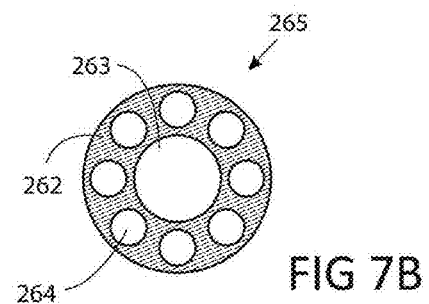
FIG 7B

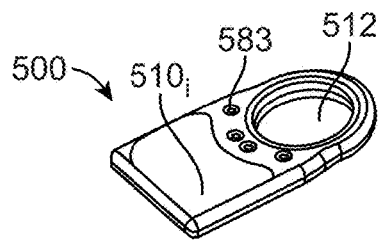 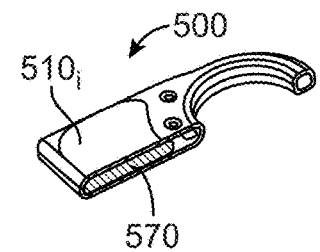
FIG. 18A
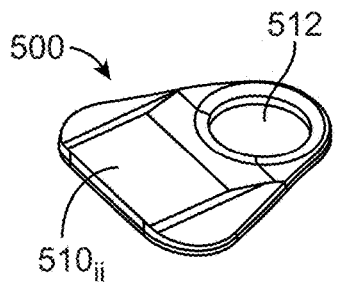 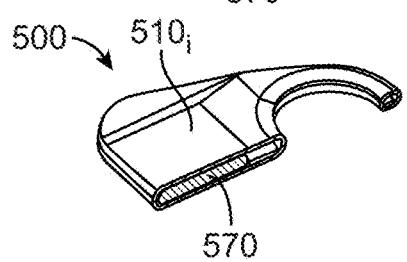
FIG. 18B
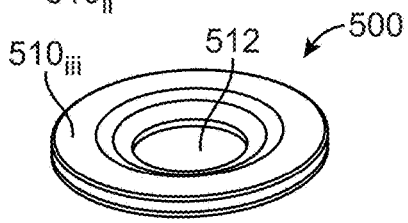 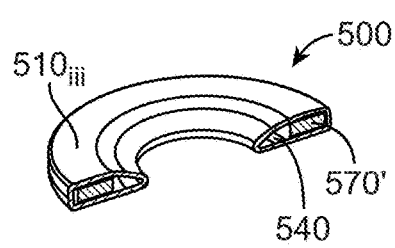
FIG. 18C
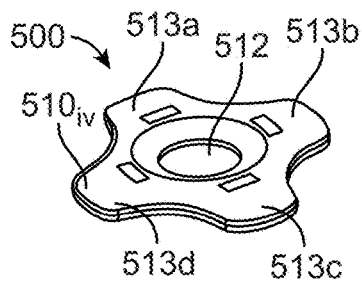 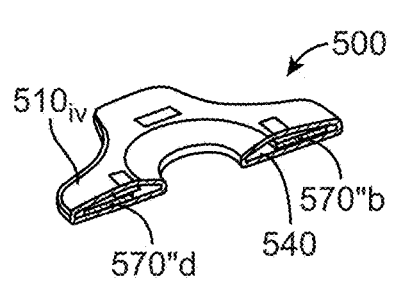
FIG. 18D
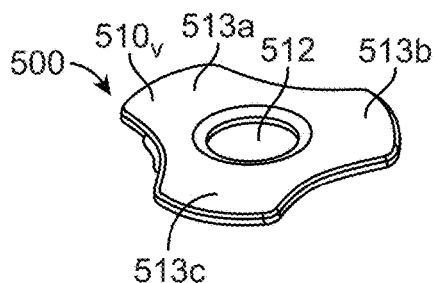 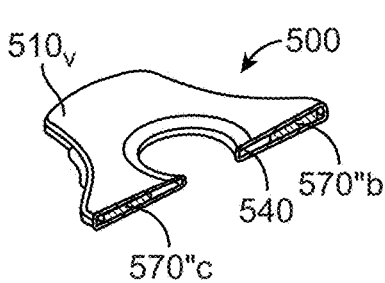
FIG. 18E
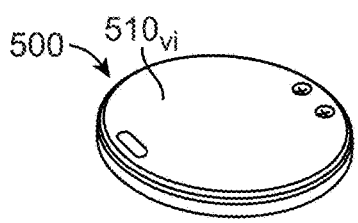 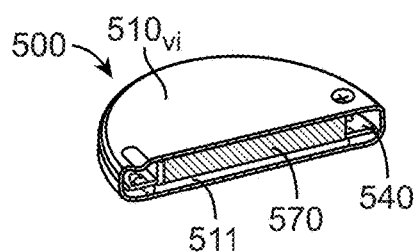
FIG. 18F

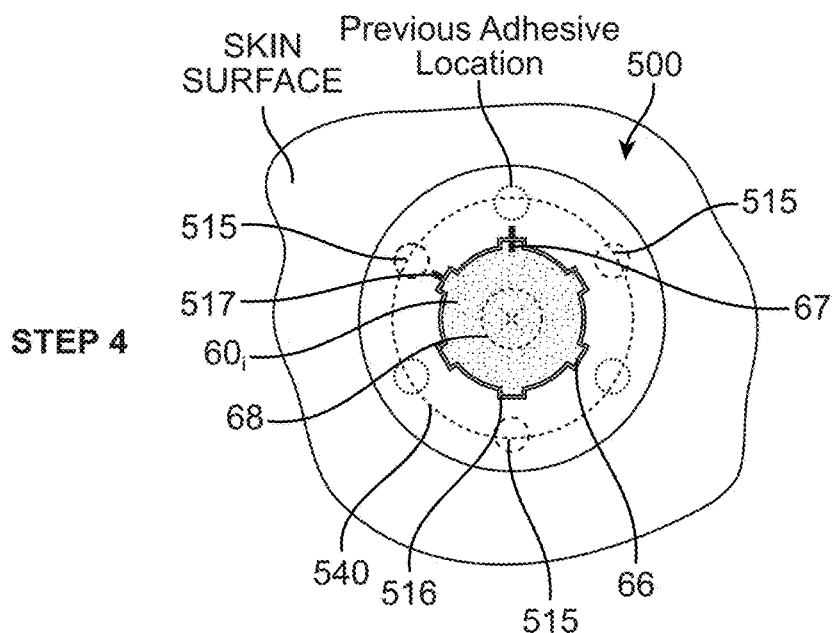
FIG. 20D
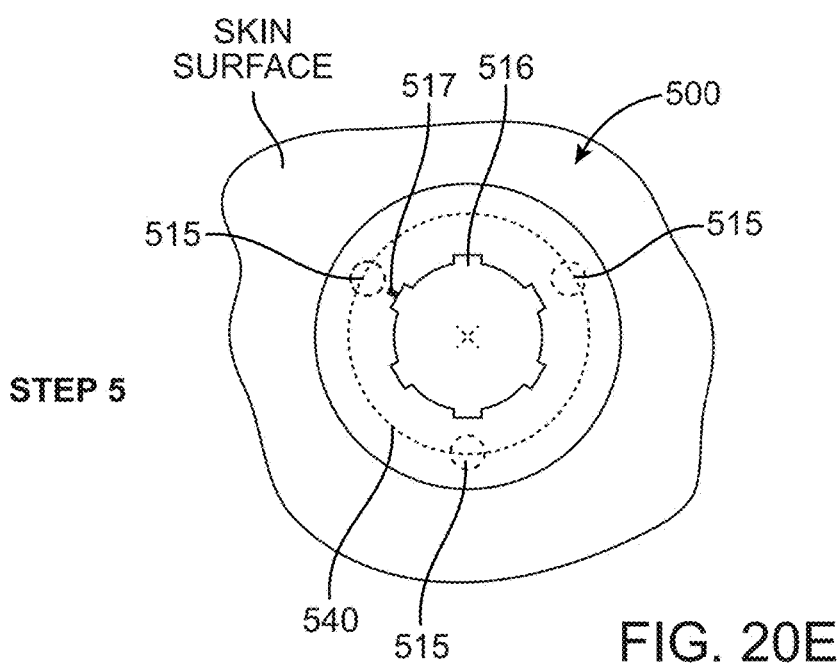 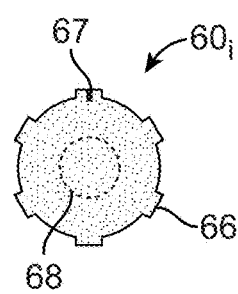
FIG. 20E

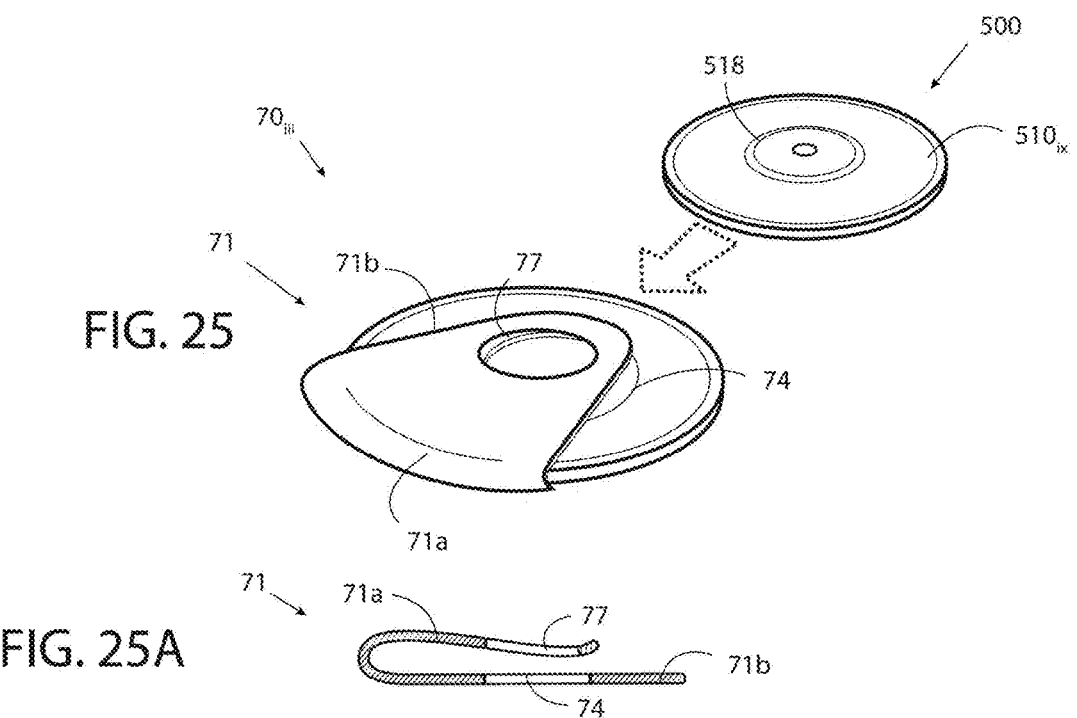
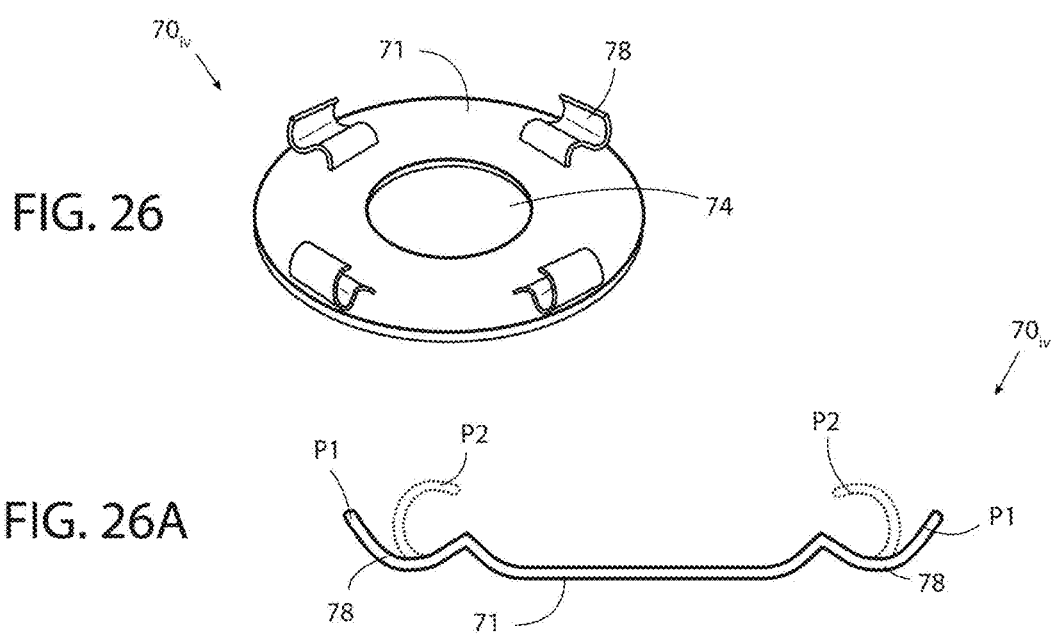

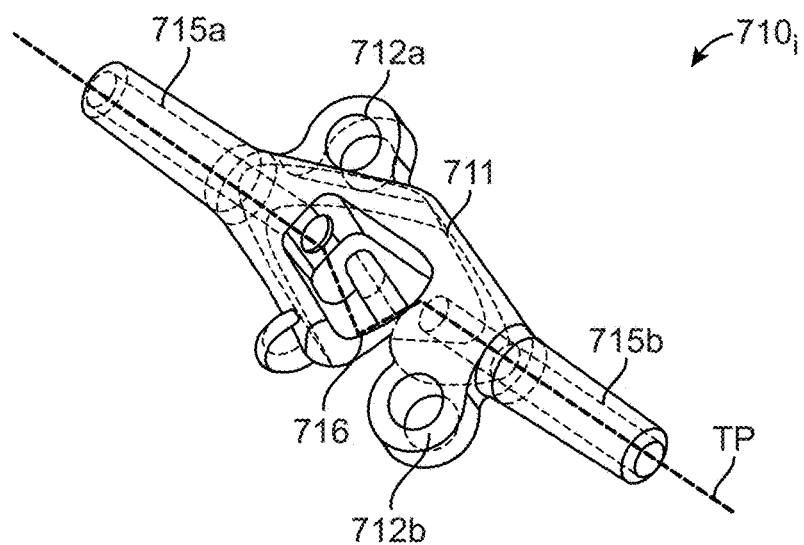
FIG. 27
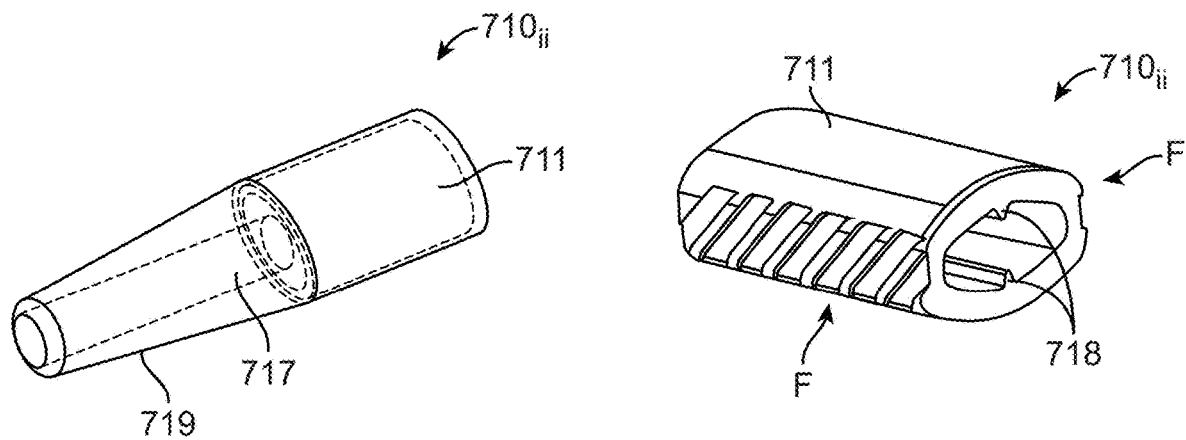
FIG. 28A
FIG. 28B

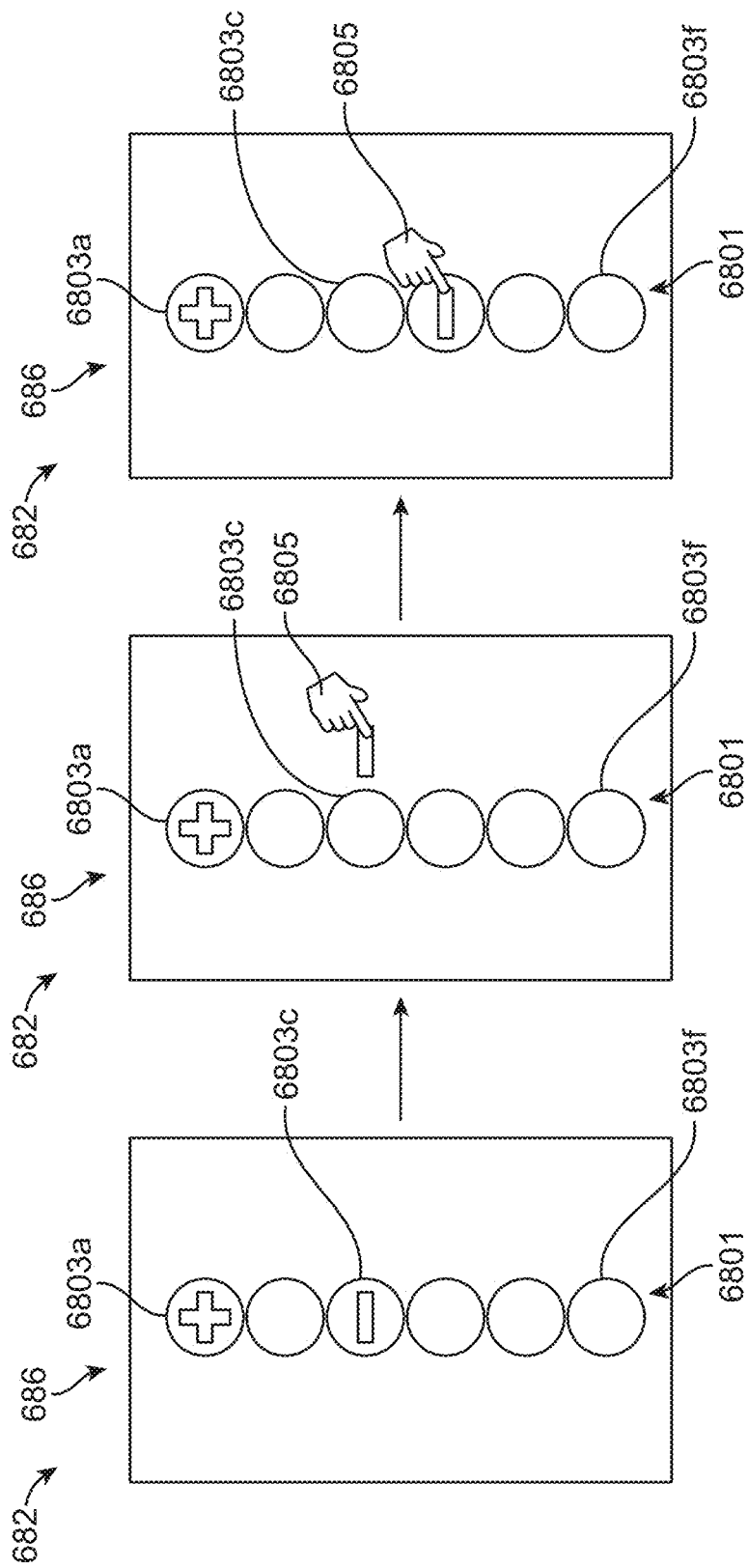

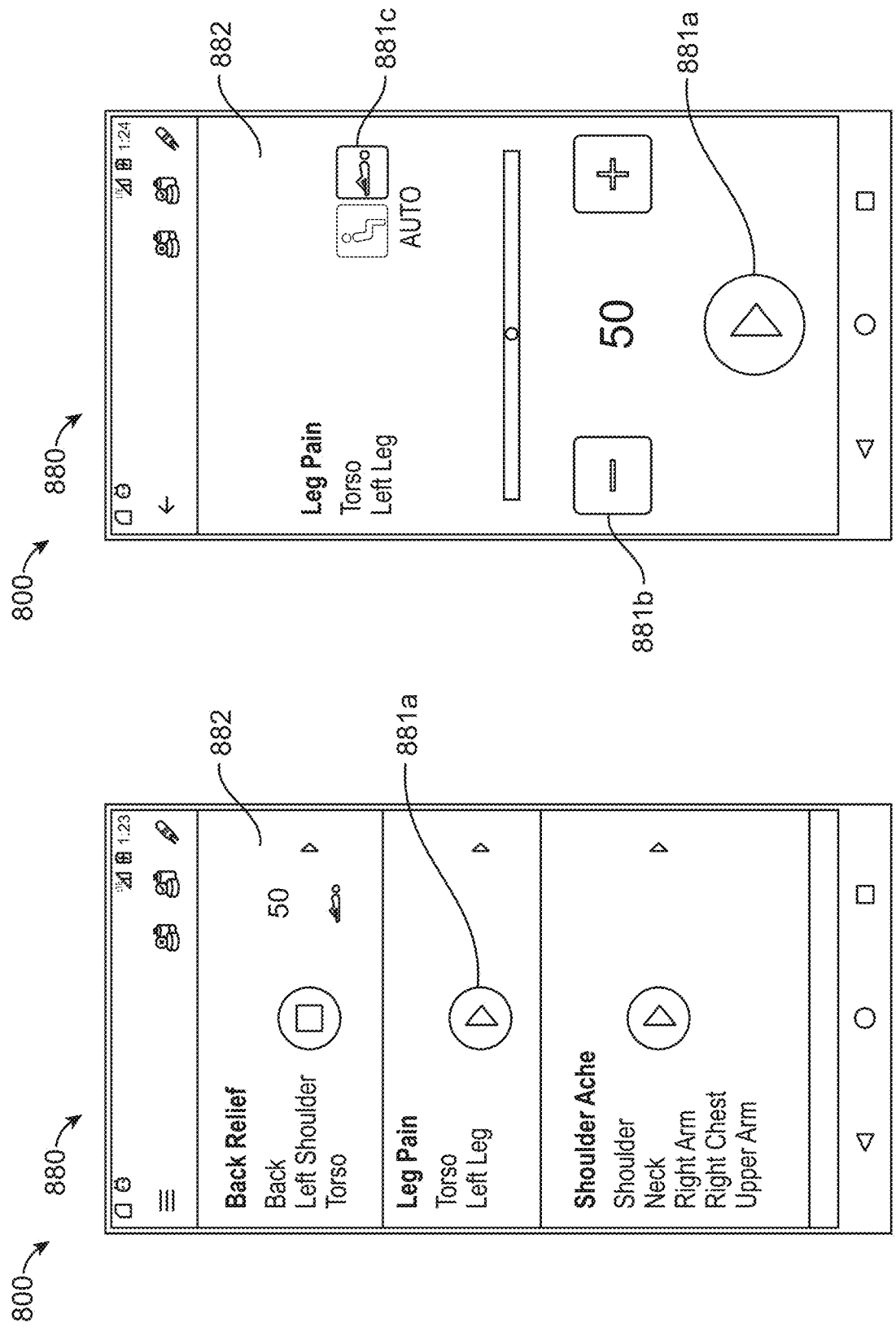

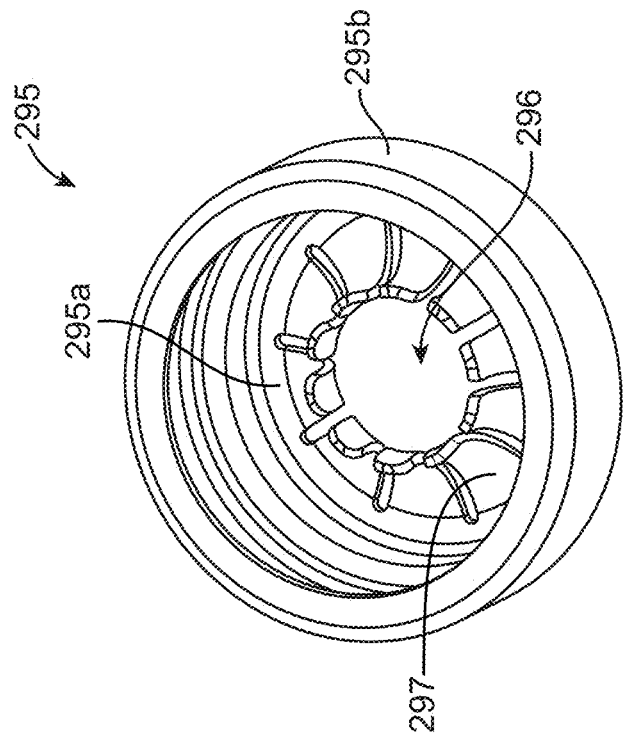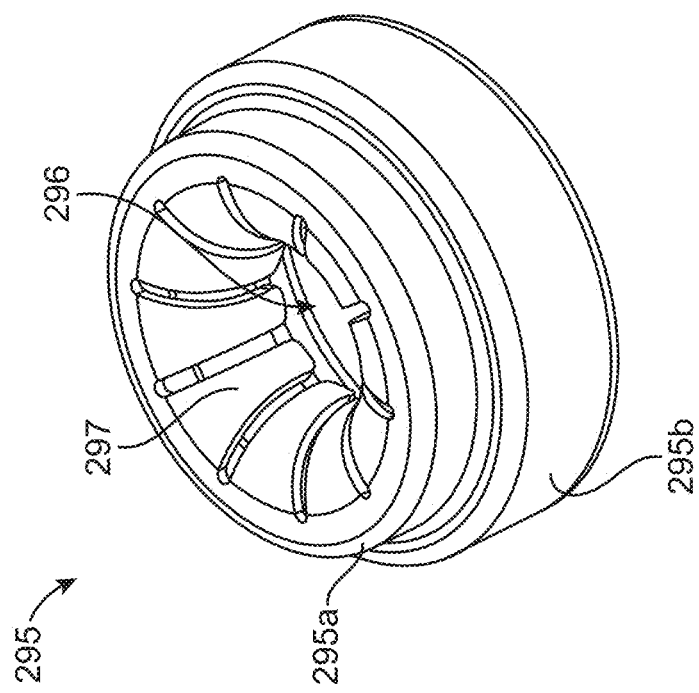
FIG. 66A

STIMULATION APPARATUS

CROSS-REFERENCE

The present application is a continuation of U.S. patent application Ser. No. 16/672,921, filed Nov. 4, 2019, now U.S. Pat. No. 11,097,096; is a continuation of PCT Application No. PCT/US18/31904, filed May 9, 2018; which claims priority to U.S. Provisional Patent Application Ser. No. 62/503,772, filed on May 9, 2017; U.S. Provisional Patent Application Ser. No. 62/555,557, filed on Sep. 7, 2017; and U.S. Provisional Patent Application Ser. No. 62/652,449, filed on Apr. 4, 2018; the entire disclosures of which are incorporated herein by reference in their entirety for all purposes.

RELATED APPLICATIONS

This application is related to: U.S. patent application Ser. No. 14/424,303, titled "Wireless Implantable Sensing Devices", filed Feb. 26, 2015, now Abandoned; U.S. patent application Ser. No. 14/975,358, titled "Method and Apparatus for Minimally Invasive Implantable Modulators", filed Dec. 18, 2015; U.S. patent application Ser. No. 15/264,864, titled "Method and Apparatus for Versatile Minimally Invasive Neuromodulators", filed Sep. 14, 2016, now U.S. Patent Application No. 10,238,872; U.S. patent application Ser. No. 15/385,729, titled "Method and Apparatus for Neuromodulation Treatments of Pain and Other Conditions", filed Dec. 20, 2016, now U.S. Pat. No. 10,335,596; International PCT Patent Application Serial Number PCT/US2016/016888, titled "Medical Apparatus Including an Implantable System and an External System", filed Feb. 5, 2016; International PCT Patent Application Serial Number PCT/US2016/051177, titled "Apparatus for Peripheral or Spinal Stimulation", filed Sep. 9, 2016; International PCT Patent Application Serial Number PCT/US2017/017978, titled "Apparatus with Enhanced Stimulation Waveforms", filed Feb. 15, 2017; International PCT Patent Application Serial Number PCT/US2017/023400, titled "Devices and Methods for Positioning External Devices in Relation to Implanted Devices", filed Mar. 21, 2017; U.S. Provisional Patent Application Ser. No. 62/341,418, titled "Methods and Systems for Insertion and Fixation of Implantable Devices", filed May 25, 2016; U.S. Provisional Patent Application Ser. No. 62/363,742, titled "Methods and Systems for Treating Pelvic Disorders and Pain Conditions", filed Jul. 18, 2016; U.S. Provisional Patent Application Ser. No. 62/441,056, titled "Stimulation Apparatus", filed Dec. 30, 2016; U.S. Provisional Patent Application Ser. No. 62/463,328, titled "Apparatus with Sequentially Implanted Stimulators", filed Feb. 24, 2017; U.S. Provisional Patent Application Ser. No. 62/503,772, titled "Stimulation Apparatus", filed May 9, 2017; U.S. Provisional Patent Application Ser. No. 62/555,557, titled "Stimulation Apparatus", filed Sep. 7, 2017; and U.S. Provisional Patent Application Ser. No. 62/652,449, titled "Stimulation Apparatus", filed Apr. 4, 2018; the content of each of which is incorporated herein by reference in its entirety for all purposes.

BACKGROUND OF THE INVENTION

Field of the Invention

The present invention relates generally to medical apparatus for a patient, and in particular, apparatus that deliver enhanced stimulation to effectively deliver a therapy while avoiding undesired effects.

Background

Implantable devices that treat a patient and/or record patient data are known. For example, implants that deliver energy such as electrical energy, or deliver agents such as pharmaceutical agents are commercially available. Implantable electrical stimulators can be used to pace or defibrillate the heart, as well as modulate nerve tissue (e.g. to treat pain). Most implants are relatively large devices with batteries and long conduits, such as implantable leads configured to deliver electrical energy or implantable tubes (i.e. catheters) to deliver an agent. These implants require a fairly invasive implantation procedure, and periodic battery replacement, which requires additional surgery. The large sizes of these devices and their high costs have prevented their use in a variety of applications.

Nerve stimulation treatments have shown increasing promise recently, showing potential in the treatment of many chronic diseases including drug-resistant hypertension, motility disorders in the intestinal system, metabolic disorders arising from diabetes and obesity, and both chronic and acute pain conditions among others. Many of these implantable device configurations have not been developed effectively because of the lack of miniaturization and power efficiency, in addition to other limitations.

There is a need for apparatus, systems, devices and methods that provide one or more implantable devices and are designed to provide enhanced treatment of pain and other enhanced benefits.

SUMMARY

According to an aspect of the present inventive concepts, a medical apparatus for a patient comprises an external system configured to transmit one or more transmission signals, each transmission signal comprising at least power or data, an implantable system configured to receive the one or more transmission signals from the external system. The external system comprises a first external device comprising: at least one external antenna configured to transmit a first transmission signal to the implantable system, the first transmission signal comprising at least power or data; an external transmitter configured to drive the at least one external antenna; an external power supply configured to provide power to at least the external transmitter; and an external controller configured to control the external transmitter. The implantable system comprises a first implantable device comprising: at least one implantable antenna configured to receive the first transmission signal from the first external device; an implantable receiver configured to receive the first transmission signal from the at least one implantable antenna; at least one implantable stimulation element configured to deliver stimulation energy to the patient; an implantable controller configured to control the energy delivered to the at least one implantable stimulation element; an implantable energy storage assembly configured to provide power to an element selected from the group consisting of: the at least one stimulation element; the implantable controller; the implantable receiver; and combinations thereof; and an implantable housing surrounding at least the implantable controller and the implantable receiver.

In some embodiments, the apparatus further comprises an O-ring connector and housing assembly into which the O-ring connector is inserted and operably connected. The apparatus can further comprise a trialing interface which includes the O-ring connector and housing assembly. The first implantable device can comprise the O-ring connector.

The O-ring connector can comprise an O-ring stack including multiple O-rings. The multiple O-rings can comprise an electrically conductive material. The O-ring stack can further comprise multiple isolating elements positioned between each O-ring, the isolating elements can be configured to electrically and/or fluidly isolate the O-rings. The O-rings can comprise an anti-microbial agent.

In some embodiments, the first implantable device comprises an electronics assembly constructed and arranged to be positioned within the implantable housing in a folded state. The electronics assembly can comprise a printed circuit board with traces and integrated circuits, and the at least one implantable antenna can be positioned away from the board traces and/or integrated circuits.

In some embodiments, the first implantable device comprises an electronics assembly including a flexible printed circuit board with multiple metal layers, and the at least one implantable antenna comprises the multiple metal layers.

In some embodiments, the at least one external antenna comprises a loop with a first diameter, and the at least one implantable antenna comprises a loop with a second diameter, and the first diameter is greater than the second diameter, and the at least one external antenna is positioned to surround the at least one implantable antenna during transmissions of data and/or power between the first external device and the first implantable device. The at least one external antenna can comprise a circular, elliptical, square, or rectangular loop.

In some embodiments, the at least one external antenna comprises a single-turn loop antenna, and the at least one implantable antenna comprises a single-turn loop antenna, and the apparatus operates near an optimal frequency to maximize communication bandwidth.

In some embodiments, the at least one external antenna comprises a loop antenna with a first diameter, and the at least one implantable antenna comprises a loop antenna with a second diameter, and the at least one external antenna is positioned from the at least one implantable antenna at a distance less than approximately one-fifth of the wavelength of the frequency of operation during transmissions of data and/or power between the first external device and the first implantable device. The at least one external antenna can be positioned from the at least one implantable antenna at a distance less than approximately one-twentieth of the wavelength of the frequency of operation during transmissions of data and/or power between the first external device and the first implantable device.

In some embodiments, the apparatus comprises an operating point, and the operating point is optimized based on a Z-parameter matrix. The Z-parameter matrix can be multiple variables that vary due to lateral displacement, rotational displacement, depth displacement, and/or changes in transmission medium, and the optimization is performed over a range in variation of the multiple variables. The optimization, $A_p$, can be computed from the Z-parameters and maximized at the frequency of operation and over conditions that define a desired operating range.

In some embodiments, the first implantable device comprises a power harvesting mechanism configured to efficiently recover low voltage signals. The first implantable device can comprise variable loading.

In some embodiments, the apparatus further comprises at least one matching network tuned to improve transmissions between the first external device and the first implantable device. The at least one matching network can be operatively attached to the at least one external antenna and/or the at least one implantable antenna. The at least one matching network comprises a first matching network operatively attached to the at least one external antenna and a second matching network operatively attached to the at least one implantable antenna. The at least one matching network can be selected by evaluating transmissions between the first external device and the first implantable device at a fixed positioned between the two, over a desired operating range, and determining the settings with the highest performance. The at least one matching network can be configured to tune the at least one external antenna and/or the at least one implantable antenna. The at least one matching network can be configured to tune the at least one external antenna.

In some embodiments, the apparatus further comprises a feedback drive configured to provide auditory and/or visual feedback to a user, and the feedback indicates an apparatus condition selected from the group consisting of: first implantable device connectivity status; battery status; communication status between the external system and the implantable system; therapy level; program number; and combinations thereof.

In some embodiments, the apparatus further comprises a detector configured to detect changes to a parameter selected from the group consisting of: impedance of the at least one external antenna; a loading condition; an environmental condition; an interference condition; a fault condition; and combinations thereof. The detector can comprise an RF detector. The detector can provide a signal related to the implant depth of the first implantable device.

In some embodiments, the first implantable device comprises an adjustable load, and adjustments to the load affect the impedance of the at least one external antenna and create a detectable signal in the output power of the first external device.

In some embodiments, the first implantable device is configured to apply and/or adjust a load operatively connected to the at least one implantable antenna to send signals back to the first external device. The load can comprise an impedance between 1 ohm and 100 ohms.

In some embodiments, the first implantable device is configured to provide an open circuit to the at least one implantable antenna to send signals back to the first external device.

In some embodiments, the first external device comprises an accelerometer configured to provide a signal based on the position of the patient, and the apparatus is configured to adjust the stimulation energy delivered to the patient based on the patient position. The apparatus can be configured to debounce the signal provided by the accelerometer.

In some embodiments, the first external device is configured to perform a function selected from the group consisting of: tracking of activity, such as gait and/or sleep as determined by an accelerometer; use of time of day and/or activity patterns to make stimulation adjustments, such as activity patterns determined by an accelerometer; correlation of therapy efficacy with amount of activity; recording of therapy changes associated with an increase and/or decrease in activity; detection of dropping of the first external device, such as to track durability; tracking of the first external device connection state as a function of activity and/or position, such as connectivity state as the patient walks or sleeps; detection of the first external device being disconnected and providing of feedback regarding repositioning of the first external device based on a detected positional change; use of a tapping or shaking motion on the first external device to convey a command; enabling and/or disabling of a control of the first external device with a specific tap gesture; changing of the functionality of a control of the first external device with a specific tap gesture; and combinations thereof.

In some embodiments, the first external device comprises a magnetic sensor configured to produce a signal used to detect the presence of another device.

In some embodiments, the first external device includes a shield comprising a copper shield and a ferrite shield. The shield can be configured to provide a function selected from the group consisting of: reduce deleterious effects of electromagnetic components of the first external device; improve transmissions of the at least one external antenna to the first implantable device; and combinations thereof.

In some embodiments, the first external device comprises a power supply and a housing, and the housing includes a first housing portion that surrounds the power supply, and a second housing portion that surrounds the at least one external antenna.

In some embodiments, the apparatus further comprises a tool for positioning and/or repositioning the first external device on the patient's skin, and the tool includes alignment markings corresponding to multiple positions of placement of the first external device in the tool, each of the positions resulting in sufficient alignment between the at least one external antenna and the at least one implantable antenna to support transmissions between the first external device and the second external device. The tool can comprise at least one replaceable skin attachment patch. The at least one replaceable skin attachment patch can comprise a first area and a second area, and the first area can be attached to the patient's skin for a first time period, and the second area can be attached to the patient's skin for a subsequent, second time period. At least the second area can be covered by a removable liner.

In some embodiments, the first external device comprises an external housing including at least one adhesive patch, and the adhesive patch comprises at least one ring.

In some embodiments, the implantable housing comprises a geometry configured to allow a user to palpate the patient's skin to locate the first implantable device. The apparatus can further comprise a patient attachment device, and the palpation can be used to position the patient attachment device.

In some embodiments, the apparatus further comprises a patient attachment device for securing the first external device to the patient, and the patient attachment device includes a strap and a housing, and the housing is removably attachable to the strap.

In some embodiments, the apparatus further comprises a patient attachment device for securing the first external device to the patient, and the patient attachment device includes a housing with a first portion and a second portion arranged in a clip-like structure.

In some embodiments, the apparatus further comprises a patient attachment device for securing the first external device to the patient, and the patient attachment device includes multiple clips that transition from a first position to a second position to frictionally engage the first external device.

In some embodiments, the apparatus further comprises an implantable lead including the at least one implantable stimulation element, and a lead anchor including a tortuous path for receiving the implantable lead.

In some embodiments, the apparatus further comprises an implantable lead including the at least one implantable stimulation element, and a lead anchor including a housing, a lumen for receiving the implantable lead, and a securing element for frictionally engaging the implantable lead.

In some embodiments, the apparatus further comprises a tool for inserting at least a portion of the first implantable device into the patient, and the tool comprises a first portion for performing blunt tissue dissection to create a tunnel and a subcutaneous pocket, and a second portion for controlling the depth of the tunnel and subcutaneous pocket. The first portion can comprise markings for providing information related to the length of the tunnel being created. The first portion can comprise a first length, and the second portion can comprise a second length greater than the first length, and the second portion can be introduced relatively perpendicular to the patient's skin, and can be subsequently turned relatively parallel to create the tunnel.

In some embodiments, the apparatus further comprises a tool for inserting at least a portion of the first implantable device into the patient, and the tool comprises a handle, a shaft, and a distal end, and the tool further comprises a housing positioned on the distal end and comprising two projections that extend toward a median line of the tool.

In some embodiments, the apparatus further comprises a tool including a clamp and an adaptor, and the clamp includes finger receiving rings, a latching mechanism, two arms, two jaws, and a connecting hinge. The adaptor can comprise a housing with at least two parallel projections.

In some embodiments, the first implantable device comprises an electronic assembly including multiple combined SDSR stages. The electronic assembly can further include a DC-DC conversion stage. The DC-DC conversion stage can comprise an inductive boost converter. The SDSR stages can comprise a first stage, subsequent stages, and capacitive input coupling, and the SDSR stages can rectify power received from the at least one implantable antenna and can multiply the voltage using capacitive input coupling to all but the first stage. The SDSR stages can comprise four stages and while receiving RF amplitudes in the 0.5V to 2V range produces an intermediate DC voltage in the 2V to 4V range. The intermediate DC voltage can be provided to an inductive boost converter. The inductive boost converter can perform further voltage multiplication. The inductive boost converter can output voltage in the 2V to 15V range. The inductive boost converter can provide line and/or load regulation and adjustable output voltage. The inductive boost converter can pass its input to its output without regulation if the voltage commanded by the boost converter is smaller than the input voltage. The intermediate DC voltage can be provided to a buck-boost converter. The electronic assembly may not include a DC-DC conversion stage. The DC output voltage of the SDSR stages can be controlled by the transmissions of the first external device to the first implantable device. The output voltage can be controlled via RF telemetry back to the first external device. The output voltage can be controlled via feedforward control using characterized load data to predict a required RF power. The electronics assembly can comprise an energy storage element in an intermediate stage, the energy storage element can be configured to maintain relatively constant rectifier loading as power is drawn intermittently. Power flow can be adjusted to control the input and output voltages of the SDSR stages at a given loading condition. Power can be controlled by adjusting power levels and/or by performing different forms of power cycling over time. A load impedance can be set to a first order by the DC voltage divided by a constant charging current. An optimal match of the at least one implantable antenna can be chosen to achieve a maximum RF efficiency by powering the first implantable device at a level required to maintain a certain intermediate DC voltage. Flexibility in power and loading can allow the first external device to operate efficiently while operating near an optimal point in the first implantable device.

In some embodiments, the apparatus uses a modulation that doesn't require linearity. The apparatus can use an amplitude modulation with data encoded in a pulse width.

In some embodiments, the apparatus further comprises an amplifier, and the modulation depth is configured to operate in an optimized range of the amplifier to minimize efficiency losses during the transmissions.

In some embodiments, the apparatus is configured to minimize amplitude changes of power transmissions to keep power transfer relatively constant.

In some embodiments, the apparatus can be configured to perform power cycling with adjustable amplitudes of transmissions, and different non-zero levels of power are transferred to the first implantable device. The adjustments to power cycling and/or power transfer amplitude can be based on the apparatus operation and/or apparatus efficiencies. The apparatus efficiencies can comprise efficiencies of a transmitter of the first external device and/or an efficiency of a receiver of the first implantable device.

In some embodiments, efficiencies of the apparatus are monitored and efficiency information is transmitted between the first external device and the first implantable device. The apparatus can be configured to make adjustments to power transfer in real-time and/or at desired intervals.

In some embodiments, the first external device comprises parameters that are sensitive to changes in impedance. The apparatus can be configured to set output power based on the impedance. The impedance can comprise the impedance of the at least one external antenna. The impedance can be changed based on the relative position between the first implantable device and the first external device. The apparatus can be configured to sense a change in output power. The apparatus can be configured to estimate relative position, implantation depth, and/or the link gain to the at least one implantable antenna, based on the sensed change in output power, and to adjust an operating parameter of the first external device. The adjusted operating parameter can comprise a parameter selected from the group consisting of: power output; power cycling; data rate; modulation depth; and combinations thereof.

In some embodiments, the first implantable device comprises an electronic assembly including address-mapped registers. The first implantable device can comprise an electronic assembly including address-mapped registers that are written via the transmissions from the first external device. The first implantable device can comprise a Stimulation Control Table that autonomously generates stimulation pulses and maintains precise stimulation control of timing and amplitude. The registers can comprise one or more parameters selected from the group consisting of: pulse width; inter phase gap; inter pulse interval; and combinations thereof, and the one or more parameters drive the Stimulation Control Table.

In some embodiments, the apparatus comprises loops used to implement stimulation pulse trains and/or stimulation pulse bursts.

In some embodiments, the apparatus comprises a Stimulation Control Table that is configured to implement a 1-level subroutine that minimizes usage of memory of the first implantable device. The subroutine can be configured to deliver complex and/or arbitrary stimulation waveforms.

In some embodiments, the apparatus comprises a Stimulation Control Table and status registers, and the Stimulation Control Table can check the status registers and autonomously takes action as a result. The status registers can comprise contents that are set from comparison between registers and/or measured quantities. The first implantable device can transmit results of the status register checking to the first external device. The first implantable device can halt stimulation if errors are detected in the status register checking.

In some embodiments, the first implantable device comprises one or more tissue anchoring elements. The one or more tissue anchoring elements can comprise an element selected from the group consisting of: a sleeve; a silicone sleeve; a suture tab; a suture eyelet; a bone anchor; wire loops; a porous mesh; a penetrable wing; a penetrable tab; a bone screw eyelet; a tine; pincers; suture slits; and combinations thereof. The one or more tissue anchoring elements can comprise an overmold positioned about at least a portion of the first implantable device.

In some embodiments, the first external device is configured to prevent adversely affecting at least a portion of the patient skin in contact with the first external device. The first external device can be configured to clean and/or promote healing of at least a portion of the patient skin in contact with the first external device. The at least a portion of the first external device can comprise an agent selected from the group consisting of: a bactericidal agent; an anti-fungal agent; and combinations thereof.

In some embodiments, the apparatus further comprises an implantable lead including at least one implantable stimulation element, and a lead anchor including a clamping assembly. The clamping assembly can include a clamp and an actuator, the clamp can comprise external threads, the actuator can comprise one or more engagement elements that include a retention element, and the actuator can further comprise internal threads configured to rotatably engage the clamp external threads. The clamp external threads can comprise male threads and the actuator internal threads can comprise female threads.

In some embodiments, the apparatus further comprises a tool for inserting at least a portion of the first implantable device into the patient, and the tool comprises one or more tissue anchoring elements configured to anchor the first implantable device to patient tissue. The one or more tissue anchoring elements can comprise a mesh and/or wrap configured to surround at least a portion of the first implantable device, and the mesh and/or wrap can be configured to engage the patient tissue. The mesh and/or wrap can engage the patient tissue via tissue ingrowth. The mesh and/or wrap can engage the patient via suture and/or clips.

In some embodiments, the apparatus further comprises a tool for inserting at least a portion of the first implantable device into the patient, the tool comprises a handle, a shaft, and a distal portion, and the distal portion further comprises a projection that extends axially from the shaft. The projection can be sized and oriented to be positioned in a mating opening of the first implantable device. The shaft can comprise a first diameter and the projection can comprise a second diameter, and the first diameter can be larger than the second diameter.

In some embodiments, the apparatus further comprises a patient attachment device for securing the first external device to the patient, and the patient attachment device is configured to prevent adversely affecting at least a portion of the patient skin in contact with the patient attachment device and/or in contact with the first external device. The patient attachment device can be configured to clean and/or promote healing of at least a portion of the patient skin in contact with the patient attachment device and/or in contact with the first external device. The at least a portion of the patient attachment device can comprise an agent selected from the group consisting of: a bactericidal agent; an anti-fungal agent; and combinations thereof.

In some embodiments, the apparatus is configured to apply one or more suppression waveforms to a pulse train to create a stimulation waveform, wherein the stimulation waveform comprises a series of stimulation pulses that remain after the suppression. The one or more suppression waveforms can comprise a series of on time periods and off time periods, and the on time periods can permit the stimulation pulses and the off time periods can suppress the stimulation pulses. The percentage of on time periods can be comparable to the off time periods.

In some embodiments, the apparatus is configured to apply one or more addition waveforms to a pulse train to create a stimulation waveform, wherein the stimulation waveform comprises a series of stimulation pulses that include pulses added via the addition waveform. The one or more addition waveforms can comprise a series of on time periods and off time periods, and stimulation pulses can be added during the on time periods and no stimulation pulses can be added during the off time periods.

In some embodiments, the apparatus further comprises an implantable lead including the at least one stimulation element and one or more tissue engagement elements proximate the at least one stimulation element. The one or more tissue engagement elements can comprise one or more circumferential arrangements. The one or more circumferential arrangements can comprise a unidirectional orientation configured to resist a migration of the implantable lead in an opposing direction. The apparatus can further comprise an introducer device constructed and arranged to introduce the implantable lead during an implantation procedure, and the implantable lead can comprise an effective lead length configured to provide exposure of at least one contact and at least one stimulation element to allow for a test stimulation during the implantation procedure without the removal of the introducer device. The introducer device can comprise a Tuohy needle. The introducer device can comprise a tear-away lead introducer.

In some embodiments, the apparatus further comprises a programmer configured to allow a user to control one or more components of the apparatus. The programmer can comprise a user interface with an electrode interface configured to allow the user to change a configuration of at least two stimulation elements, and the configuration can comprise a polarity of the stimulation element, and the polarity can comprise an anode or a cathode. The anode polarity can be visually represented as a plus-sign icon and the cathode polarity can be visually represented as a minus-sign icon. The user can reassign the anode or cathode polarity of a first stimulation element to a second stimulation element. The user can reassign the polarity using a cursor to reposition a polarity icon of the first stimulation element to the second stimulation element. The programmer can comprise a user interface with a patient posture interface configured to allow the user to change one or more stimulation programs based on a patient position. The patient posture interface can comprise one or more user input components configured to enable a user to manually indicate when the patient is in an upright or a supine position. The first external device can be configured to automatically detect when the patient is in an upright or a supine position. The user interface can comprise an icon to indicate to the patient posture is automatically detected by the first external device. The user can manually change the patient position when the patient position detected by the first external device is incorrect. The first external device can be configured to recalibrate one or more posture vectors in response to a manual change of the patient position by the user.

In some embodiments, the apparatus is configured to adjust the power delivery between the first external device and the first implantable device. The apparatus can be configured to adjust the amplitude of power transmitted by the first external device to change the output of power of the transmission signal. The transmission signal can comprise an RF signal. The apparatus can be configured to turn the power transmitted by the first external device on and off. The power transmitted by the first external device can be turned on and off via a duty cycle, and the duty cycle can be set and/or adjusted via an algorithm. The algorithm can comprise an optimization algorithm. The optimization algorithm can be configured to control the amplitude of the power transmitted. The optimization algorithm can be configured to track a targeted voltage of the first implantable device based on a measurement that occurs at a rate lower than the stimulation rate. The optimization algorithm can be configured to measure a stored energy in the first implantable device once every stimulation period and can adjust the duty cycle based on an analysis of energy requirements for the stimulation period, and the stimulation period can comprise a period of time during which one or more forms of stimulation energy can be delivered to the patient. The stored energy can be measured prior to a first stimulation pulse during the stimulation period. The stored energy can comprise voltage. The optimization algorithm can be configured to measure and/or achieve a target energy level of the first implantable device. The optimization algorithm can be configured to measure and/or achieve the target energy level by setting a target voltage level slightly below the maximum allowed voltage level, increasing the duty cycle for a period of time, and then measuring the energy level. The optimization algorithm can be configured to measure and/or achieve the target energy level by performing at least one of the following: setting a target voltage level slightly below the maximum allowed voltage level, increasing the duty cycle for a period of time, and then measuring the energy level; or increasing the energy level over a period of time until a maximum can be achieved, and adjusting the target energy level to be slightly below the maximum to allow for an optimized energy storage within a control loop. The optimization algorithm can be configured to feed the duty cycle of each stimulation cycle to a lowpass digital filter with a time constant configured to be slower than the stimulation rate, and the output of the lowpass digital filter can be sampled after several time constants, and the filtered value can comprise the average duty cycle during the sampling period. The output power of the first external device can be increased when the average duty cycle is too high, and the output power of the first external device can be decreased when the average duty cycle is too low.

In some embodiments, the apparatus further comprises one or more arrangements configured to enhance the reliability of the apparatus. The one or more arrangements can be configured to provide uninterrupted delivery of stimulation energy to the first implantable device. A first arrangement can be configured to perform a duty cycle modulation of power transferred from the first external device to the first implantable device. The first external device can transfer power to the first implantable device in bursts via the duty cycle modulation. The power can be transferred before and/or after one or more stimulation pulses. The power can be transferred before and/or after the one or more stimulation pulses in a symmetric pattern. The power transferred before the one or more stimulation pulses can be configured to prevent a significant voltage drop when the first implantable device transitions from operating at a quiescent current to delivering a stimulation energy to tissue. The power transferred after the one or more stimulation pulses can be configured to replenish energy used during the one or more stimulation pulses and/or reduce the impact of disturbances in the power transfer. The apparatus can further comprise an idle mode during which no stimulation energy is delivered to the patient, and the duty cycle modulation can be performed during the idle mode. The apparatus can further comprise one or more low frequency stimulation modes, and the duty cycle modulation can be performed during the one or more low frequency modes. The one or more low frequency stimulation modes can comprise a stimulation frequency less than approximately 1.5 kHz. The one or more low frequency stimulation modes can comprise a stimulation frequency less than approximately 1 kHz. The first arrangement can be configured to utilize duty cycle modulation during a stimulation period comprising a period of time during which one or more forms of stimulation energy can be delivered to the patient, and the stimulation energy can comprise multiple stimulation pulses. The power transferred from the first external device to the first implantable device can be allocated based on the energy of the multiple stimulation pulses and/or when the multiples stimulation pulses occur during the stimulation period. A periodic measurement of available energy in the first implantable device can be performed immediately prior to the stimulation pulse configured to deliver the greatest energy to the patient. A second arrangement can be configured to control a duty cycle of power transfer between the first external device to the first implantable device. The second arrangement can comprise a block configured to calculate an error between a setpoint energy level and a measured energy level, and the calculated error can be provided to a proportional integrator controller, and the proportional integrator controller can be configured to determine a power transmission duty cycle based on the calculated error. The proportional integrator controller can comprise a derivate control. The second arrangement can comprise a control loop, and a high proportional path gain can allow the control loop to respond quickly to power transfer disturbances. The second arrangement can be configured to periodically update the amplitude of power transfer to keep the average duty cycle low. Periodically updating the amplitude can provide a large dynamic range in the duty cycle and the proportional path can comprise a required dynamic range to respond quickly to power transfer disturbances.

In some embodiments, the apparatus is configured to provide one or more therapies with multiple stimulation pulses per a stimulation period. Each of the multiple stimulation pulses can comprise different pulse energy. Each of the multiple stimulation pulses can be configured to occur at arbitrary times during the stimulation period. The apparatus can further comprise a control loop configured to calculate a total amount of charging time to occur during the stimulation period. The charging time can be carried over and charging can be delivered after subsequent pulses when the charging time exceeds the time between the stimulation pulses. The amplitude of the power transfer can be adjusted if the charge time exceeds the total time of the stimulation period.

In some embodiments, the apparatus comprises an amplitude modulation mode. The amplitude modulation mode can be configured to continuously enable a power transmission componentry of the first external device. The amplitude modulation mode can be configured to control the energy received by the first implantable device via a control loop, and the control loop can be configured to adjust the amplitude of the transmitted power from the first external device.

In some embodiments, the control loop is adjusted using one or more of the following settings: asymmetric gain settings; gain settings that are altered over time based on previous measurements; operation specific gain settings; and combination thereof. The amplitude modulation mode can be used when the stimulation energy rate is high and the energy of the individual stimulation pulses is low.

In some embodiments, a desired available energy of the first implantable device is configured to be dynamically determined via a periodic measurement of an energy storage limit of the energy storage assembly. The available energy can be tracked and controlled via a measurement that occurs immediately before a delivery of stimulation energy. The duty cycle of the power delivered from the first energy device to the first implantable device can be adjusted to minimize an error between the energy storage assembly and the available energy. The adjustment can comprise an increase in power transfer from the first external device to the first implantable device when the first implantable device is rapidly losing power.

In some embodiments, the apparatus further comprises an implantable lead including a proximal portion and a distal portion, the proximal portion including the at least one implantable stimulation element, and the implantable lead further comprises one or more markers positioned along the length of the implantable lead between the proximal portion and distal portion. The apparatus can further comprise an insertion tool comprising a sheath extending distally from a hub, and the insertion tool can slidingly receive the lead distal portion via an opening in the hub. The one or more markers can be configured to indicate a position of the implantable lead relative to the insertion tool. At least one marker can be configured to align with the hub opening to indicate approximately one-half of the stimulation elements are exposed to patient tissue. At least one marker can be configured to align with the hub opening to indicate at least one-half of the stimulation elements are exposed to patient tissue. At least one marker can be configured to align with the hub opening to indicate at least one but less than all of the stimulation elements are exposed to patient tissue. At least one marker can be configured to align with the hub opening to indicate at least two of the stimulation elements are exposed to patient tissue. At least one marker can be configured to align with the hub opening, and a test stimulation can be performed once the marker aligns with the hub opening.

In some embodiments, the apparatus further comprises an implantable lead including a proximal portion and a distal portion, the proximal portion including the at least one implantable stimulation element, and the proximal portion further comprises one or more arrangements including one or more projections positioned proximal to the at least one implantable stimulation element. The one or more projections can be configured to transition between a collapsed state and an expanded state, and the projections can be resiliently biased in the expanded state. The one or more arrangements can comprise a hub comprising a first portion and second portion, and the second portion can comprise the one or more projections. The one or more projections can comprise a proximal portion including a recessed inner surface, and the projections can taper in thickness proximally. The one or more projections can be configured to extend laterally from the second portion and can overlap the first portion of an adjacent arrangement in the collapsed state. The overlapping of the one or more arrangements in the collapsed state can be configured to provide: a greater number of projections per a unit length of the arrangements; a longer length of the projections; a continuous diameter of the implantable lead; and combinations thereof.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same or like elements. The drawings are not necessarily to scale, emphasis instead being placed upon illustrating the principles of the preferred embodiments.

FIG. 3 is a perspective view of an implantable device comprising a universal connector, consistent with the present inventive concepts.

FIG. 3A is a perspective view of a single connector of an implantable device operably attached to a lead connection assembly, consistent with the present inventive concepts.

FIG. 3B is a perspective view of a dual connector of an implantable device operably attached to a dual lead connection assembly, consistent with the present inventive concepts.

FIG. 3C is a perspective view of a single connector of an implantable device operably attached to an implantable lead, consistent with the present inventive concepts.

FIG. 3D is a perspective view of a dual connector of an implantable device operably attached to dual implantable leads, consistent with the present inventive concepts.

FIG. 6 is a perspective view of a lead connection assembly, consistent with the present inventive concepts.

FIG. 6A is a sectional view of a lead connection assembly, consistent with the present inventive concepts.

FIG. 6B is a perspective view of a proximal portion of an implantable lead comprising multiple contacts, consistent with the present inventive concepts.

FIG. 7A is a perspective view of an implantable lead comprising a distal portion with multiple stimulation elements and a proximal portion with a conduit, consistent with the present inventive concepts.

FIG. 7B is a cross-sectional view of an implantable lead comprising a conduit and multiple tubes, consistent with the present inventive concepts.

FIGS. 18A-18F are pairs of perspective and sectional views of various embodiments of an external device, consistent with the present inventive concepts.

FIGS. 20A-20E are perspective views of the steps of method for repositioning an external device on a patient's skin using a tool, consistent with the present inventive concepts.

FIG. 25 is a perspective view of an embodiment of a patient attachment device for attaching an external device to a patient and the external device, consistent with the present inventive concepts.

FIG. 25A is a sectional view of an embodiment of a patient attachment device, consistent with the present inventive concepts.

FIG. 26 is a perspective view of an embodiment of a patient attachment device for an external device, consistent with the present inventive concepts.

FIG. 26A is a sectional view of an embodiment of a patient attachment device consistent with the present inventive concepts.

FIG. 27 is a perspective view of an embodiment of a lead anchor for an implantable lead, consistent with the present inventive concepts.

FIG. 28A is a transparent perspective view of an embodiment of a lead anchor for an implantable lead, consistent with the present inventive concepts.

FIG. 28B is a perspective view of an embodiment of a lead anchor for an implantable lead, consistent with the present inventive concepts.

FIGS. 56A-C illustrates a series of steps of manipulating a user interface of a programmer to modify a stimulation electrode configuration, consistent with the present inventive concepts.

FIGS. 58A-C illustrate a user interface of a programmer, consistent with the present inventive concepts.

FIG. 66A are front and back views of a radially contacting conductor of a lead connection assembly, consistent with the present inventive concepts.

DETAILED DESCRIPTION OF THE DRAWINGS

Figure 1:
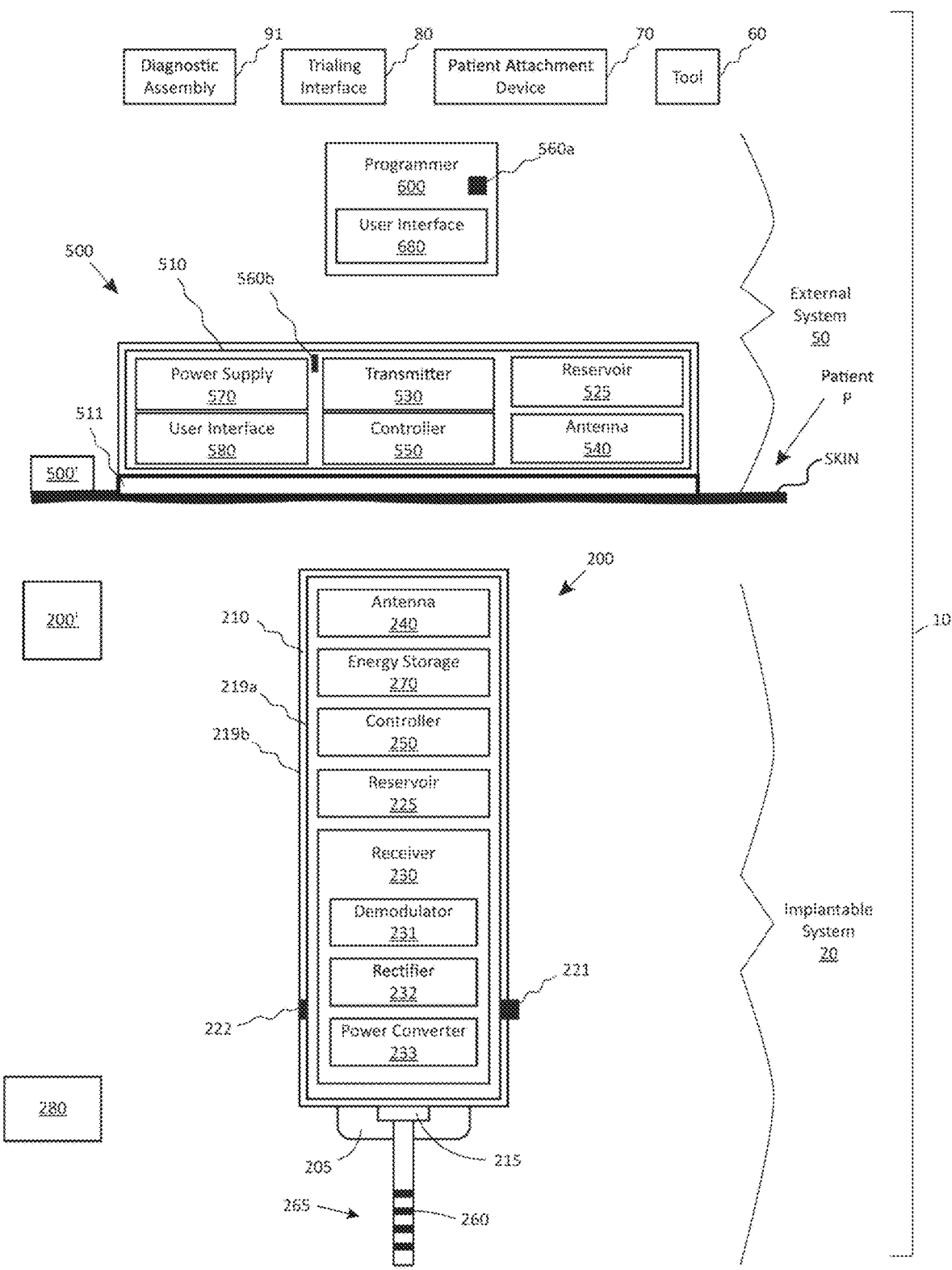
FIG. 1 is a schematic anatomical view of a medical apparatus comprising an external system and an implantable system, consistent with the present inventive concepts.

The terminology used herein is for the purpose of describing particular embodiments and is not intended to be limiting of the inventive concepts. Furthermore, embodiments of the present inventive concepts may include several novel features, no single one of which is solely responsible for its desirable attributes or which is essential to practicing an inventive concept described herein. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers, and/or sections, these limitations, elements, components, regions, layers, and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present Other words used to describe the relationship between elements should be interpreted in a like fashion (e.g. "between" versus "directly between," "adjacent" versus "directly adjacent," etc.). A first component (e.g. a device, assembly, housing or other component) can be "attached", "connected" or "coupled" to another component via a connecting filament (as defined below). In some embodiments, an assembly comprising multiple components connected by one or more connecting filaments is created during a manufacturing process (e.g. pre-connected at the time of an implantation procedure of the apparatus of the present inventive concepts). Alternatively or additionally, a connecting filament can comprise one or more connectors (e.g. a connectorized filament comprising a connector on one or both ends), and a similar assembly can be created by a user (e.g. a clinician) operably attaching the one or more connectors of the connecting filament to one or more mating connectors of one or more components of the assembly.

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one or more of these.

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

As used herein, the term "proximate" shall include locations relatively close to, on, in, and/or within a referenced component or other location.

The term "and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross-sectional area as the cross section of the component being described.

The terms "major axis" and "minor axis" of a component where used herein are the length and diameter, respectively, of the smallest volume hypothetical cylinder which can completely surround the component.

The term "functional element" where used herein, is the be taken to include a component comprising one, two or more of: a sensor; a transducer; an electrode; an energy delivery element; an agent delivery element; a magnetic field generating transducer; and combinations of one or more of these. In some embodiments, a functional element comprises a transducer selected from the group consisting of: light delivery element; light emitting diode; wireless transmitter; Bluetooth device; mechanical transducer; piezoelectric transducer; pressure transducer; temperature transducer; humidity transducer; vibrational transducer; audio transducer; speaker; and combinations of one or more of these. In some embodiments, a functional element comprises a needle, a catheter (e.g. a distal portion of a catheter), an iontophoretic element or a porous membrane, such as an agent delivery element configured to deliver one or more agents. In some embodiments, a functional element comprises one or more sensors selected from the group consisting of: electrode; sensor configured to record electrical activity of tissue; blood glucose sensor such as an optical blood glucose sensor; pressure sensor; blood pressure sensor; heart rate sensor; inflammation sensor; neural activity sensor; muscular activity sensor; pH sensor; strain gauge; accelerometer; gyroscope; GPS; respiration sensor; respiration rate sensor; temperature sensor; magnetic sensor; optical sensor; MEMs sensor; chemical sensor; hormone sensor; impedance sensor; tissue impedance sensor; body position sensor; body motion sensor; physical activity level sensor; perspiration sensor; patient hydration sensor; breath monitoring sensor; sleep monitoring sensor; food intake monitoring sensor; urine movement sensor; bowel movement sensor; tremor sensor; pain level sensor; orientation sensor; motion sensor; and combinations of one or more of these.

The term "transducer" where used herein is to be taken to include any component or combination of components that receives energy or any input, and produces an output. For example, a transducer can include an electrode that receives electrical energy, and distributes the electrical energy to tissue (e.g. based on the size of the electrode). In some configurations, a transducer converts an electrical signal into any output, such as light (e.g. a transducer comprising a light emitting diode or light bulb), sound (e.g. a transducer comprising a piezo crystal configured to deliver ultrasound energy), pressure, heat energy, cryogenic energy, chemical energy, mechanical energy (e.g. a transducer comprising a motor or a solenoid), magnetic energy, and/or a different electrical signal (e.g. a Bluetooth or other wireless communication element). Alternatively or additionally, a transducer can convert a physical quantity (e.g. variations in a physical quantity) into an electrical signal. A transducer can include any component that delivers energy and/or an agent to tissue, such as a transducer configured to deliver one or more of: electrical energy to tissue (e.g. a transducer comprising one or more electrodes); light energy to tissue (e.g. a transducer comprising a laser, light emitting diode and/or optical component such as a lens or prism); mechanical energy to tissue (e.g. a transducer comprising a tissue manipulating element); sound energy to tissue (e.g. a transducer comprising a piezo crystal); thermal energy to tissue (e.g. heat energy and/or cryogenic energy); chemical energy; electromagnetic energy; magnetic energy; and combinations of one or more of these.

The term "transmission signal" where used herein is to be taken to include any signal transmitted between two components, such as via a wired or wireless communication pathway. For example, a transmission signal can comprise a power and/or data signal wirelessly transmitted between a component external to the patient and one or more components implanted in the patient. A transmission signal can include one or more signals transmitted using body conduction. Alternatively or additionally, a transmission signal can comprise reflected energy, such as energy reflected from any power and/or data signal.

The term "data signal" where used herein is to be taken to include a transmission signal including at least data. For example, a data signal can comprise a transmission signal including data and sent between a component external to the patient and one or more components implanted in the patient. Alternatively, a data signal can comprise a transmission signal including data sent from an implanted component to one or more components external to the patient. A data signal can comprise a radiofrequency signal including data (e.g. a radiofrequency signal including both power and data) and/or a data signal sent using body conduction.

The term "implantable" where used herein is to be taken to define a component which is constructed and arranged to be fully or partially implanted in a patient's body and/or a component that has been fully or partially implanted in a patient. The term "external" where used herein is to be taken to define a component which is constructed and arranged to be positioned outside of the patient's body.

The terms "attachment", "attached", "attaching", "connection", "connected", "connecting" and the like, where used herein, are to be taken to include any type of connection between two or more components. The connection can include an "operable connection" or "operable attachment" which allows multiple connected components to operate together such as to transfer information, power, and/or material (e.g. an agent to be delivered) between the components. An operable connection can include a physical connection, such as a physical connection including a connection between two or more: wires or other conductors (e.g. an "electrical connection"), optical fibers, wave guides, tubes such as fluid transport tubes, and/or linkages such as translatable rods or other mechanical linkages. Alternatively or additionally, an operable connection can include a non-physical or "wireless" connection, such as a wireless connection in which information and/or power is transmitted between components using electromagnetic energy. A connection can include a connection selected from the group consisting of: a wired connection; a wireless connection; an electrical connection; a mechanical connection; an optical connection; a sound propagating connection; a fluid connection; and combinations of one or more of these.

The term "connecting filament" where used herein is to be taken to define a filament connecting a first component to a second component. The connecting filament can include a connector on one or both ends, such as to allow a user to operably attach at least one end of the filament to a component. A connecting filament can comprise one or more elements selected from the group consisting of: wires; optical fibers; fluid transport tubes; mechanical linkages; wave guides; flexible circuits; and combinations of one or more of these. A connecting filament can comprise rigid filament, a flexible filament or it can comprise one or more flexible portions and one or more rigid portions.

The term "connectorized" where used herein is to be taken to refer to a filament, housing or other component that includes one or more connectors (e.g. clinician or other user-attachable connectors) for operably connecting that component to a mating connector (e.g. of the same or different component).

The terms "stimulation parameter", "stimulation signal parameter" or "stimulation waveform parameter" where used herein can be taken to refer to one or more parameters of a stimulation waveform (also referred to as a stimulation signal). Applicable stimulation parameters of the present inventive concepts shall include but are not limited to: amplitude (e.g. amplitude of voltage and/or current); average amplitude; peak amplitude; frequency; average frequency; period; phase; polarity; pulse shape; a duty cycle parameter (e.g. frequency, pulse width, and/or off time); inter-pulse gap; polarity; burst-on period; burst-off period; inter-burst period; pulse train; train-on period; train-off period; inter-train period; drive impedance; duration of pulse and/or amplitude level; duration of stimulation waveform; repetition of stimulation waveform; an amplitude modulation parameter; a frequency modulation parameter; a burst parameter; a power spectral density parameter; an anode/cathode configuration parameter; amount of energy and/or power to be delivered; rate of energy and/or power delivery; time of energy delivery initiation; method of charge recovery; and combinations of one or more of these. A stimulation parameter can refer to a single stimulation pulse, multiple stimulation pulses, or a portion of a stimulation pulse. The term "amplitude" where used herein can refer to an instantaneous or continuous amplitude of one or more stimulation pulses (e.g. the instantaneous voltage level or current level of a pulse). The term "pulse" where used herein can refer to a period of time during which stimulation energy is relatively continuously being delivered. In some embodiments, stimulation energy delivered during a pulse comprises energy selected from the group consisting of: electrical energy; magnetic energy; electromagnetic energy; light energy; sound energy such as ultrasound energy; mechanical energy such as vibrational energy; thermal energy such as heat energy or cryogenic energy; chemical energy; and combinations of one or more of these. In some embodiments, stimulation energy comprises electrical energy and a pulse comprises a phase change in current and/or voltage. In these embodiments, an inter-phase gap can be present within a single pulse. The term "quiescent period" where used herein can refer to a period of time during which zero energy or minimal energy is delivered (e.g. insufficient energy to elicit an action potential and/or other neuronal response). The term "inter-pulse gap" where used herein can refer to a quiescent period between the end of one pulse to the onset of the next (sequential) pulse. The terms "pulse train" or "train" where used herein can refer to a series of pulses. The terms "bunt", "burst of pulses" or "burst stimulation" where used herein can refer to a series of pulse trains, each separated by a quiescent period. The term "train-on period" where used herein can refer to a period of time from the beginning of the first pulse to the end of the last pulse of a single train. The term "train-off period" where used herein can refer to a quiescent period between the end of one train and the beginning of the next train. The term "burst-on period" where used herein can refer to a period of time from the beginning of the first pulse of the first train to the end of the last pulse of the last train of a single burst. The term "burst-off period" where used herein can refer to a quiescent period between the end of one burst and the beginning of the next burst. The term "inter-train period" where used herein can refer to a quiescent period between the end of one train and the beginning of the next train. The term "inter-burst period" where used herein can refer to a quiescent period between the end of one burst and the beginning of the next burst. The term "train envelope" where used herein can refer to a curve outlining the amplitude extremes of a series of pulses in a train. The term "burst envelope" where used herein can refer to a curve outlining the amplitude extremes of a series of pulses in a burst. The term "train ramp duration" where used herein can refer to the time from the onset of a train until its train envelope reaches a desired target magnitude. The term "bunt ramp duration" where used herein can refer to the time from the onset of a burst until its burst envelope reaches a desired target magnitude.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

The present inventive concepts include a medical apparatus and clinical methods for treating a patient, such as to treat pain. The patient can comprise a human or other mammalian patient. The medical apparatus can comprise a stimulation apparatus. The medical apparatus can comprise an implantable system and an external system. The implantable system can comprise one or more similar and/or dissimilar implantable devices. In some embodiments, the implantable system comprises a first implantable device that delivers stimulation energy via energy received wirelessly from one or more external devices, and a second implantable device that delivers stimulation energy via an integral (e.g. implanted) battery. In these embodiments, the first implantable device can be configured to deliver stimulation energy during a limited period of time (e.g. a trial period in which stimulation settings are determined and/or acceptability of the apparatus is determined), and the second implantable device can be configured to deliver stimulation energy for a prolonged period of time in which long-term stimulation therapy is provided to a patient. In these embodiments, a single implantable lead comprising one or more stimulation energy delivery elements (e.g. electrodes) can be connected to the first implantable device and then the second implantable device. In some embodiments, a first implantable device can be configured to remain implanted in the patient for a limited period of time, such as to reduce cost of manufacture, and a second implantable device is configured for a longer implant life. The first implantable device can be used in a trialing procedure in which the stimulation apparatus is assessed for acceptable use (e.g. by the patient and/or clinician) and/or one or more stimulation settings are optimized or otherwise determined.

Each implantable device can comprise one or more implantable antennas configured to receive power and/or data. Each implantable device can comprise an implantable receiver configured to receive the power and/or data from the one or more implantable antennas. Each implantable device can comprise one or more implantable functional elements (e.g. an implantable stimulation element). An implantable functional element can be configured to interface with the patient (e.g. interface with tissue of the patient or interface with any patient location). Alternatively or additionally, an implantable functional element can interface with a portion of an implantable device (e.g. to measure an implantable device parameter). In some embodiments, the one or more implantable functional elements can comprise one or more transducers, electrodes, and/or other elements configured to deliver energy to tissue. Alternatively or additionally, the one or more implantable functional elements can comprise one or more sensors, such as a sensor configured to record a physiologic parameter of the patient. In some embodiments, one or more implantable functional elements are configured to record device information and/or patient information (e.g. patient physiologic or patient environment information).

Each implantable device can comprise an implantable controller configured to control (e.g. modulate power to, send a signal to and/or receive a signal from) the one or more implantable functional elements. In some embodiments, an implantable controller of a first implantable device is configured to control one or more other implantable devices. Each implantable device can comprise an implantable energy storage assembly (e.g. a battery and/or a capacitor) configured to provide power to the implantable controller (e.g. a controller comprising a stimulation waveform generator), the implantable receiver and/or the one or more implantable functional elements. In some embodiments, an implantable energy storage assembly is further configured to provide power to an assembly that transmits signals via the implantable antenna (e.g. when the implantable device is further configured to transmit data to one or more external devices). Each implantable device can comprise an implantable housing surrounding the implantable controller and the implantable receiver. In some embodiments, one or more implantable antennas are positioned within the implantable housing. Alternatively or additionally, one or more implantable antennas and/or implantable functional elements can be tethered (e.g. electrically tethered) to the implantable housing. In some embodiments, one or more implantable functional elements are positioned on an implantable lead, such as a flexible lead mechanically fixed or attachable to the implantable housing and operably connected (e.g. electrically, fluidly, optically and/or mechanically) to one or more components internal to the implantable housing. The implantable lead can be inserted (e.g. tunneled) through tissue of the patient, such that its one or more functional elements are positioned proximate tissue to be treated and/or positioned at an area in which data is to be recorded. In some embodiments, the implantable lead is configured to operably attach to and/or detach from, multiple implantable devices.

The external system of the medical apparatus of the present inventive concepts can comprise one or more similar and/or dissimilar external devices. Each external device can comprise one or more external antennas configured to transmit power and/or data to one or more implanted components of the implantable system. Each external device can comprise an external transmitter configured to drive the one or more external antennas. Each external device can comprise an external power supply configured to provide power to at least the external transmitter. Each external device can comprise an external programmer configured to control the external transmitter and/or an implantable device (e.g. when an external power transmitter is not included in the apparatus or otherwise not present during use). Each external device can comprise an external housing that surrounds at least the external transmitter. In some embodiments, the external housing surrounds the one or more external antennas, the external power supply and/or the external programmer.

The external programmer can comprise a discrete controller separate from the one or more external devices, and/or a controller integrated into one or more external devices. The external programmer can comprise a user interface, such as a user interface configured to set and/or modify one or more treatment and/or data recording settings of the medical apparatus of the present inventive concepts. In some embodiments, the external programmer is configured to collect and/or diagnose recorded patient information, such as to provide the information and/or diagnosis to a clinician of the patient, to a patient family member and/or to the patient themselves. The collected information and/or diagnosis can be used to adjust treatment or other operating parameters of the medical apparatus.

In some embodiments, a medical apparatus comprises a stimulation apparatus for activating, blocking, affecting or otherwise stimulating (hereinafter "stimulate" or "stimulating") tissue of a patient, such as nerve tissue or nerve root tissue (hereinafter "nerve", "nerves", "nerve tissue" or "nervous system tissue"). The stimulation apparatus comprises an external system configured to transmit power, and an implanted system configured to receive the power from the external system and to deliver stimulation energy to tissue. The delivered stimulation energy can comprise one or more stimulation waveforms, such as a stimulation waveform configured to enhance treatment of pain while minimizing undesired effects. The stimulation signal (also referred to as "stimulation energy" herein) delivered by the implanted system can be independent of the power received from the external system, such as to be independent of one or more of: the position of one or more components of the external system; the changing position of one or more components of the external system; the frequency of the power received from the external system; the amplitude of the power received from the external system; changes in amplitude of the power received from the external system; duty cycle of the power received from the external system; envelope of the power received from the external system; and combinations of one or more of these.

Referring now to FIG. 1, a schematic anatomical view of a stimulation apparatus for providing a therapy to a patient is illustrated, consistent with the present inventive concepts. Apparatus 10 comprises implantable system 20 and external system 50. External system 50 transmits transmission signals to one or more components of implantable system 20. These transmission signals can comprise power and/or data. Implantable system 20 comprises implantable device 200 shown implanted beneath the skin of patient P. In some embodiments, implantable system 20 comprises multiple similar or dissimilar implantable devices 200 (singly or collectively implantable device 200), such as is described in applicant's co-pending application International PCT Patent Application Serial Number PCT/US2017/017978, titled "Apparatus with Enhanced Stimulation Waveforms", filed Feb. 15, 2017, the content of which is incorporated herein in its entirety for all purposes. Each implantable device 200 can be configured to receive power and data from a transmission signal transmitted by external system 50, such as when stimulation energy delivered to the patient (e.g. to nerve or other tissue of the patient) by implantable device 200 is provided via wireless transmissions signals from external system 50. In some embodiments, implantable system 20 comprises at least two implantable devices, such as implantable device 200 and implantable device 200' shown in FIG. 1. Implantable device 200' can be of similar construction and arrangement to implantable device 200, and it can include components of different configuration.

External system 50 can comprise an external device 500, which includes housing 510. In some embodiments, external system 50 comprises multiple external devices 500 (singly or collectively external device 500), also as is described in applicant's co-pending Application Serial Number PCT/US2017/017978, titled "Apparatus with Enhanced Stimulation Waveforms", filed Feb. 15, 2017. In some embodiments, external system 50 comprises at least two external devices (e.g. at least two external devices configured to deliver power and/or data to one or more implantable devices 200), such as external device 500 and external device 500' shown in FIG. 1. External device 500' can be of similar construction and arrangement to external device 500, and it can include components of different configuration.

External system 50 can comprise external programmer 600, which can comprise a user interface, such as user interface 680. External programmer 600 can be configured to control one or more external devices 500. Alternatively or additionally, external programmer 600 can be configured to control one or more implantable devices 200 (e.g. when no external device 500 is included in apparatus 10 or otherwise no external device 500 is available to communicate with an implantable device 200.

Apparatus 10 can be configured to stimulate tissue (e.g. stimulate nerve tissue such as tissue of the central nervous system or tissue of the peripheral nervous system, such as to neuromodulate nerve tissue), such as by having one or more implantable devices 200 deliver and/or provide energy (hereinafter "deliver energy") and/or deliver an agent (e.g. a pharmaceutical compound or other agent) to one or more tissue locations. In some embodiments, one or more implantable devices 200 deliver energy and/or an agent while receiving power and/or data from one or more external devices 500. In some embodiments, one or more implantable devices 200 deliver energy and/or an agent (e.g. continuously or intermittently) using an internal power source (e.g. a battery and/or capacitor) without receiving externally supplied power, such as for periods of at least 1 hour, at least 1 day, at least 1 month or at least 1 year. In some embodiments, one or more stimulation parameters are varied (e.g. systematically and/or randomly), during that period.

In some embodiments, apparatus 10 is further configured as a patient diagnostic apparatus, such as by having one or more implantable devices 200 record a patient parameter (e.g. a patient physiologic parameter) from one or more tissue locations, such as while receiving power and/or data from one or more external devices 500. In some embodiments, during its use, one or more implantable devices 200 at least receives power from one or more external devices 500 (e.g. with or without also receiving data).

Alternatively or additionally, apparatus 10 can be configured as a patient information recording apparatus, such as by having one or more implantable devices 200 and/or one or more external devices 500 record patient information (e.g. patient physiologic information and/or patient environment information). In some embodiments, one or more implantable devices 200 and/or one or more external devices 500 further collect information (e.g. status information or configuration settings) of one or more of the components of apparatus 10.

In some embodiments, apparatus 10 is configured to deliver stimulation energy to tissue to treat pain. In particular, apparatus 10 can be configured to deliver stimulation energy to tissue of the spinal cord and/or tissue associated with the spinal cord ("tissue of the spinal cord", "spinal cord tissue" or "spinal cord" herein), the tissue including roots, dorsal root, dorsal root ganglia, spinal nerves, ganglia, and/or other nerve tissue. The delivered energy can comprise energy selected from the group consisting of: electrical energy; magnetic energy; electromagnetic energy; light energy such as infrared light energy. visible light energy and/or ultraviolet light energy; mechanical energy; thermal energy such as heat energy and/or cryogenic energy; sound energy such as ultrasonic sound energy (e.g. high intensity focused ultrasound and/or low intensity focused ultrasound) and/or subsonic sound energy; chemical energy; and combinations of one or more of these. In some embodiments, apparatus 10 is configured to deliver to tissue energy in a form selected from the group consisting of: electrical energy such as by providing a controlled (e.g. constant or otherwise controlled) electrical current and/or voltage to tissue; magnetic energy (e.g. magnetic field energy) such as by applying controlled current or voltage to a coil or other magnetic field generating element positioned proximate tissue; and/or electromagnetic energy such as by providing both current to tissue and a magnetic field to tissue. The coil or other magnetic field generating element can surround (e.g. at least partially surround) the target nerve and/or it can be incorporated as part of an anchoring system to the target tissue. Alternatively, or additionally, the magnetic energy can be applied externally and focused to specific target tissue via an implant comprising a coil and/or ferromagnetic materials. In some embodiments, the magnetic energy is configured to induce the application of mechanical energy. Delivered energy can be supplied in one or more stimulation waveforms, each waveform comprising one or more pulses of energy, as described in detail herebelow.

In some embodiments, apparatus 10 is configured as a stimulation apparatus in which external system 50 transmits a power signal to one or more implantable devices 200, and the one or more implantable devices 200 deliver stimulation energy to tissue with a stimulation signal (also referred to as a stimulation waveform), with the power signal and the stimulation signal having one or more different characteristics. The power signal can further be modulated with data (e.g. configuration or other data to be sent to one or more implantable devices 200). In these embodiments, the characteristics of the stimulation signal delivered (e.g. amplitude, frequency, duty cycle and/or pulse width), can be independent (e.g. partially or completely independent) of the characteristics of the power signal transmission (e.g. amplitude, frequency, phase, envelope, duty cycle and/or modulation). For example, the frequency and modulation of the power signal can change without affecting the stimulation signal, or the stimulation signal can be changed (e.g. via external programmer 600), without requiring the power signal to change. In some embodiments, implantable system 20 is configured to rectify the power signal, and produce a stimulation waveform with entirely different characteristics (e.g. amplitude, frequency and/or duty cycle) from the rectified power signal. Each implantable device 200 can comprise an oscillator and/or controller configured to produce the stimulation signal. In some embodiments, one or more implantable devices 200 is configured to perform frequency multiplication, in which multiple signals are multiplexed, mixed, added, and/or combined in other ways to produce a broadband stimulation signal.

In some embodiments, apparatus 10 is configured such that external system 50 transmits data (e.g. data and power) to implantable system 20, and implantable system 20 recovers (e.g. decodes, demodulates or otherwise recovers) the transmitted data without synchronizing to the carrier and/or data symbol rate of the transmitted signal from external system 50. In some embodiments, the transmitted signal comprises a power signal, and a clock and/or data is recovered without synchronizing to the power signal. In some embodiments, the transmitted signal comprises a clock and/or data signal, and a clock and/or data is recovered without synchronizing to the transmitted clock and/or data signal. In some embodiments, the recovered signal comprises a clock and/or data and a clock and/or data is recovered from the transmission signal without synchronizing to the recovered clock and/or data. Avoiding synchronization reduces power consumption of each implantable device 200, such as by obviating the need for (and avoiding the power consumed by) a frequency locked loop (FLL); phase locked loop (PLL); high frequency clock; and/or crystal oscillator needed to perform the synchronization. Avoiding these components can also be correlated to reduced package size of each implantable device 200 (e.g. avoidance of a relatively large sized crystal oscillator). Asynchronous data transfer between external system 50 and implantable system 20 is also advantageous as it relates to: increased communication data rate; power transfer efficiency; operation with more than one implantable device 200; and combinations of one or more of these. In some embodiments, one or more components of apparatus 10 are of similar construction and arrangement as similar components described in U.S. patent application Ser. No. 13/591,188, titled "Method of Making and Using an Apparatus for a Locomotive Micro-Implant using Active Electromagnetic Propulsion", filed Aug. 21, 2012, the content of which is incorporated herein by reference in its entirety for all purposes. In some embodiments, external system 50 and implantable system 20 provide asynchronous data transfer or are otherwise configured as described in U.S. patent application Ser. No. 13/734,772, titled "Method and Apparatus for Efficient Communication with Implantable Devices", filed Jan. 4, 2013, the content of which is incorporated herein by reference in its entirety for all purposes.

Apparatus 10 can be configured to treat pain, such as back pain and/or leg pain treated by stimulating dorsal root ganglia and/or other nerves or locations of the spinal cord or other nervous system locations. In some embodiments, apparatus 10 is configured to treat a type of pain selected from the group consisting of: back pain; joint pain; neuropathic pain; tennis elbow; muscle pain; shoulder pain; chronic, intractable pain of the back and/or lower limbs including unilateral or bilateral pain; neuropathic groin pain; perineal pain; phantom limb pain; complex regional pain syndrome; failed back surgery syndrome; cluster headaches; migraines; inflammatory pain; arthritis; abdominal pain; pelvic pain; and combinations of one or more of these.

In some embodiments, apparatus 10 is configured to treat a patient disease or disorder selected from the group consisting of: chronic pain; acute pain; migraine; cluster headaches; urge incontinence; pelvic dysfunction such as overactive bladder; fecal incontinence; bowel disorders; tremor; obsessive compulsive disorder; depression; epilepsy; inflammation; tinnitus; hypertension; heart failure; carpal tunnel syndrome; sleep apnea; obstructive sleep apnea; dystonia; interstitial cystitis; gastroparesis; obesity; mobility issues; arrhythmia; rheumatoid arthritis; dementia; Alzheimer's disease; eating disorder; addiction; traumatic brain injury; chronic angina; congestive heart failure; muscle atrophy; inadequate bone growth; post-laminectomy pain; liver disease; Crohn's disease; irritable bowel syndrome; erectile dysfunction; kidney disease; and combinations of one or more of these.

In some embodiments, apparatus 10 is configured to treat one or more diseases or disorders by delivering stimulation to perform renal modulation. In some embodiments, apparatus 10 is configured to treat hypertension, such as when apparatus 10 is configured to deliver stimulation to perform renal neuromodulation.

Apparatus 10 can be configured to treat heart disease, such as heart failure of a patient. In these embodiments, stimulation of the spinal cord can be performed. In canine and porcine animals with failing hearts, spinal cord stimulation has been shown to reverse left ventricular dilation and improve cardiac function, while suppressing the prevalence of cardiac arrhythmias. In canines, coronary artery occlusion has been associated with increased intracardiac nerve firing, and stimulation at spinal segment T1 has been shown to suppress that nerve firing. Stimulation via apparatus 10 at one or more spinal cord locations can be used to suppress undesired cardiac nerve firing in humans and other mammalian patients. In some embodiments, stimulation via apparatus 10 at multiple spinal cord locations is used to enhance a cardiac treatment. For example, one or more stimulation elements 260 of one or more implantable devices 200 can be implanted at one or more spinal cord locations, such as to deliver stimulation to tissue proximate those locations. In some embodiments, stimulation elements 260 comprise two or more stimulation elements (e.g. electrodes) that span multiple vertebra of the spinal column (e.g. multiple stimulation elements that span at least T8 to T9 and/or T-9 to T-10). Power and/or data can be transmitted to the one or more implantable devices 200 via one or more external devices 500 of external system 50. One or more stimulation signals can be delivered to spinal cord tissue, such as to treat heart failure or other cardiac disease or disorder. In some embodiments, one or more stimulation elements 260 are configured to deliver energy (e.g. electrical energy) to tissue to treat heart failure, such as tissue selected from the group consisting of: spinal canal; nerves in the spinal canal; nerves in the epidural space; peripheral nerves; posterior spinal nerve root; dorsal root; dorsal root ganglion; pre-ganglionic tissue on posterior spinal nerve root; post-ganglionic tissue on posterior nerve root; dorsal ramus; grey ramus communicans; white ramus communicans; ventral ramus; and combinations of one or more of these. In some embodiments, one or more functional elements of apparatus 10 (e.g. one or more stimulation elements 260 of implantable system 20) are used to record a patient parameter, such as a patient heart or spine parameter, and the information recorded is used to adjust the delivered stimulation signals. The at least one heart parameter can comprise a parameter selected from the group consisting of: EKG; blood oxygen; blood pressure; heart rate; ejection fraction; wedge pressure; cardiac output; and combinations of one or more of these.

Apparatus 10 can be configured to pace and/or defibrillate the heart of a patient. One or more stimulation elements 260 can be positioned proximate cardiac tissue and deliver a stimulation signal as described herein (e.g. based on power and/or data received by implantable system 20 from external system 50). The stimulation signal can be used to pace, defibrillate and/or otherwise stimulate the heart. Alternatively or additionally, apparatus 10 can be configured to record cardiac activity (e.g. by recording EKG, blood oxygen, blood pressure, heart rate, ejection fraction, wedge pressure, cardiac output, lung impedance and/or other properties or functions of the cardiovascular system), such as to determine an onset of cardiac activity dysfunction or other undesired cardiac state. In some embodiments, apparatus 10 is configured to both record cardiac or other information and deliver a stimulation signal to cardiac tissue (e.g. stimulation varied or otherwise based on the recorded information). For example, apparatus 10 can be configured such that external system 50 transmits power and/or data to implantable system 20. Implantable system 20 monitors cardiac activity, and upon detection of an undesired cardiovascular state, implantable system 20 delivers a pacing and/or defibrillation signal to the tissue that is adjacent to one or more stimulation elements 260 configured to deliver a cardiac stimulation signal.

Apparatus 10 can be configured to perform a diagnostic procedure including measuring one or more patient parameters (e.g. patient physiologic or other patient parameters), such as are described in detail herebelow. In some embodiments, apparatus 10 is configured to measure a physiologic parameter that can be sensed from one or more sensor-based stimulation elements 260 positioned in subcutaneous tissue. In these embodiments, external system 50 can comprise an external device 500 configured for placement proximate an implantable device 200 implanted in a position to record data from subcutaneous tissue (e.g. blood glucose data). External device 500 can comprise a wrist band, a wrist watch or an arm band configuration such as when the implantable device 200 is positioned in subcutaneous tissue proximate the patient's wrist or upper arm. The external device 500 can comprise a leg, knee or ankle band configuration, such as when one or more implantable devices 200 are positioned in subcutaneous tissue proximate the patient's ankle, knee, and/or thigh. In some embodiments, external device 500 comprises a band or other attachment device for positioning about the thorax, neck, groin, and/or head of the patient. Power and/or data can be sent to the implantable device 200 from the external device 500, and data (e.g. blood glucose data) can be sent to external device 500 (or another component of external system 50) by implantable device 200, such as using a communication configuration known to those of skill in the art. In some embodiments, external device 500 comprises a functional element 560 configured to deliver an agent (e.g. insulin or glucose delivered by a needle-based functional element 560), based on the information received from implantable device 200. Alternatively, or additionally, implantable device 200 comprises a stimulation element 260 configured to deliver an agent (e.g. insulin or glucose delivered by a needle-based stimulation element 260), based on the information recorded by implantable device 200. Various closed loop sensing and agent delivery combinations and configurations should be considered within the spirit and scope of the present inventive concepts, including but not limited to: sensing a blood parameter such as white blood cell count and delivering a chemotherapeutic or other agent based on the blood parameter; sensing a hormone level and delivering a hormone or a hormone affecting agent; sensing blood pressure and delivering stimulation energy and/or a blood pressure affecting agent; sensing neural activity and delivering stimulation energy and/or a neural affecting agent or other agent based on the neural activity, such as for treating epilepsy; and combinations of one or more of these.

External system 50 can be configured to transmit power and/or data (e.g. implantable system 20 configuration data) to one or more implantable devices 200 of implantable system 20. Configuration data provided by external system 50 (e.g. via one or more antennas 540 of one or more external devices 500) can include when to initiate stimulation delivery (e.g. energy delivery), when to stop stimulation delivery, and/or data related to the value or change to a value of one or more stimulation variables as described hereabove. The configuration data can include a stimulation parameter such as an agent (e.g. a pharmaceutical agent) delivery stimulation parameter selected from the group consisting of: initiation of agent delivery; cessation of agent delivery; amount of agent to be delivered; volume of agent to be delivered; rate of agent delivery; duration of agent delivery; time of agent delivery initiation; and combinations of one or more of these. The configuration data can include a sensing parameter, such as a sensing parameter selected from the group consisting of: initiation of sensor recording; cessation of sensor recording; frequency of sensor recording; resolution of sensor recording; thresholds of sensor recording; sampling frequency of sensor recording; dynamic range of sensor recording; initiation of calibration of sensor recording; and combinations of one or more of these.

External system 50 can comprise one or more external devices 500. External system 50 can comprise one or more antennas 540, such as when a single external device 500 comprises one or more antennas 540 or when multiple external devices 500 each comprise one or more antennas 540. The one or more antennas 540 can transmit power and/or data to one or more antennas 240 of implantable system 20, such as when a single implantable device 200 comprises one or more antennas 240 or when multiple implantable devices 200 each comprise one or more antennas 240. In some embodiments, one or more antennas 540 define a radiation footprint (e.g. a footprint defining a volume, such as a volume of tissue, in which electromagnetic transmissions radiated by antennas 540 can be properly received by antennas 240), such as is described in applicant's co-pending International PCT Patent Application Serial Number PCT/US2016/016888, titled "Medical Apparatus including an Implantable System and an External System", filed Feb. 5, 2016; the content of which is incorporated herein by reference in its entirety for all purposes.

External system 50 transmits power and/or data with a transmission signal comprising at least one wavelength, $\lambda$. External system 50 and/or implantable system 20 can be configured such that the distance between an external antenna 540 transmitting the power and/or data and one or more implantable antennas 240 receiving the power and/or data transmission signal is equal to between $0.1\lambda$ and $10.0\lambda$, such as between $0.2\lambda$ and $2.0\lambda$. In some embodiments, one or more transmission signals are delivered at a frequency range between 10 MHz and 10.6 GHz, such as between 0.1 GHz and 10.6 GHz, between 10 MHz and 3.0 GHz, between 40 MHz and 1.5 GHz, between 10 MHz and 100 MHz, between 0.902 GHz and 0.928 GHz, in a frequency range proximate to 40.68 MHz, in a frequency range proximate to 866 MHz, or approximately between 863 MHz and 870 MHz. Transmitter 530 can comprise a transmitter that produces a transmission signal with a power level between 0.01 W and 4.0 W, such as a transmission signal with a power level between 0.01 W and 2.0 W or between 0.2 W and 1.0 W. In some embodiments, transmitter 530 is configured as described herebelow in reference to transmitter 530 of FIG. 16.

In addition to transmitting power and/or data to implantable system 20, external system 50 can be further configured to provide information (e.g. patient information and/or apparatus 10 performance information) to one or more other devices of apparatus 10, such as tool 60 shown in FIG. 1 and described in detail herebelow.

One or more external devices 500 (singly or collectively external device 500) can be configured to transmit power and/or data (e.g. implantable system 20 configuration data) to one or more implantable devices 200. In some embodiments, one or more external devices 500 are configured to transmit both power and data (e.g. simultaneously and/or sequentially) to one or more implantable devices 200. In some embodiments, one or more external devices 500 are further configured to receive data from one or more implantable devices 200 (e.g. via data transmitted by one or more antennas 240 of one or more implantable devices 200). Each external device 500 can comprise housing 510, power supply 570, a transmitter 530, a controller 550, and/or one or more antennas 540, each described in detail herebelow. Each external device 500 can further comprise one or more functional elements 560, such as a functional element comprising a sensor, electrode, energy delivery element, a magnetic-field generating transducer, and/or any transducer, also described in detail herebelow. In some embodiments, a functional element 560 comprises one or more sensors configured to monitor performance of external device 500 (e.g. to monitor voltage of power supply 570, quality of transmission of power and/or data to implantable system 20, temperature of a portion of an external device 500, and the like).

One or more housings 510 (singly or collectively housing 510) of each external device 500 can comprise one or more rigid and/or flexible materials which surround various components of external device 500 such as antenna 540, transmitter 530, controller 550, and/or power supply 570 shown in FIG. 1. In some embodiments, a single external device 500 comprises multiple discrete (i.e. separate) housings 510, two or more of which can transfer data or other signals via a wired or wireless connection. In some embodiments, a housing 510 further surrounds an external programmer 600 and/or a power supply 570. In some embodiments, housing 510 comprises both a rigid material and a flexible material. In some embodiments, housing 510 comprises a material selected from the group consisting of: plastic; injection-molded plastic; an elastomer; metal; and combinations of one or more of these. In some embodiments, housing 510 comprises a shielded portion (e.g. shielded to prevent transmission of electromagnetic waves), and an unshielded portion, such as an unshielded portion surrounding antenna 540.

Housing 510 can comprise an adhesive element, not shown but such as an adhesive element configured to temporarily attach an external device 500 to the patient's skin. Housing 510 can be constructed and arranged to engage (e.g. fit in the pocket of) a patient attachment device, such as patient attachment device 70 described herebelow.

One or more antennas 540 (singly or collectively antenna 540) can each comprise one, two, three, or more external antennas. Antenna 540 can comprise one or more polarizable antennas, such as one or more antennas with adjustable polarization. Antenna 540 can comprise an array of antennas, such as an array of antennas configured to: support beam shaping and/or focusing; allow adjustment of the amplitude and/or phase of the transmission signal; increase the radiation footprint; and combinations of one or more of these. An array of antennas 540 can be configured to be selectively activated, such as to improve coupling with one or more implanted antennas 240, such as to adjust for movement of the array of the antennas 540 relative to the implanted antennas 240. Antenna 540 can comprise an array of selectable conductors configured to adjust a radiation pattern and/or an electromagnetic field of a resultant antenna. Antenna 540 can comprise a surface and shield material positioned on the surface, such as when the shield material is positioned on the side facing away from the patient's skin. The shield material can comprise radio-absorptive shield material and/or radio-reflective shield material. For antenna 240 to operate effectively at higher frequencies, the shield material can comprise a ferrite material that has a low conductivity and low magnetic loss tangent at a frequency of interest, and whereby a higher permeability is achieved. By placing a material with a high magnetic permeability ($\mu'$), low magnetic loss tangent ($\mu''/\mu'$), and low conductivity at the operating frequency (such as a high frequency ferrite) between the antenna and other elements of the transmitter, the losses or loading effects due to these elements can be dramatically reduced. In some cases, the magnetic field magnification of this shielding layer will enhance the overall performance. Additionally, this layer shields the outside environment from unwanted radiation from the antenna, and it protects the antenna from radiation originating in the environment.

In some embodiments, a spacing layer is positioned between antenna 540 and the shield material. The spacing layer can comprise a thickness of between 0 mm and 5 mm, such as between 0.25 mm and 1 mm. The spacing layer can comprise non-conductive dielectric materials, air, or other materials that have minimal impact on antenna performance. The spacing layer can also be incorporated into a board thickness, with the antenna being constructed on the opposite side of the board in relation to the shielding layer. The shielding layer can comprise a ferrite material as described hereabove, or any material with the desired permeability, magnetic loss, and conductivity at the frequency of interest. The thickness of the shielding layer can be dependent on its specific material properties and the application. In some embodiments, a conductive layer on the side of the shielding layer is positioned opposite the antenna to further shield unwanted radiation. To reduce weight, the shielding layer material can be porous or incorporate holes or slots spaced in a way to minimize the reduction in performance. The holes and spacings can be sized smaller than a wavelength of the RF signal. If no spacing layer is used, the shielding layer can extend inside the antenna. Additionally or alternatively, the shielding layer can be positioned on the other side or both sides of the antenna because of the field magnification effect. In some embodiments, the shielding layer is constructed to increase the directivity of the antenna or focus the electromagnetic energy.

One or more antennas 540 can be positioned in a housing 510 that is otherwise void of other components (e.g. void of power supply 570, controller 550 and/or transmitter 530), such as when an antenna 540 is positioned within a first housing 510 and communicates with components positioned in a second housing 510.

In some embodiments, a spacer 511 is positioned between antenna 540 and the patient's skin, such as a spacer comprising a thickened portion of housing 510 or a discrete spacer 511 placed on aside of housing 510 (as shown) or on aside of antenna 540. Spacer 511 can comprise one or more materials that match the impedance of antenna 540 to the impedance of the patient's tissue. Spacer 511 can comprise a thickness of between 0.1 cm to 3 cm, such as a thickness between 0.2 cm and 1.5 cm. Spacer 511 can comprise materials which isolate heat (e.g. a spacer 511 comprising thermally insulating material). Alternatively, or additionally, housing 510 can comprise a heat insulating and/or dissipating material. Spacer 511 can comprise a soft or otherwise compressible material (e.g. foam) for patient comfort. Spacer 511 can be inflatable, such as to control the separation distance of an external antenna 540 from the patient's skin. An inflatable spacer 511 can be compartmentalized into several sections with independently controlled air pressure or volume to adjust the separation distance of an external antenna 540 and the patient's skin and/or its angle (e.g. tilt) with respect to the tissue surface.

In some embodiments, antenna 540 comprises a multi-feed point antenna, such as a multi-feed point antenna configured to: support beam shaping and/or focusing; allow adjustment of amplitude and/or phase of a transmission signal; increase the radiation footprint; or combinations of one or more of these.

In some embodiments, antenna 540 comprises one or more antennas selected from the group consisting of: patch antenna; slot antenna; array of antennas; a loop antenna (e.g. a concentric loop antenna); antenna loaded with reactive elements; dipole antenna; polarizable antenna; selectable conductors that form an antenna; and combinations of one or more of these.

Antenna 540 can comprise a major axis between 1 cm and 10 cm, such as a major axis between 2 cm and 5 cm. Antenna 540 can be further configured to receive a signal, such as when an antenna 240 is configured to transmit data to an external device 500. Antenna 540 can be positioned on (e.g. fabricated onto) a substrate, such as a flexible printed circuit board or other printed circuit board (e.g. a single or multiple layer printed circuit board comprising electrical traces connecting components).

A single external antenna 540 can be configured to transmit power and/or data to multiple implantable devices 200 (e.g. each containing one or more antennas 240). In some embodiments, a single external device 500, comprising one or more antennas 540 can be configured to transmit power and/or data to multiple implantable devices 200.

One or more antennas 540 can comprise a multi-turn spiral loop antenna, such as a multi-turn spiral loop antenna configured to desensitize coupling sensitivity and/or boost input voltage. In some embodiments, one or more antennas 540 comprise multiple concentric loops with varied dimensions, such as concentric loops configured to desensitize coupling sensitivity. In these embodiments, the multiple concentric loops can be: connected in parallel and driven from the same feed point; driven from the same feed point and connected using one or more of a capacitor, inductor, varactor, and combinations of one or more of these; and/or driven from multiple feed points.

In some embodiments, one or more external devices 500 comprise a first antenna 540 and a second antenna 540. In these embodiments, the first antenna 540 can be similar or dissimilar to the second antenna 540. In some embodiments, a first antenna 540 and a dissimilar second antenna 540 are positioned within a single external device 500 (e.g. within housing 510). In other embodiments, a first antenna 540 is positioned in a first external device 500, and a dissimilar second antenna 540 is positioned in a second external device 500. The similarity or dissimilarity of the antennas can be configured to enhance one or more design and/or performance parameters selected from the group consisting of: implantable device 200 operation depth; polarization; power efficiency; a radiation footprint; directional gain; beam shaping and/or focusing; sensitivity to implantable device 200 placement; patient comfort; patient usability; data transfer; and combinations of one or more of these. In some embodiments, the first antenna 540 is optimized for a different design parameter than the second antenna 540, and each antenna 540 can be activated independently or simultaneously to realize both benefits. In some embodiments, the first antenna 540 is similar to the second antenna 540 and placed in an array to increase the radiation footprint or placed in different external locations to operate with multiple implantable devices 200 implanted at different sites.

In some embodiments, a first external antenna 540 and a second external antenna 540 transmit power and/or data to a single implantable antenna 240. In some embodiments, a first antenna 540 and a second antenna 540 transmit power and/or data to one or more antennas 240, the transmissions performed simultaneously or sequentially. In sequential power and/or data transfers, a first external device 500 comprising a first one or more antennas 540 can be replaced (e.g. swapped) with a second external device 500 comprising a second one or more antennas 540. Alternatively or additionally, sequential power and/or data transfer can be initiated by one or more of the following conditions: when a first external antenna 540 moves (e.g. moves relative to an implanted antenna 240); when a second external device 500 comprising a second antenna 540 is turned on or otherwise activated; when a second antenna 540 provides improved power and/or data transfer to antenna 240 than that which is provided by a first antenna 540; and/or when power received from a first antenna 540 decreases (e.g. decreases below a threshold). In some embodiments, an antenna 240 receives power from a first antenna 540 and a second antenna 540, but only receives data from the first antenna 540. In some embodiments, a first antenna (e.g. an antenna 240 or an antenna 540) is driven with a different carrier signal than a second antenna (e.g. an antenna 240 or an antenna 540). The two carrier signals can comprise differences in amplitudes and/or relative phases as compared to each other. Each carrier signal can include a data transmission signal (e.g. data to be transmitted to an implantable device 200 from an external device 500 or to an external device 500 from an implantable device 200).

External device 500 can comprise an electronics module, controller 550 shown, configured to control one or more other components of external device 500. In some embodiments, controller 550 is configured as described herebelow in reference to controller 550 of FIG. 16.

One or more transmitters 530 (singly or collectively external transmitter 530) can each comprise one or more external transmitters that drive one or more antennas 540 (e.g. one or more antennas 540 positioned in a single external device 500 or multiple external devices 500). Transmitter 530 is operably attached to antenna 540 and is configured to provide one or more drive signals to antenna 540, such as one or more power signals and/or data signals transmitted to one or more implantable devices 200 of implantable system 20. Transmitter 530 can be configured to perform multi-level amplitude shift keying. The amplitude shift-keying can be configured to provide adjustable-depth modulation between 0-100% depth, such as between 5-75% depth, or such as between 10-50% depth.

As described herein, one or more external devices 500 can be configured to transmit data (e.g. configuration data) to one or more implantable devices 200, such as via a data transmission produced by transmitter 530 and sent to one or more antennas 540. In some embodiments, a transmitter 530 is configured to perform data modulation comprising amplitude shift keying with pulse width modulation. In these embodiments, the transmitter can be configured to perform multi-level amplitude shift keying. The amplitude shift-keying can be configured to provide adjustable-depth modulation between 0-100% depth, such as between 5-75% depth, or such as between 10-50% depth. In some embodiments, one or more external devices 500 transmit data to one or more implantable devices 200 using time division multiple access (TDMA). In some embodiments, one or implantable devices 200 are independently addressable through unique identification (ID) codes. Alternatively or additionally, transmitter 530 can be configured to transmit one or more data signals with a bandwidth between 1 kHz and 100 MHz, between 0.1 MHz and 100 MHz, or between 1 MHz and 26 MHz.

As described herein, one or more external devices 500 can be configured to transmit power to one or more implantable devices 200, such as via a power transmission produced by transmitter 530 and set to one or more antennas 540. One or more transmitters 530 can deliver power to one or more implantable devices 200 simultaneously or sequentially. In some embodiments, one or more transmitters 530 are configured to adjust the level of power transmitted to one or more implantable devices 200, such as by adjusting one or more duty cycling parameters. In these embodiments, power transmitted can be adjusted to: set a power transfer based on a stimulation level produced by implantable system 20; prevent oversaturation; to reduce interference with implantable system 20 data transmissions (e.g. when one or more implantable devices 200 are further configured to transmit data to external system 50); set a power transfer based on charge information and/or discharge information related to an implantable device 200 (e.g. charge rate and/or discharge rate of an implantable energy storage assembly 270); and combinations of one or more of these. In some embodiments, implantable system 20 comprises a first receiver 230 (e.g. of a first implantable device 200) and a second receiver 230 (e.g. of a second implantable device 200'). One or more transmitters 530 can be configured to transmit a first power transmission to the first receiver 230, and a second power transmission to the second receiver 230. The first power transmission and the second power transmission can be adjusted or otherwise be different, such as to prevent oversaturation.

In some embodiments, transmitter 530 (and/or another component of external system 50) is further configured as a receiver, such as to receive data from implantable system 20. For example, a transmitter 530 can be configured to receive data via one or more antennas 240 of one or more implantable devices 200. Data received can include patient information (e.g. patient physiologic information, patient environment information or other patient information) and/or information related to an implantable system 20 parameter (e.g. an implantable device 200 stimulation parameter and/or other configuration parameter as described herein).

In some embodiments, transmitter 530 comprises a first transmitter to transmit power and/or data to one or more implantable devices 200, and a second transmitter to transmit data to a different device, as described herein. In these embodiments, a second transmitter of transmitter 530 can be configured to transmit data to tool 60 or another device such as an external programmer 600; cell phone; computer; tablet; computer network such as the internet or a LAN; and combinations of one or more of these. In some embodiments, the second transmitter of transmitter 530 comprises a wireless transmitter; a Bluetooth transmitter; a cellular transmitter; and combinations of one or more of these. In some embodiments, a functional element 560 comprises a transmitter such as a Bluetooth transmitter.

Each power supply 570 (singly or collectively power supply 570) can be operably attached to a transmitter 530, and one or more other electrical components of each external device 500. Power supply 570 can comprise a power supplying and/or energy storage element selected from the group consisting of: battery; replaceable battery (e.g. via a battery door of housing 510); rechargeable battery; AC power converter; capacitor; and combinations of one or more of these. In some embodiments, power supply 570 comprises two or more batteries, such as two or more rechargeable batteries, such as to allow the first battery to be replaced (e.g. serially replaced) by the second battery. In some embodiments, power supply 570 is configured to provide a voltage of at least 3V. In some embodiments, power supply 570 is configured to provide a capacity between 1 Watt-hour and 75 Watt-hours, such as a battery or capacitor with a capacity of approximately 5 Watt-hours. In some embodiments, power supply 570 comprises an AC power source. Power supply 570 can include voltage and/or current control circuitry. Alternatively or additionally, power supply 570 can include charging circuitry, such as circuitry configured to interface a rechargeable battery with an external charging device. In some embodiments, power supply 570 is configured as described herebelow in reference to power supply 570 of FIG. 16.

Each external device 500 can include one or more user interface components, user interface 580 shown, such as to allow the patient or other user to adjust one or more parameters of apparatus 10. User interface 580 can include one or more user input components (e.g. buttons, slides, knobs, and the like) and/or one or more user output components (e.g. lights, displays and the like). In some embodiments, user interface 580 is configured as described herebelow in reference to user interface 580 of FIG. 16.

Each external programmer 600 (singly or collectively external programmer 600 or programmer 600) comprises a programming device configured to control one or more components of apparatus 10. Programmer 600 can comprise a user interface 680. Programmer 600 can send and/or receive commands to and/or from one or more external devices 500 via a wireless or wired connection (wired connection not shown but such as one or more insulated conductive wires). In some embodiments, one or more external devices 500 comprise programmer 600, such as when user interface 680 is integrated into housing 510 of external device 500. In some embodiments, apparatus 10 comprises multiple programmers 600.

External programmer 600 can be configured to adjust one or more parameters of apparatus 10, such as a stimulation parameter (e.g. a stimulation waveform parameter as described herein); a sensing parameter; a therapy parameter; a data recording parameter (e.g. a patient data recording parameter and/or an implantable device 200 data recording parameter); power transfer; data rate; activity of one or more external transmitters 530; activity of one or more external antennas 540; a stimulation element 260 parameter; a functional element 560 parameter; and combinations of one or more of these, such as is described hereabove. Programmer 600 can be further configured to provide information, such as patient physiologic information recorded by one or more implantable devices 200, or apparatus 10 information, such as performance and/or configuration information (singly or collectively "status information") of one or more external devices 500 and/or implantable devices 200. In some embodiments, the programmer 600 uses information recorded by one or more implantable devices 200, apparatus 10 information, and/or information from external devices 500 to adapt configuration parameters of one or more components of apparatus 10.

In some embodiments, external programmer 600 is configured to confirm that an adequate power transmission and/or an adequate data transmission has occurred between one or more external devices 500 and one or more implantable devices 200. In these embodiments, programmer 600 can comprise diagnostic assembly 91 described hereabove, or otherwise be configured to detect one or more of: power transmission to the implantable system 20 (e.g. to detect power transmission to implantable system 20 below a threshold); power transmission to the implantable system 20 trending in an undesired direction; improper and/or inadequate data transfer to the implantable system 20; and combinations of one or more of these. In some embodiments, the programmer 600 monitors power transfer in real time and adjusts power transmission accordingly to optimize the rectifier 232 efficiency of one or more implantable devices 200. In some embodiments, apparatus 10 can be configured to adjust (e.g. in real time) the power transmission from one or more external devices 500 of external system 50 to one or more implantable devices 200 of implantable system 20, such as to optimize or otherwise improve an efficiency of apparatus 10, such as to improve the efficiency of transmissions between an external device 500 and an implantable device 200. These adjustments can include adjustment to one or more of: power transmission amplitude, duty cycle, frequency, phase, and periodicity.

In some embodiments, programmer 600 and/or another component of apparatus 10 comprises a matching network configured to match the impedance of one or more antennas 540 to one or more transmitters 530. The matching network can comprise an adjustable matching network. The matching network can comprise a directional coupler configured to measure a reflection coefficient. A transmitter 530 can comprise an output, and a programmer 600 can be configured to monitor a standing wave pattern at the output of the transmitter 530.

In some embodiments, external programmer 600 comprises a lookup table of stimulation signal waveform patterns, such as to allow a clinician, patient and/or other operator of apparatus 10 to select a predetermined stimulation pattern. In some embodiments, programmer 600 comprises a set of adjustable stimulation signal parameters configured to be varied to allow an operator to construct customized waveforms, such as to vary one or more stimulation parameters described hereabove. In some embodiments, the programmer 600 is configured to allow an operator to create a customized waveform by specifying an amplitude of one or more discrete pulses or steps of a stimulation signal.

In some embodiments, external programmer 600 comprises a transmitter configured to transmit data to tool 60 or another device such as a cell phone; computer; tablet; computer network such as the internet or a LAN; and combinations of one or more of these. In these embodiments, programmer 600 can comprise a wireless transmitter; a Bluetooth transmitter; a cellular transmitter; and combinations of one or more of these. In some embodiments, external programmer 600 comprises a receiver configured to receive data, or a transceiver configured to both transmit and receive data.

User interface 680 of external programmer 600 can comprise one or more user input components and/or user output components, such as a component selected from the group consisting of: keyboard; mouse; keypad; switch; membrane switch; touchscreen; display; audio transducer such as a speaker or buzzer; vibrational transducer; light such as an LED; and combinations of one or more of these.

In some embodiments, one or more components of external system 50 and/or other external component of apparatus 10, comprises one or more functional elements 560, such as functional elements 560a and/or 560b (singly or collectively functional element 560), shown positioned in programmer 600 and in external device 500, respectively. Each functional element 560 can comprise a functional element as defined hereabove (e.g. a sensor, a transducer, and/or other functional element as described herein). In some embodiments, functional element 560 comprises a needle, a catheter (e.g. a distal portion of a catheter), an iontophoretic element or a porous membrane, such as an agent delivery element configured to deliver one or more agents contained (e.g. one or more agents in a reservoir, such as reservoir 525 described herebelow) within an external device 500 and delivered into the patient (e.g. into subcutaneous tissue, into muscle tissue and/or into a blood vessel such as a vein).

In some embodiments, the functional element 560 comprises an electrode for sensing electrical activity and/or delivering electrical energy. In some embodiments, apparatus 10 is configured to cause stochastic resonance, and the addition of white noise can enhance the sensitivity of nerves to be stimulated and/or boost weak signals to be recorded by the one or more stimulation elements 260.

In some embodiments, one or more functional elements 560 comprise a sensor, such as a sensor configured to record data related to a patient parameter (e.g. a patient physiologic parameter), an external system 50 parameter and/or an implantable system 20 parameter. In some embodiments, operation of one or more implantable devices 200 (e.g. stimulation energy delivered by one or more implantable devices 200) is configured to be delivered based on the data recorded by one or more sensor-based functional elements 560, such as in a closed-loop energy delivery mode.

Functional element 560 can comprise one or more sensors configured to record data regarding a patient parameter selected from the group consisting of: blood glucose; blood pressure; EKG; heart rate; cardiac output; oxygen level; pH level; pH of blood; pH of a bodily fluid; tissue temperature; inflammation level; bacteria level; type of bacteria present; gas level; blood gas level; neural activity; neural spikes; neural spike shape; action potential; local field potential (LFP); EEG; muscular activity (e.g. as measured using electromyography, EMG); electrical activity produced by skeletal muscles (e.g. as measured using EMG); gastric volume; peristalsis rate; impedance; tissue impedance; electrode-tissue interface impedance; physical activity level; pain level; body position; body motion; organ motion; respiration rate; respiration level; perspiration rate; sleep level; sleep cycle; digestion state; digestion level; urine production; urine flow; bowel movement; tremor; ion concentration; chemical concentration; hormone level; viscosity of a bodily fluid; patient hydration level; and combinations of one or more of these.

Functional element 560 can comprise one or more sensors configured to record data representing a parameter of external system 50 or any component of apparatus 10. Functional element 560 can comprise one or more sensors selected from the group consisting of: an energy sensor; a voltage sensor; a current sensor; a temperature sensor (e.g. a temperature of one or more components of external device 500 or programmer 600); an antenna matching and/or mismatching assessment sensor; power transfer sensor; link gain sensor; power use sensor; energy level sensor; energy charge rate sensor; energy discharge rate sensor; impedance sensor; load impedance sensor; instantaneous power usage sensor; average power usage sensor; bit error rate sensor; signal integrity sensor; and combinations of one or more of these. Apparatus 10 can be configured to analyze (e.g. via controller 250 described herebelow) the data recorded by functional element 560 to assess one or more of: power transfer; link gain; power use; energy within power supply 570; performance of power supply 570; expected life of power supply 570; discharge rate of power supply 570; ripple or other variations of power supply 570; matching of antennas 240 and 540; communication error rate between implantable device 200 and external device 500; integrity of transmission between implantable device 200 and external device 500; and combinations of one or more of these.

In some embodiments, one or more functional elements 560 are positioned on a housing 510. A functional element 560 can comprise a body conduction sensor, such as a body conduction sensor configured to record and/or receive data via skin conduction. A functional element 560 can be configured to record data associated with stimulation delivered by one or more implantable devices 200 (e.g. record data associated with stimulation energy delivered by one or more stimulation elements 260), such as to provide closed loop or semi-closed loop stimulation. A functional element 560 can be configured to record temperature, such as when apparatus 10 is configured to deactivate or otherwise modify the performance of an external device 500 when the recorded temperature (e.g. patient temperature and/or external device 500 temperature) exceeds a threshold.

In some embodiments, external programmer 600 and/or an external device 500 comprises a temperature sensor, such as functional elements 560a and 560b. The temperature-based functional element 560 can be positioned proximate a portion of programmer 600, housing 510 and/or one or more antennas 540 (e.g. to measure the temperature of one or more portions of a programmer 600 and/or external device 500). In these embodiments, the temperature data recorded by the functional element 560 is used to adjust one or more of: matching network; stimulation level (e.g. stimulation energy delivered by one or more implantable devices 200); power transmission level (e.g. level of power transmitted between one or more external devices 500 and one or more implantable devices 200); and combinations of one or more of these. In some embodiments, the temperature sensor-based functional element 560 is a part of a safety mechanism that deactivates programmer 600 and/or an external device 500 if the recorded temperature exceeds a threshold. Alternatively or additionally, a temperature sensor-based functional element 560 can be configured to measure temperature of the patient, such as when placed on housing 510, such as to adjust energy and/or agent delivery performed by implantable device 200 based on the recorded patient temperature.

In some embodiments, external programmer 600 and/or external device 500 comprise an accelerometer, vibration sensor, and/or other motion or shock sensor, such as functional elements 560a and 560b shown. In these embodiments, functional elements 560a and/or 560b can comprise a sensor configured to produce a signal used to detect when either external programmer 600 and/or an external device 500 is dropped, and the forces generated during the drop. Alternatively or additionally, this sensor can be configured to produce a signal configured to detect a tap (e.g. on a housing) of the device, such that a tap gesture can be used in place of a control (e.g. a discrete switch) on the device.

Implantable system 20 comprises one or more implantable devices 200, such as one or more implantable devices 200 provided sterile or configured to be sterilized for implantation into the patient. A first implantable device 200 can be of similar or dissimilar construction and arrangement to a second implantable device 200. Each implantable device 200 can be configured to treat a patient (e.g. treat pain of the patient) and/or record patient information, such as by delivering energy and/or an agent to tissue and/or by recording one or more physiologic parameters of tissue.

One or more portions of an implantable device 200 or other component of implantable system 20 can be configured to be visualized or contain a visualizable portion or other visualizable element, such as visualizable element 222 shown. Visualizable element 222 can comprise a material selected from the group consisting of: radiopaque material; ultrasonically reflective material; magnetic material; and combinations of one or more of these. In these embodiments, each implantable device 200 can be visualized (e.g. during and/or after implantation) via an imaging device such as a CT, X-ray, fluoroscope, ultrasound imager and/or MRI.

In some embodiments, implantable system 20 comprises multiple implantable devices 200 (e.g. implantable device 200 and implantable device 200' shown in FIG. 1) and implantable system 20 comprises a "multi-point ready" system, in which the operation (e.g. energy delivery, agent deliver, data recording and/or other function) of the multiple implantable devices 200 is performed simultaneously, asynchronously, and/or sequentially. The implantable devices 200 can be part of a network including one or more external devices 500 (e.g. external device 500 and external device 500' shown in FIG. 1) in which the treating of a patient and/or the recording of patient information relies on operation of the implantable devices 200 at one or more implantation sites in a synchronized, asynchronized, and/or otherwise coordinated way. The synchronization or otherwise coordination can be controlled by a single or multiple external devices 500, which can further be synchronized to a single clock. Each implantable device 200 of implantable system 20 can receive a power signal and/or a data signal from one or more external devices 500. In some embodiments of the multi-point ready implantable system 20, each implantable device 200 comprises a unique ID, such that each implantable device 200 is individually addressed (e.g. receive unique signals from external system 50). In some embodiments, external system 50 transmits high-bandwidth signals to implantable system 20, such that time-domain multiple access communication is performed while operating in near real time. In some embodiments, implantable system 20 is configured as a multi-point ready system such that stimulation energy delivered by implantable system 20 is independent of power received by implantable system 20 from external system 50.

Two implantable devices 200, or two discrete components of a single implantable device 200 (e.g. two components comprising or positioned in different housings), can be attached to each other by a connecting filament as defined hereabove. In some embodiments, a connecting filament comprises a user-attachable (e.g. clinician-attachable) connector on at least one end. The filament connector is configured to operably attach to a mating connector on a component (e.g. a housing 210) of an implantable device 200.

Each implantable device 200 is configured to receive power and/or data (e.g. implantable system 20 configuration data) from one or more external devices 500. In some embodiments, one or more implantable devices 200 are configured to receive both power and data (e.g. simultaneously and/or sequentially) from one or more external devices 500. In some embodiments, a single external device 500 sends power and/or data to multiple implantable devices 200. Alternatively or additionally, a single implantable device 200 can receive power and/or data from multiple external devices 500. In some embodiments, a first external device 500 is positioned on or near the patient's skin at a location proximate an implanted first implantable device 200, and a second external device 500 is positioned on or near the patient's skin (generally "on" the patient's skin) at a location proximate an implanted second implantable device 200. In these embodiments, the first external device 500 transmits data and/or power to at least the first implantable device 200 and the second external device 500 transmits data and/or power to at least the second implantable device 200.

Each implantable device 200 can comprise one or more stimulation elements 260, configured to stimulate, deliver energy to, deliver an agent to, record information from and/or otherwise interface with the patient. Alternatively or additionally, the one or more stimulation elements 260 can be configured to record patient information. Each implantable device 200 can comprise housing 210, receiver 230, controller 250, energy storage assembly 270 and/or one or more antennas 240, each described in detail herein. Each stimulation element 260 can comprise a sensor and/or any transducer, as described in detail herein. One or more stimulation elements 260 can be positioned on a lead 265 (e.g. a flexible filament including wires or other conductors that connect each stimulation element to electronics within housing 210). Each implantable device 200 can comprise one or more leads 265, such as two leads attached to a single housing 210, or a first lead 265 attached to a first housing 210 and a second lead 265 attached to a second housing 210. Each implantable device 200 can further comprise one or more anchor elements 221, as described in detail hereinbelow.

In some embodiments, one or more implantable devices 200 are further configured to transmit data to one or more external devices 500, such as via one or more antennas 240 transmitting a signal to one or more antennas 540, or otherwise. Data transmitted by an implantable device 200 can comprise patient information (e.g. patient physiologic information recorded by one or more stimulation elements 260 configured as a physiologic sensor), or implantable device 200 information (e.g. data recorded by one or more stimulation elements 260 configured as a sensor and positioned in implantable device 200, or other implantable device 200 configuration and/or performance data).

Housing 210 of each implantable device 200 can comprise one or more rigid and/or flexible materials which surround various components, such as antenna 240, energy storage assembly 270, controller 250 and/or receiver 230 as shown in FIG. 1. In some embodiments, one or more stimulation elements 260 are positioned in, on and/or within housing 210. In some embodiments, housing 210 surrounds a substrate, such as a flexible and/or foldable printed circuit board, such as multiple discrete or continuous printed circuit boards positioned in different planes (e.g. a flexible or foldable printed circuit board).

Housing 210 can comprise one or more shapes or combination of shapes, such as one or more shapes selected from the group consisting of: disc; pill; cylinder; sphere; oblate spheroid; dish-like shape; bowl-like shape; cone; rectangular prism; trapezoidal prism; a portion of a toroid; and combinations of one or more of these.

Housing 210 can comprise a major axis and a minor axis, defined hereabove. In some embodiments, housing 210 comprises a major axis less than or equal to 20 mm, such as a major axis less than or equal to 15 mm, 12 mm or 10 mm. In some embodiments, housing 210 comprises a minor axis less than or equal to 8 mm, such as a minor axis less than or equal to 6 mm, or less than or equal to 5 mm. Housing 210 can comprise a wall thickness between 0.1 mm and 1.0 mm, such as a wall thickness between 0.2 mm and 0.5 mm, such as a wall thickness of approximately 0.3 mm. Housing 210 can comprise a displacement volume less than or equal to 2000 $mm^3$, such as less than or equal to 600 $mm^3$.

Housing 210 can comprise one or more portions that are transmissive to radiofrequency (RF) signals. In some embodiments, housing 210 comprises glass. In some embodiments, housing 210 comprises a material selected from the group consisting of: glass; ceramic; stainless steel; titanium; polyurethane; an organic compound; liquid crystal polymer (LCP); gold; platinum; platinum iridium; tungsten; epoxy; a thermoplastic; a thermoset plastic; and combinations of one or more of these. In some embodiments, one or more portions of housing 210 comprises one or more coatings, such as one or more coatings configured to cause or prevent a physiologic reaction and/or a coating configured to block (e.g. shield) an electromagnetic transmission.

Housing 210 can comprise one or more passageways or other feedthroughs, such as for the passage of a lead, wire, optical fiber, fluid delivery tube, mechanical linkage and/or other conduit through a wall of housing 210, such as is described in applicant's co-pending International PCT Patent Application Serial Number PCT/US2016/016888, titled "Medical Apparatus including an Implantable System and an External System", filed Feb. 5, 2016; the content of which is incorporated herein by reference in its entirety for all purposes.

In some embodiments, one or more inner or outer surfaces (or portions of surfaces) of housing 210 includes an insulating and/or shielding layer (e.g. a conductive electromagnetic shielding layer), such as inner coating 219a and/or outer coating 219b shown (singly or collectively coating 219). Coating 219 can comprise an electrically insulating and/or a thermally insulating layer or other coating. In some embodiments, one or more portions of housing 210 comprise an electrically shielding coating 219, while other portions are transmissive to electromagnetic signals such as radiofrequency signals.

In some embodiments, housing 210 comprises an array of feedthroughs, not shown. In some embodiments, housing 210 is surrounded by a covering, such as a flexible and/or non-conductive covering, such as a covering made of an elastomer.

In some embodiments, implantable device 200 and/or another component of apparatus 10 can include one or more features to prevent or at least reduce migration of implant 200 within the patient's body. In some embodiments, one or more implantable devices 200 comprises one or more anchor elements configured to secure one or more portions of implantable device 200 to tissue (e.g. anchor element 221 described hereabove and/or an anchor element in an overmold positioned about a portion of housing 210). Anchor element 221 can comprise one or more anchoring elements selected from the group consisting of: a sleeve such as a silicone sleeve; suture tab; suture eyelet; bone anchor, wire loops; porous mesh; penetrable wing; penetrable tab; bone screw eyelet; tine; pincers; suture slits; and combinations of one or more of these.

One or more antennas 240 (singly or collectively antenna 240) can be configured to receive power and/or data, and receiver 230 can receive the power and/or data from the one or more antennas 240. Each antenna 240 can comprise one or more implantable antennas, such as one or more antennas positioned within housing 210, and/or one or more antennas electrically attached to a connecting filament. In some embodiments, one or more implantable devices 200 comprise at least two antennas 240, or at least three antennas 240. Antenna 240 can be configured to receive power and/or data from one or more external devices 500, such that an attached receiver 230 receives the power and/or data. In some embodiments, implantable system 20 comprises at least two implantable devices 200, each of which comprise one or more (e.g. two or three) antennas 240 which are positioned within a housing 210 and/or electrically tethered to a housing 210. In some embodiments, an implantable device 200 comprises a first antenna 240 positioned in a first plane and a second antenna 240 positioned in a second plane. The first plane and second plane can be relatively orthogonal planes, or planes oriented between 30° and 90° relative to each other, such as between 40° and 90°, approximately 30°, approximately 45° and/or approximately 60° relative to each other. In some embodiments, an implantable device 200 comprises a first antenna 240 positioned in a first plane, a second antenna 240 positioned in a second plane, and a third antenna 240 positioned in a third plane.

In some embodiments, implantable device 200 comprises one or more antennas 240 positioned on a substrate, such as a printed circuit board (PCB), a flexible printed circuit board and/or a foldable substrate (e.g. a substrate comprising rigid portions and hinged portions). In some embodiments, the substrate is folded or otherwise pivoted to position the various antennas 240 on differently oriented planes, such as multiple planes oriented between 5° and 90° relative to each other, such as two antennas 240 positioned on two planes oriented between 30° and 90° or between 40° and 90° relative to each other, or three antennas 240 positioned on three planes oriented between 5° and 60° relative to each other. Two or more antennas 240 can be positioned on two or more different planes that are approximately 45° relative to each other, or approximately 60° or approximately 90° relative to each other.

Implantable device 200 can comprise three antennas 240. In some embodiments, a first antenna 240 comprises an electrical dipole antenna, and the second and third antennas 240 can be positioned in different planes than the first antenna 240. In some embodiments, the three antennas 240 each comprise a loop antenna, such as when each loop antenna is positioned on a different plane. In some embodiments, a first antenna 240 comprises an electrical dipole antenna, and a second antenna 240 and a third antenna 240 each comprise a loop antenna. In these embodiments, the second antenna 240 and the third antenna 240 can be positioned relatively orthogonal to each other (e.g. positioned on two relatively orthogonal planes). In some embodiments, a first antenna (e.g. an electrical dipole antenna) is positioned outside of housing 210, while a second antenna (e.g. a loop antenna) and a third antenna (e.g. a loop antenna) are each positioned on, in and/or within housing 210. In some embodiments, implantable device 200 comprises one or more antennas 240 in which any combination of antenna types (as described herein) are used in combination.

One or more antennas 240 can comprise an antenna selected from the group consisting of: loop antenna; multiple-turn loop antenna; planar loop antenna; coil antenna; dipole antenna; electric dipole antenna; magnetic dipole antenna; patch antenna; loaded dipole antenna; concentric loop antenna; loop antenna with ferrite core; and combinations of one or more of these. One or more antennas 240 can comprise a loop antenna, such as an elongated loop antenna or a multiple-turn loop antenna.

One or more antennas 240 can comprise a multi-turn spiral loop antenna, such as a multi-turn spiral loop antenna configured to desensitize coupling sensitivity and/or boost input voltage. In some embodiments, one or more antennas 240 comprise multiple concentric loops with varied dimensions, such as concentric loops configured to desensitize coupling sensitivity. In these embodiments, the multiple concentric loops can be: connected in parallel and driven from the same feed point; driven from the same feed point and connected using one or more of a capacitor, inductor, varactor, and combinations of one or more of these; and/or driven from multiple feed points.

One or more antennas 240 can comprise a minor axis and a major axis. In some embodiments, one or more antennas 240 comprise a minor axis between 1 mm and 8 mm, such as between 2 mm and 5 mm. In some embodiments, one or more antennas 240 comprise a major axis between 3 mm and 15 mm, such as between 4 mm and 8 mm. In some embodiments, one or more antennas 240 comprise a major axis above 3 mm, such as between 3 mm and 15 mm, such as when the antenna 240 is positioned outside of housing 210.

One or more antennas 240 can comprise a foldable and/or unfoldable antenna, such as is described in applicant's co-pending U.S. patent application Ser. No. 14/975,358, titled "Method and Apparatus for Minimally Invasive Implantable Modulators", filed Dec. 18, 2015, the content of which is incorporated herein by reference in its entirety for all purposes.

One or more antennas 240 can be positioned inside of housing 210. Alternatively or additionally, one or antennas 240 can be positioned outside of housing 210.

Implantable system 20, one or more implantable devices 200 and/or one or more antennas 240 can be configured to be positioned at a desired depth beneath the patient's skin, such as at a depth between 0.5 cm and 7.0 cm, such as a depth of between 1.0 cm and 3.0 cm.

One or more energy storage assemblies 270 (singly or collectively energy storage assembly 270) can comprise one or more implantable energy storage components, such as one or more batteries (e.g. rechargeable batteries) and/or capacitors (e.g. a supercapacitor). Energy storage assembly 270 can be configured to provide power to one or more of: one or more stimulation elements 260; controller 250; receiver 230; and combinations of one or more of these. In some embodiments, energy storage assembly 270 further provides power to one or more antennas 240 and/or circuitry configured to transmit data via antenna 240. In some embodiments, energy storage assembly 270 includes digital control for charge/discharge rates, voltage outputs, current outputs, and/or system power distribution and/or management.

Energy storage assembly 270 can comprise one or more capacitors with a single or collective capacitance between 0.01 µF and 10 F, such as a capacitance between 1 µF and 1.0 mF, or between 1 µF and 10 µF. The energy storage assembly 270 can comprise one or more capacitors with capacitance between 1 mF and 10 F, such as when energy storage assembly 270 comprises a super-capacitor and/or an ultra-capacitor. Such large capacitance can be used to store sufficient charge to maintain operation (e.g. maintain delivery of stimulation energy and/or delivery of an agent)

without the use (e.g. sufficient proximity) of an associated external device 500. A capacitor or other energy storage element (e.g. a battery) can be chosen to provide sufficient energy to maintain operation for at least 30 seconds, at least 2 minutes, at least 5 minutes, at least 30 minutes, and up to several hours or more (e.g. during showering, swimming or other physical activity). In some embodiments, energy storage assembly 270 is configured to provide continuous and/or intermittent stimulation energy for at least one charge-balanced pulse (e.g. for the duration of at least one charge-balanced pulse). In some embodiments, a capacitor, battery or other energy storage element is configured to provide stimulation energy without receiving externally supplied power for periods of at least 1 hour, at least 1 day, at least 1 month or at least 1 year. Energy storage assembly 270 can comprise one or more capacitors with a breakdown voltage above 1.0V, such as a breakdown voltage above 1.5V, 4.0V, 10V, or 15V. In some embodiments, energy storage assembly 270 can comprise capacitors distributed outside of housing 210, such as when one or more capacitors are distributed along lead 265. Energy storage assembly 270 can comprise one or more capacitors with low self-leakage, such as to maintain stored energy for longer periods of time.

In some embodiments, energy storage assembly 270 comprises a temporary energy storage component, such as a super-capacitor, configured to store a sufficient quantity of energy to provide uninterrupted stimulation, such as during time periods in which the link gain may be of poor quality or it may be temporarily unavailable (e.g. an external device 500 not being in place such as during a shower, swimming, and the like). An energy storage assembly 270 comprising an ultra-capacitor, super-capacitor or flexible battery can be charged via the wireless power transmission of the present inventive concepts, such as to store a sufficient amount of energy for one or more stimulation elements 260 to deliver stimulation energy during subsequent (intended or unintended) unavailability of one or more external devices 500 (e.g. an external device 500 is intentionally removed or unintentionally falls off or otherwise loses its position sufficiently proximate one or more implantable devices 200). An energy storage assembly 270 comprising one or more high capacity energy storage components can be beneficial in applications where therapy interruption provides a significant risk or is otherwise relatively unacceptable, such as for life support therapies, cardiac resynchronization therapies, and the like. The high capacity energy storage components of energy storage assembly 270 can be positioned in an assembly positioned within housing 210, on an inner or outer surface of housing 210, within a separate housing, and/or within lead 265.

In some embodiments, implantable device 200 receives power regularly from external system 50 (e.g. relatively continuously while implantable device 200 delivers stimulation energy), and energy storage assembly 270 comprises a relatively small battery or capacitor, such as a battery or capacitor that has an energy storage capacity of less than or equal to 0.6 Joules, 7 Joules or 40 Joules.

One or more controllers 250 (singly or collectively controller 250) can be configured to control one or more stimulation elements 260, such as a stimulation element 260 comprising a stimulation-based transducer (e.g. an electrode or other energy delivery element) and/or a sensor (e.g. a physiologic sensor and/or a sensor configured to monitor an implantable device 200 parameter). In some embodiments, controller 250 is configured to transmit a stimulation signal (e.g. transmit stimulation energy configured in one or more stimulation waveforms) to one or more stimulation elements 260 (e.g. one or more stimulation elements 260 comprising an electrode and/or other energy delivery element), independent of the power signal received by one or more antennas 240 (e.g. independent of power transmitted by external system 50), such as by using energy stored in energy storage assembly 270. In these embodiments, the power signal and/or the RF path for the power signal can be adjusted to optimize power efficiency (e.g. by tuning matching network on transmitter 530 and/or receiver 230; configuring antennas 540 and/or 240 in an array; tuning operating frequency; duty cycling the power signal; adjusting antenna 540 and/or 240 position; and the like), and a stimulation signal can be precisely delivered (e.g. by using energy stored on energy storage assembly 270 and generating stimulation signal locally on the implantable device 200) to ensure clinical efficacy. Also, if the power signal transmission (also referred to as "power link") is perturbed unexpectedly, the stimulation signal can be configured so that it is not significantly affected (e.g. unaffected). In some configurations, the stimulation signal being delivered by one or more implantable devices 200 is insensitive to interference that may be present. In these embodiments, a power transmission signal and stimulation signal can vary in one or more of: amplitude; changes in amplitude; average amplitude; frequency; changes in frequency; average frequency; phase; changes in phase; average phase; waveform shape; pulse shape; duty cycle; polarity; and combinations of one or more of these.

Controller 250 can receive commands from receiver 230, such as one or more commands related to one or more implantable device 200 configuration parameters selected from the group consisting of: stimulation parameter; data rate of receiver; data rate of data transmitted by the first implantable device 200 at least one implantable antenna 240; stimulation element 260 configuration; state of controller 250; antenna 240 impedance; clock frequency; sensor configuration; electrode configuration; power management parameter; energy storage assembly parameter; agent delivery parameter; sensor configuration parameter; and combinations of one or more of these.

In some embodiments, one or more stimulation elements 260 comprise a stimulation element configured to deliver energy (e.g. one or more electrodes configured to deliver monopolar or bipolar electrical energy) to tissue, and controller 250 is configured to control the energy delivery, such as to control one or more stimulation parameters. Each of these stimulation parameters can be held relatively constant, and/or varied, such as a variation performed in a continuous or intermittent manner. In some embodiments, one or more stimulation parameters are varied in a random or pseudo-random (hereinafter "random") manner, such as a variation performed by apparatus 10 using a probability distribution as described in applicant's co-pending International PCT Patent Application Serial Number PCT/US2017/017978, titled "Apparatus with Enhanced Stimulation Waveforms", filed Feb. 15, 2017, the content of which is incorporated herein by reference in its entirety for all purposes. In some embodiments, stimulation (e.g. stimulation comprising high frequency and/or low frequency signal components) is varied randomly to eliminate or at least reduce synchrony of neuronal firing with the stimulation signal (e.g. to reduce paresthesia or other patient discomfort). In some embodiments, one or more stimulation elements 260 comprise a stimulation element configured to stimulate a target (e.g. nerve tissue such as spinal nerve tissue and/or peripheral nerve tissue). The amount of stimulation delivered to the target can be controlled by varying a parameter selected from the group consisting of: stimulation element 260 size and/or configuration (e.g. electrode size and/or configuration); stimulation element 260 shape (e.g. electrode shape, magnetic field generating transducer shape or agent delivering element shape); shape of a generated electric field; shape of a generated magnetic field; stimulation signal parameters; and combinations of one or more of these.

In some embodiments, one or more stimulation elements 260 comprise an element configured to deliver electrical energy to tissue (e.g. one or more electrodes configured to deliver monopolar or bipolar electrical energy), and controller 250 is configured to control charge balance, such as to actively and/or passively control charge balance, as described herebelow. Charge balance can be essential for patient safety in electrical stimulation of nerves or other tissue. Imbalanced stimulation waveforms can cause electrode corrosion and/or dissolution which can lead to deposition of toxic materials in tissue, implant rejection, and nerve damage. The stimulation waveform can be balanced such that net outflow charge approximately equals net inflow charge. With stimulation waveform amplitudes that can vary between 0.01 mA to 15 mA (such as between 0.1 mA and 15 ma, between 0.1 mA and 12 mA, or between 0.1 mA and 10 mA), depending on the treatment, the error in charge balance can be on the order of 0.001% to 0.01%. Alternatively or additionally, controller 250 can comprise AC coupling capacitors that are configured to balance stimulation waveforms passively. The AC coupling capacitance can be fairly large (e.g. greater than 10 µF), in order to pass the stimulation waveform with minimal filtering. In some embodiments, apparatus 10 is configured to perform active charge balancing. In some embodiments, an implantable device 200 comprises a precise resistor in series with a stimulation electrode-based stimulation element 260. The precise resistor can be used to measure outflow and inflow currents, such as when controller 250 comprises an analog to digital converter (ADC). Controller 250 can integrate current over time during a first phase in which stimulation energy is delivered, and during a second phase in which a reverse current is applied (e.g. a reverse current used to balance charge). Controller 250 can be configured to balance the total charge in the two phases, to ensure that the net DC current is approximately zero. The integration can be achieved using an analog integrator and/or a digital summer of controller 250, with controller 250 keeping track of one or more parameters of the pulses delivered (e.g. pulses delivered within a train or a burst). Implantable device 200 can comprise a precise series resistance comprising an "on-chip" trimmed resistor or an "off-chip resistor". In some embodiments, implantable device 200 comprises a bank of trimmed resistors that are used to control the net series resistance, such as to adjust resistance based on stimulation amplitude requirements (e.g. to take advantage of the full dynamic range of an ADC of controller 250). In some embodiments, controller 250 comprises a shunt path with an RC-based low pass filter used for both outflow and inflow of current. RC elements of controller 250 can be chosen such that the shunt current is only a fraction of the stimulation current. Since the same RC elements can be used for both outflow and inflow current, the precision required for the RC components can be lower. An ADC can be used to sense the voltage on the capacitor at the end of a stimulation pulse. After the stimulation pulse, the capacitor can be discharged and the polarity of the stimulation current can be reversed and set to any amplitude, until the capacitor is charged to approximately the same voltage (according to the ADC precision) as it was charged during the stimulation pulse. The ADC resolution can be high enough to ensure the residual error is less than what would cause an undesired charge accumulation. ADC resolution requirements can be further reduced by reducing the net capacitance in a shunt RC circuit, to cause accelerated charging of the capacitor. The capacitor can be discharged every time the voltage exceeds a certain predefined threshold, while controller 250 keeps track of the number of times the capacitor has been charged and reset. By resetting the capacitor through a low resistance path, the discharge time can be insignificant compared to the charge time, reducing the error due to the discharge period. Since the net charge equivalent to full scale voltage on the ADC can be divided into multiple cycles, the required resolution of the ADC to achieve the same residual error can be divided by the number of cycles.

In some embodiments, controller 250 is configured to produce a stimulation signal comprising a waveform or a waveform pattern (hereinafter stimulation waveform), for one or more stimulation elements 260 configured as a stimulation element (e.g. such that one or more stimulation elements 260 deliver stimulation energy comprising or at least resembling that stimulation waveform). Controller 250 can produce a stimulation signal comprising a waveform selected from the group consisting of: square wave; rectangle wave; sine wave; sawtooth; triangle wave (e.g. symmetric or asymmetric); trapezoidal; ramp; waveform with exponential increase; waveform with exponential decrease; pulse shape which minimizes power consumption; Gaussian pulse shape; pulse train; root-raised cosine; bipolar pulses; and combinations of one or more of these. In some embodiments, controller 250 is configured to produce a stimulation signal comprising a waveform including a combination of two or more waveforms selected from the group consisting of: square wave; rectangle wave; sine wave; triangle wave (symmetric or asymmetric); ramp; waveform with exponential increase; waveform with exponential decrease; pulse shape which minimizes power consumption; Gaussian pulse shape; pulse train; root-raised cosine; bipolar pulses; and combinations of one or more of these. In some embodiments, controller 250 is configured to construct a custom waveform (e.g. an operator customized waveform), such as by adjusting amplitude at specified time steps (e.g. for one or more pulses). In some embodiments, controller 250 is configured to generate a waveform including one or more random parameters (e.g. random timing of pulses or random changes in frequency, rate of change or amplitude).

In some embodiments, controller 250 is configured to provide a stimulation signal comprising waveforms and/or pulses repeated at a frequency (e.g. includes a frequency component) between 1.0 Hz and 50 KHz, such as between 10 Hz and 500 Hz, between 40 Hz and 160 Hz and/or between 5 KHz and 15 KHz. In some embodiments, controller 250 is configured to produce a stimulation signal comprising a frequency between 1 Hz and 1000 Hz, such as a stimulation signal with a frequency between 10 Hz and 500 Hz. In some embodiments, controller 250 is configured to produce a stimulation signal comprising a duty cycle between 0.1% and 99%, such as a duty cycle between 1% and 10% or between 1% and 25%. In some embodiments, controller 250 is configured to produce a stimulation signal comprising a frequency modulated stimulation waveform, such as a stimulation waveform comprising a frequency component (e.g. signal) between 1 kHz and 20 kHz. In some embodiments, controller 250 is configured to produce a stimulation signal comprising a mix and/or modulation of low frequency and high frequency signals, which comprise any of the waveform types, shapes and other configurations. In these embodiments, the stimulation signal can comprise low frequency signals between 1 Hz and 1000 Hz, and high frequency signals between 600 Hz and 50 kHz, or between 1 kHz and 20 kHz. Alternatively or additionally, the stimulation signal can comprise a train of high frequency signals and bursts of low frequency signals, and/or a train of low frequency signals and bursts of high frequency signals. Alternatively or additionally, the stimulation signal can comprise one or more high frequency signals modulated with one or more low frequency signals, such as one or more high frequency signals frequency modulated (FM), amplitude modulated (AM), phase modulated (PM) and/or pulse width modulated (PWM) with one or more low frequency signals. The stimulation signal can cycle among different waveforms shapes at specified time intervals. The stimulation signal can comprise a pseudo random binary sequence (PRBS) non-return-to-zero or return-to-zero waveform, such as with a fixed and/or time-varying pulse width and/or frequency of the pulses.

Controller 250 can comprise a clamping circuit configured to allow fast charging and/or discharging of the energy storage assembly 270, stimulation element 260 drivers (e.g. electrode drivers) of controller 250, and/or other components of implantable device 200. The clamping circuit can improve pulse shape by offering additional control and/or configuration of rise and fall times in the shape of the waveform (e.g. to create rapid rise or fall times). In some embodiments, the clamping circuit can be configured to limit the rise and/or fall time to be less than or equal to one-tenth (10%) of the pulse width of an applied stimulation pulse (e.g. less than or equal to 1 µs rise and/or fall time for a 10 µs stimulation pulse).

In some embodiments, controller 250 comprises a matching network configured to match the impedance of a first antenna 240 with the impedance of the receiver 230. In these embodiments, controller 250's matching network can be adjustable. Alternatively or additionally, controller 250 can comprise an adjustable loading impedance to stabilize the load seen at an antenna 240 under different operating conditions. In some embodiments, the adjustable loading impedance is controlled according to the charge rate of the energy storage assembly 270.

Controller 250 and/or any other component of each implantable device 200 can comprise an integrated circuit comprising one or more components selected from the group consisting of: matching network; rectifier; DC-DC converter; regulator; bandgap reference; overvoltage protection; overcurrent protection; active charge balance circuit; analog to digital converter (ADC); digital to analog converter (DAC); current driver; voltage driver; digital controller; clock generator; data receiver; data demodulator; data modulator; data transmitter; electrode drivers; sensing interface analog front end; power management circuit; energy storage interface; memory register; timing circuit; and combinations of one or more of these.

One or more receivers 230 (singly or collectively receiver 230) can comprise one or more components, such as demodulator 231, rectifier 232 and/or power converter 233 shown in FIG. 1. In some embodiments, receiver 230 can comprise a DC-DC converter such as a boost converter. Receiver 230 can comprise a data receiver, such as a data receiver including an envelope detector and demodulator and/or an envelope averaging circuit. In some embodiments, one or more antennas 240 separately connect to one or more receivers 230. In some embodiments, one or more antennas 240 connect to a single receiver 230, such as via a series connection or a parallel connection.

One or more implantable devices 200 can be configured to transmit a data signal to external system 50. In some embodiments, receiver 230 is configured to drive one or more antennas 240 to transmit data to external system 50 (e.g. to an antenna 540 of an external device 500). Alternatively or additionally, implantable device 200 can be configured to transmit a data signal by having receiver 230 adjust a load impedance to backscatter energy, such as a backscattering of energy which can be detected by external system 50. In some embodiments, data transmission is accomplished by receiver 230 manipulating a signal at a tissue interface, such as to transmit a data signal using body conduction.

In some embodiments, receiver 230 comprises a matching network, such as a matching network configured to detune to prevent oversaturation. For example, implantable system 20 can comprise two or more implantable devices 200 each of which includes a receiver 230 comprising a matching network. A first implantable device 200's receiver 230's matching network can be configured to detune based on power received by the second implantable device 200's receiver 230.

Demodulator 231 can comprise circuitry that asynchronously recovers signals modulated on the power signal provided by external system 50, and converts the modulated signals into digital signals. In some embodiments, demodulator 231 asynchronously recovers the modulated signal by comparing a dynamically generated moving average with the envelope, outputting a high voltage when the envelope is greater than the moving average and a low voltage when the envelope is less than the moving average. Data can then be extracted from this resulting digital signal from the width and/or amplitude of the pulses in the signal, according to the encoding method used by external system 50. In some embodiments, demodulator 231 recovers a digital signal that is used as timing information for an implantable device 200, similar to an on-chip clock. The recovered clock signal can also be used to synchronize an on-chip clock generator of controller 250, such as through the use of a frequency and/or phase locked loop (FLL or PLL).

Rectifier 232 can comprise a power signal rectifier, such as to provide power to the energy storage assembly 270 and/or controller 250. In some embodiments, rectifier 232 comprises one or more self-driven synchronous rectifier (SDSR) stages connected in charge-pump configuration, to boost the voltage from input RF amplitude to the rectifier to a higher voltage. The boosted voltage can directly charge energy storage assembly 270, or be further boosted by a DC-DC converter or boost converter. In some embodiments, rectifier 232 comprises diode-capacitor ladder stages instead of, or in addition to, SDSR stages. On-chip diodes, such as Schottky diodes, or off-chip diodes can be used in one or more rectifier 232 stages. For maximum efficiency, the rectification elements, such as diodes, can be optimized to minimize forward conduction and/or reverse conduction losses by properly sizing the components and selecting appropriate number of stages based on the input RF voltage and load current.

Power converter 233 can comprise one or more voltage conversion elements such as DC-DC converters that boost or otherwise change the voltage to a desired level. In some embodiments, voltage conversion is achieved with a buck-boost converter, a boost converter, a switched capacitor, and/or charge pumps. One or more power converters 233 can interface with energy storage assembly 270 and charge up associated energy storage components to desired voltages. In some embodiments, power converter 233 receives control signals from controller 250, such as to configure voltages, currents, charge/discharge rates, switching frequencies, and/or other operating parameters of power converter 233.

One or more implantable leads 265 (singly or collectively lead 265) can be attached to one or more housings 210, such as a lead 265 comprising one or more stimulation elements 260. Lead 265 can comprise one or more stimulation elements 260 configured as a stimulation element (e.g. an electrode configured to deliver electrical energy in monopolar or bipolar mode or an agent delivery element such as an output port fluidly connected to a reservoir within housing 210). Alternatively or additionally, lead 265 can comprise one or more stimulation elements 260 configured as a physiologic sensor (e.g. an electrode configured to record electrical activity of tissue or other physiologic sensor as described herein). Alternatively or additionally, lead 265 can comprise one or more stimulation elements 260 configured to transmit signals through tissue to external system 50, such as through body conduction.

In some embodiments, implantable device 200 comprises a connector, connector 215, that operably attaches (e.g. electrically attaches) one or more stimulation elements 260 to one or more components (e.g. electronic components) internal to housing 210 (e.g. to transfer power and/or data therebetween). Connector 215 can be constructed and arranged as described herebelow in reference to any of FIGS. 2A-D, 3, 3A-D, 4A-B, 5C and/or 8. In some embodiments, connector 215 is operably attached (e.g. in a manufacturing process) or attachable (e.g. in a clinical procedure) to lead 265 as shown in FIG. 1. Alternatively, connector 215 can be operably attached and/or attachable to a lead connection assembly 280, which in turn can be attached to a lead 265, such as is described herebelow in reference to any of FIGS. 2C, 3A and/or, 3B. In some embodiments, connector 215 passes through an opening in housing 210, in a feedthrough arrangement. In some embodiments, an overmold or other sealing element, sealing element 205 shown, provides a seal about connector 215, the opening in housing 210 and/or the interface between connector 215 and housing 210.

In some embodiments, lead 265 comprises a removable stylet configured to aid in the implantation of lead 265, such as is described in applicant's co-pending International PCT Patent Application Serial Number PCT/US2016/016888, titled "Medical Apparatus including an Implantable System and an External System", filed Feb. 5, 2016; the content of which is incorporated herein by reference in its entirety for all purposes. In some embodiments, implantable system 20 comprises more than one lead 265, comprising one or more stimulation elements 260 and attached to one or more housings 210 of one or more implantable devices 200. In some embodiments, one or more leads 265 can be attached to a single housing 210.

In some embodiments, lead 265 comprises a diameter between 1 mm and 4 mm, such as a diameter between 1 mm and 2 mm. In some embodiments, lead 265 comprises a length between 3 cm and 60 cm, such as a length between 6 cm and 30 cm. One or more leads 265 can include between 2-64 stimulation elements 260, such as when a lead 265 comprises between 2 and 64 electrodes, such as between 4 and 32 electrodes. In some embodiments, lead 265 comprises a paddle lead. In some embodiments, lead 265 comprises a single or multi-lumen catheter, such as when an attached implantable device 200 is configured as an agent delivery apparatus as described herein (e.g. a stimulation element 260 configured as a catheter comprises at least a portion of lead 265).

One or more stimulation elements 260 (singly or collectively stimulation element 260) can comprise one or more sensors, transducers and/or other functional elements. In some embodiments, stimulation elements 260 comprise at least one sensor and/or at least one transducer (e.g. a single stimulation element 260 or multiple stimulation elements 260). In some embodiments, stimulation element 260 comprises a functional element configured to provide a therapy, such as one or more stimulation elements 260 configured to deliver an agent to tissue (e.g. a needle or catheter), to deliver energy to tissue and/or to otherwise therapeutically affect tissue. In some embodiments, stimulation element 260 comprises one or more stimulation elements 260 configured to record patient information, such as when stimulation element 260 comprises one or more sensors configured to measure a patient physiologic parameter, as described herein. In some embodiments, stimulation element 260 comprises one or more sensors configured to record an implantable device 200 parameter, also as described herein.

One or more stimulation elements 260 can be positioned on lead 265 as shown in FIG. 1. Alternatively or additionally, one or more stimulation elements 260 can be positioned on housing 210.

Functional element 260 can comprise one or more stimulation elements positioned at one or more internal body locations. Functional element 260 can comprise one or more stimulation elements positioned to interface with (e.g. deliver energy to and/or record a physiologic parameter from) spinal cord tissue, spinal canal tissue, epidural space tissue, spinal root tissue (dorsal or ventral), dorsal root ganglion, nerve tissue (e.g. peripheral nerve tissue, spinal nerve tissue or cranial nerve tissue), brain tissue, ganglia (e.g. sympathetic or parasympathetic) and/or a plexus. In some embodiments, stimulation element 260 comprises one or more elements positioned proximate and/or within one or more tissue types and/or locations selected from the group consisting of: one or more nerves; one or more locations along, in and/or proximate to the spinal cord; peripheral nerves of the spinal cord including locations around the back; the knee; the tibial nerve (and/or sensory fibers that lead to the tibial nerve); the occipital nerve; the sphenopalatine ganglion; the sacral and/or pudendal nerve; brain tissue, such as the thalamus; baroreceptors in a blood vessel wall, such as in the carotid artery; one or more muscles; the medial nerve; the hypoglossal nerve and/or one or more muscles of the tongue; cardiac tissue; the anal sphincter; the dorsal root ganglion; motor nerves; muscle tissue; the spine; the vagus nerve; the renal nerve; an organ; the heart; the liver; the kidney; an artery; a vein; bone; and combinations of one or more of these, such as to stimulate and/or record data from the tissue and/or location in which the stimulation element 260 is positioned proximate to and/or within. In some embodiments, apparatus 10, implantable device 200 and/or stimulation element 260 are configured to stimulate spinal nerves, peripheral nerves and/or other tissue as described in applicant's co-pending application International PCT Patent Serial Number PCT/US2016/051177, titled "Apparatus for Peripheral or Spinal Stimulation", filed Sep. 9, 2016.

In some embodiments, stimulation element 260 comprises one or more sensors configured to record data representing a physiologic parameter of the patient. Functional element 260 can comprise one or more sensors selected from the group consisting of: electrode; sensor configured to record electrical activity of tissue; blood glucose sensor; gas sensor; blood gas sensor; ion concentration sensor; oxygen sensor; pressure sensor; blood pressure sensor; heart rate sensor; cardiac output sensor; inflammation sensor; neural activity sensor; neural spike sensor; muscular activity sensor; EMG sensor, bladder volume sensor, bladder pressure sensor, gastric volume sensor; peristalsis rate sensor; pH sensor; strain gauge; accelerometer; gyroscope; GPS; respiration sensor; respiration rate sensor; flow sensor; viscosity sensor; temperature sensor; magnetic sensor; optical sensor; MEMs sensor; chemical sensor; hormone sensor; impedance sensor; tissue impedance sensor; electrode-tissue interface impedance sensor; body position sensor; body motion sensor; organ motion sensor; physical activity level sensor; perspiration sensor; patient hydration sensor; breath monitoring sensor; sleep monitoring sensor; food intake monitoring sensor; digestion monitoring sensor; urine movement sensor; bowel movement sensor; tremor sensor; pain level sensor; and combinations of one or more of these.

Apparatus 10 and stimulation element 260 can be configured to record a patient parameter (e.g. patient physiologic and/or patient environment parameter) selected from the group consisting of: blood glucose; blood pressure; EKG; heart rate; cardiac output; oxygen level; pH level; pH of blood; pH of a bodily fluids; tissue temperature; inflammation level; bacteria level; type of bacteria present; gas level; blood gas level; neural activity; neural spikes; neural spike shape; action potential; local field potential (LFP); EEG; muscular activity (e.g. as measured using EMG); skeletal muscle activity; bladder volume; bladder pressure; gastric volume; peristalsis rate; impedance; tissue impedance; electrode-tissue interface impedance; physical activity level; pain level; body position; body motion; organ motion; respiration rate; respiration level; perspiration rate; sleep level; sleep cycle; digestion state; digestion level; urine production; urine flow; bowel movement; tremor; ion concentration; chemical concentration; hormone level; viscosity of a bodily fluid; patient hydration level; and combinations of one or more of these.

In some embodiments, stimulation element 260 comprises one or more sensors configured to record data representing a parameter of implantable device 200. In these embodiments, stimulation element 260 can comprise one or more sensors selected from the group consisting of: an energy sensor; a voltage sensor; a current sensor; a temperature sensor (e.g. a temperature of one or more components of implantable device 200); a contamination detector (e.g. to detect undesired material that has passed through housing 210); an antenna matching and/or mismatching assessment sensor; power transfer sensor; link gain sensor; power use sensor; energy level sensor; energy charge rate sensor; energy discharge rate sensor; impedance sensor; load impedance sensor; instantaneous power usage sensor; average power usage sensor; bit error rate sensor; signal integrity sensor; and combinations of one or more of these. Apparatus 10 can be configured to analyze (e.g. via implantable controller 250, programmer 600 and/or diagnostic assembly 91 described herebelow) the data recorded by stimulation element 260 to assess one or more of: power transfer; link gain; power use; energy within energy storage assembly 270; performance of energy storage assembly 270; expected life of energy storage assembly 270; discharge rate of energy storage assembly 270; ripple or other variations of energy storage assembly 270; matching of antenna 240 and 540; communication error rate between implantable device 200 and external device 500; integrity of transmission between implantable device 200 and external device 500; and combinations of one or more of these. A stimulation element 260 can be configured to record temperature, such as when apparatus 10 is configured to deactivate or otherwise modify the performance of an implantable device 200 when the recorded temperature exceeds a threshold.

In some embodiments, one or more stimulation elements 260 comprise a transducer configured to deliver energy to tissue, such as to treat pain and/or to otherwise stimulate or affect tissue. In some embodiments, stimulation element 260 comprises a stimulation element, such as one or more transducers selected from the group consisting of: an electrode; an energy delivery element such as an electrical energy delivery element, a light energy delivery element, a laser light energy delivery element, a sound energy delivery element, a subsonic sound energy delivery element and/or an ultrasonic sound delivery element; an electromagnetic field generating element; a magnetic field generating element; a mechanical transducer (e.g. delivering mechanical energy to tissue); a tissue manipulating element; a heat generating element; a cooling (e.g. cryogenic or otherwise heat extracting energy) element; an agent delivery element such as a pharmaceutical drug delivery element; and combinations of one or more of these.

In some embodiments, one or more stimulation elements 260 comprises a drug or other agent delivery element, such as a needle, port, iontophoretic element, catheter, or other agent delivering element that is connected to a reservoir of agent positioned within housing 210 (e.g. reservoir 225 described herebelow). In some embodiments, one or more stimulation elements 260 comprise a drug eluting element configured to improve biocompatibility of implantable system 20.

In some embodiments, one or more stimulation elements 260 comprise one or more electrodes configured to deliver energy to tissue and/or to sense a patient parameter (e.g. electrical activity of tissue or other patient physiologic parameter). In these embodiments, one or more stimulation elements 260 can comprise one or more electrodes selected from the group consisting of: microelectrode; cuff electrode; array of electrodes; linear array of electrodes; circular array of electrodes; paddle-shaped array of electrodes; bifurcated electrodes; and combinations of one or more of these.

In some embodiments, apparatus 10 and stimulation element 260 are configured to both record one or more patient parameters, and also to perform a medical therapy (e.g. stimulation of tissue with energy and/or an agent). In these embodiments, the medical therapy can be performed in a closed-loop fashion, such as when energy and/or agent delivery is modified based on the measured one or more patient physiologic parameters.

In some embodiments, one or more stimulation elements 260 comprise an agent delivery element, such as a fluid delivery element (e.g. a catheter, a porous membrane, an iontophoretic element or a needle) in fluid communication with a reservoir of the agent positioned within housing 210, such as reservoir 225 described herebelow.

In some embodiments, apparatus 10 comprises tool 60. Tool 60 can comprise a data logging and/or analysis tool configured to receive data from external system 50 or implantable system 20, such as data comprising: diagnostic information recorded by external system 50 and/or implantable system 20; therapeutic information recorded by external system 50 and/or implantable system 20; patient information (e.g. patient physiologic information) recorded by implantable system 20; patient environment information recorded by implantable system 20; and combinations of one or more of these. Tool 60 can be configured to receive data from wired or wireless (e.g. Bluetooth) means. Tool 60 can comprise a tool selected from the group consisting of: a data logging and/or storage tool; a data analysis tool; a network such as a LAN or the Internet; a cell phone; and combinations of one or more of these.

Figure 16:
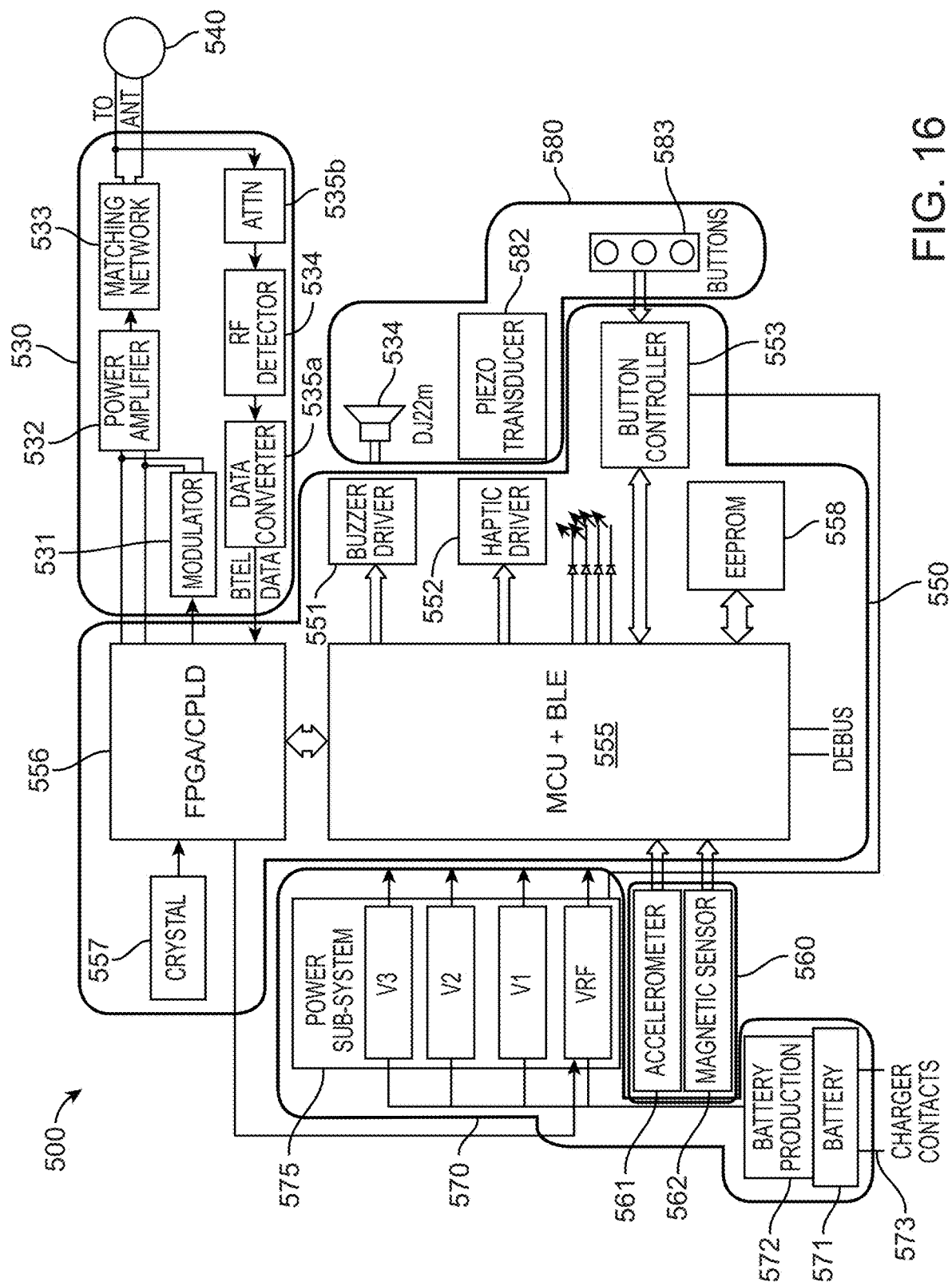
FIG. 16 is an electronic block diagram of an external device, consistent with the present inventive concepts.

In some embodiments, tool 60 comprises a battery charging assembly, such as an assembly configured to recharge one or more power supplies 570 comprising a rechargeable battery or capacitor, such as is described herebelow in reference to tool 60$_{ii}$ of FIGS. 16 and/or 32.

In some embodiments, tool 60 comprises an implantation tool, such as an introducer or other implantation tool constructed and arranged to aid in the implantation of housing 210, implantable antenna 240, lead 265 and/or one or more stimulation elements 260. In some embodiments, tool 60 comprises a component configured to anchor implantable device 200 to tissue, such as a mesh or wrap that slides around at least a portion of implantable device 200 and is configured to engage tissue (e.g. via tissue ingrowth) or be engaged with tissue (e.g. via suture or clips).

In some embodiments, tool 60 comprises a tool configured to aid in the placement of one or more external devices 500 on the patient's skin (e.g. at a location proximate an implanted implantable device 200), such as is described herebelow in reference to tool 60$_i$ of FIG. 20.

In some embodiments, lead 265 comprises a paddle lead or other stimulating lead and tool 60 comprises an introducer (e.g. a needle or an extended-width introducer) configured to deliver at least a distal portion of lead 265 into an epidural space of a patient. Tool 60 can comprise an introducer comprising a Tuohy needle, such as a Tuohy needle of 12 gauge or smaller. Tool 60 can comprise a handle for manipulating lead 265. Tool 60 can be configured to place lead 265 at an entry point above the lumbar spinal column (e.g. between L1 and L2 vertebrae). Tool 60 can include extension tubing used to insert lead 265. Tool 60 can further comprise a tool configured to anchor lead 265, such as when tool 60 comprises sutures, clips, other anchoring elements and/or an anchor securing tool (e.g. a needle or a stapling device), such as to secure lead 265 in subcutaneous tissue. Lead 265 and/or tool 60 can comprise extension tubing used to place lead 265, such as extension tubing that remains in place after removal of an introducer of tool 60. Tool 60 can be configured to place lead 265 against the dura of the spinal cord of the patient.

In some embodiments, tool 60 and/or lead 265 are constructed and arranged to implant lead 265 to stimulate one or more multifidus (MF) muscle fascicles, such as at least three sets of multifidus muscle fascicles. Lead 265 can be secured to a vertebra (e.g. on the transverse process, lamina or vertebral body). Lead 265 can be placed via tool 60 such that one or more stimulation elements 260 (e.g. electrodes) are positioned within the multifidus muscle structures. One or more stimulation elements 260 can be positioned to deliver electrical energy and/or to otherwise stimulate tissue selected from the group consisting of: muscle motor point(s) or the deep fibers of lumbar multifidus; quadratus lumborum; the erector spinae; psoas major; transverse abdominis; connective tissue such as the annulus or facet capsule; ligaments coupling bony structures of the spine; and combinations of one or more of these. Functional elements 260 can be positioned to: depolarize, hyperpolarize and/or block innervated sections of the muscle that will then propagate an activating and/or inhibiting stimulus along the nerve fibers recruiting muscle tissue remote from the site of stimulation and/or modulate nerve activity (including inhibiting nerve conduction, improving nerve conduction and/or improving muscle activity). In some embodiments, stimulation elements 260 are positioned to cause transvascular stimulation (e.g. transvascular stimulation from arteries and/or veins in a leg or arm). In some embodiments, stimulation elements 260 are positioned to stimulate nerve tissue selected from the group consisting of: dorsal ramus nerve; medial branch of dorsal ramus nerve; nervous tissue associated with multifidus muscle; and combinations of one or more of these. In some embodiments, stimulation elements 260 are configured to deliver stimulation energy to contract the multifidus muscle. In some embodiments, stimulation elements 260 are configured to stimulate tissue by providing episodic electrical stimulation. In some embodiments, apparatus 10 comprises a tool 60 configured to diagnose a defect in spinal muscle or the motor control system. In some embodiments, apparatus 10 comprises a tool 60 configured to test function of the multifidus muscle, such as when tool comprises an MRI; ultrasound imager; electromyogram; tissue biopsy device; and/or a device configured to test displacement as a function of load for a spine.

In some embodiments, two or more external system 50 components are connected by a connecting filament, such as is described hereabove. Alternatively or additionally, two or more implantable system 20 components are connected by a conduit, such as a connecting filament as described herein. Alternatively or additionally, two more external system 50 components and/or two or more implantable system 20 components transmit information and/or power via a wireless transmitter (e.g. an RF transmitter), magnetic coupling, inductive coupling; capacitive coupling and/or other wireless transmission means.

Apparatus 10 can include one or more devices, such as patient attachment device 70 shown in FIG. 1, that is used to attach one or more portions of external system 50 to a location on or proximate the patient. In some embodiments, patient attachment device 70 is constructed and arranged as described in applicant's co-pending U.S. patent application Ser. No. 15/385,729, titled "Method and Apparatus for Neuromodulation Treatments of Pain and Other Conditions", filed Dec. 20, 2016, the content of which is incorporated herein by reference in its entirety for all purposes.

Patient attachment device 70 can comprise one or more elements configured to attach one or more external devices 500 and/or programmer 600 at one or more locations on or proximate the patient's skin, that are relatively close to one or more implantable devices 200 that have been implanted in the patient. Patient attachment device 70 can comprise a component selected from the group consisting of: belt; belt with pockets; belt with adhesive; adhesive; strap; strap with pockets; strap with adhesive shoulder strap; shoulder band; shirt; shirt with pockets; clothing; clothing with pockets; epidural electronics packaging; clip; bracelet; wrist band; wrist watch; anklet; ankle bracelet; knee strap; knee band; thigh strap; thigh band; necklace; hat; headband; collar; glasses; goggles; earpiece; behind-the-earpiece; and combinations of one or more of these. In some embodiments, patient attachment device 70 comprises a belt configured to surround at least one antenna 540 (e.g. at least one antenna 540 mounted to or otherwise positioned on a printed circuit board such as a flexible printed circuit board). Patient attachment device 70 can include one or more pockets, such as one or more pockets configured to collectively surround one or more of: external device 500; one or more antennas 540; power supply 570; programmer 600; and combinations of one or more of these. In some embodiments, patient attachment device 70 comprises multiple pockets, such as to allow repositioning of an external antenna 540, programmer 600, external transmitter 530 and/or external power supply 570 to various different locations, such as to improve transmission of power and/or data to one or more implantable devices 200 and/or improve patient comfort. In some embodiments, one or more antennas 540, power supplies 570, and/or transmitters 530 are connected through flexible cables positioned in patient attachment device 70. In some embodiments, the flexible cables are small coax cables that accommodate the power levels and frequencies of the carried signals. In some embodiments, the one or more antennas 540 are connected to one or more additional components of external device 500 through a single cable with a local power splitting component and/or active matching element that adjusts signal power to each of the one or more antennas 540.

In some embodiments, patient attachment device 70 and/or external device 500 can be configured to prevent adversely affecting portions of the skin contacted by either device. Alternatively or additionally, patient attachment device 70 and/or external device 500 can be configured to clean and/or to promote healing of one or more skin-contacting portions. For example, patient attachment device 70 can include an agent (e.g. a coating or other included agent) selected from the group consisting of: a bactericidal agent; an anti-fungal agent; and combinations thereof.

In some embodiments, an anchoring-based tool, patient attachment device 70, is used on a patient-by-patient basis, such as when used on overweight patients and/or to otherwise avoid migration of implantable device 200 sideways and/or downward (e.g. into fat tissue).

Apparatus 10 can comprise a device configured to operate (e.g. temporarily operate) one or more implantable devices 200, such as trialing interface 80 shown in FIG. 1. Trialing interface 80 can be configured to deliver power to an implantable device 200, deliver data to an implantable device 200, and/or receive data from an implantable device 200. Trialing interface 80 can be configured to interface with one or more implantable devices 200 during an implantation procedure in which one or more implantable device 200 are implanted in a patient (e.g. a sterile clinical procedure). Trialing interface 80 can be configured to be sterilized one or more times. Trialing interface 80 can comprise one or more antennas, such as an antenna similar to antenna 540 of an external device 500. Trial interface 80 can comprise a transmitter, such as a transmitter similar to transmitter 530 of external device 500, and a power supply, such as a power supply similar to power supply 570 of external device 500. In some embodiments, trialing interface is of similar construction and arrangement to the trialing interface described in applicant's co-pending U.S. patent application Ser. No. 15/385,729, titled "Method and Apparatus for Neuromodulation Treatments of Pain and Other Conditions", filed Dec. 20, 2016, the content of which is incorporated herein by reference in its entirety for all purposes. In some embodiments, trialing interface 80 includes a housing to be positioned proximate at least a portion of implantable device 200, such as a housing that surrounds an antenna and a transmitter that is configured to operatively couple to (e.g. transmit power and/or data to) one or more antennas 240 of one or more implantable devices 200.

In some embodiments, trialing interface 80 is constructed and arranged as shown in FIGS. 39 and 40A-C. For example, trialing interface 80 includes an O-ring connector 81 and a housing assembly 89 into which O-ring connector 81 is inserted. O-ring connector 81 includes an O-ring stack 82 including multiple O-rings, O-rings 83. O-rings 83 can comprise electrically conductive (e.g. silver or other conductive material doped medical grade silicone) O-rings that are interleaved with electrical and/or fluid isolating non-conductive O-rings and/or spacers 84. In some embodiments, O-rings 83 comprise silver and/or other material provided as an anti-microbial agent. Additionally or alternatively, other material coatings or dopants can be included in the O-rings 83. The interleaved O-ring arrangement (e.g. of O-rings 83 and spacers 84, which can take many forms) can be designed to match a particular attachable lead 265 geometry (e.g. matching of contact pitch, diameter, contact count, and the like). O-ring connector 81 can include a stylet channel, such as to provide steering through the connector. O-ring connector 81 can include a covering (e.g. an overmold) and/or other features that facilitate anchoring to tissue, anchoring to lead 265, or both. Trialing interface 80 (and/or implantable device 200 and/or other implantable portions of apparatus 10) can include hermetic or other seals (e.g. a seal between O-ring connector 81 (e.g. O-ring stack 82) and the housing portion of trialing interface 80, such as sealing elements and/or methods that include shrink wrapping, LCP encapsulation, overmolding, potting, coating, dipping, casting, ultrasonic or laser welding materials, and the like.

O-ring stack 82 can be attached within connector 81 and/or other portions of trialing interface 80 via one or more of: conductive epoxy, a compression fitting, discrete attachment wires, a weld, sealing adhesive (e.g. silicone), and the like, between housing halves to capture and seal; and/or a clamshell style compression of two housing halves.

In some embodiments, connector 81 includes a projection 86, and housing assembly 89 includes a channel configured to receive projection 86 (e.g. in a tongue and groove arrangement). Housing assembly 89 includes one or more exposed contacts 88 (e.g. iridium oxide coated pads exposed through an LCP or polyimide substrate). O-rings 83, when inserted into housing assembly 89, can provide a robust, wiping electrical connection between O-rings 83 and contacts 88. Housing assembly 89 also provides a perimeter sealing compression that can creates a fluidically sealed inner chamber of connector 81, and provide a proper fit with the subsequently inserted lead 265.

A lead extension of trialing interface 80 can comprise O-ring connector 81 (or simply an O-ring stack 82), that is encapsulated (e.g. in a soft durometer material) and connected electrically to a conduit (e.g. one or more conductive wires) of the lead extension. In some embodiments, the conduit terminates in a standard connector (e.g. a micro-HDMI or a RJ-45 connector). O-ring connector 81 and/or O-ring stack 82 can be configured as a female connector that mates with a male connector of an implantable lead 265, such that the conduit passes through the patient's skin (e.g. to subsequently connect to an external device 500 or other external device of apparatus 10). In some embodiments, implantable device 200 is constructed and arranged similar to trialing interface 80 of FIGS. 40A-C, such as when implantable device 200 includes connector 81 which can be slidingly received by housing 210 such that O-ring stack 82 is operably connected to contacts within housing 210 (e.g. contacts similar to contacts 88 of trialing interface 80).

In some embodiments, one or more implantable devices 200 of implantable system 20 comprises an implantable transmitter configured to transmit data, such as to transmit data (e.g. stimulation information, patient physiologic information, patient environment information, implantable device 200 performance and/or configuration information, and the like) to one or more external devices 500. In these embodiments, receiver 230 can be configured as both a receiver and a transmitter. One or more implantable devices 200 can be configured to transmit data by sending a signal to (i.e. "driving") one or more antennas 240 or another antenna of implantable device 200. An implantable device 200 can be configured to transmit data using one or more of: load modulation; a signal carrier; and/or body conduction. An implantable device 200 can be configured to adjust the transmission, such as to adjust a data transmission parameter selected from the group consisting of: data rate; pulse width; duration of carrier signal; amplitude of carrier signal; frequency of carrier signal; configurable load; and combinations of one or more of these.

In some embodiments, apparatus 10 comprises a diagnostic assembly, diagnostic assembly 91 shown in FIG. 1. In some embodiments, programmer 600 and/or implantable controller 250 comprise all or a portion of diagnostic assembly 91. Diagnostic assembly 91 can be configured to assess, monitor, determine and/or otherwise analyze patient information and/or implantable device 200 information, such as when one or more stimulation elements 260 and/or 560 are configured as a sensor configured to record patient information (e.g. patient physiologic information and/or patient environment information) and/or apparatus 10 information (e.g. implantable device 200 information) as described herein. Diagnostic assembly 91 can be configured to analyze communication and/or the power link between an implantable device 200 and an external device 500. In some embodiments, such a communication link analysis can be performed by measuring bit error rate (BER) of a known data stream during communication signal transmission (also referred to as "communication link") measurement phase (e.g. such as during a calibration procedure). The BER can be tracked by the implant controller 250 or programmer 600, such as to monitor and keep track of any trends in the link. This trend can be used to adjust the link and/or provide feedback to an operator of apparatus 10 (e.g. the patient), in case the link cannot be automatically adjusted to compensate for a negative trend (e.g. such that the operator can perform physical re-adjustment of the external system 50). Alternatively or additionally, a power link analysis can be performed by monitoring charge/discharge rate of the implanted energy storage assembly 270. Similar to the communication link, the power link status and/or trending can be monitored and recorded for link adjustment and/or feedback purposes. Diagnostic assembly 91 can be configured to analyze a result of stimulation energy delivered by implantable device 200, such as when a stimulation element 260 comprises an electrode to record electrical activity of tissue (e.g. in addition to delivering electrical energy to stimulate tissue). A stimulation element 260 and/or functional element 560 can comprise a sensor configured to record neural activity and/or muscular activity, and the diagnostic assembly configured to analyze the recorded sensor data. In some embodiments, diagnostic assembly 91 is configured to analyze impedance, such as when a stimulation element 260 and/or functional element 560 comprises a sensor configured to record data related to impedance, such as when implantable device 200 performs a frequency sweep, performs an impulse response and/or compares voltage and current of a stimulation waveform. In some embodiments, diagnostic assembly 91 is configured to assess the impedance of one or more implantable antennas 240 and/or one or more external antennas 540. In these embodiments, impedance can be assessed by performing a function selected from the group consisting of: performing a frequency sweep; performing an impulse response; comparing voltage and current of a waveform; and combinations of one or more of these.

In some embodiments, diagnostic assembly 91 is configured to test or otherwise assess the link between one or more implantable antennas 240 and one or more external antennas 540 (e.g. during a procedure in which one or more implantable devices 200 are implanted in a patient). In these embodiments, diagnostic assembly 91 can be configured to perform a test prior to anchoring housing 210 to tissue (e.g. prior to initial or final suturing into tissue such as the fascia layer). For example, lead 265 can be implanted at a location to stimulate target tissue (e.g. one or more nerves identified to treat pain or another patient condition). Prior to suturing housing 210 in its implant location, diagnostic assembly 91 can be configured to confirm that one or more external antenna 540 transmission links to one or more implantable antennas 240 are above an efficiency threshold, for example such that sufficient power will be received by the one or more implantable devices 200. Additionally, the procedure can be performed to optimize or otherwise improve the position of the one or more implantable devices 200 to be implanted and subsequently secured to tissue.

In these link testing embodiments, diagnostic assembly 91 can comprise a handheld assembly (e.g. a sterile assembly comprising a wand or other handheld housing). Diagnostic assembly 91 can be configured to send a simple signal to one or more implantable devices 200 (e.g. a diagnostic assembly 91 with similar power and/or data transmission capabilities as an external device 500). Each implantable device 200 can respond (e.g. via data sent via an implantable antenna 240 or other transmitter) with information related to the quality of the transmission link (e.g. information about the power received by the one or more implantable devices 200). Diagnostic assembly 91 could provide a user interface (e.g. a speaker, a text screen and/or a video display) that provides quality or other information (go/no go information, digital or other discrete level information, and/or analog information). Diagnostic assembly 91 could be further configured to provide information confirming detection of one or more implantable devices 200, status of one or more implantable devices 200 (e.g. parameter level and/or fault detection status), and/or self-diagnostic status (i.e. diagnostic assembly 91 status).

Each implantable device 200 can be configured to specifically identify and/or specifically reply to diagnostic assembly 91 (e.g. in a different form than communications with an external device 500). Each implantable device 200 can be configured to provide information related to one or more of: the charge and/or discharge rate of energy storage assembly 270 (e.g. the charge and/or discharge rate of a capacitor or battery of energy storage assembly 270); or the frequency of a voltage-controlled oscillator that is driven by an unregulated voltage of power converter 233. Diagnostic assembly 91 can be configured to perform numerous performance tests (e.g. of one or more implantable devices 200 or implantation locations for one or more implantable devices 200), prior to completion of the implantation procedure (e.g. prior to closing one or more incisions).

In some embodiments, apparatus 10 is configured to provide a therapy by delivering stimulation energy to tissue, such as electrical energy delivered to tissue by one or more stimulation elements 260 comprising one or more electrodes. Alternatively or additionally, apparatus 10 can be configured as an agent-delivery apparatus (e.g. a pharmaceutical or other agent delivery apparatus). In some embodiments, apparatus 10 comprises one or more reservoirs for storing the agent, such as reservoir 525 of external device 500 and/or reservoir 225 of implantable device 200, each shown in FIG. 1. Reservoirs 525 and/or 225 can be fluidly connected to one or more functional elements 560 and/or stimulation elements 260, respectively (e.g. via one or more tubes). Reservoirs 525 and/or 225 can comprise one or more chambers (e.g. independent chambers configured to separately contain incompatible drugs or otherwise prevent undesired multiple drug interactions). Reservoirs 525 and/or 225 can comprise a volume (e.g. a volume to store one or more agents) between 0.1 ml and 50 ml, such as between 0.1 ml and 3.0 ml, or between 0.1 ml and 1.0 ml. Reservoirs 525 and/or 225 can comprise pressurized reservoirs or otherwise comprise a fluid pumping mechanism (e.g. a peristaltic mechanism, syringe pump or other fluid pump). Reservoirs 525 and/or 225 and can comprise refillable reservoirs (e.g. when reservoir 225 of an implantable device 200 comprises a valved opening such as a silicone septum or a mechanical valve, either accessible via a needle for refilling). The fluidly attached functional elements 560 and/or stimulation element 260 can comprise a fluid delivery element selected from the group consisting of: a catheter; a porous membrane; an iontophoretic element; a needle; or combinations of one or more of these. Delivered and/or stored (e.g. in a reservoir) agents can comprise an agent selected from the group consisting of: an analgesic agent such as morphine, fentanyl, lidocaine or other agent delivered to treat pain; a chemotherapeutic agent such as a chemotherapeutic agent delivered systemically (e.g. throughout the blood system of the patient) and/or to a location in or proximate an organ such as the liver or brain to treat cancer; an antibiotic configured to treat or prevent an infection; a hormone such as a hormone delivered intravenously in hormonal therapy; heart medications such as nitroglycerin, a beta blocker or a blood pressure lowering medication; a carbohydrate such as glucose or dextrose delivered to treat a low blood sugar condition; insulin such as to treat a high blood sugar condition; a diabetic medication; a neurological medication; an epilepsy medication; and combinations of one or more of these. In some embodiments, apparatus 10 comprises the one or more agents stored in reservoir 225 and/or 525. In some embodiments, apparatus 10 is constructed and arranged to deliver the agent (e.g. via a catheter-based functional element 560 and/or stimulation element 260) to a patient location selected from the group consisting of: a vessel; a blood vessel; a vein; an artery; heart; brain; liver; spine; epidural space; intrathecal space; subcutaneous tissue; bone; intraperitoneal space, intraventricular space, and combinations of one or more of these.

In some embodiments, an external device 500 is attached to the patient via a patient attachment device 70 comprising a wrist band, wrist watch, leg band, ankle band or other band configured to position an external device 500 about a limb of the patient (i.e. arm or leg of the patient). In these embodiments, one or more implantable devices 200 are implanted under the skin proximate the intended (limb) location of external device 500 and patient attachment device 70. Apparatus 10 can be configured such that external device 500 comprises one or more antennas 540; one or more implantable devices 200 each comprise one or more antennas 240; and each implantable device 200 one or more antennas 240 receive power and/or data from the one or more antennas 540 of the limb-attached external device 500. The limb-attached external device 500 can comprise one or more reservoirs 525 described hereabove and/or one or more functional elements 560 configured as agent delivery elements and/or sensors. The one or more implantable devices 200 can comprise one or more reservoirs 225 described hereabove and/or one or more stimulation elements 260 configured as agent delivery elements and/or sensors.

In some embodiments, apparatus 10 comprises an agent delivery apparatus and agent is delivered into the patient (e.g. into a blood vessel, muscle or subcutaneous tissue) by an external device 500 functional element 560 (e.g. a needle) based on signals recorded by an implantable device 200 stimulation element 260 (e.g. a sensor). Alternatively or additionally, agent can be delivered into the patient (e.g. into a blood vessel, muscle or subcutaneous tissue) by an implantable device 200 stimulation element 260 (e.g. a needle, catheter, porous membrane or iontophoretic delivery element). The amount of agent delivered by stimulation element 260 can be based on signals recorded by an implantable device 200 stimulation element 260 (e.g. a sensor) and/or an external device 500 functional element 560 (e.g. a sensor). External device 500 can provide power to one or more implantable devices 200 and/or it can send data (e.g. sensor data from a functional element 560) to implantable device 200, such as to control agent delivery by implantable device 200.

Apparatus 10 can be configured to prevent an electromagnetic field (e.g. an electromagnetic field produced by one or more devices not included in apparatus 10 and/or other present in the patient environment) from adversely affecting and/or otherwise affecting the patient treatment and/or patient information recording (e.g. patient tissue stimulation and/or patient physiologic information gathering) performed by apparatus 10. Electromagnetic fields from one or more apparatus 10 devices and/or otherwise present in the patient environment can potentially interfere with apparatus 10. The architecture of the wireless signal transmissions of apparatus 10 can be configured to include certain unique and/or identifiable patterns in the signals transmitted by apparatus 10 to confirm (upon receipt) that the signal originated from a component of apparatus 10. Alternatively or additionally, the stimulation signal produced by an implantable device 200 can be created independent from a power signal received from an external device 500, so that any electromagnetic interference in the wireless link does not affect generation and delivery of the stimulation signal. In some embodiments, each implantable device 200 and/or external device 500 includes unique identification codes that are required to be transmitted prior to any changes in stimulation or other implantable device 200 configuration, ensuring correct operation in the presence of interference. Alternatively or additionally, the communication link can incorporate handshaking protocols, confirmation protocols, data encryption and/or scrambling, coding and other security measures to ensure that interfering signals do not adversely affect the implantable system 20 performance (e.g. stimulation). In some embodiments, external system 50 and/or implantable system 20 incorporate electromagnetic absorptive and/or reflective materials to minimize external interference from other sources and/or minimize the probability of apparatus 10 interfering with other systems. Alternatively or additionally, apparatus 10 can incorporate error detection and protocols for entering an alarm state (e.g. and shutting down normal operation) and/or otherwise ensuring safe operation.

In some embodiments, implantable system 20 of apparatus 10 is configured to perform magnetic field modulation, such as targeted magnetic field neuromodulation (TMFN), electro-magnetic field neuromodulation, such as targeted electro-magnetic field neuromodulation (TEMFN), transcutaneous magnetic field stimulation (TMS), or any combination of these. Each implantable device 200, via one or more of its stimulation elements 260 (e.g. electrodes) can be configured to provide localized (e.g. targeted) magnetic and/or electrical stimulation. Combined electrical field stimulation and magnetic field stimulation can be applied by using superposition, and can reduce the overall energy requirement. In some embodiments, implantable apparatus 10 comprises one or more stimulation elements 260 comprising a magnetic field generating transducer (e.g. microcoils or cuff electrodes positioned to partially surround or otherwise be proximate to one or more target nerves). Functional elements 260 comprising microcoils can be aligned with nerves to minimize affecting non-targeted tissue (e.g. to avoid one or more undesired effects to non-target tissue surrounding or otherwise proximate the target tissue). In some embodiments, the target tissue comprises dorsal root ganglia (DRG) tissue, and the non-target tissue comprises ventral root tissue (e.g. when the stimulation energy is below a threshold that would result in ventral root tissue stimulation).

In some embodiments, external system 50 of apparatus 10 is configured to provide mechanically adjustable alignment of one or more external antennas 540 alignment. Link gain between one or more external antennas 540 and one or more implantable antennas 240 can degrade over time due to physical misalignment of the antennas, relative orientation changes between antennas and/or relative angular misalignment between antennas. In order to compensate for misaligned antennas, electrical beam steering can be included in apparatus 10. Antennas comprising a multi-feed antenna structure and/or an array of antennas can be incorporated (e.g. into external antenna 540, implantable antenna 240 or both) for electrical beam steering. Alternatively or additionally, mechanical antenna steering can be implemented to physically realign one or more external antennas 540 with one or more implanted antennas 240 (or vice versa). A substrate of an implantable antenna 240 and/or an external antenna 540 can be flexible and/or rigid (e.g. a substrate comprising polyamide, polyimide, liquid crystal polymer (LCP), Rogers, FR4, or a similar material). One or more antennas 540 can be connected to electronics (e.g. a transmitter, receiver or transceiver) using a flexible waveguide or cable (e.g. 50 ohm 0.047" coaxial cable designed to provide patient comfort) and/or a flexible PCB substrate transmission line. Mechanical or physical realignment of antennas 240 and/or 540 can be accomplished using one or more of: use of motorized positioners, such as a mechanism including one or more small pulleys and/or tensioners used to translate one or more antennas 240 and/or 540 about one or more axes; an actuator (e.g. a piezoelectric actuator) with directional gears configured to translate one or more antennas 240 and/or 540 about one or more axes; a micro-pump with fluid reservoir (e.g. liquid or gas reservoir) configured to hydraulically and/or pneumatically translate one or more antennas 240 and/or 540 about one or more axes, such as by creating a local pressure difference. In some embodiments, a micropump with fluid reservoir is used to move one or more antennas 240 and/or 540, such as to move an external antenna 540 away from tissue to reduce specific absorption rate (SAR). In these embodiments, external antenna 540 can be positioned in mechanical contact with an expandable reservoir (e.g. a balloon) positioned between external antenna 540 and tissue. The reservoir can be inflated or deflated to control separation distance of the external antenna 540 from the patient's skin surface. In some embodiments, apparatus 10 comprises one or more algorithm positioning algorithms, beam steering functionality and/or mechanical antenna steering as described in applicant's co-pending U.S. patent application Ser. No. 14/975, 358, titled "Method and Apparatus for Minimally Invasive Implantable Modulators", filed Dec. 18, 2015, or International PCT Patent Application Serial Number PCT/US2016/016888, titled "Medical Apparatus including an Implantable System and an External System", filed Feb. 5, 2016, the content of each of which is incorporated herein in its entirety for all purposes.

In some embodiments, implantable system 20 of apparatus 10 is configured to provide paresthesia-reduced (e.g. paresthesia-free) high frequency pain management and rehabilitation therapy (e.g. via delivery of a stimulation signal above 600 Hz or 1 kHz, or other stimulation signal resulting in minimal paresthesia). Apparatus 10 can be configured to provide both low frequency (e.g. <1 kHz) stimulation and high frequency stimulation, such as when providing low frequency stimulation to elicit feedback from a patient during intraoperative or other (e.g. post-implantation) stimulation configuration. For example, trialing interface 80 can be used during an intra-operative titration of stimulation configuration using low frequency stimulation (e.g. to position and/or confirm position of one or more stimulation elements 260, such as to confirm sufficient proximity to target tissue to be stimulated and/or sufficient distance from non-target tissue not to be stimulated). In some embodiments, high frequency stimulation is delivered to reduce pain over extended periods of time, and low frequency stimulation is used in these intraoperative and/or post-implantation titration or other stimulation configuration procedures. Intentional elicitation of paresthesia (e.g. via low frequency stimulation and/or high frequency stimulation) is beneficial during stimulation element 260 (e.g. electrode) implantation because a patient can provide feedback to the implanting clinician to ensure that the stimulation elements 260 are positioned close to the target neuromodulation or energy delivery site. This implantation position-optimizing procedure can advantageously reduce the required stimulation energy due to stimulation elements 260 being closer to target tissue, since a minimum threshold for efficacious stimulation amplitude is proportional to the proximity of stimulation elements 260 to target tissue (e.g. target nerves). The patient can inform the clinician of the sensation of paresthesia coverage, and the clinician can adjust stimulation element 260 position to optimize stimulation element 260 location for efficacious treatment while minimizing unintentional stimulation of non-target tissue (e.g. motor nerves or other nerves which are not causing the patient's pain). These paresthesia-inducing techniques (e.g. using low frequency stimulation and/or high frequency stimulation) can be used during or after implantation of one or more implantable devices 200.

In some embodiments, apparatus 10 is configured to deliver low frequency stimulation energy (e.g. electrical energy comprising a low frequency signal) to stimulate motor nerves, such as to improve tone and structural support (e.g. physical therapy). In these embodiments, apparatus 10 can be further configured to provide high frequency stimulation, such as to treat pain (e.g. suppress and/or control pain). The combined effect can be used not only for pain management but also muscle strengthening and gradual healing of supportive structures. Alternatively or additionally, as described herein, apparatus 10 can be configured to deliver low frequency stimulation energy (e.g. electrical energy) to induce paresthesia, which can also be accompanied by the delivery of high frequency stimulation (e.g. to suppress and/or control pain). In some embodiments, apparatus 10 is configured to deliver low frequency stimulation (e.g. electrical energy comprising a low frequency signal) and burst stimulation, delivered simultaneously or sequentially. The low frequency stimulation and the burst stimulation can be delivered on similar and/or dissimilar stimulation elements 260 (e.g. similar or dissimilar electrode-based stimulation elements 260).

As described herein, apparatus 10 can be configured for treating numerous disease and disorders, such as when apparatus 10 is configured to deliver electrical or other stimulation energy to treat pain (e.g. by delivering electrical or other energy to the spine or other neural location). Apparatus 10 can be configured to stimulate tissue with various stimulation waveforms, such as those described in applicant's co-pending application International PCT Patent Application Serial Number PCT/US2017/017978, titled "Apparatus with Enhanced Stimulation Waveforms", filed Feb. 15, 2017 [Docket nos. 47476-708.601; NAL-014-PCT-Parent], the content of which is incorporated herein by reference for all purposes.

Apparatus 10 can be configured to treat neuropathy, neuralgia and/or other nerve pain that is related to: surgery; trauma; infection (e.g. a herpetic infection); and/or diabetes (e.g. diabetic neuropathy). One or more stimulation elements 260 can be configured to deliver stimulation energy (e.g. electrical energy, magnetic energy, light energy, thermal energy, sound energy, and/or chemical energy (e.g. energy from a drug or reagent) to nerve tissue such as tissue of the central nervous system and/or peripheral nervous system. One or more leads 265 (each comprising one or more stimulation elements 260) can be implanted in and/or proximate the spinal cord, the groin and/or a joint such as the hip. For example, apparatus 10 can be configured to treat one or more of: post-surgical neuralgia (e.g. following hernia repair such as a hernia repair including an implanted mesh); headache (e.g. due to occipital neuralgia); post-herpetic neuralgia; chronic pelvic and/or hip pain; knee pain; and combinations of one or more of these.

To treat pain related to hernia or hernia repair, one or more stimulation elements 260 (e.g. on a lead 265 and/or on a housing 210) can be positioned to stimulate tissue of the peripheral nervous system and/or the central nervous system. In some embodiments, one or more stimulation elements 260 are positioned to stimulate the cutaneous branch of the ilioinguinal, inguinal and/or genital branch of the genitofemoral nerves. In some embodiments, one or more stimulation elements 260 are positioned to stimulate corresponding branches of spinal nerves correlating to one or more dermatomes related to pain associated with at least one of hernia or hernia repair.

Hernia or hernia repair can lead to: inguinal pain; ilioinguinal neuralgia; post-traumatic neuropathic pain; ilioinguinal nerve entrapment; neuropathic pain of ilioinguinal origin; post-surgical inguinal pain; genitofemoral pain; genitofemoral neuralgia; genitofemoral nerve entrapment; neuropathic pain of genitofemoral origin; post-surgical genitofemoral pain; iliohypogastric pain; iliohypogastric neuralgia; iliohypogastric nerve entrapment; neuropathic pain of iliohypogastric origin; post-surgical iliohypogastric pain; testicular pain; scrotal pain; penis pain; groin pain; thigh pain; anal pain; rectal pain; perineal pain; abdominal adhesions; pelvic adhesions; scar pain; diffuse polyneuropathy; and combinations of one or more of these. In some embodiments, apparatus 10 is configured to treat hernia pain by delivering a low frequency stimulation signal (e.g. an electrical signal less than or equal to 1 kHz delivered by one or more electrode-based stimulation elements 260). Alternatively or additionally, apparatus 10 can treat hernia pain with a high frequency stimulation signal, such as a signal comprising a frequency greater than 1 kHz Stimulation can be accomplished either via subcutaneous field stimulation and/or by stimulation elements 260 positioned adjacent or at least near the nerves and/or their branches. In some embodiments, stimulation is accomplished transvascularly (e.g. stimulation including low and/or high frequencies).

The apparatus of the present inventive concepts can be configured to stimulate the ilioinguinal nerve, genitofemoral nerve and/or iliohypogastric nerves, such as to ameliorate pain following hernia repair. One or more leads 265 (e.g. one or more leads 265 comprising one or more electrode-based or otherwise stimulation-based stimulation elements 260) can be inserted over the inguinal region (which may include the inguinal ring) to stimulate any or all three of these nerves (e.g. in a unilateral or bilateral fashion). Both the ilioinguinal and genital branch of the genitofemoral nerves pass through the inguinal ring. The anterior cutaneous iliohypogastric and femoral branch of the genitofemoral nerve can be stimulated at one or more locations proximate but rostral (iliohypogastric) or lateral (genitofemoral) to the inguinal ring. Leads 265 can comprise one or more stimulation elements 260 comprising cylindrical, paddle, cuff and/or hemi-cuff electrodes (electrodes placed surgically near and/or around these nerves). The nerves can be localized via ultrasound or other imaging modalities. Contrast can be used to image the vessels nearby (e.g. the testicular and/or ovarian vein and/or artery). The genital branch of the genitofemoral nerve can be stimulated in a transvascular manner through the testicular vein and/or artery. The genitofemoral and/or the ilioinguinal nerves can also be stimulated (e.g. transvascularly stimulated) through the femoral vein and/or artery, or via the superficial or deep external pudendal vein and/or artery, and/or via the superficial epigastric vein and/or artery.

The painful areas innervated by the ilioinguinal nerve, genitofemoral nerve and/or iliohypogastric nerves, can also be treated via spinal cord stimulation provided by apparatus 10 in the L1-L5 region of the spinal cord. In some embodiments, direct stimulation of the L1-L2 dorsal root ganglia is provided in a similar treatment. Leads 265 (e.g. percutaneous or paddle) including stimulation-based stimulation elements 260 can be placed over the dorsal columns, over the dorsal roots and/or in the dorsal root entry zone, in a unilateral, bilateral and/or midline fashion.

To treat occipital neuralgia, also known as C2 neuralgia, one or more stimulation elements 260 can be positioned to stimulate peripheral nerve tissue to reduce pain. Occipital neuralgia is a medical condition characterized by chronic pain in the upper neck, back of the head and/or behind the eyes (areas corresponding to the locations of the lesser and greater occipital nerves). In some embodiments, one or more leads 265, each comprising one or more stimulation elements 260, are implanted transversely, either unilaterally or bilaterally, at the level of the appropriate target cervical nerve (C1, C2, etc.). The C1, 2, 3 cervical roots include the greater occipital nerve which originates primarily from C2, and the lesser occipital nerves. Relevant trigeminal branches include both the supraorbital and supratrochlear nerves from V1, the infraorbital branches from V2, and the superficial temporal nerves from V3. A partial convergence of these two systems occurs at the Trigemino-Cervical Complex (TCC). In some embodiments, one or more stimulation elements 260 are positioned to stimulate the trigeminal and/or occipital nerves. One or more leads 265 can be anchored to the fascia proximate the tissue to be stimulated.

To treat post-herpetic neuralgia (e.g. neuralgia associated with shingles), one or more stimulation elements 260 can be positioned to stimulate corresponding branches of the spinal nerves and/or peripheral nerves correlating to one or more dermatomes related to the patient's shingles.

In some embodiments, apparatus 10 is configured to treat pelvic, bladder and/or bowel disorders, such as by stimulating sacral, pudendal and/or tibial nerves. In some embodiments, apparatus 10 is configured to treat pelvic pain by stimulating the tibial nerve.

Apparatus 10 can be configured to treat a bladder, bowel or other dysfunction selected from the group consisting of: overactive bladder; urinary urgency; urinary frequency; urinary urgency frequency; urinary urge incontinence; urinary stress incontinence; urge incontinence; stress incontinence; non-obstructive urinary retention; female sexual dysfunction; fecal incontinence; accidental bowel leakage; constipation; diarrhea; irritable bowel syndrome; colitis; detrusor instability; detrusor dysfunction; spastic bladder; neurogenic bladder; detrusor sphincter dyssynergia; detrusor hyperreflexia; detrusor areflexia; and combinations of one or more of these.

Apparatus 10 can be configured to treat a pelvic disorder selected from the group consisting of: pelvic pain; painful bladder syndrome; Hunner's ulcers or lesions; interstitial cystitis; pelvic floor dysfunction; endometriosis; vulvodynia; dyspareunia; pelvic adhesions; abdominal adhesions; irritable bowel syndrome; pelvic girdle pain; pudendal nerve entrapment; pudendal neuralgia; dysmenorrhea; MOllerian abnormalities; pelvic inflammatory disease; ovarian cysts; ovarian torsion; Loin pain hematuria syndrome; proctitis; prostatitis; prostadynia; post-abdominal surgical pain; post-pelvic surgical pain; hernia pain; post-hernia surgical pain; anal pain; rectal pain; perineal pain; groin pain; vulvar pain; vaginal pain; clitoral pain; colitis; and combinations of one or more of these.

Apparatus 10 can be configured to treat one or more of the pelvic disorders, bladder dysfunctions and/or and bowel dysfunctions listed above, by stimulating (e.g. using bilateral and/or unilateral stimulation) one or more of the targets listed below.

In some embodiments, the stimulated targets include the sacral nerves (roots) S2, S3 and/or S4. One or more leads 265 (e.g. each including one or more stimulation-delivering stimulation elements 260) can be positioned to stimulate any or all of the three roots, on a single side or both sides, in any bilateral or unilateral combination. The roots can be accessed, with the patient lying in the prone position, by positioning one or more leads 265 (e.g. percutaneously), with or without the use of fluoroscopy, ultrasound or any other imaging modality, into one/any of the sacral foramen (a) from the posterior aspect of the sacrum. One or more leads 265 can be passed through the foramen to the anterior side of the sacrum, and/or one or more leads 265 can remain inside the foramen(a).

In some embodiments, the sacral roots are approached rostrally, via the sacral canal in a retrograde manner. In these embodiments, one or more leads 265 can be passed through the ligamentum flavum, just caudal to L5 or via any of the intervertebral spaces from L5 to T12, into the spinal canal. One or more leads 265 are then threaded, with or without the aid of visualization (fluoroscopy, ultrasound or other imaging modality), in a caudal (retrograde) manner to enter the sacral canal. One or more leads 265 can be placed along the sacral canal, and each root can be stimulated individually and/or each root can be stimulated in concert, via one or more leads 265 positioned along the internal surface of the sacral canal, and spanning one or more foramina.

In some embodiments, one or more leads 265 are threaded from the spinal canal into each and/or all sacral foramen(a), in an anterior direction. The sacral canal can also be accessed caudally by one or more leads 265, via the sacral hiatus in an anterograde manner.

In some embodiments, the sacral roots (S2, S3 and/or S4) are accessed as they enter the spinal cord at the cauda equina. This access can be achieved by inserting the one or more leads 265 through the ligamentum flavum, at a location just caudal to L5, or via any of the intervertebral spaces from L5 to T12, into the spinal canal. The one or more leads 265 can then be threaded, with or without the aid of visualization (fluoroscopy, ultrasound or other imaging modality), up to the cauda equina, where the S2, S3 and/or S4 roots can be stimulated where they enter the spinal cord, and/or the conus medullaris can be stimulated directly (e.g. in the same location).

In some embodiments, the pudendal nerve is stimulated through one or more different approaches. The pudendal nerve contains both afferent and efferent fibers carried by S2, S3 and S4 roots. The pudendal fibers exit Alcock's canal near the ischial spine, where they spread out to innervate to the bladder wall, perineum, anus, genitals and urethra. Pelvic and voiding disorders can be treated by stimulating pudendal nerve fibers. The fibers can be accessed at the Alcock's canal via various approaches. In one embodiment, a transperineal approach is achieved by positioning the patient in the lithotomy position and inserting the lead 265 midpoint between the ischial tuberosity and the anus. A lead 265 is inserted toward the ischial spine, which can be palpated transvaginally or transrectally. The ischial spine can also be visualized through a number of imaging modalities (e.g. fluoroscopy, x-ray, ultrasound, and the like). In another embodiment, a transvaginal approach is achieved by positioning the patient in the lithotomy position and inserting a lead 265 through the vaginal wall, adjacent to the ischial spine (e.g. through the vaginal wall toward the ischial spine). In another embodiment, a posterior approach is achieved by laying the patient in the prone position and inserting a lead 265 just medial to the ischial tuberosity toward the ischial spine. This insertion can be facilitated by rectal palpation of the ischial spine and through visualization via a number of imaging modalities (e.g. fluoroscopy, x-ray, ultrasound, and the like).

In some embodiments, apparatus 10 is configured to stimulate pudendal afferents, such as by stimulating the dorsal genital nerve. These fibers are located just below the skin on the dorsum of the penis or just rostral to the clitoris. In some embodiments, pudendal afferents are stimulated periurethrally. One or more leads 265 can be inserted alongside the urethra to stimulate the pudendal fibers.

In some embodiments, apparatus 10 is configured to stimulate tibial nerve fibers, such as to treat one or more pelvic disorders (e.g. voiding dysfunction). The tibial nerve can be accessed a few mm below the skin surface in the ankle immediately posterior to the medial malleolus. Lead 265 can comprise a cylindrical SCS-type lead, which can be inserted percutaneously in this location. Alternatively or additionally, a direct (surgical) cut-down can be used to insert a cylindrical lead or to apply a cuff electrode directly to the nerve. The tibial nerve can also be accessed approximately half way up the lower leg adjacent to the tibia. One or more leads 265 can be inserted percutaneously in this location. Alternatively or additionally, a direct cut-down can be used to insert lead 265 (e.g. a cylindrical lead or a cuff electrode and/or hemi-cuff electrode applied directly to the nerve in the mid-shin location). Tibial nerve fibers can be accessed in the popliteal fossa behind the knee, for example percutaneously with a lead 265 comprising a cylindrical lead, and/or via a direct cut-down, for example with a lead 265 comprising either a cylindrical or cuff electrode.

In some embodiments, apparatus 10 and one or more leads 265 are constructed and arranged to stimulate the tibial and/or pudendal nerves via a transvascular approach (i.e. stimulation energy delivered from inside a blood vessel to nerve tissue proximate the blood vessel), such as via the femoral vein and/or artery, each of which provide intraluminal access to many other blood vessels (e.g. using standard interventional techniques). The tibial nerve can be transvascularly stimulated by the popliteal vein and/or artery (e.g. by placing one or more stimulation elements 260 in the popliteal vein and/or artery), at a location behind the knee. The popliteal vein and/or artery can be intraluminally accessed from the femoral artery and vein. The tibial nerve also passes near the small saphenous vein, where it branches off of the popliteal vein. The posterior tibial vein and/or artery are positioned adjacent to the tibial nerve, from the knee to the foot. One or more leads 265 can utilize one or more of these above locations to stimulate the tibial nerve.

In some embodiments, apparatus 10 and one or more leads 265 are constructed and arranged to stimulate the pudendal nerve and/or sacral roots, such as using a lead 265 placed via the femoral vein and/or artery, which in turn provides intraluminal access to many vessels. One or more leads 265 can be configured to utilize any of the following arteries and veins to stimulate the pudendal nerve and/or the sacral roots. One or more leads 265 can be constructed and arranged to stimulate a target site via a blood vessel selected from the group consisting of: the internal pudendal artery or vein (which branch off of common iliac artery or vein, respectively); the inferior and superior gluteal vein and/or artery; middle rectal, pudendal plexus and internal iliac vein and/or artery; medial and lateral sacral vein and/or artery; uterine and obturator vein and/or artery; and combinations of one or more of these.

In some embodiments, apparatus 10 is configured to treat pelvic dysfunction, overactive bladder, and/or urinary incontinence (singly or collectively "overactive bladder" herein). In some embodiments, apparatus 10 is configured to treat overactive bladder such as to reduce the effects of overactive bladder and/or to decrease use of one or more medications taken by the patient to treat overactive bladder. In some embodiments, one or more stimulation elements 260 are positioned to stimulate tissue of the central nervous system or tissue and/or tissue of the peripheral nervous system to treat overactive bladder, such as to stimulate one or more nerves that control and/or are otherwise related to bladder function (e.g. to increase bladder capacity, improve bladder emptying, reduce urge incontinence and/or reduce stress incontinence). For example, one or more stimulation elements 260 are be positioned to stimulate tibial nerve tissue and/or sacral nerve tissue (e.g. at least the S3 nerve root) to treat overactive bladder. In some embodiments, one or more stimulation elements 260 can be positioned to stimulate sacral nerve tissue to treat urinary urgency, urinary frequency (e.g. urinary urgency frequency), and/or painful bladder syndrome. In some embodiments, lead 265 is constructed and arranged to be positioned along one or more locations of the tibial nerve, such as a positioning performed using percutaneous technique (e.g. when lead 265 comprises a cylindrical SCS-type lead) and/or surgical (cut-down) techniques (e.g. when lead 265 comprise a cuff electrode and/or hemi-cuff electrode applied directly to the nerve). The tibial nerve branches off of the sciatic nerve just above the knee, and runs along the length of the tibia, medial and lateral to the tibia. The tibial nerve then passes posterior to the medial malleolus prior to innervating the plantar surface of the foot. Lead 265 can be constructed and arranged to access sites proximate the tibial nerve percutaneously and/or through an incision at the back of the knee in the popliteal fossa, along the tibia or behind the medial malleolus. The housing 210 can be placed anywhere in the leg when stimulating the tibial nerve. Lead 265 can be constructed and arranged to stimulate the tibial nerve through a transvascular approach, via the femoral vein and/or artery, each of which provide intraluminal access to many vessels. The tibial nerve can be accessed by the popliteal artery and vein behind the knee, which are intraluminally accessible from the femoral artery and vein, respectively. The tibial nerve also passes near the small saphenous vein, where it branches off of the popliteal vein. The posterior tibial vein and artery travel adjacent to the tibial nerve from the knee to the foot. One or more leads 265 can be constructed and arranged to utilize any of these locations to transvascularly stimulate the tibial nerve (e.g. transvascularly stimulate the tibial nerve via the popliteal artery, popliteal vein, saphenous vein, posterior tibial artery and/or posterior tibial vein via a lead 265 advanced via the femoral vein and/or artery). In these transvascular embodiments, the housing 210 can be placed near the femoral or popliteal access point at locations in the groin, perineum, scrotum, pelvis, hip, thigh, leg, behind the knee, buttocks, abdomen and/or low back. In the case of sacral nerve stimulation, one or more leads 265 can be inserted through an incision(s) made in the lower back, such that one or more stimulation elements 260 are positioned proximate (e.g. in contact) with the sacral nerve root(s). The housing 210 can be placed anywhere in the groin, perineum, scrotum, pelvis, hip, thigh, leg, behind the knee, buttocks, abdomen and/or low back. Lead 265 (e.g. a lead 265 comprising a lead extension) can be extended underneath the skin (e.g. tunneled) to a second incision (e.g. across the flank to the lower abdomen, across the midline to the buttocks, or low back), and a third incision can be made (e.g. in the abdomen, back or buttocks) where housing 210 can be inserted and connected to lead 265. Alternatively, housing 210 can be inserted at another internal location. If lead 265 is already connected (e.g. attached in manufacturing) to housing 210, lead 265 can be advanced in the opposite direction, such as from the third incision, to the second incision, to the first incision (if three incisions are made), or housing 210 can be advanced under the tissue from incision 1 to incision 2 or from incision 2 to incision 3. In some embodiments, only 1 or 2 incisions are performed. In some embodiments, such as when lead 265 is already connected (e.g. attached in manufacturing) to housing 210, lead 265 and housing 210 are implanted. In some embodiments, a first lead 265 and a first housing 210 (pre-attached or attachable) are utilized in a dose titration or other "trialing procedure", and a second lead 265 and housing 210 (pre-attached or attachable) are implanted in the patient for subsequent treatment of the patient.

In some embodiments, one or more stimulation elements 260 are positioned to perform posterior tibial nerve stimulation (PTNS), also referred to as percutaneous tibial nerve stimulation, such as to perform an indirect form of neuromodulation to treat bladder voiding dysfunction. The posterior tibial nerve is derived from the lumbar-sacral nerves (L4-S3), which innervate the bladder detrusor and pelvic floor. In some embodiments, one or more stimulation elements 260 are positioned to perform retrograde stimulation of the sacral nerve plexus and restore the balance between bladder inhibitory and excitatory control systems of the bladder. One or more stimulation elements 260 can be positioned above the ankle, proximate and/or into the tibial nerve. Implantable device 200 can deliver stimulation energy to the stimulation elements 260 comprising low-voltage electrical stimulation configured to produce sensor and/or motor responses. Apparatus 10 can be configured to provide continuous and/or intermittent stimulation to tissue, such as to modulate transmission of excitatory nerve signals to the bladder muscles. In some embodiments, implantable system 20 is configured to deliver a series of repeated stimulation periods, such as a regimen of approximately: weekly thirty-minute sessions of stimulation for twelve weeks. In some embodiments, implantable system 20 is configured to provide weekly, daily and/or hourly sessions that deliver stimulation for between 10 minutes and 60 minutes. Implantable system 20 can deliver stimulation for any number of minutes per day. In some embodiments, apparatus 10 is configured to achieve an approximate 50% reduction in urinary urge incontinence and/or urinary urgency/frequency episodes.

In some embodiments, apparatus 10 is configured to provide temporary stimulation of tissue to treat overactive bladder, such as by using trialing interface 80 described hereabove in reference to FIG. 1, such as to provide power and/or date to one or more implantable devices 200 to confirm acceptable improvement of the patient's overactive bladder (e.g. successful stimulation of one or more sacral nerves, tibial nerves or other tissue), before closing an incision or otherwise fully implanting one or more implantable devices 200. In some embodiments, a temporary stimulation (for overactive bladder or in a trialing procedure for any therapy) is provided for up to one week, up to one month, more than 1 month, more than 2 months, or more than 3 months. In some embodiments, one or more implantable devices 200 are left in place if the temporary stimulation period is successful or unsuccessful (e.g. left implanted due to its small size or otherwise minimal impact on the patient).

In some embodiments, apparatus 10 is configured to stimulate a region of the pelvic floor, such as to: change the reflex thresholds of the bladder muscles responsible for bladder emptying, strengthen and/or otherwise improve the condition of the muscles that maintain closure on the bladder outlet; change the state of the neural pathways, musculature and/or bladder during and beyond the period stimulation; and/or otherwise decrease the severity of urinary incontinence. In some embodiments, one or more stimulation elements 260 are positioned to stimulate periurethral muscles. In some embodiments, one or more stimulation elements 260 are positioned to stimulate tissue of the vagina or anus. In some embodiments, one or more stimulation elements 260 are positioned to stimulate sphincter muscles for controlling the bladder, such as two stimulation elements 260 positioned on either side of the urethral orifice. In these embodiments, housing 210 can be implanted in suprapubic region or in the perineum. In some embodiments, lead 265 comprises (e.g. on a distal portion) a pessary ring comprising two stimulation elements 260. In some embodiments, stimulation elements 260 comprise periurethral electrodes configured to stimulate pudendal afferents.

As described above, apparatus 10 can be configured for treating numerous diseases, disorders or other undesirable patient conditions, such as fecal incontinence. Injury of nerves that sense stool in the rectum can lead to fecal incontinence. In some embodiments, one or more stimulation elements 260 (e.g. one or more electrical, magnetic, light or other energy delivery elements) of one or more leads 265 and/or one or more implantable devices 200 are configured to stimulate tissue to treat fecal incontinence, such as to treat tissue selected from the group consisting of: sacral nerve tissue; tissue whose stimulation strengthens muscles of the bowel and/or rectum; and combinations of one or more of these. In these fecal incontinence applications, leads 265 can be implanted in a location selected from the group consisting of: the pelvic girdle; the sacral foramina; the lower back; the upper buttock; and combinations of one or more of these, such as to stimulate sacral nerve tissue. Leads 265 can be anchored via lead anchors (silicone or other materials), suture, staples, clips, adhesive and the like, such as an attachment to the underlying fascia of target tissue to be stimulated. In some embodiments, apparatus 10 is configured to treat both fecal incontinence and a bladder disorder such as overactive bladder, such as when one or more stimulation elements 260 are configured to deliver energy to sacral nerve or other tissue.

In some embodiments, apparatus 10 is configured to treat fecal incontinence, overactive bladder (i.e. overactive bladder and/or urinary incontinence), and/or pelvic disorders, and implantable device 200: comprises between 1 and 16 stimulation elements 260, such as four or more electrodes; delivers electrical stimulation energy at a range of approximately between 10 Hz and 15 Hz (or a range of between 5 Hz and 25 Hz); delivers electrical stimulation energy with a pulse width of approximately between 180 µsec and 240 µsec (or between 1 µsec and 200 µsec); provides electrical stimulation energy with an amplitude of approximately 0.1V to 8.5V (e.g. providing a current between 0.1 mA to 10 mA, which can be adjusted in increments between 0.01 mA and 0.1 mA), such as an amplitude between 0.4V and 2.0V; delivers continuous electrical stimulation energy; delivers intermittent electrical stimulation energy, such as with a period between 8 seconds and 24 seconds and/or an on time between 8 seconds and 16 seconds; or an on time of several hours followed by an off time of several hours (such as 8 hours of stimulation ON and 16 hours of stimulation OFF or 16 hours on and 8 hours off, and 12 hour on and 12 hours off; delivers monopolar electrical energy; delivers bipolar electrical energy; and combinations of one or more of these.

In some embodiments, apparatus 10 is configured to treat an occipital neuralgia, such as migraine headache, headache and/or cluster headache, and one or more stimulation elements 260 (e.g. small column paddle electrodes, standard paddle electrodes or other electrodes) are positioned to stimulate nerve tissue selected from the group consisting of: occipital; supraorbital; infraorbital; greater occipital nerve (GON); lesser occipital nerve (LON); both supraorbital and GON; supratroclear; sphenopalantine (SPG); and combinations of one or more of these.

In some embodiments, apparatus 10 is configured to treat neuralgia, such as a neuralgia resulting from surgery (e.g. groin, shoulder, lung and/or amputation), trauma and/or phantom pain, and one or more stimulation elements 260 are positioned to stimulate nerve tissue.

In some embodiments, apparatus 10 is configured to treat neuralgia, such as a neuralgia resulting from groin surgery (e.g. hernia or other groin surgery), and one or more stimulation elements 260 are positioned to stimulate nerve tissue selected from the group consisting of: ilioinguinal; genitofemoral; iliohypogastric; and combinations of one or more of these.

In some embodiments, apparatus 10 is configured to treat neuralgia, such as a neuralgia resulting from shoulder surgery, and one or more stimulation elements 260 are positioned to stimulate axial nerve tissue (e.g. one or more stimulation elements 260 positioned on a lead 265 implanted in a suprascapular location).

In some embodiments, apparatus 10 is configured to treat neuralgia, such as a neuralgia resulting from lung surgery, and one or more stimulation elements 260 are positioned to stimulate intercostal nerve tissue.

In some embodiments, apparatus 10 is configured to treat neuralgia, such as a neuralgia associated with carpal tunnel syndrome, and one or more stimulation elements 260 are positioned to stimulate median nerve tissue.

In some embodiments, apparatus 10 is configured to treat neuralgia, such as a neuralgia associated with temporomandibular joint disorder (TMJ), and one or more stimulation elements 260 are positioned to stimulate V2 of trigeminal nerve tissue.

In some embodiments, apparatus 10 is configured to treat neuralgia, such as a facial neuralgia, and one or more stimulation elements 260 are positioned to stimulate trigeminal nerve tissue.

In some embodiments, apparatus 10 is configured to treat neuralgia, such as a leg (sciatic) neuralgia, and one or more stimulation elements 260 are positioned to stimulate nerve tissue proximal a contributing lesion.

In some embodiments, apparatus 10 is configured to treat pelvic pain, such as interstitial cystitis and/or bladder pain, and one or more stimulation elements 260 are positioned to stimulate peripheral nervous system tissue (e.g. pudendal tissue and/or S-2, S-3 and/or S-4 roots) and/or central nervous system tissue (e.g. lower spinal cord and/or S3 neural foramen).

In some embodiments, apparatus 10 is configured to treat pelvic pain, such as anal pain, and one or more stimulation elements 260 are positioned to stimulate peripheral nerve tissue such as pudendal tissue and/or S-2, S-3 and/or S-4 roots.

In some embodiments, apparatus 10 is configured to treat subcutaneous pain, and one or more stimulation elements 260 (e.g. paddle electrodes) are positioned to stimulate nerve tissue.

In some embodiments, apparatus 10 is configured to treat diabetic neuropathy, such as painful diabetic neuropathy, and one or more stimulation elements 260 are positioned proximate the lower spinal cord (e.g. to stimulate S3 nerves) or other body location to stimulate nerve tissue.

In some embodiments, apparatus 10 is configured to treat visceral pain, angina and/or other pain, and one or more stimulation elements 260 are positioned to stimulate the vagus nerve.

In some embodiments, apparatus 10 is configured to treat peripheral vascular disease, diabetic neuropathy and/or other conditions associated with diabetes, such as to treat a disease or disorder selected from the group consisting of: peripheral diabetic neuropathic pain; painful diabetic peripheral neuropathy; peripheral vascular disease; peripheral arterial disease; peripheral artery disease; cardiac autonomic neuropathy; diabetic autonomic neuropathy; diabetic sensory neuropathy; diabetic motor neuropathy; diabetic sensorimotor neuropathy; diabetic muscular atrophy; diabetic neurovascular disease; and combinations of one or more of these. In these embodiments, lead 265 can be positioned proximate a nerve in the foot, leg, arm and/or sacrum (e.g. such that one or more stimulation elements 260 are positioned proximate the nerve to be stimulated). In some embodiments, lead 265 is positioned to stimulate the dorsal root ganglia to treat diabetic neuropathy (e.g. diabetic neuropathy of the hand and/or foot). Lead 265 can be implanted percutaneously and/or surgically as described herein. Lead 265 and/or one or more stimulation elements 260 can comprise a paddle electrode, such as one or more paddle electrodes implanted in the foot, leg and/or arm. Lead 265 and/or one or more stimulation elements 260 can comprise a cuff or hemi-cuff electrode surgically implanted around a nerve in the foot, leg and/or arm. Apparatus 10 can be configured to provide spinal cord stimulation, either through percutaneous insertion of one or more leads 265 in the epidural space or surgical implantation of a lead 265 comprising a paddle lead positioned in the epidural space. Apparatus 10 can be configured to provide transvascular stimulation of nerves in the foot, leg and/or arm, (e.g. to treat diabetic neuropathy) such as when one or more leads 265 are interventionally advanced into the venous or arterial system. Leads 265 can be positioned using percutaneous transforaminal placement in the sacral foramina, such as for treatment of foot or leg disorders. Leads 265 can be constructed and arranged for cephalocaudal insertion (retrograde) into the epidural space or sacral canal, such as for treatment of foot or leg disorders. Leads 265 can be constructed and arranged to provide dorsal root ganglion stimulation, such as for treatment of trunk, neck, head, back, foot, leg, arm and/or hand disorders.

One or more leads 265 (e.g. each including one or more stimulation elements 260) can be constructed and arranged to stimulate tibial nerve fibers, such as to treat diabetic neuropathy and/or diabetic related maladies of the foot. The tibial nerve can be accessed as described herein.

One or more leads 265 can be configured to stimulate the peroneal nerve or saphenous nerve, such as at one or more locations described herebelow. The peroneal nerve can be accessed percutaneously or surgically behind the knee in the popliteal fossa where it branches off the sciatic nerve. It can also be accessed as it wraps around the lateral aspect of the knee just prior to diving under the fibularis longus and extensor digitorum longus muscles. The deep fibular nerve (a branch of the peroneal nerve) innervates top medial foot, whereas the superficial fibular (peroneal) innervates top of both medial and lateral foot. In some embodiments, stimulation element 260 comprises one or more electrodes positioned in the anterior tibial vein and/or artery to transvascularly stimulate the deep fibular nerve. The saphenous nerve comes off the femoral nerve deep in the thigh. It passes around the medial aspect of the knee medial to the patella. It then runs down the medial shin adjacent to the tibia, gastrocnemius and soleus muscles where it can be accessed surgically or percutaneously. It then surfaces just as it warps around the anterior aspect of the medial malleolus where it supplies the medial posterior foot in front of heel. The medial sural cutaneous nerve comes off the tibial at the popliteal fossa, then runs down the back of the calf (over the gastrocnemius) and wraps around the posterior aspect of the lateral malleolus before innervating the lateral aspect of the sole and heel. In some embodiments, the saphenous nerve is transvascularly stimulated by positioning one or more stimulation elements 260 in a blood vessel selected from the group consisting of: femoral vein; femoral artery; great saphenous vein; great saphenous artery; and combinations of one or more of these. In some embodiments, the sural nerve is stimulated. In these embodiments, the sural nerve can be transvascularly stimulated by positioning one or more stimulation elements 260 in the saphenous vein.

One or more leads 265 can be configured to stimulate the median nerve, ulnar nerve and/or radial nerve. The median nerve can be accessed percutaneously in the upper arm lateral to the brachial vein and/or artery, but medial to the biceps muscle, whereas the ulnar nerve runs medial to the brachial artery in the upper arm. The median nerve passes through the anterior aspect of the elbow under the bicipital aponeurosis. The ulnar nerve runs medial and posterior to the medial epicondyle of the humerus. The median nerve can also be accessed in the wrist just proximal to the palm and the palmar carpal ligament. The ulnar nerve can be accessed just proximal to the palmar carpal ligament adjacent to the pisiform. The radial nerve can be accessed percutaneously just as it passes anterior to the lateral epicondyle. In some embodiments, apparatus 10 is configured to transvascularly stimulate at least one of a median nerve, an ulnar nerve or a radial nerve, and stimulation element 260 comprises one or more electrodes positioned in a vessel selected from the group consisting of: brachial vein; brachial artery; basilic vein; basilic artery; deep vein of the arm; deep artery of the arm; and combinations of one or more of these. In some embodiments, apparatus 10 is configured to transvascularly stimulate at least one of a median nerve or an ulnar nerve, and stimulation element 260 can comprise one or more electrodes positioned in a vessel selected from the group consisting of: brachial vein; brachial artery; and combinations of one or more of these. In some embodiments, apparatus 10 is configured to transvascularly stimulate the radial nerve, and stimulation element 260 comprises one or more electrodes positioned in a vessel selected from the group consisting of: deep vein of arm; deep artery of arm; basilic vein; radial collateral vein; radial collateral artery; medial collateral vein; medial collateral artery; radial vein; radial artery; and combinations of one or more of these. In some embodiments, apparatus 10 can be configured to transvascularly stimulate the medial cutaneous nerve, and stimulation element 260 comprises one or more electrodes positioned in the basilic vein. In some embodiments, apparatus 10 is configured to transvascularly stimulate the ulnar nerve, and stimulation element 260 comprises one or more electrodes positioned in a vessel selected from the group consisting of: ulnar collateral vein; ulnar collateral artery; ulnar vein; ulnar artery; and combinations of one or more of these. In some embodiments, apparatus 10 is configured to transvascularly stimulate the median nerve, and stimulation element 260 can comprise one or more electrodes positioned in a vessel selected from the group consisting of: brachial vein; brachial artery; ulnar vein; ulnar artery; and combinations of one or more of these.

As described herein, one or more leads 265 can be positioned to stimulate the spinal cord, such as via percutaneous insertion of a lead 265 in the epidural space or surgical implantation of the lead 265 (e.g. a paddle lead) in the epidural space. A lead 265 can be placed such that one or more stimulation elements 260 (e.g. one or more electrodes) are positioned from T5-S5, such as to capture the area of pain or reduced circulation of the leg or foot. One or more stimulation elements 260 of one or more leads 265 can be positioned from C2 to T8, such as to capture the area of pain or reduced circulation of the arm or hand. One or more leads 265 can be placed along the midline, unilaterally and/or bilaterally over the dorsal columns, in the gutter (over dorsal roots) and/or in the dorsal root entry zone. Leads 265 can span several vertebral levels or they can be positioned to span a single level.

One or more stimulation elements 260 (e.g. one or more electrodes attached to one or more leads 265) can be positioned to transvascularly stimulate one or more nerves, such as one or more nerves in the foot, leg and/or arm, such as when the one or more stimulation elements 260 are implanted within one or more blood vessels of the venous and/or arterial system.

In the leg, the tibial nerve, sacral roots and/or deep fibular nerve can be stimulated, such as when a lead 265 accesses the tissue to be stimulated through a transvascular approach, such as via the femoral vein and/or artery, as described herein. The deep fibular nerve can be stimulated by one or more stimulation elements 260 positioned in the anterior tibial vein and/or the anterior tibial artery. In the arm, the median nerve, ulnar nerve, superior ulnar nerve, medial cutaneous nerve and/or radial nerve can be stimulated, such as when lead 265 accesses the tissue to be stimulated through a transvascular approach, such as via the brachial vein and/or artery, the basilic vein and/or artery, and/or the deep vein and/or artery.

One or more stimulation elements 260 (e.g. one or more electrodes attached to one or more leads 265) can be positioned to stimulate dorsal root ganglia that supply the following nerves (e.g. to treat the leg and/or foot): common peroneal (L4-S2); tibial (L4-S3); femoral (L2-L4); and combinations of one or more of these. One or more stimulation elements 260 (e.g. one or more electrodes attached to one or more leads 265) can be positioned to stimulate dorsal root ganglia that supply the following nerves (e.g. to treat the hand and/or arm): radial (C5-T1); median (C5-T1); ulnar (C7-T1); and combinations of one or more of these. In these embodiments, one or more leads 265 can be passed through the intervertebral foramina, either unilaterally or bilaterally, at a single vertebral level or at multiple vertebral levels.

In some embodiments, apparatus 10 is configured to treat post-amputation pain, such as to treat a disease or disorder selected from the group consisting of: phantom limb pain; phantom stump pain; acute and persistent stump pain; limb pain; neuroma; Morton's neuroma; neurilemoma; neurolemoma; Schwann cell tumor; phantom limb itch; phantom limb sensations; and combinations of one or more of these. Apparatus 10 can be configured to treat the conditions associated with post-amputation pain (i.e., stump pain), such as by using a high frequency alternating current (HFAC) block approaches. In these embodiments, one or more leads 265 can be implanted such that one or more stimulation elements 260 stimulate one or more nerves in the leg, arm and/or sacrum. One or more leads 265 can be surgically implanted, such as when lead 265 comprises a paddle electrode positioned near a nerve in the foot, leg or arm and/or a cuff electrode or hemi-cuff electrode positioned to at least partially surround a nerve in the foot, leg or arm. One or more leads 265 can be positioned to stimulate the spinal cord, such as via a percutaneous insertion of the leads 265 in the epidural space or surgical implantation of the lead 265 (e.g. a paddle lead) in the epidural space. One or more leads 265 can be positioned to provide transvascular stimulation of nerves in the leg or arm, such as when one or more stimulation elements 260 are implanted within a vein or artery. One or more leads 265 can be implanted using percutaneous transforaminal placement in the sacral foramina, such as for treatment of leg stump pain. One or more leads 265 can be implanted using cephalocaudal insertion (retrograde) into the epidural space or sacral canal, such as for treatment of leg stump pain. One or more leads 265 can be positioned to perform dorsal root ganglion stimulation and/or block, such as for treatment of leg and/or arm stump pain.

In some embodiments, apparatus 10 is configured to treat occipital and/or headache (HA) pain, such as when apparatus 10 is configured to treat a disease or disorder selected from the group consisting of: occipital neuralgia; cervicogenic headache; tension headache; chronic and episodic migraine headache; tension headache; hemicrania continua; trigeminal autonomic cephalalgias (TACs); chronic and episodic cluster headache; chronic and episodic paroxysmal hemicranias; short-lasting unilateral neuralgiform headache attacks with conjunctival injection and tearing (SUNCT); short-lasting unilateral neuralgiform headache attacks with cranial autonomic symptoms (SUNA); long-lasting autonomic symptoms with hemicrania (LASH); post-traumatic headache; and combinations of one or more of these.

Apparatus 10 can be configured to treat the conditions associated with headache pain and/or occipital neuralgia by stimulating one or more nerves in the head, such as one or more nerves selected from the group consisting of: greater and/or lesser occipital nerve (e.g. which arise from C2 and C3); the greater and/or lesser auricular nerves (e.g. which also arise from C2/C3); the third (least) occipital nerve (e.g. which arises from C3); and combinations of one or more of these. The infraorbital or supraorbital nerves can be access subcutaneously below and above the eye, respectively. Apparatus 10 can be configured to stimulate auriculotemporal, supratrochlear and/or sub-occipital nerves. To stimulate any of these nerves, lead 265 (e.g. a cylindrical SCS-type lead) can be inserted percutaneously either subcutaneously or under the muscle. Alternatively, surgery (e.g. direct cut-down) can be performed to insert lead 265 (e.g. a cylindrical lead, a paddle lead, a cuff or hemi-cuff electrode) proximate, one and/or around these nerves. Alternatively or additionally, the nerves can be accessed transvascularly as described herein (e.g. when one or more stimulation elements 260 are implanted in a blood vessel). Housing 210 can be implanted anywhere in the head under the skin, including: behind the ear, back of the head, the neck, in the face, and the like, where one or more external devices 500 can be positioned in, on and/or within a hat, headband, glasses, goggles, earpiece, necklace, patch, and the like. Apparatus 10 can be configured to treat headache pain and/or occipital neuralgia by stimulating tissue in the cervical spinal cord (C2-C3), for example proximate the location the nerve enters the cord from the foramen. One or more leads 265 can be placed over the dorsal columns, in the gutter, over the dorsal root entry zone and/or out in the foramen at the dorsal root ganglion. In some embodiments, the trigeminal and pterygopalatine ganglia are accessed by inserting one or more leads 265 through the face or the roof of the mouth. In these embodiments, housing 210 can be placed anywhere in the head under the skin, as described herein.

In some embodiments, apparatus 10 is configured to treat post-herpetic neuralgia, such as to treat a disease or disorder selected from the group consisting of: shingles; herpes zoster; zoster; zona; varicella zoster virus infection; zoster sine herpete; fever blisters; herpes zoster blisters; herpes zoster rash; and combinations of one or more of these. In some embodiments, apparatus 10 is configured to treat post-herpetic neuralgia using high frequency alternating current (HFAC) block approaches. In these embodiments, one or more leads 265 can be implanted such that one or more stimulation elements 260 stimulate one or more nerves in the leg, arm, torso and/or sacrum. One or more leads 265 can be surgically implanted, such as when lead 265 comprises a paddle electrode positioned near a nerve in the foot, leg, torso and/or arm and/or a cuff electrode or hemi-cuff electrode positioned to at least partially surround a nerve in the foot, leg, torso or arm. One or more leads 265 can be positioned to stimulate the spinal cord, such as via a percutaneous insertion of the leads 265 in the epidural space or surgical implantation of the lead 265 (e.g. a paddle lead) in the epidural space. One or more leads 265 can be positioned to provide transvascular stimulation of nerves in the leg, torso and/or arm, such as when one or more stimulation elements 260 are implanted within a vein or artery. One or more leads 265 can be implanted using percutaneous transforaminal placement in the sacral foramina, such as for treatment of leg or foot pain. One or more leads 265 can be implanted using cephalocaudal insertion (retrograde) into the epidural space or sacral canal, such as for treatment of leg or foot pain. One or more leads 265 can be positioned to perform dorsal root ganglion stimulation and/or block, such as for treatment of leg, torso and/or arm pain.

In some embodiments, apparatus 10 is configured to treat angina, such as to treat a disease or disorder selected from the group consisting of: angina; chest pain caused by reduced blood flow to the heart muscle; chest pain associated with coronary artery disease such as squeezing, pressure, heaviness, tightness or pain in the chest; recurring angina pectoris; acute angina pectoris; chronic angina pectoris; acute coronary syndrome; chest pain; coronary artery spasms; microvascular angina; Prinzmetal's angina; angina inversa; stable or common angina; unstable angina; variant angina; and combinations of one or more of these.

In some embodiments, apparatus 10 is configured to treat carpal tunnel syndrome, such as to treat a disease or disorder selected from the group consisting of: median nerve entrapment; tingling and/or numbness in fingers or hand; median nerve irritation or compression; narrowing of the carpal tunnel; and combinations of one or more of these. In these embodiments, apparatus 10 can be configured to deliver stimulation to median nerve tissue; ulnar nerve tissue and/or radial nerve tissue.

In some embodiments, apparatus 10 is configured to treat erectile dysfunction (ED), such as to treat a disease or disorder selected from the group consisting of: impotence; male sexual dysfunction; inability to develop or maintain an erect penis; cardiogenic ED; vasculogenic ED; diabetic ED; neurogenic ED; traumatic ED; post-prostatectomy ED; hormonal ED; hyopogonadism; pharmacological ED; and combinations of one or more of these.

In some embodiments, apparatus 10 is configured to treat complex regional pain syndrome (CRPS), such as to treat a disease or disorder selected from the group consisting of: CRPS type 1; CRPS type 2; reflex sympathetic dystrophy; causalgia; reflex neurovascular dystrophy; amplified musculoskeletal pain syndrome; systemic autonomic dysregulation; neurogenic edema; musculoskeletal pain; and combinations of one or more of these.

In some embodiments, apparatus 10 is configured to treat knee pain. Knee pain from joint degeneration or join replacement surgery can be treated via stimulation of the nerves innervating the knee and/or via stimulation of the tissue surrounding the knee (sometimes referred to as peripheral field stimulation). Apparatus 10 can comprise between one and eight leads 265 whose stimulation elements 260 are placed near and around the knee. In some embodiments, four leads 265 are placed, in locations medial, lateral, superior and inferior to the knee. The leads 265 can be placed subcutaneously for field stimulation, or they can be placed directly adjacent to specific nerve targets. Applicable nerve targets are as follows: medial knee can include medial femoral cutaneous and infrapatellar cutaneous branches of saphenous nerve; lateral knee can include constant articular branches of common peroneal, lateral retinacular nerve; anterior knee can include lateral, medial, and anterior cutaneous femoral nerve, infrapatellar branch of saphenous nerve, medial and lateral retinacular nerve and articular branches of peroneal nerve; posterior knee can include obturator, posterior tibial and sciatic nerves. In addition, the following nerves can be stimulated via stimulation elements 260 to treat knee pain: nerves arising from the tibial nerve such as the superior, middle and inferior genicular nerves; nerves arising from the common peroneal such as the superior lateral, inferior lateral, and recurrent genicular nerves; and nerves arising from the obturator nerve such as the genicular branch of obturator; and nerves arising from the femoral nerve such as the saphenous nerve. Each of these targets can be stimulated transvascularly by one or more stimulation elements 260.

In some embodiments, implantable device 200 has an internal battery or other power supply such that stimulation (e.g. stimulation energy and/or a stimulation agent) is delivered to one or more locations within a patient for an extended time period (e.g. at least 1 hour, at least 1 day, at least 1 month or at least 1 year), without receiving a power transmission (e.g. as described herein from an external device such as external device 500) during that time period. In some embodiments, at least a portion of a single pulse of energy (e.g. at least a single phase) is delivered by implantable device 200 using energy provided by an internal power supply such as a battery or a capacitor. In these embodiments, data can be transmitted by one or more of an external device 500 and/or programmer 600, such as to activate or modify stimulation being delivered, with or without also transmitting power.

In some embodiments, implantable device 200 comprises one or more components configured to receive transmitted power (e.g. via an external device 500), receive transmitted data (e.g. via an external device 500 and/or programmer 600) and/or deliver stimulation (e.g. deliver stimulation energy and/or a stimulation agent).

In some embodiments, one or more implantable devices 200 are configured to deliver stimulation energy (e.g. via one or more stimulation elements 260 comprising an electrode) with a stimulation waveform comprising one or more high frequency signals (e.g. a signal comprising one or more high frequency components). For example, one or more implantable devices 200 can deliver one or more stimulation waveforms comprising one or more signals above 600 Hz, such as one or more signals above 1.0 kHz, 1.2 kHz, 5 kHz, 10 kHz or 25 kHz.

In these embodiments, the delivered stimulation waveform can be configured to be void of (i.e. not include) one or more lower frequency signals, such as by not including any signals at a frequency below 100 Hz, below 500 Hz, below 1000 Hz, below 1200 Hz or below 1500 Hz.

One or more implantable devices 200 can be configured to deliver stimulation energy with a stimulation waveform that varies over time. In some embodiments, one or more stimulation parameters of the stimulation waveform are randomly varied over time, such as by using a probability distribution as described in applicant's co-pending application International PCT Patent Application Serial Number PCT/US2017/017978, titled "Apparatus with Enhanced Stimulation Waveforms", filed Feb. 15, 2017. Each stimulation waveform can comprise one or more pulses, such as a group of pulses that are repeated at regular and/or irregular intervals. In some embodiments, a pulse can comprise delivery of electrical energy, such as electrical energy delivered in one or more phases (e.g. a pulse comprising at least a cathodic portion and an anodic portion). In some embodiments, single or groups of pulses are provided at time-varying modes of repetition (e.g. regular intervals for a period, then a period of irregular intervals) or at regular intervals with occasional (random) spurious pulses inserted (creating a single irregular event in an otherwise regular series). Non-limiting examples of waveform variations include: a variation in frequency (e.g. frequency of one or more signals of the waveform); variation of a signal amplitude; variation of interval time period (e.g. at time period between pulses or a time period between pulse trains); variation of a pulse width; multiple piecewise or continuous variations of one of more stimulation parameters in a single pulse (e.g. multi-step, multi-amplitude in one "superpulse"); variation of pulse symmetry (e.g. via active drive, passive recovery and/or active-assisted passive recovery); variation of stimulation energy over a time window and/or overlapping time windows; variation of the power in the frequency spectrum of the stimulation waveform; and combinations of one or more of these. In some embodiments, apparatus 10 and/or implantable device 200 can be configured to vary a stimulation waveform "systematically" such as a variation performed temporally (e.g. on predetermined similar or dissimilar time intervals) and/or a variation performed based on a parameter, such as a measured parameter that can be based on a signal produced by a sensor of implantable device 200 or another component of apparatus 10. Alternatively or additionally, apparatus 10 and/or implantable device can be configured to vary a stimulation waveform randomly. Random variation shall include discrete or continuous variations that can be selected from a distribution, such as a probability distribution selected from the group consisting of: a uniform distribution; an arbitrary distribution; a gamma distribution; a normal distribution; a log-normal distribution; a Pareto distribution; a Gaussian distribution; a Poisson distribution; a Rayleigh distribution; a triangular distribution; a statistic distribution; and combinations of one or more of these. Random pulses or groups of pulses can be generated based on randomly varying one or more stimulation signal parameters. One or more stimulation parameters can be varied randomly through the use of one or more probability distributions, as described herebelow.

In some embodiments, the amplitude of a signal delivered by one or more implantable devices 200 is adjusted to prevent discomfort to the patient (e.g. paresthesia or other undesired condition) from the stimulation signal. In some embodiments, the amplitude of the stimulation signal can be ramped (e.g. up and/or down), a single time or multiple times (e.g. continuously or intermittently). In some embodiments, a titration procedure is performed to "set" one or more stimulation parameters based on avoiding patient discomfort.

In some embodiments, one or more implantable devices 200 are configured to deliver stimulation energy (e.g. via one or more stimulation elements 260 comprising an electrode) with a stimulation waveform comprising one or more waveform patterns. The stimulation waveforms delivered can be configured to treat various conditions of a patient. Each stimulation waveform can comprise a series of continuous pulses, intermittent pulses, and/or spurious pulses (e.g. occasional events in an otherwise continuous stream). Each pulse can comprise a pulse train that is repeatedly delivered by implantable device 200, the train comprising one or more cathodic pulses and/or one or more anodic pulses. In some embodiments, implantable device 200 delivers a multiphasic pulse comprising at least two cathodic pulses and/or anodic pulses, with or without any time between each pulse. For example, implantable device 200 can deliver a biphasic pulse comprising a cathodic pulse followed by an anodic pulse, a triphasic pulse comprising a cathodic pulse followed by an anodic pulse followed by a second cathodic pulse, or any series of two or more cathodic and/or anodic pulses. In some embodiments, delivered pulses are exponential in nature (e.g. comprise an exponential portion), such as dynamic return pulses that exceed a minimum current (e.g. at least 1 mA, 10 mA or 50 mA) for a short duration (e.g. for approximately 1 μsec), and then decay to lower current levels (e.g. a level of approximately 100 nA), with a time constant on the order of 1 μsec to 100 μsec.

The stimulation waveforms delivered by implantable device 200 can comprise one or more high frequencies. The stimulation waveform frequency or other stimulation parameter can be set and/or adjusted (hereinafter "adjusted") to optimize therapeutic benefit to the patient and minimize undesired effects (e.g. paresthesia or other patient discomfort). In some embodiments, a stimulation waveform is adjusted based on a signal produced by a sensor of apparatus 10 (e.g. a sensor of implantable device 200, such as a stimulation element 260 configured as a sensor or other sensor of implantable device 200 as described hereabove). Adjustment of a stimulation waveform parameter can be performed automatically by the implantable device 200 and/or via an external device 500 and/or programmer 600).

In some embodiments, a pulse shape of a stimulation waveform can be varied, such as a pulse shape comprising: a sinusoidal geometry; a square geometry (e.g. a waveform comprising a square wave); a rectangular geometry; a triangular geometry; (e.g. symmetric or asymmetric); a trapezoidal geometry; a sawtooth geometry; a ramped geometry; an exponential geometry; a piece-wise step function geometry; a root-raised cosine geometry; and combinations of one or more of these.

In some embodiments, a charge recovery phase (e.g. anodal phase) of a stimulation waveform is varied by implantable device 200.

Inter-pulse gap, the time between one or more pulses (e.g. a biphasic or other multiphasic pulse that is repeated continuously), can be varied systematically and/or randomly by implantable device 200. In some embodiments, inter-pulse gap between one or more pulses comprises zero time (i.e. a first pulse is immediately followed by a similar or dissimilar second pulse). In some embodiments, inter-pulse gap is varied systematically, such as on a routine basis (i.e. temporally) and/or varied based on a signal produced by a sensor of apparatus 10. Alternatively or additionally, inter-pulse gap can be varied randomly, such as a random variation based on a distribution (e.g. a probability distribution with a pre-determined shape) as described herebelow.

In some embodiments, implantable device 200 delivers a stimulation waveform comprising a series of frequency modulated (FM) pulses, such that the frequency of stimulation varies. Implantable device 200 can be configured to deliver a frequency modulated stimulation waveform comprising a carrier signal, at a carrier frequency, that is modulated continuously between a first frequency and a second frequency. For example, implantable device 200 can deliver a stimulation waveform that modulates between 2.0 kHz and 3.0 kHz every second (e.g. comprising a carrier signal at 2.5 kHz that is modulated at 1 Hz) with a modulation range (the excursion from the carrier signal) of +/−500 Hz. In some embodiments, implantable device 200 can deliver a stimulation waveform that comprises: a carrier frequency between 1 kHz and 50 kHz, a modulation frequency between 0.1 Hz and 10 kHz and/or a modulation range between 1 Hz and the carrier frequency.

In some embodiments, implantable device 200 delivers a stimulation waveform comprising a series of amplitude modulated (AM) pulses, such that the amplitude of stimulation varies (e.g. varying the amplitude of the voltage and/or current of the stimulation signal). The amplitude of delivered current can be varied in a single amplitude modulated sweep, such as a sweep from 2 mA to 3 mA. In some embodiments, amplitude of a signal can be varied continuously, such as when current is varied between 2 mA and 3 mA every second (e.g. a signal comprising a modulation frequency of 1 Hz). In these embodiments, the depth of modulation would be 33%, where depth of modulation is equal to 1−[lower range/upper range]. In some embodiments, amplitude of delivered current fluctuates between 1 mA and 3 mA (i.e. a depth of modulation of 66%), while in other embodiments, current fluctuates between 0 mA and 3 mA (e.g. a depth of modulation of 100%). In some embodiments, implantable device 200 is configured to deliver an amplitude modulated signal comprising: a carrier frequency between 1 Khz and 50 kHz; a modulation frequency between 0.1 Hz and the carrier frequency and/or a depth of modulation between 0.1% and 100%.

In some embodiments, implantable device 200 delivers a stimulation waveform comprising delivery of continuously balanced analog current waveforms, for example from a differential Howland current source. In these embodiments, there are not independent pulses, but rather there is true analog frequency and amplitude modulation. Periods of delivering stimulation (or presence of balanced differential analog stimulation) and periods of no stimulation (e.g. a quiescent period) can be included. In some embodiments, controller 250 comprises one or more reconfigurable stimulation blocks including one or more Howland or other current sources. The one or more current sources (e.g. two or more current sources) can each be attached to a stimulation element 260 (e.g. in a monopolar configuration when the current source is also connected to housing 210 or in a bipolar configuration when the current source is connected to a pair of stimulation elements 260). Alternatively, controller 250 can comprise one or more current sources that are attached to a matrix of switches that selectively connect the one or more current sources to multiple stimulation elements 260 (e.g. connect a single current source to 2, 4, 8, 12 or 16 electrodes). In some embodiments, controller 250 is configured such that a stimulation waveform signal provided to the current source passes through a capacitor (e.g. capacitor C1 shown), the capacitor providing DC balance.

In some embodiments, implantable device 200 delivers a stimulation waveform comprising delivery of multiple trains of pulses that are delivered intermittently, a "burst stimulation" waveform as defined hereabove. For example, implantable device 200 can be configured to deliver a series or train of five pulses, each with a 1 msec pulse width. The each of the five pulses can be separated by an inter-pulse gap of 4 msec, creating a train-on period of 16 msec. These five pulses can be repeated every 25 msec (the "inter-train period"). In some embodiments, implantable device 200 can be configured to deliver a burst stimulation waveform comprising a pulse width between 5 μsec and 1 msec. Implantable device 200 can deliver a train or burst stimulation waveform comprising pulses with constant pulse widths and/or varying pulse widths, such as when the pulse widths (and/or other stimulation parameters) are varied randomly and/or systematically. Implantable device 200 can deliver a train or burst stimulation waveform with a varied or constant pulse shape selected from the group consisting of: sinusoid; square, rectangle; triangle (symmetric or asymmetric); trapezoid; sawtooth; ramp (e.g. a linear ramp); exponential curve; piece-wise step function; and combinations of one or more of these. Implantable device 200 can deliver a train or burst stimulation waveform with an inter-pulse gap less than inter-train period. The inter-pulse gap can be relatively constant or it can be varied, such as when implantable device 200 randomly varies the inter-pulse gap or varies the inter-pulse gap systematically. In some embodiments, the inter-pulse gap between any two pulses within a pulse train (or burst) can be varied between 0.1 μsec and the inter-train period (or inter-burst period). Implantable device 200 can deliver a train stimulation waveform with an inter-pulse gap between 1 μsec and 1 second. Implantable device 200 can deliver a burst stimulation waveform with an inter-train period between 1 μsec and 1 second. Implantable device 200 can deliver a burst stimulation waveform with an inter-burst period between 20 μsec and 24 hours. The inter-burst period can be relatively constant or it can be varied, such as when implantable device 200 randomly varies the inter-burst period or varies the inter-burst period systematically. In some embodiments, inter-burst period is varied by the user, such as via a user using external programmer 600. In these embodiments, user activation can be regulated with one or more safeguards or other limits such as those incorporated into patient controlled analgesia devices. The inter-train period can be varied between 1 μsec and 24 hours. Implantable device 200 can deliver a train or burst stimulation waveform with a train-on period (the time between the onset of a first pulse in a pulse train to the end of the last pulse in a pulse train) between 10 μsec and 24 hours. The train-on and/or burst-on period can be relatively constant or it can be varied, such as when implantable device 200 randomly varies the train-on and/or burst-on period or varies the train-on and/or burst-on period systematically. Implantable device 200 can deliver a train or burst stimulation waveform with a train or burst envelope selected from the group consisting of: cosine; cosine-squared; sine; square; rectangle; triangle (symmetric or asymmetric); trapezoid: sawtooth; ramp (e.g. linear ramp); and combinations of one or more of these. Implantable device 200 can deliver a train and/or burst stimulation waveform with a train ramp duration or burst ramp duration between 1 μsec to 10 minutes. Implantable device 200 can deliver a train and/or burst stimulation waveform with a depth of modulation between train and/or bursts of between 1% and 99%. For example, between some or all of the trains and/or bursts (burst-off or train-off periods), a signal may be present and may contain the same or different elements contained in the train-on and/or burst-on period. These burst-off or train-off periods may comprise a quiescent period. The amplitude of the signal contained in these quiescent periods can be from 0% to 99% of the signal amplitude during the train-on and/or burst-on period, such as a signal with an amplitude less than 50% of the signal amplitude during the train-on and/or burst-on period or another amplitude below a neuronal excitation threshold.

In some embodiments, apparatus 10 is configured to deliver stimulation energy to dorsal root ganglion and/or spinal cord tissue to treat a condition such as pain. In these and other embodiments, apparatus 10 can be configured to provide a stimulation waveform comprising: a combination of low frequency stimulation (e.g. electrical energy comprising a low frequency signal) and burst stimulation; burst stimulation (e.g. burst stimulation alone); a combination of low frequency stimulation and high frequency stimulation; a combination of low frequency stimulation, high frequency stimulation and burst stimulation; and combinations of one or more of these. The stimulation energy provided by apparatus 10 can be delivered to tissue via one or more stimulation elements 260, such as two or more electrodes which deliver similar or dissimilar stimulation waveforms simultaneously and/or sequentially. Each of the stimulation waveforms can comprise one or more pulses comprising an entire phase or at least a portion of a phase at a superthreshold level. Alternatively or additionally, each of the stimulation waveforms can comprise one or more pulses comprising an entire phase or at least a portion of a phase at a subthreshold level.

In some embodiments, apparatus 10 is configured to vary one or more stimulation parameters. The stimulation parameters can be varied to optimize (e.g. balance the benefits of) therapeutic benefit, system efficiency, stimulation efficiency, avoidance and/or reduction of paresthesia, and/or reduction of charge.

Referring now to FIGS. 2A-D, perspective views of four embodiments of an implantable device are illustrated, consistent with the present inventive concepts. Each implantable device 200 comprises a housing 210 and a connector 215. Each implantable device 200 can be of similar construction and arrangement to implantable device 200 described hereabove in reference to FIG. 1 and/or otherwise as described herein. Connector 215 is configured to provide an electrical and/or other operable connection between components of implantable device 200 internal to housing 210, and one or more components of one or more leads 265 (e.g. directly and/or via one or more connectors 285, as described herebelow). Each lead 265 can comprise one or more stimulation elements 260 (e.g. one or more electrodes) and/or other components (e.g. sensors or other functional elements as described herein) configured to receive (via connector 215) energy (e.g. electrical energy) from components within housing 210 and/or transmit (via connector 215) a signal to one or more components within housing 210. In some embodiments, a lead connection assembly 280 is operably connected between connector 215 and lead 265.

Figure 2A:
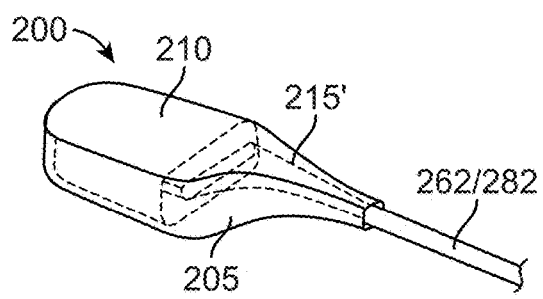
FIG. 2A is a perspective view of an implantable device comprising a single connector, consistent with the present inventive concepts.

In FIG. 2A, connector 215 comprises a "single connector", connector 215' configured to attach to conduit 262 (e.g. a flexible conduit comprising one or more conductors and/or other energy or signal carrying filaments) of a single lead 265, not shown (e.g. an attachment made in the manufacturing process of implantable device 200 or an attachment made during an implantation procedure for implantable device 200). Alternatively, connector 215' can attach to conduit 282 (e.g. a flexible conduit comprising one or more conductors and/or other energy or signal carrying filaments) of a lead connection assembly 280, not shown, as described herebelow in reference to FIG. 2C.

Figure 2B:
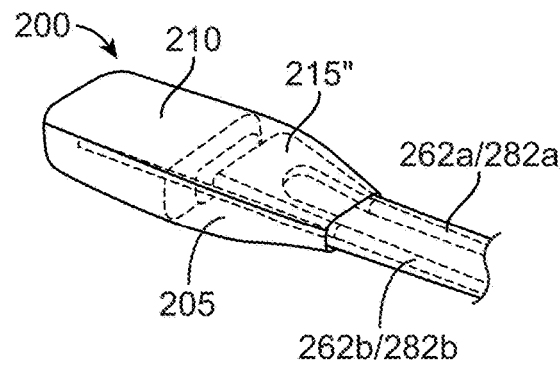
FIG. 2B is a perspective view of an implantable device comprising a dual connector, consistent with the present inventive concepts.

In FIG. 2B, connector 215 comprises a "dual connector", connector 215" configured to attach to two conduits 262a-b of dual leads 265, not shown (e.g. either or both attachments made in the manufacturing process of implantable device 200 and/or attachments made during an implantation procedure for implantable device 200). Alternatively, connector 215" can attach to two conduits 282a-b of two lead connection assemblies 280, not shown, each as described herebelow in reference to FIG. 2C.

Figure 2C:
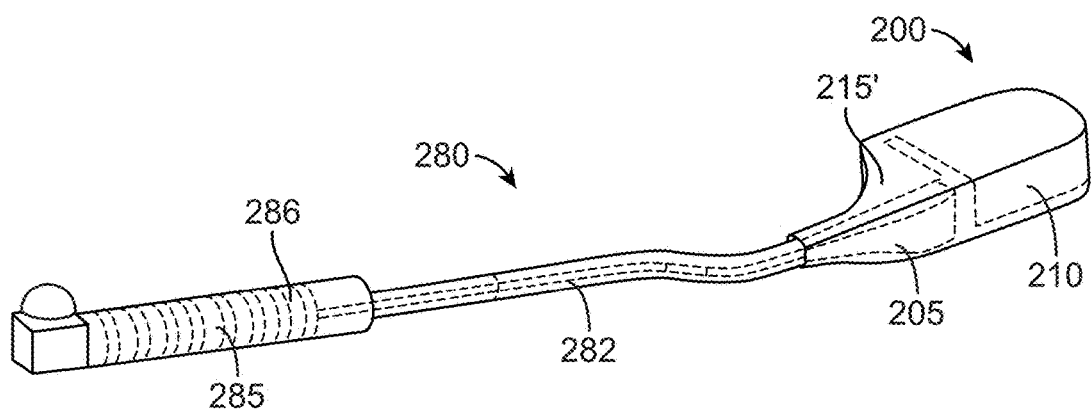
FIG. 2C is a perspective view of an implantable device comprising a single connector operably connected to a conduit of a lead connection assembly, consistent with the present inventive concepts.

In some embodiments, connector 215, such as single connector 215', is operably connected to conduit 282 (e.g. a flexible conduit comprising one or more conductors) of lead connection assembly 280, as shown in FIG. 2C. Lead connection assembly 280 comprises (e.g. on its distal end as shown or at a different location) connector 285 which includes one or more electrical contacts, contacts 286, that are operably connected to connector 215 via conduit 282.

Contacts 286 are configured to operably (e.g. electrically) connect to one or more mating contacts of an attached lead 265, not shown, such as described herebelow in reference to FIGS. 6, 6A and 6B.

Figure 2D:
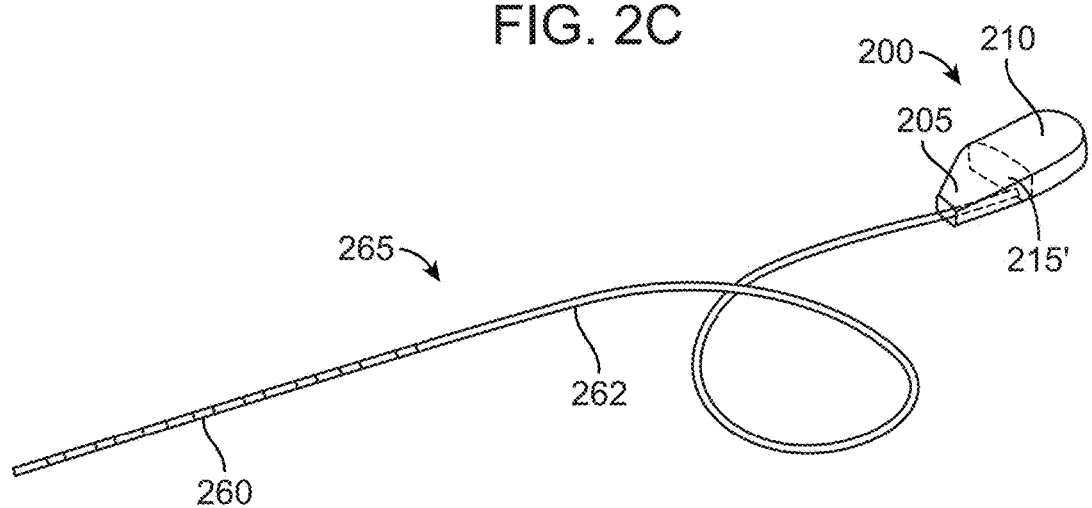
FIG. 2D is a perspective view of an implantable device comprising a single connector that includes an implantable lead, consistent with the present inventive concepts.

In some embodiments, implantable device 200 includes a lead 265 that is attached to connector 215 in manufacturing (e.g. pre-attached in the clinical setting, avoiding the need for attachment during implantation), as shown in FIG. 2D.

In some embodiments, implantable device 200 includes an overmold or other sealing element, sealing element 205, configured to surround at least the interface between housing 210 and connector 215, as shown in FIGS. 2A-D, such as to prevent contamination from entering housing 210 and/or adversely affecting the connection made between connector 215 and an attached component.

Referring now to FIG. 3, a perspective view of an implantable device comprising a universal connector is illustrated, consistent with the present inventive concepts. Implantable device 200 comprises housing 210 and a connector, connector 220, positioned on housing 210 (e.g. passing through a wall of housing 210). Implantable device 200 can be of similar construction and arrangement to implantable device 200 described hereabove in reference to FIG. 1 and/or otherwise as described herein. Housing 210 can comprise one or more rigid and/or flexible portions constructed and arranged to surround various components of implantable device 200. Connector 220 comprises one or more exposed conductors, such as the array of pins 206 shown. Pins 206 are operably connected to one or more components (e.g. electrical components) of implantable device 200 positioned within housing 210. Connector 220 can be configured to operably attach (e.g. electrically attach) to one or more leads 265 and/or one or more lead connection assemblies 280. In some embodiments, connector 220 is configured to "universally" attach to multiple different leads 265, to multiple different lead connection assemblies 280, and/or to at least one lead 265 and at least one lead connection assembly 280.

Referring additionally to FIGS. 3A-D, perspective views of various conduits for attachment to connector 220 of FIG. 3 are illustrated, consistent with the present inventive concepts. In FIGS. 3A-D, a connector 215, 215' and/or 215" (generally connector 215) is included for attachment to connector 220 of FIG. 3. Each connector 215 comprises multiple conductive receptacles, such as the array of receptacles 216 shown, which are constructed and arranged to mate with (e.g. slidingly receive) the array of pins 206 of connector 220, such that energy and/or data can be transferred to and/or from components internal to housing 210 to components of lead 265 (e.g. to at least stimulation elements 260). In some embodiments, lead connection assembly 280 (as described herebelow in reference to FIGS. 6, 6A and 6B) is positioned between connector 220 and lead 265.

In the embodiment shown in FIG. 3A, connector 215 comprises a single connector 215', including receptacles 216, that is operably attached to lead connection assembly 280 (e.g. at a first end). Lead connection assembly 280 includes conduit 282 and connector 285 for operative attachment to a lead 265 (e.g. at an opposite end of lead connection assembly 280 as shown).

In the embodiment shown in FIG. 3B, connector 215 comprises a dual connector 215", including receptacles 216, that is operably attached to dual lead connection assembly 280' (e.g. at a first end). Lead connection assembly 280 includes two conduits, conduits 282a-b, and associated connectors, connectors 285a-b respectively, for attachment to two separate leads 265 (e.g. at an opposite end of lead connection assembly 280' as shown).

In the embodiment shown in FIG. 3C, connector 215 comprises a single connector 215', including receptacles 216, that is operably attached to a single lead 265 (e.g. at a first end). Lead 265 includes conduit 262 and one or more stimulation elements 260. A lead assembly 360 comprises lead 265 and operably attached connector 215'.

In the embodiment shown in FIG. 3D, connector 215 comprises a dual connector 215", including receptacles 216, that is operably attached to two leads 265a-b (e.g. at a first end). Leads 265a-b include conduits 262a-b and one or more stimulation elements 260a-b, respectively. A lead assembly 360' comprises leads 265a-b and connector 215 operably attached to both.

Figure 4A:
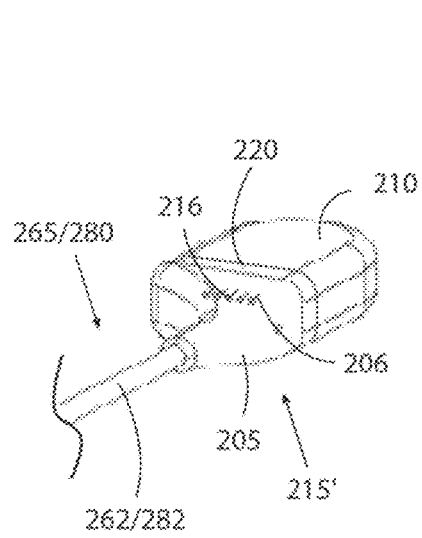
FIG. 4A is a perspective view of a single connector operably attached to an implantable device, consistent with the present inventive concepts.
Figure 4B:
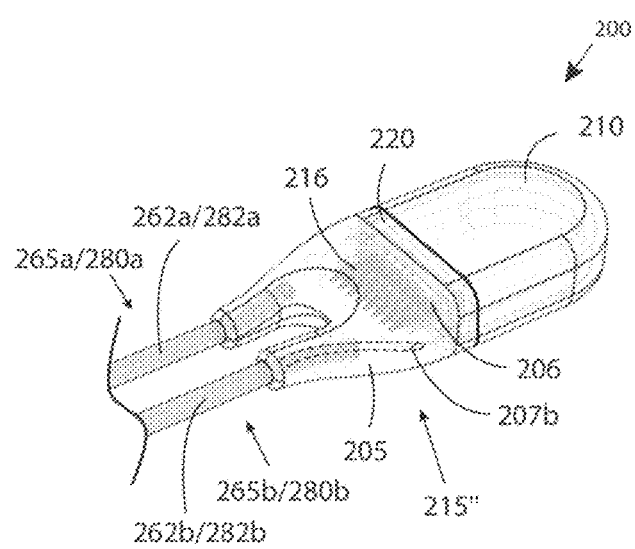
FIG. 4B is a perspective view of a dual connector operably attached to an implantable device, consistent with the present inventive concepts.
Figure 4C:
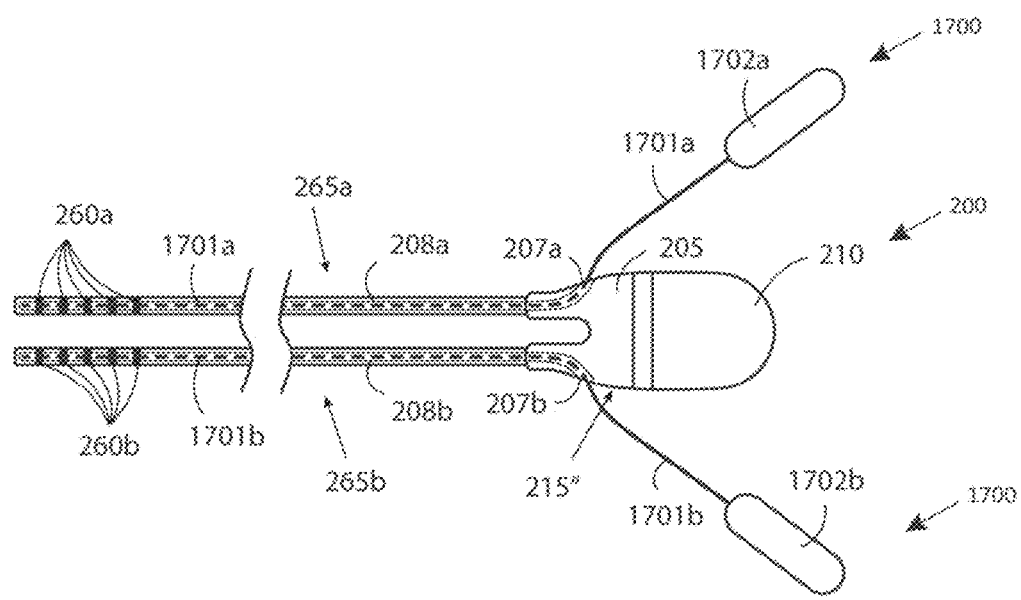
FIG. 4C is a top view of an implantable device with a dual connector assembly and two stylets, consistent with the present inventive concepts.

Referring additionally to FIGS. 4A and 4B, perspective views of a single connector 215' attached to a connector 220 and a dual connector 215" attached to a connector 220, respectively, are illustrated, consistent with the present inventive concepts. As shown in FIG. 4A, the array of pins 206 of connector 220 are slidingly received by the array of receptacles 216 of connector 215'. Connector 215' includes single conduit 262 of lead 265 or a single conduit 282 of lead connection assembly 280. As shown in FIG. 4B, the array of pins 206 of connector 220 are slidingly received by the array of receptacles 216 of connector 215". Connector 215" includes dual conduits 262a, 262b of two leads 265 or conduits 282a, 282b of two lead connection assemblies 280 or a dual lead connection assembly 280'. In some embodiments, as shown in both FIGS. 4A and 4B, a sealing element 205 is applied to surround at least a portion of housing 210, connector 220, and/or connector 215, such that sealing element 205 prevents contamination from entering housing 210 and/or adversely affecting the connection made between connector 215 and an attached component Referring additionally to FIG. 4C, apparatus 10 can include one or more stylets 1700, such as stylets 1700a and 1700b shown, and implantable device 200 can comprise one or more stylet entry ports, such as openings 207a and 207b shown. Each entry port 207 can be connected to a lumen of a lead 265 and/or lead connection assembly 280, such as lumens 208a and 208b. Each stylet 1700 can include an elongate filament 1701 which can be connected to a handle 1702, (e.g. filaments 1701a and 1701b connected to handles 1702a and 1702b, respectively). Each filament 1701 can be inserted into a lumen 208 such as to provide rigidity in the advancement of the lead 265 (or lead connection assembly 280) through tissue. Filament 1701 can comprise a filament that is flexible and/or malleable, such as a malleable filament whose shape can be curved or otherwise modified as desired to assist in the insertion of a lead 265 through tissue (e.g. a lead comprising one or more stimulation elements 260 as shown). In some embodiments, a single stylet 1700 is used to sequentially advance a first lead 265a and then a second lead 265b. While the embodiment of FIG. 4C shows a stylet 1700 working in cooperation with an implantable device 200 with dual openings 207a and 207b which provide access to dual leads 265a and 265b, a stylet 1700 can work similarly with an implantable device with a single lead 265.

Figure 5A:
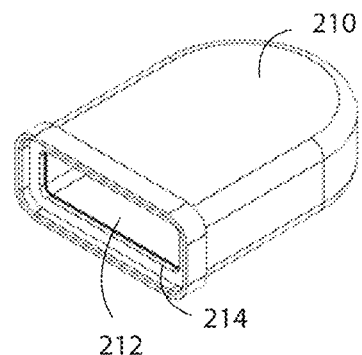
FIG. 5A is a perspective view of a housing of an implantable device, consistent with the present inventive concepts.

Refering now to FIGS. 5A-F, perspective views of a housing and a foldable electronics assembly of an implantable device are illustrated, consistent with the present inventive concepts. Housing 210 and electronics assembly 300 shown can be included in an implantable device which can be of similar construction and arrangement to implantable device 200 described hereabove in reference to FIG. 1 and/or otherwise as described herein. In FIG. 5A, a perspective view of a housing 210 is illustrated, housing 210 including an opening, opening 212. Opening 212 can include a projection along its inner perimeter, flange 214. Flange 214 can be constructed and arranged to engage (e.g. frictionally engage and/or sealingly engage, such as via a weld, such as a laser weld) a region of foldable electronics assembly 300 (e.g. when folded), forming connector 220 (e.g. connector 220 comprising connecting portions of electronics assembly 300 and portions of housing 210 proximate flange 214). In some embodiments, housing 210 comprises a material selected from the group consisting of: ceramic material; molded and/or machined zirconia; and combinations thereof. In some embodiments, at least flange 214 comprises titanium. In some embodiments, flange 214 of housing 210 is brazed with at least one of pure gold or a gold active braze alloy.

Figure 5B:
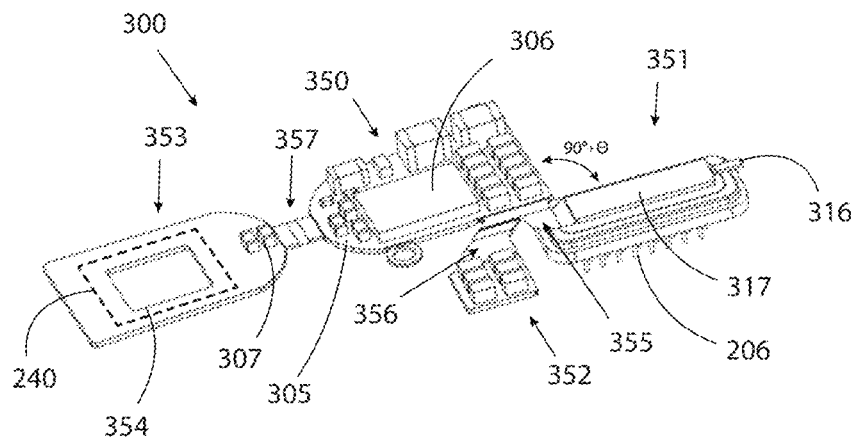
FIG. 5B is a perspective view of a foldable electronics assembly of an implantable device, consistent with the present inventive concepts.

In FIG. 5B, a perspective view of a foldable electronics assembly 300 in an unfolded (e.g. planar) configuration is illustrated. Foldable electronics assembly 300 is constructed and arranged to be folded (e.g. during a manufacturing process of implantable device 200), and inserted into housing 210 via its opening 212. In some embodiments, foldable electronics assembly 300 can include energy storage assembly 270, controller 250, and/or receiver 230, each as described herein. Foldable electronics assembly 300 can comprise a multi-layer circuit board, board 305, comprising regions 350-353 and bendable portions 355-357. Region 350 comprises a main board of foldable electronics assembly 300, including control electronics 306. In some embodiments, any of bendable portions 355-357 do not include a solder mask on an outer layer (e.g. their top and/or bottom layer) and/or any of bendable portions 355-357 only include conductive traces on an inner layer (e.g. do not include conductive traces on an outer layer), such as to provide electrical isolation between traces (e.g. prevent shorting of traces that could occur during and/or after bending), and/or to ensure all traces are protected from physical damage (e.g. during assembly, all traces are "within" the PCB, protected by at least the outer insulative layer). PCB traces running along the bendable portions 355-357 can be positioned proximate either side of a neutral axis of each bend, such as to prevent physical damage due to tensile and/or compressive forces that result at each bend.

Region 351 comprises a connecting portion, portion 317. Portion 317 is configured to slidingly receive (e.g. through one or more holes in portion 317), and operably attach pins 206 to board 305. Alternatively, pins 206 are surface mounted to portion 317. Region 351 is configured to be positioned orthogonal to region 350 via bendable portion 355 as shown in assembled view illustrated in FIG. 5C (i.e. rotated approximately 90 degrees about each of the two bendable edges of bendable portion 355). In some embodiments, bendable portion 355 includes a slight angular offset, θ, configured to provide a tolerance for the repositioning of region 351 relative to region 350 (e.g. to compensate for an internal tapered included to mold or otherwise manufacture housing 210). Angle θ can comprise an angle of at least 0.5°, or an angle of approximately 1.5° (such that region 351 is offset approximately 91.5° from region 350). In some embodiments, region 351 and region 350 can be positioned (e.g. positioned opposite each other, connected via bendable portion 355), such that a single fold repositions region 351 perpendicular to region 350.

Figure 5C:
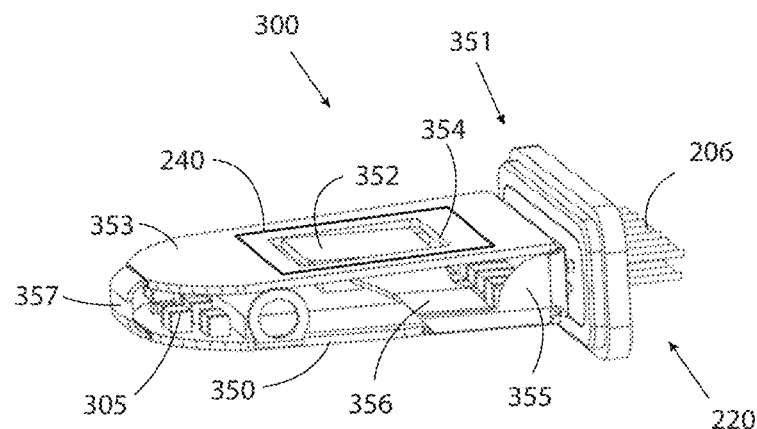
FIG. 5C is a perspective view of an assembled foldable electronics assembly of an implantable device, consistent with the present inventive concepts.

Region 352 can be configured to fold over region 350 via bendable portion 356, such that region 352 is positioned on top of region 350. Region 353 can contain one or more traces configured as an antenna 240, and antenna 240 can be constructed and arranged to fold over regions 352 and 350 via bendable portion 357 (also as shown in FIG. 5C). In some embodiments, region 353 includes an opening, opening 354, which can be constructed and arranged to create a space sized to accept other components of foldable electronics assembly 300. As shown in FIG. 5C, opening 354 can accept region 352 such that the thickness of the assembled foldable electronics assembly 300 (i.e. regions 351-353 are folded via bendable portions 355-357, respectively) can be minimized or at least decreased.

In some embodiments, foldable electronics assembly 300 is held in the assembled position by a securing element selected from the group consisting of: a molded tray; a soft elastomer part compressed between board 305 and housing 210; an adhesive; and combinations thereof.

In order to minimize size of implantable device 200, antenna 240 can be constructed on the same PCB as other electronic components of implantable device 200. For a loop antenna 240 construction, antenna 240 can be positioned on or near the perimeter of a PCB, enclosing the other elements on the PCB. Antenna 240 can comprise a single loop antenna. To maximize the distance between antenna 240 and elements that can degrade the antenna's performance (e.g. control electronics 306), antenna 240 can be folded over the top of control electronics 306 via bendable portion 357. In some embodiments, traces are positioned to follow along bendable portion 357, and a matching network 307 is positioned adjacent to control electronics 306, opposite bendable portion 357 on region 353. Such an arrangement increases the distance between antenna 240 and the other conductive materials of foldable electronics assembly 300 (e.g. to improve performance of antenna 240). In other embodiments, antenna 240 comprises more than one layer of the board 305, such as to minimize resistance and increase the performance of the antenna. Increasing the thickness of the antenna 240 traces, as well as adding redundant traces on other layers of board 305, decreases the resistance of antenna 240, which increases its quality factor and improves efficiency. Additionally, the thicker antenna 240 traces and additional antenna 240 trace layers can result in reduced inductance, which would in turn reduce antenna 240's sensitivity to variation in the matching components. The distance between region 353 and one or more (e.g. all or the majority) of the components and/or other conductive components of region 350 can comprise a distance of at least 10 µm, such as a distance between 10 µm and 100 µm.

Figure 5D:
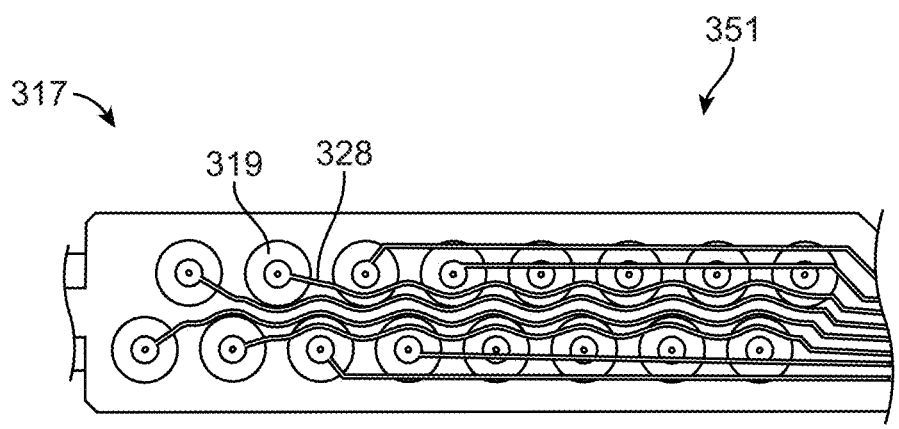
FIG. 5D is a perspective view of a connection portion of a foldable electronics assembly comprising a series of serpentine traces, consistent with the present inventive concepts.
Figure 5E:
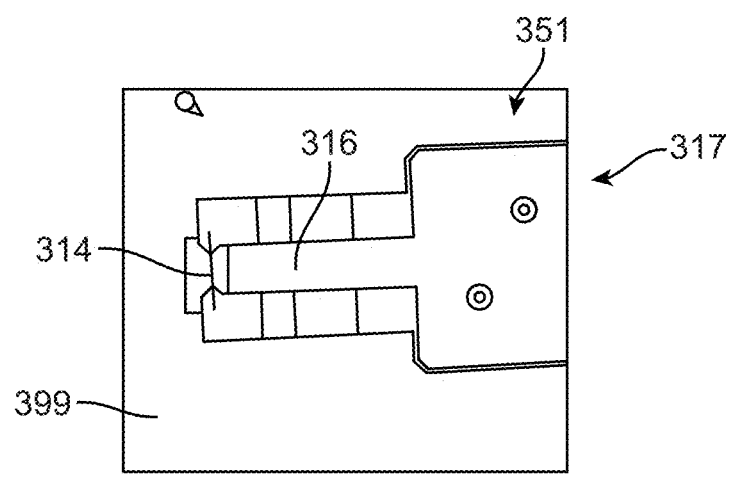
FIG. 5E is a perspective view of a connection portion of a foldable electronics assembly comprising a projection, consistent with the present inventive concepts.

Referring now to FIGS. 5D-E, connection portion 317 of region 351 can comprise a densely packed series of connection points (e.g. surface mount pads) configured to electrically connect to (e.g. be soldered to or otherwise electrically connect with) the heads of pins 206. Portion 317 can comprise a geometric routing scheme comprising a series of serpentine traces 328 (as shown in FIG. 5D), traces 328 comprising arcs of increasing radius that are interconnected in an alternating fashion to weave around one or more vias 319 (e.g. on an offset grid), such as to allow increased inter-trace width and spacing. The geometric scheme can be provided to address at least one of the following constraints: managing edge to edge dimensions (which correlates to minimizing height of housing 210); providing clearance for one or more vias (to connect to feedthrough pads); allow for a relatively large quantity of traces (one for each pin 206, e.g. approximately 16); maintaining reliable manufacturing offset of traces from PCB edge; maintaining reliable manufacturing trace width and spacing; minimizing housing 210 outer diameter; and combinations thereof.

In some embodiments, region 351 includes a projection, tab 316, configured to reduce risk of damage to connecting portion 317 during manual or automated (e.g. laser) removal of the board 305 from a manufacturing carrier, carrier 399 (e.g. after laser cutting the profile of board 305, a portion of which as shown in FIG. 5E). Following the cutting of board 305 from manufacturing carrier 399, board 305, including tab 316, are disconnected from carrier 399 via breakable portion 314. In some embodiments, tab 316 is configured to aid in the attachment (e.g. solder, glue, rivet) of region 351 to one or more portions of connector 215 and/or housing 210 following the folding of region 352 via bendable portion 355, as described hereabove in reference to FIG. 5B.

Referring now to FIG. 6, a perspective view of a lead connection assembly is illustrated, consistent with the present inventive concepts. Lead connection assembly 280 comprises a connector 285 positioned on the distal end of conduit 282. Connector 285 further includes a distal end opening, opening 289, and lead retention element, set screw 288. Opening 289 is configured to slidingly receive a proximal portion of a lead 265 (not shown), wherein subsequently set screw 288 can be rotated to apply a frictional force to lead 265 to maintain the connection between lead 265 and lead connection assembly 280.

Referring to FIG. 6A, a sectional view of a lead connection assembly is illustrated, consistent with the present inventive concepts. Connector 285 comprises one or more contacts 286 (e.g. electrical contacts) and one or more spacing elements, spacers 287. Contacts 286 can be oriented in a coaxial stack arrangement, and positioned proximal to set screw 288, as shown. Additionally, connector 285 includes one or more wires or other connecting filaments, wires 283 that extend beyond the proximal end of connector 285 to connector 215 (not shown), via conduit 282.

Referring additionally to FIG. 6B, the proximal portion of a lead 265 is illustrated. Lead 265 includes multiple contacts 269 (8 shown), which are operably connected (e.g. electrically connected) to corresponding multiple stimulation elements 260 on the distal portion of lead 265 (e.g. via a set of wires). The proximal portion of lead 265 can be inserted into connector 285, such as to correspondingly connect stimulation elements 260 to contacts 286 via contacts 269.

Referring to FIGS. 7A and 7B, a perspective view and a cross-sectional view, respectively, of a lead comprising multiple stimulation elements are illustrated, consistent with the present inventive concepts. Lead 265 comprises conduit 262 (e.g. a flexible conduit comprising one or more wires or other energy carrying filaments) and one or more stimulation elements 260 positioned on a distal portion of conduit 262. Lead 265 can comprise one or more tubes 266, each including lumens 264 constructed and arranged to surround one or more wires 267 and/or other filaments. In some embodiments, lead 265 comprises a central lumen 263 (as shown in FIG. 7B) for the passage of a stylet or other implanting tool used during surgical placement of implantable device 200. In some embodiments, the proximal end of wires 267 are exposed (e.g. stripped of insulation or other coating) and include platinum iridium ferrules, ferrules 268 (also as shown in FIG. 7A), such as ferrules configured for enhanced attachment of lead 265 to the array of pins 206 of connector 220 (described hereabove). In some embodiments, ferrules 268 are crimped and/or welded to the proximal end of wires 267.

In some embodiments, a silicone sleeve 290 is positioned over a proximal portion of tubes 266, such as a positioning performed in a manufacturing process in which sleeve 290 is expanded (e.g. using heptane) and subsequently positioned over tubes 266. Silicone sleeve 290 frictionally engages tubes 266, and silicone sleeve 290 can serve as an anchoring point (e.g. an adhesive attachment point) for a subsequent overmolding or other sealing process (e.g. an overmolding or other sealing process using a material also including silicone).

Figure 8:
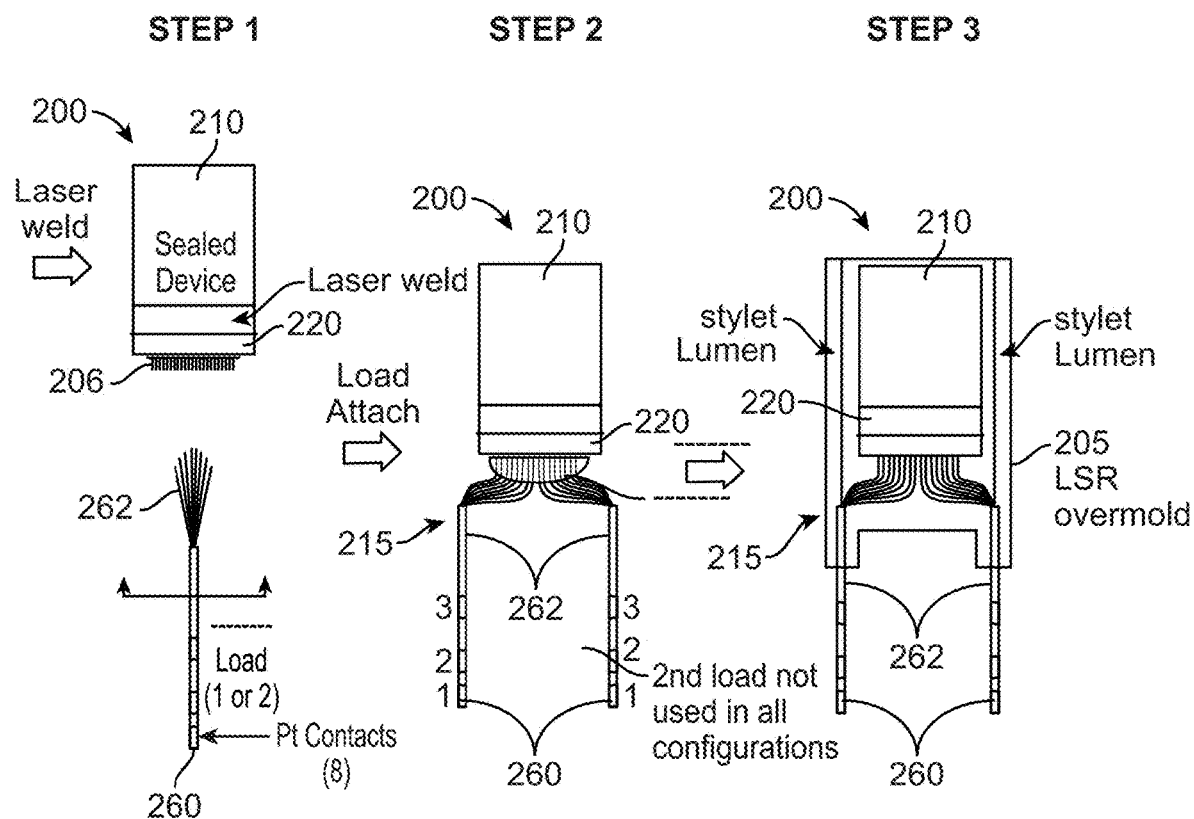
FIG. 8 is a top view of an implantable system undergoing an assembly process, consistent with the present inventive concepts.

Referring to FIG. 8, a top view of an implantable system undergoing an assembly process is illustrated, consistent with the present inventive concepts. In Step 1, foldable electronics assembly 300 is inserted into housing 210, such as in a process to manufacture an implantable device 200 as described herein. In some embodiments, a getter or other moisture-absorbing material ("getter material" herein) is applied to one or more portions of implantable device 200, such as to absorb any moisture that remains within housing 210 and/or moisture that enters housing 210 over time (e.g. while implanted in a patient). Alternatively or additionally, a getter material can be applied directly to foldable electronics assembly 300, such that the foldable electronics assembly 300 can be maintained within housing 210 in a moisture-free environment. Helium or other identifiable gas can be placed within housing 210, such as to serve as a leak tracer during subsequent seal testing (e.g. hermeticity or other seal testing) performed during and/or after manufacturing of implantable device 200. In some embodiments, implantable device 200 is maintained in a heated oven for a time period, such as to remove any remaining moisture. Subsequently, connector 220 and housing 210 can be sealed, such as by a perimeter laser weld.

In Step 2, the array of pins 206 of connector 220 slidingly receives the array of receptacles 216 of connector 215, such as to provide at least an electrical connection between pins 206 and receptacles 216.

In Step 3, sealing element 205 (e.g. an overmold, adhesive or other sealing element) is applied to surround one or more portions of housing 210, connector 220, and/or connector 215. In some embodiments, sealing element 205 is constructed and arranged to include one or more openings or lumens, such as a lumen configured to allow insertion of a styled into lead 265 as described herein.

Figure 9:
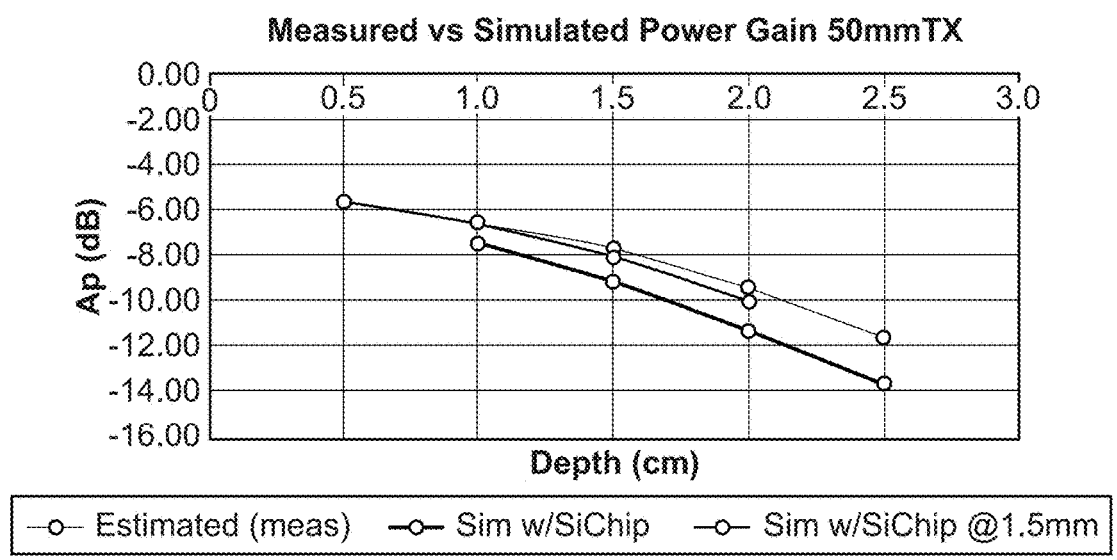
FIG. 9 is a graph of power gain versus depth of a 50 mm antenna, consistent with the present inventive concepts.

Referring now to FIG. 9, a graph of link gain versus depth is illustrated consistent with the present inventive concepts. Implantable device 200 can comprise a folded electronics assembly 300 configuration (e.g. as shown in FIGS. 5A-E) that allows antenna 240 to be positioned away from loss-inducing board traces and components (i.e. integrated circuits), with minimal or no penalty to implantable device 200 size. In FIG. 9, antenna 240 and circuitry of implantable device 200 was simulated using an assembly including a silicon chip (representing the application-specific integrated circuits of implantable device 200). In one configuration (Sim w/SiChip plotted), antenna 240 surrounded the chip on a single PCB. In a second configuration (Sim w/SiChip @1.5 mm), antenna 240 was folded over the top of the silicon chip, and spaced at a distance of 1.5 mm from the chip. As illustrated in FIG. 9, the second configuration shows approximately 2 dB of improvement as compared to the first configuration. Measurements of a prototype construction of a folded electronics assembly 300 is also plotted. The measured performance of the graph of FIG. 9 shows a recovery in link gain, which matches a simulation with a 1.5 mm separation between the antenna 240 and application-specific integrated circuits. Additionally, a high efficiency can be achieved by utilizing numerous (e.g. all) available metal layers in a multi-layer flex board of electronics assembly 300 for antenna 240, such that the antenna 240 resistance is significantly reduced.

Figure 10:
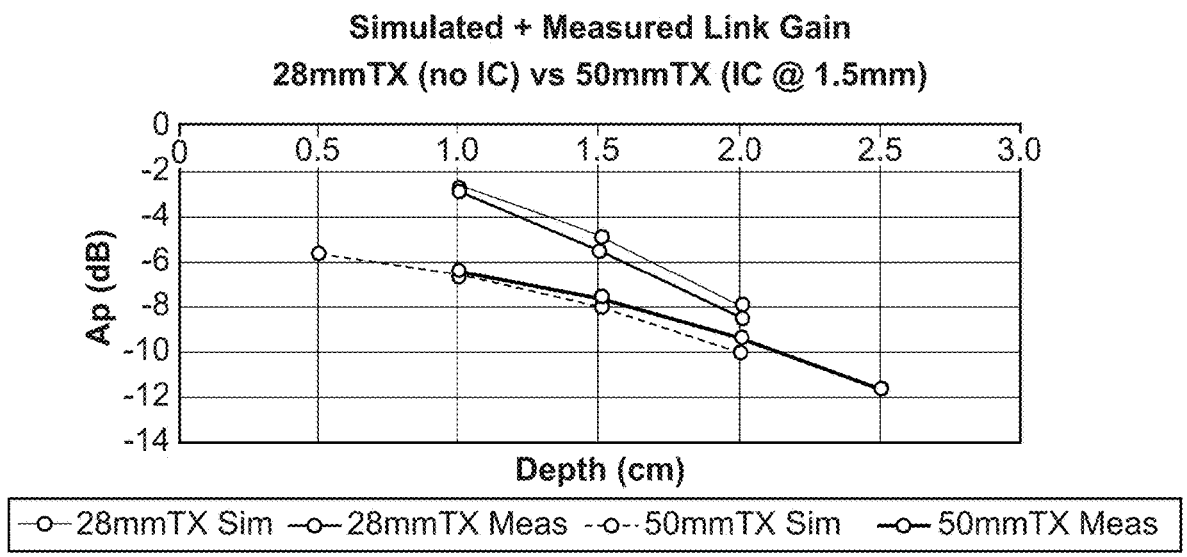
FIG. 10 is a graph of link gain versus depth of a 28 mm antenna compared to a 50 mm antenna, consistent with the present inventive concepts.
Figure 11:
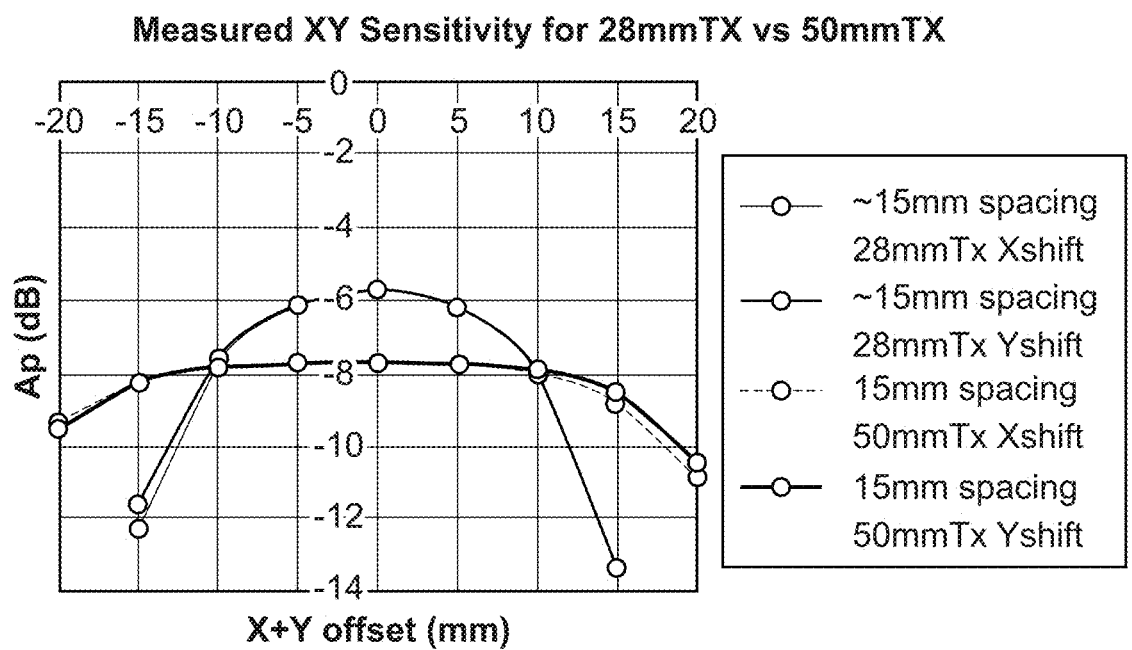
FIG. 11 is a graph of lateral sensitivity of a 28 mm antenna compared to a 50 mm antenna, consistent with the present inventive concepts.

Referring now to FIGS. 10 and 11, graphs of link gain versus depth are illustrated, consistent with the present inventive concepts. FIGS. 10 and 11 illustrate simulated and measured data for an external device 500 antenna, antenna 540 described herein, that comprises a loop transmitter with a first configuration comprising a 28 mm diameter and an antenna 540 in a second configuration comprising a 50 mm diameter. FIG. 10 shows the change in antenna 540 performance with depth, and FIG. 11 shows the change in antenna 540 performance with lateral offset. The 50 mm antenna shows less sensitivity to lateral or depth variation (as shown in FIG. 10), but achieves a lower efficiency (as shown in FIG. 11) when in perfect alignment as compared with the 28 mm antenna. The dimensions of the antenna can be designed based on efficiency requirements as well as the anticipated operating depth and alignment precision of the transmitter and the receiver. Apparatus 10 can be constructed and arranged to minimize sensitivity to lateral, rotational, and/or depth displacement by using an external device 500 comprising a single external antenna 540 and an implantable device 200 comprising one or more implantable antennas 240, where the external antenna 540 is larger than the one or more implantable antennas 240. In these embodiments, antenna 240 maintains suitable performance when covered by the larger external antenna 540. An example of such an arrangement is an external antenna 540 having a large loop (e.g. a circular, elliptical, square, or rectangular loop) that transmits to an implanted antenna 240 having a smaller receiving loop (e.g. a circular, elliptical, square, or rectangular loop) that functions acceptably as long as antenna 240 is underneath and enclosed by the larger loop of the external antenna 540. For example, a single-turn loop antenna for both antenna 540 (at least a transmitter) and antenna 240 (at least a receiver) achieves lowest quality factor and, therefore, maximum bandwidth for communications, such that it results in higher efficiency for systems operating near the optimal frequency (i.e. multi-turn loops near these frequencies exhibit cancelling effects, reducing efficiency). Additionally, maximum link gain can be achieved by using maximization techniques in conjunction with low-voltage power harvesting electronics without requiring a large turns ratio or area ratio to boost the output voltage received by the receiver.

These antennas 540 and 240 perform best when the size of the loops and distance between them is less than approximately one-fifth of the wavelength of the frequency of operation, such as when the distance is less than one-twentieth of the wavelength of the frequency of operation. Other factors play a role, such as tissue absorption and antenna construction which can also be considered in selecting an operating frequency. As used herein, the "operating point" of apparatus 10 can refer to a design parameter value(s) of apparatus 10, such as one or more design parameters selected from the group consisting of: external antenna 540 size, shape and/or construction; external antenna 540 matching network configuration; implantable antenna 240 size, shape and/or construction; implantable antenna 240 matching network configuration; and combinations of one or more of these. Alternatively or additionally, the operating point can refer to environmental conditions encountered during use of apparatus 10; such as an environmental condition selected from the group consisting of: tissue type (e.g. tissue proximate one or more portions of implantable device 200); depth of implantation of implantable device 200 and/or implantable antenna 240; distance between implantable antenna 240 and external antenna 540; alignment between implantable antenna 240 and external antenna 540 (e.g. lateral offset and/or angular offset of the antennas); frequency of transmissions sent from external device 500 to implantable device 200; frequency of transmissions sent between implantable device 200 and external device 500; and combinations of one or more of these. An optimal operating point can be derived by the Z-parameter matrix describing apparatus 10. The maximum efficiency depends not only on the cross terms that represent coupling, but also on the driving and driven impedances of the transmitter (e.g. external device 500) and receiver (e.g. implantable device 200). These impedances vary with frequency, and the coupling terms vary with the relative position, transmission medium, and characteristics of the antenna 540 and 240 structures themselves. Therefore, a multi-variable optimization is necessary to determine the best design parameters for a specific system.

The efficiency of such communication between the antennas 540 and 240 is dictated by a Z-parameter matrix, which captures the antenna impedances and their quality factors (Q) as well as the associated coupling relationships. Near-field inductive power transfer functions like a transformer, and medical devices that use this implementation typically use a coupling coefficient (k) that is essentially the cross-coupling term in the Z-parameter matrix. With this coupling coefficient (k), an optimal coupling point is determined, usually referred to as critical coupling, that results from reflecting the load on the receiver to the primary transmitter. In doing this, the power transfer efficiency can be represented and analyzed by the voltage transfer, which results in designs that use multiple turns, ferrite cores, and other optimizations around a specific coupling point (which is most strongly influenced by separation distance), and results in reduced performance as coupling is altered (such as lateral, rotational, or depth displacement). More turns also tend to increase the quality factor (Q), which results in reduced bandwidth in the link between the transmitter and receiver. These additional loops improve efficiency when power can be related to voltage transfer to a fixed load. Essentially, these systems function as a transformer, meaning that the additional loops do not fundamentally improve efficiency, instead they improve efficiency for a fixed loading condition by altering the voltage transformation and the coil impedance. In contrast to this approach, the antenna assembly considers all the variables in the Z-parameter matrix and the variation of the matrix (that can be due to lateral, rotational, or depth displacement, as well as changes in the transmission medium itself) and optimizes over the range. As part of maximizing power transfer efficiency, the antenna impedances, input and output impedances both affect power transfer efficiency and vary with frequency at a given relative position. To be specific, it can be shown that the link gain ($A_p$) can be written in terms of the Z-parameter matrix illustrated by the following equation $$A_p = \frac{|Z_{21}|^2 \cdot \text{Re}(Z_L)}{|Z_{22} + Z_L|^2 \cdot \text{Re}(Z_{in})}$$

where $Z_{in}$ and $Z_L$ are the input impedance and load impedance respectively, and where each impedance (Z) term is a function of frequency. Hence in this approach, $A_p$ is computed from the Z-parameters and maximized both at the frequency of operation and also over all the conditions that define the desired operating range.

It may be desirable to maximize the minimum link gain that is encountered over a depth displacement range of 10 mm to 20 mm and a lateral displacement range of +/−15 mm. For example, to maximize link gain over a depth up to 20 mm, and over a lateral translation less than or equal to 10 mm, a smaller antenna 540 size approximating 28 mm can be used (these are the regions where the 28 mm antenna 540 outperforms the 50 mm antenna 540, as shown in FIGS. 9 and 10). However, to cover a depth of up to 25 mm and/or a lateral translation of up to 15 mm to 20 mm, the minimum link gain is maximized by using a larger antenna 540 size approximating 50 mm. The performance with respect to depth and lateral offset is continuous (i.e. an operating point can be selected anywhere at any location along the curve), so antenna 540 dimensions greater than 50 mm, smaller than 28 mm, or in between 28 mm and 50 mm may perform better as the implantable device 200 and/or other apparatus 10 component design requirements change. The data presented shows an example of the performance tradeoff.

Figure 12:
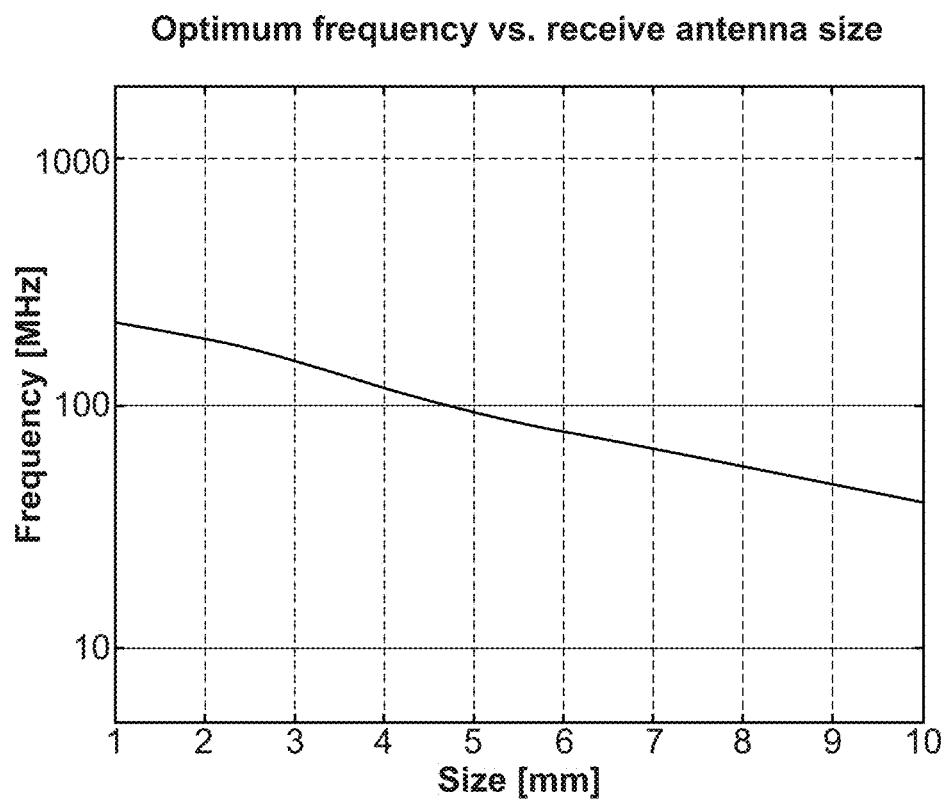
FIG. 12 is a graph of frequency versus antenna size, consistent with the present inventive concepts.

Referring now to FIG. 12, a graph of frequency versus antenna size is illustrated, consistent with the present inventive concepts. In this figure, the frequency at which the highest transfer efficiency can be achieved (for various antenna diameters) is depicted, for an antenna 240 comprising a single turn circular or square loop receiver. In some embodiments, antenna 240 and/or 540 comprise single-loop antenna structures, which perform best near an optimal frequency. In some embodiments utilizing a near field design, it would be expected that decreasing the frequency would offer advantages to power transfer efficiency as long as the appropriate number of loops can be used to achieve the ideal voltage transfer. However, an approach that considers the effect of these impedances in addition to the coupling relationships shows that higher efficiencies can be achieved at a specific frequency for a single loop antenna. Additionally, it is apparent that the antenna structures are not behaving as a transformer (e.g. the power transfer efficiency is higher than would be expected by purely analyzing the magnetic flux captured by the receiver, suggesting the behavior is more antenna-like with resonant effects). Achieving the best efficiencies for a given application introduces considerations in the implementations of both the transmitting antenna (e.g. antenna 540) and the receiving antenna (E.g. antenna 240), such as methods for adjusting transferred power or receiving low-voltage RF signals. The specific optimal frequency for a system can vary significantly depending on the details of the antenna shapes, sizes, materials, and operating environment. The optimal frequency for a given system can be estimated using 3D electromagnetic simulations of the link gain.

Figure 13:
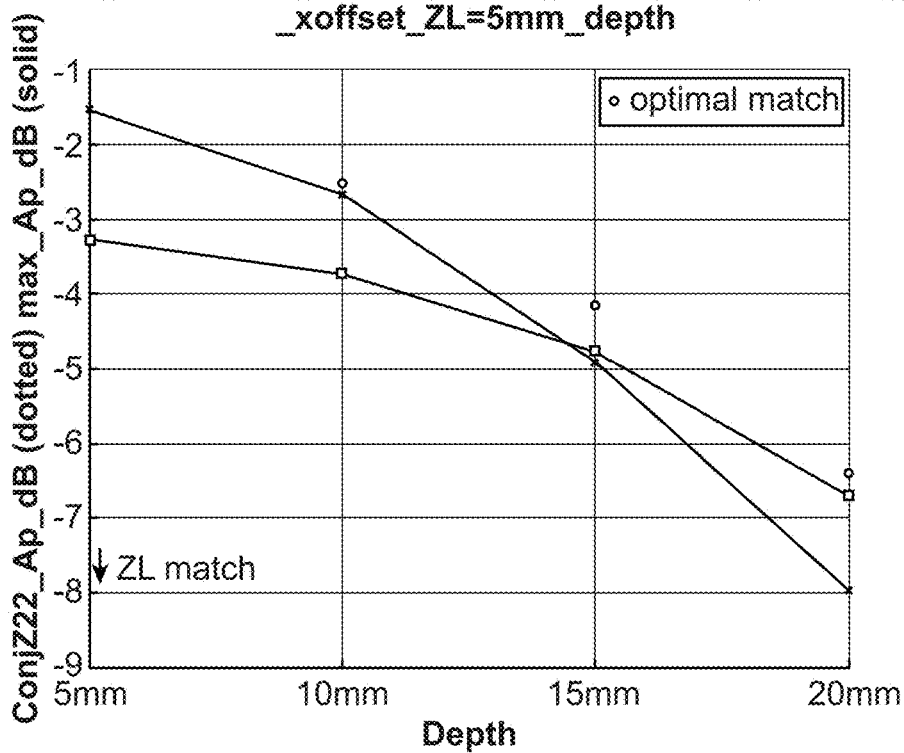
FIG. 13 is a graph of transfer efficiency versus depth of different transmitter matching conditions, consistent with the present inventive concepts.

Referring now to FIG. 13, a graph of transfer efficiency versus depth, with different transmitter matching conditions is illustrated, consistent with the present inventive concepts. FIG. 13 illustrates that the optimal matching network is different at each depth, with the optimal performance represented by circles. A conjugate match to the antenna impedance is represented with squares, and has the best performance at farther separation distances. Lastly, the data points marked with an "x" represent the performance if the optimal match at a 5 mm depth is incorporated (e.g. used for all depths). While achieving the optimal performance at 5 mm, this 5 mm optimized configuration rapidly declines and performs worse than the simple conjugate match at approximately 15 mm depth. This data provides an example of how changing the matching network impacts performance. Apparatus 10 can comprise an antenna assembly that is desensitized to coupling, which includes lateral, rotational, or depth displacement, by using an appropriate impedance transformation of a transmitter and receiver along with an appropriate power harvesting circuit. A single loop external antenna 540 allows for maximum available bandwidth, and can optimize efficiency over the widest range of operating conditions with adjustable resonant tuning or resonant tuning at a desired operating point of apparatus 10. The receiver antenna 240 can utilize a power harvesting mechanism that has the ability to efficiently recover low voltage signals and also has variable loading. As coupling increases, the impedances of the transmitting antenna 540 and receiving antenna 240 affect each other more strongly, and affect the associated antenna matching or tuning. For an apparatus 10 with a fixed network for antenna tuning, the network can be selected to achieve the best performance for the anticipated operating range. For example, if the implantation depth of implantable device 200 is anticipated to range from 0.5 cm to 1.5 cm, a simple conjugate match to the uncoupled antenna impedances will result in degraded performance as depth decreases and coupling increases (however it would be optimal for operating ranges with low coupling). Alternatively, tuning the coupled impedances at a depth of 0.5 cm may result in degraded performance as depth increases to 1.5 cm, limiting the range. However, tuning at a depth of 1.5 cm can outperform both the conjugate match and a matched tuned at 0.5 cm and hence improve the overall operating range of the antenna assembly. As shown in FIG. 13, a 30 mm transmitting antenna 540 can have its associated receiving antenna 240 tuned to a coupling at 0.5 cm depth, wherein the maximum link gain is the same as the optimal match at 0.5 cm. The maximum link gain drops quickly below the optimal match at greater depths, wherein the link gain rate of decline from 1 to 2 cm is greater than 5 dB/cm.

Figure 14:
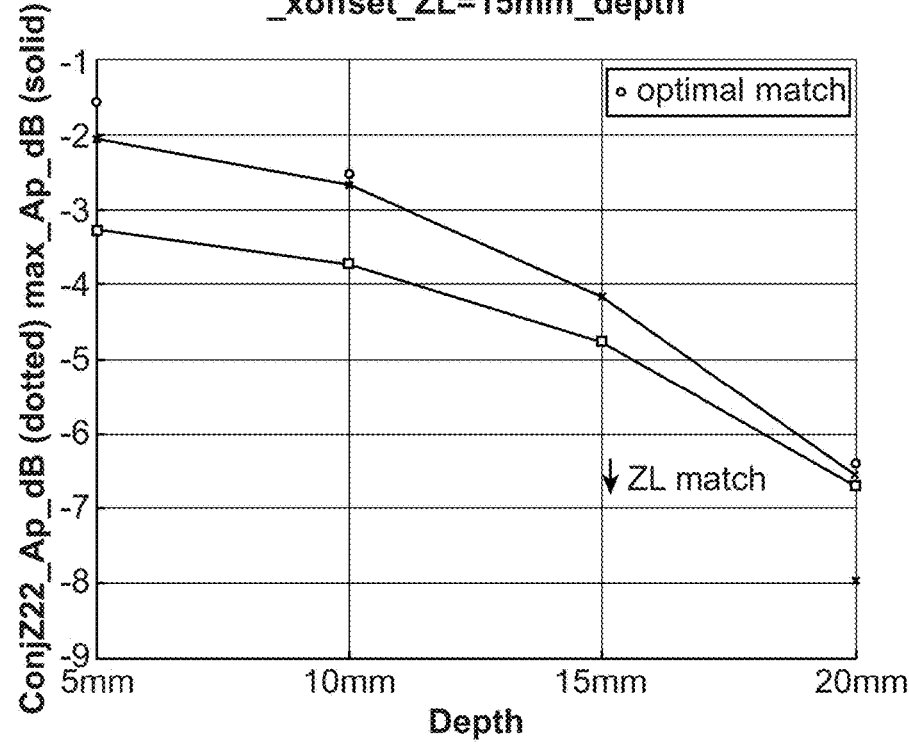
FIG. 14 is another graph of transfer efficiency versus depth of different transmitter matching conditions, consistent with the present inventive concepts.

Referring now to FIG. 14, a graph of transfer efficiency versus depth, with different transmitter matching conditions is illustrated, consistent with the present inventive concepts. FIG. 14 illustrates that the optimal matching network is different at each depth, with the optimal performance represented by circles. Similar to FIG. 13, a conjugate match to the antenna impedance is represented with squares. Lastly, the data points marked with an "x" represent the performance if the optimal match at a 15 mm depth is incorporated (e.g. used for all depths). Using a fixed network that optimizes performance at 15 mm performs significantly better than the simple conjugate match at all distances up to 20 mm. Again, this data provides an example of how a fixed network can be optimized to maximize performance over the operating range. Apparatus 10 can have its antennas 540 and 240 tuned to a coupling at a 1.5 cm depth. The maximum link gain achieved is equal to the optimal match at 1.5 cm, and by sacrificing higher performance at lower depths (i.e. higher couplings), the rate of decline in link gain from 1 cm to 2 cm is reduced to 4 dB/cm, and deviates less from the optimal match across that range. This latter tuning, as shown in FIG. 14, would therefore be the better choice if anticipated depths were between 1 cm and 2 cm, while the former tuning, as shown in FIG. 13, would be better if anticipated depths were less than 1 cm. Depending on the antenna 540 and 240 size and construction, as well as the intended application, this operating point can be different, and so analysis of the efficiency over the operating range, including all the parameters affecting the link (e. g. tissue type, depth, alignment, rotation) with different tuning points is desired. The tuning is implemented based on the antenna structure, particularly because the operating point will likely be affected by tissue absorption and the wavelength relative to the antenna 540 and 240 size and separation distance. Alternatively or additionally, the tuning can be adjustable at one or both of the transmitting antenna 540 and the receiving antenna 240. Usually, a larger antenna will be more sensitive to the tuning, and therefore implementing adjustable tuning at the transmitting antenna 540 will have the greatest benefit. The matching network of an antenna (e.g. transmitting antenna 540 and/or receiving antenna 240), can be tuned to improve the minimum link performance by evaluating the performance of the optimal matching condition at fixed positions over a desired operating range and selecting the match (e.g. set of settings) with the highest performance. Alternatively or additionally, the tuning can be adjustable at one or both of the transmitting antenna 540 and the receiving antenna 240. Usually, a larger antenna will be more sensitive to the tuning, and therefore implementing adjustable tuning at the transmitting antenna 540 will have the greatest benefit. In some embodiments, antenna 540 is operatively attached to a first matching network (e.g. of external device 500) and antenna 240 is operatively attached to a second matching network (e.g. of implantable device 200).

The bandwidth of the antenna link will influence the ability to transfer data, and depends on the operating frequency and the quality factor of the transmitting antenna 540 and receiving antenna 240. In some embodiments, data is transmitted at some fraction of the time that the power is being transferred. In these embodiments, the quality factors can be adjusted during data transmission to achieve higher data rates. This adjustment will degrade power transfer efficiency, though this negative impact will be small because of the relative infrequency (e.g. low duration) of data transmission.

Figure 15:
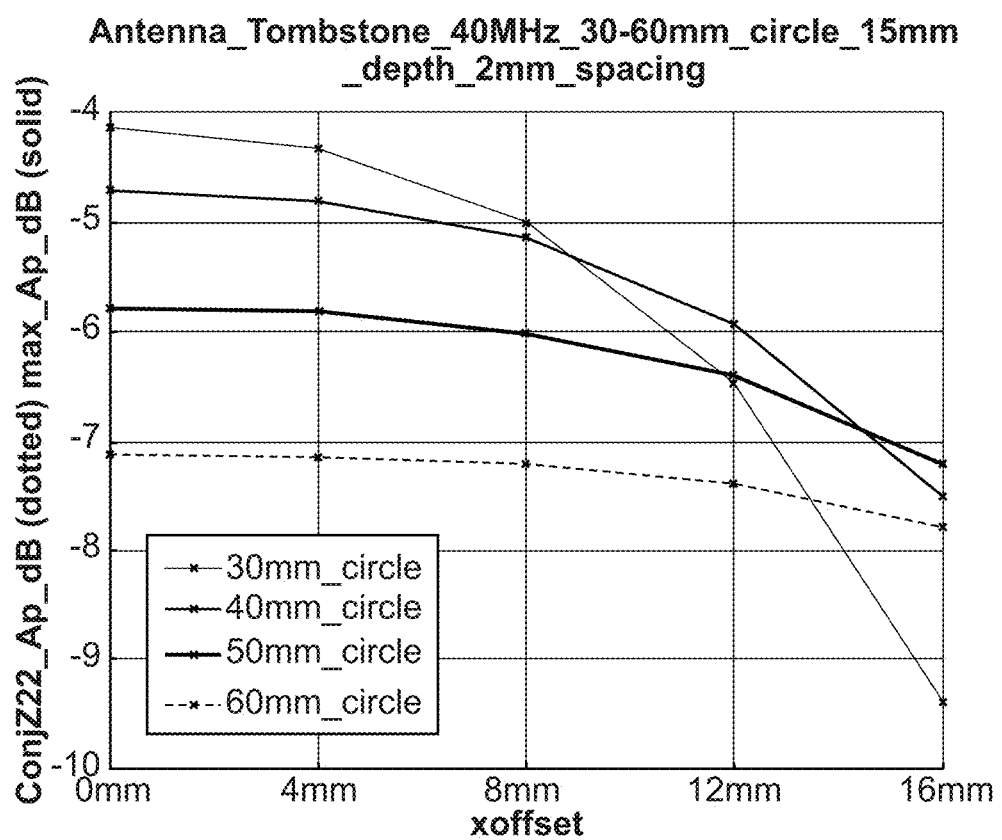
FIG. 15 is a graph of simulated performance with a lateral offset between various transmitting antennas and a receiving antenna, consistent with the present inventive concepts.

Referring now to FIG. 15, a graph of simulated performance with a lateral offset between a transmitting antenna and receiving antenna, for each of a 30 mm, 40 mm, 50 mm, and 60 mm circular transmitting antennas is illustrated, consistent with the present inventive concepts. For a given receiving antenna 240, a smaller transmitting antenna 540 may achieve better performance over a range of shallow depths and limited translational displacement. Conversely, a larger transmitting antenna 540 will "maximize the minimum" link gain if a larger range of depths and translational displacement is required. For example, a transmitting antenna size between 30 mm and 60 mm in diameter accommodates for XY misalignment error between antennas 540 and 240 on the order of order of +/−0.5" (approximately 12.7 mm). As shown in FIG. 15, simulated XY misalignment error varies with transmitting antenna 540 size.

Referring now to FIG. 16, an electronic block diagram of an external device is illustrated, consistent with the present inventive concepts. External device 500 includes power supply 570, controller 550, transmitter 530, user interface 580, and antenna 540. External device 500 can be of similar construction and arrangement to external device 500 described in reference to FIG. 1 and/or otherwise as described herein. In some embodiments, external device 500 includes one or more functional elements 560.

Power supply 570 includes battery 571, for example a rechargeable battery. Power supply 570 further includes charger contacts 573 extending from battery 571, contacts 573 positioned to align with contacts of an external charger (e.g. tool 60$_{ii}$ described herebelow in reference to FIG. 31). In some embodiments, power supply 570 comprises isolation power circuit 572, configured to protect battery 571 from hazards, such as an over current and/or an under voltage condition. Power supply 570 further includes power sub-system 575, which can be configured to interface with battery 571 to provide one or more voltages to one or more components of external device 500 (e.g. providing one or more voltages selected from the group consisting of: 3.3V; 3.0V; 2.7V; 1.8V; 1.2V; and combinations thereof, and/or providing a continuously variable voltage such as voltage that can be varied between 0V and 3.3V). In some embodiments, power sub-system 575 comprises a variable RF voltage supply.

Controller 550 can include microcontroller 555, field-programmable gate array (FPGA) 556, oscillator crystal 557, and/or memory (e.g. electrically erasable programmable read-only memory, EEPROM, 558. In some embodiments, controller 550 further comprises a Bluetooth transmitter, such as a Bluetooth transmitter integrated into microcontroller 555. Controller 550 can be configured to communicate (e.g. via Bluetooth) with one or more components of apparatus 10, such as programmer 600, implantable device 200, and/or another component of apparatus 10. FPGA 556 can be configured to modulate transmission signals communicated to implantable system 20 and/or to demodulate back telemetry data (BTEL) received from implantable system 20 (e.g. via antenna 240). Crystal 557 can be configured to operate at a frequency between 30 MHz and 50 MHz, such as a frequency between 40.66 MHz and 40.7 MHZ, such as a frequency of approximately 40.68 MHz. EEPROM 558 can be configured to store information pertaining to at least one of the following: apparatus parameters (also referred to as "system parameter" herein); therapy parameters; therapy usage; event data; error data; and combinations of these. EEPROM 558 can be further configured to provide a user with a therapeutic starting point upon turning on external device 500 for treatment, and the therapeutic starting point can be identical to the therapeutic parameters selected by the user in a preceding treatment.

Controller 550 can further include one or more drivers, such as feedback driver 551, haptic driver 552, and/or button controller 553 configured to interact with (e.g. control and/or receive signals from) one or more components of user interface 580. User interface 580 can include speaker 581, piezo transducer 582, and/or buttons 583. Feedback driver 551 can provide auditory and/or visual feedback mechanisms to a user (e.g. via a buzzer, LED lights, and the like), such that these feedback mechanisms can indicate system conditions of at least one of the following: implant connectivity status; battery status; communication status between the external system 50 and the implantable system 20; therapy level; program number; and combinations thereof. Feedback driver 551 can be configured to control speaker 581. Haptic driver 552 can provide tactile feedback to a user (e.g. the patient), and can be configured to control piezo transducer 582. In some embodiments, feedback driver 551 and haptic driver 552 provide feedback to assist a user (e.g. the patient, a family member, nurse or clinician) in the proper placement of external device 500. Button controller 553 can be configured to receive input from buttons 583, such as to provide an initiation to perform a function selected from the group consisting of: turn device on and/or off; change between two or more therapeutic programs; increase or decrease therapy levels (e.g. amount of energy delivered); and combinations thereof.

Transmitter 530 can be configured to transmit and/or receive signals (e.g. via antenna 540), to and/or from implantable system 20. Transmitter 530 can include modulator 531, power amplifier 532, matching network 533, data converter 535*a*, attenuator 535*b*, and/or RF detector 534. In some embodiments, transmitter 530 is configured to drive antenna 540, comprising one or more antennas. The RF detector 534 outputs a signal representative of the instantaneous output power of the transmitter into data converter 535*a*. The output power is strongly influenced by the specific antenna impedance. The antenna impedance changes with its surrounding environment (such as tissue), the coupling with the implantable device 200, implant loading conditions, fault conditions, received signals, interference, and/or other mechanical or electrical variations in the system. These changes in antenna impedance will be detected by the RF detector 534, which can then inform apparatus 10 to respond properly. For example, the coupling between the transmitting and receiving antenna changes with depth, so the depth of the implantable device 200 can be estimated based on the output of the RF detector. Similarly, apparatus 10 can detect and respond to different loading conditions, environments, interference, or fault conditions. To receive signals from the implantable system 20, the load on the implantable device 200 can be controllably adjusted, which will affect the transmitting antenna 540 impedance to create a detectable signal in the output power of the transmitter (e.g. one or more external devices 500). This signal can be analyzed directly as an analog signal, or it can be passed through a filter and comparator to convert it to a digital signal, which can be recovered by digital electronics such as an FPGA. The load on the implantable system 20 can be adjusted by switching a load across its antenna 240, which can be a capacitive, inductive, and/or resistive load. In some embodiments, implantable device 200 applied and/or modifies a load operatively attached to implantable antenna 240, as a method to send signals (e.g. data encoded signals) to external device 500. The applied load can comprise a static or adjustable load with an impedance between 1 ohm and 100 ohms (a load that is adjusted in order to send the signals). In some embodiments, the implantable antenna 240 is opened (i.e. an open circuit is applied to implantable antenna 240) to send signals back to external device 500. To avoid collisions with data transmitted from the external system 50, the implantable system 20 can be configured to transmit only upon request at specific timings after data transmissions from the external system 50.

Functional element 560 can include a position or motion sensor, accelerometer 561, and/or a magnetic sensor, magnetic sensor 562, as shown. Accelerometer 561 can detect (e.g. provide a signal related to) the position of the patient (e.g. sitting, standing, supine) and automatically adjusts the therapeutic parameters, such as a stimulation level and/or therapeutic program which is based on patient position. Alternatively or additionally, external device 500 can be configured to allow a user (e.g. the patient) to manually input a change in patient position. In some embodiments, apparatus 10 is configured to debounce the signal provided by accelerometer 561 (e.g. includes a "debouncing" period), to confirm the patient's new position and/or prevent undesired oscillations of the stimulation parameters due to temporary movements of the patient. Additionally or alternatively, one or more components of external device 500 can be configured to perform one or more functions selected from the group consisting of: activity tracking (e.g. gait, sleep as determined by accelerometer 561); use of time of day and/or activity patterns (e.g. as determined by accelerometer 561) to make stimulation adjustments; correlate therapy efficacy with amount of activity; record therapy changes with an increase and/or decrease in activity; detect dropping of the external device 500, such as to track durability; track external device 500 connection state as a function of activity and position (e.g. connectivity state as the patient walks, or sleeps); detect external device 500 disconnection due to motion and provide feedback about how to reposition the external device 500 based on detected positional change; use a tapping, shaking, and/or other motion and/or contact with the external device 500 (e.g. as opposed to use of buttons 583) to convey different commands; enable or disable button 583 control with specific tap gestures (e.g. tapping, shaking, and/or other contact of an operator such as the patient with housing 210 or other portion of implantable device 200); change button 583 functionality with specific tap gestures on the external device 500; and combinations thereof. In some embodiments, magnetic sensor 562 is configured to detect (e.g. produce a signal used by apparatus 10 to detect) the presence of a charging device, such as tool $60_{ii}$ described herein. Alternatively or additionally, magnetic sensor 562 is configured to detect another device of apparatus 10 whose proximity to external device 500 can be used by external device to perform a function. In these embodiments, an external device 500 can be configured to shut down (e.g. not transmit to an implantable device 200) when being charged by a tool $60_{ii}$, such as to simplify the electronics of tool $60_{ii}$ (e.g. by avoiding a transmitting or other operating load being placed on tool $60_{ii}$ by external device 500 electronics). In some embodiments, magnetic sensor 562 is used as a control (e.g. as a magnetically-activated button or other magnetically-activated control used to turn external device 500 on or off and/or program external device 500).

In some embodiments, stimulation is adjusted by monitoring electrode-based stimulation element 560 impedances and/or by monitoring evoked compound action potentials (ECAP), such as can be recorded by one or more electrode-based stimulation elements 260. Impedance changes can be used to modify compliance voltage and/or modify stimulation element 260 configuration (e.g. which stimulation elements 260 deliver energy). ECAP data can be used to routinely (e.g. continuously) modify stimulation parameters, such as an adjustment to amplitude, pulse with, frequency, and the like, such as to maintain effective treatment (e.g. effective pain relief and/or stimulation that is paresthesia-free).

Figure 17:
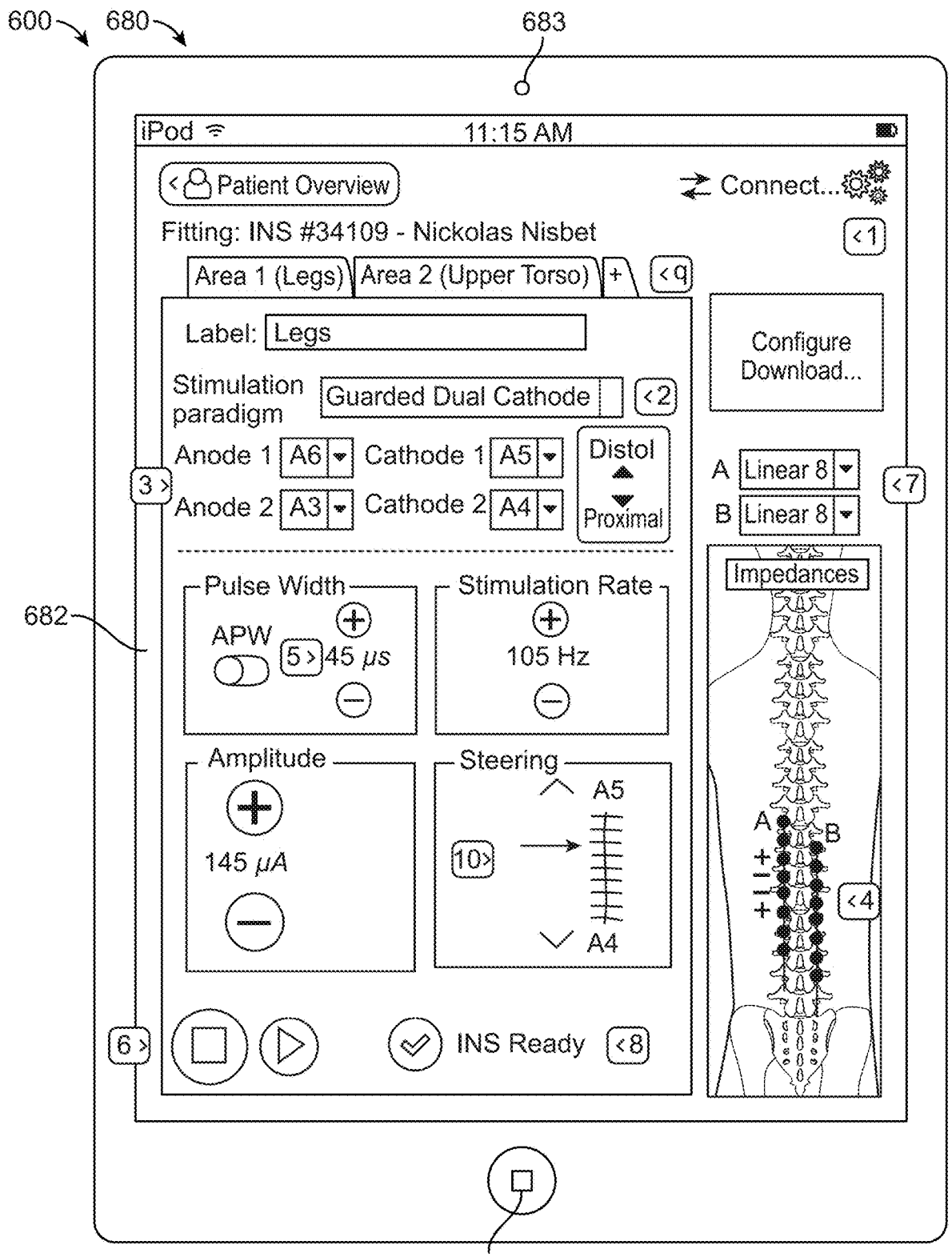
FIG. 17 is a user interface of a programmer for a stimulation apparatus, consistent with the present inventive concepts.

Referring to FIG. 17, a user interface of a programmer for a stimulation apparatus is illustrated, consistent with the present inventive concepts. Programmer 600 includes user interface 680 comprising one or more user interface components, such as one or more buttons 681, a touchscreen 682, and/or an audible alert element, speaker 683. Programmer 600 can be configured to communicate (e.g. via Bluetooth or other wireless or wired communication) with one or more components of apparatus 10, such as external device 500, implantable device 200, diagnostic assembly 91, trialing interface 80, and/or tool 60, each as described herein. In some embodiments, programmer 600 comprises a portable computer, such as a laptop, cell phone, or tablet. Programmer 600 can be configured to manipulate at least one of the following: stimulation parameters; impedance measurements; uploading of therapy log files; device parameters; patient session management; and combinations thereof.

In some embodiments, programmer 600 performs a scan identifying all available wireless communication devices, after which a user (e.g. a clinician) selects one or more of the available wireless devices in which to wirelessly communicate (e.g. to establish communication with one or more external devices 500 or other wireless devices of apparatus 10). Alternatively or additionally, one or more wireless devices of apparatus 10 (e.g. one or more external devices 500) is linked with a programmer 600 via a near field communication (NFC) and/or RFID protocol. For example, a user (e.g. clinician) can place programmer 600 and an external device 500 in proximity to each other, and via wireless information transfer (via NFC or RFID) a subsequent secure wireless communication pathway can be established (e.g. Bluetooth or Bluetooth Low Energy, BLE).

Touchscreen 682 can display stimulation and/or other apparatus 10 information, and/or allow user control (e.g. adjustment) of one or more components of external device 500 and/or implantable device 200. In some embodiments, touchscreen 682 displays (e.g. as shown in FIG. 17) and/or allows the adjustment of at least one of the following: patient name; stimulation parameters; anatomic representation of target tissue; pulse width; stimulation rate; amplitude; on/off controls; lead type selection; device status (i.e. stimulating or not stimulating); select and/or add target tissue areas; and combinations thereof.

Figure 37A:
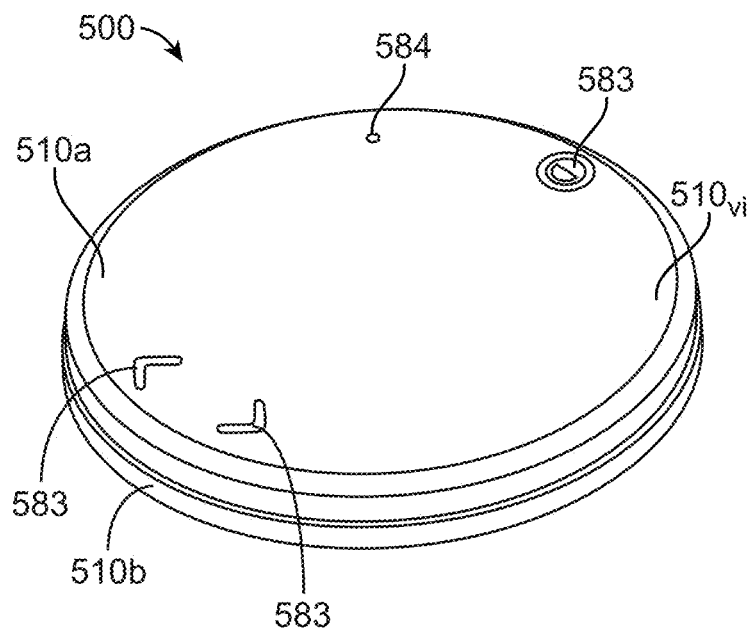
FIGS. 37A and 37B are top and bottom views of an embodiment of a housing of an implantable device, consistent with the present inventive concepts.
Figure 37B:
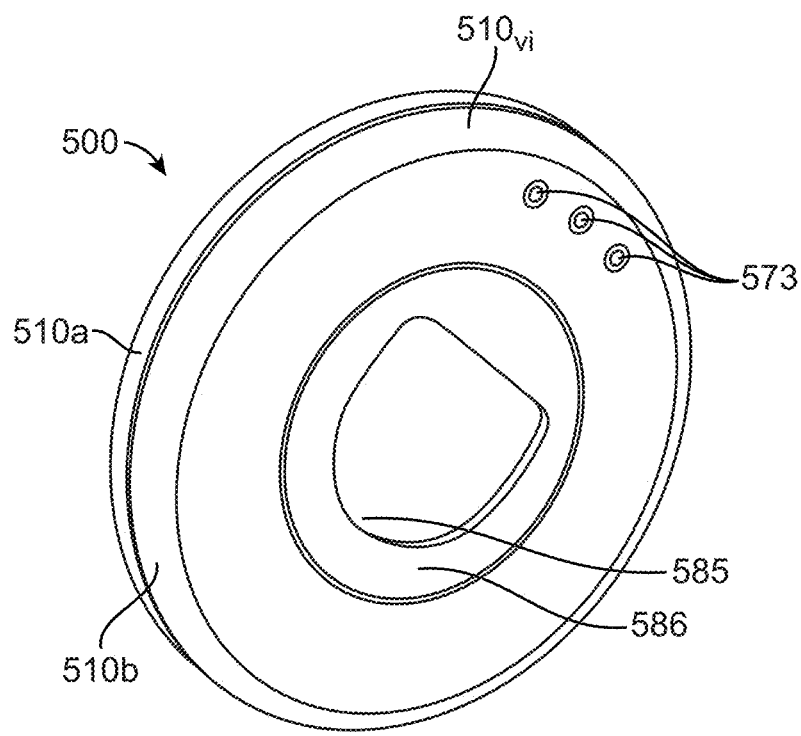

Referring to FIGS. 18A-F, pairs of perspective and sectional views of various configurations of an external device are illustrated, consistent with the present inventive concepts. External device 500 comprises a housing 510, that at least partially surrounds a power supply 570 and an antenna 540. Antenna 540 can comprise a loop configuration and include an opening 542. In some embodiments, housing 510 includes an opening 512. The diameter of opening 512 can be proportional to the diameter of opening 542 of antenna 540. In the embodiment shown in FIG. 18A, housing $510_i$ includes one or more user interface components, such as one or more buttons, buttons 583. Buttons 583 can be configured to allow a user to adjust the therapeutic parameters of apparatus 10. In the embodiment shown in FIG. 18B, housing $510_{ii}$ comprises a triangle-like geometry. In the embodiment shown in FIG. 18C, housing $510_{iii}$ comprises a toroidal geometry (e.g. a donut shape). External device 500 can include a toroidal power supply, power supply 570'. In the embodiment shown in FIG. 18D, housing $510_{iv}$ comprises at least four lobes, lobes 513a-d, which can be evenly spaced around the perimeter of antenna 540 as shown. Each of the lobes 513a-d can surround a discrete power supply, power supplies 570"a-d. In the embodiment shown in FIG. 18E, housing $510_v$ comprises at least three lobes, lobes 513a-c, which can be evenly spaced around the perimeter of antenna 540 as shown. Each of the lobes 513a-c surround a discrete power supply, power supplies 570"a-c. In the embodiment shown in FIG. 18F, housing $510_{vi}$ comprises a circular configuration, and can include a spacing element, spacer 511. Housing $510_{vi}$ can include one or more buttons 583. Antenna 540 and power supply 570 can be positioned (e.g. attached) on a top surface of spacer 511, as shown. In some embodiments, power supply 570 is constructed and arranged to fit within opening 542 of antenna 540, such that the diameter of power supply 570 is proportional to the diameter of opening 542. Referring now to FIG. 37A, in some embodiments, housing $510_{vi}$ includes at least one port, port 584 shown, configured for passage of gas out of and/or into housing $510_{vi}$, such as to provide pressure venting and/or transmission of sound. In some embodiments, housing $510_{vi}$ does not include port 584 (e.g. housing $510_{vi}$ does not include a vent or sound port). Housing $510_{vi}$ can comprise one or more user interface components, such as buttons 583 shown, which can be integrated into housing $510_{vi}$ (e.g. fabricated within the wall of housing 510vi). Buttons 583 can be configured to allow a user to adjust the therapeutic and/or other parameters of apparatus 10 (e.g. by transmitting a force or a signal to a switch or other electrical component internal to housing 510vi). Referring now to FIG. 37B, housing 510vi can include a charging orientation feature or marking, orientation guide 585, that can be integrated into housing 510vi (e.g. a recess or projection of housing 510vi) and/or simply marked on housing 510vi. Orientation guide 585 can comprise a depression or projection constructed and arranged to slidingly engage an external charger, such as tool $60_{ii}$ as described herebelow in reference to FIG. 31. Orientation guide 585 can provide for proper alignment and contact between charger contacts 573 of external device 500 and the charger contacts of tool 60ii. In some embodiments, housing 510vi further includes retention portion 586 that can be configured to secure an adhesive patch 68 (such as described herebelow in reference to FIGS. 20A-E, 21, and 22) and/or patient attachment device 70 (as described herebelow in reference to FIGS. 23, 24, 25A-C, and 26-26A) to housing 510vi. Retention portion 586 can comprise an adhesive, recess, projection, and/or other attachment element (e.g. Velcro) that can be configured to interface with adhesive patch 68 and/or patient attachment device 70. In some embodiments, retention portion 586 comprises adhesive patch 68 (avoiding the need for a separate adhesive patch).

Figure 33:
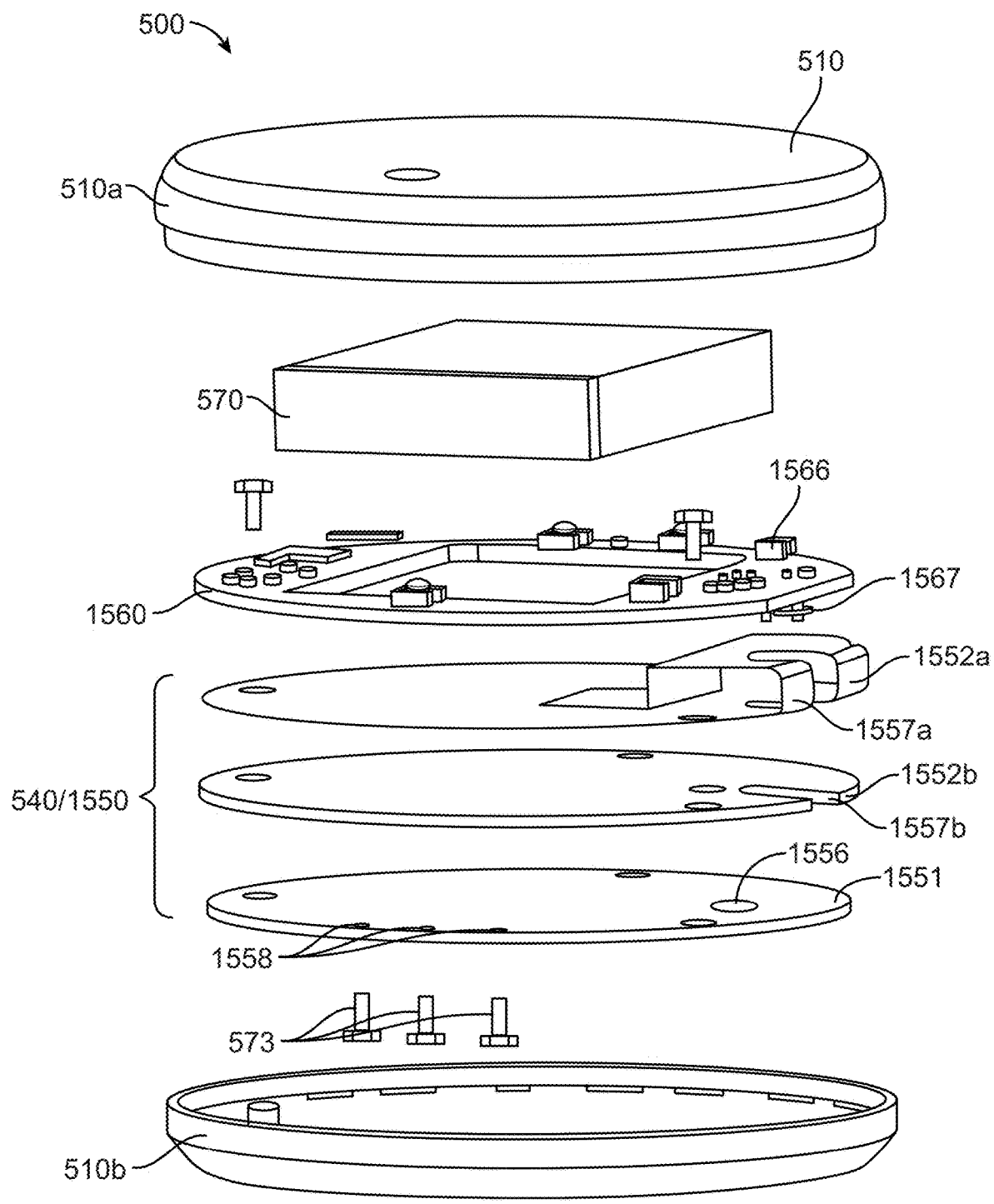
FIG. 33 is an exploded perspective view of an external device, consistent with the present inventive concepts.

Referring to FIG. 33, an exploded perspective view of an external device is illustrated, consistent with the present inventive concepts. External device 500 can be of similar construction and arrangement, and include similar components, as described hereabove in reference to FIG. 18F. External device 500 comprises a housing 510 which includes top portion 510a and bottom portion 510b. Top portion 510a and bottom portion 510b can be fixedly attached to each other via one or more attachment elements such as adhesive and/or via one or more attachment processes such as welding, such as to provide a sufficient seal to prevent a significant amount of contaminants from passing between the mating surfaces of top portion 510a and bottom portion 510b.

Housing 510, when assembled, surrounds multiple components and/or assemblies of external device 500, such as power supply 570 (e.g. including one or more batteries, capacitors, or other energy storage components) and substrate 1560. One or more electronic components 1566 can be attached to substrate 1560, and similarly electrically connected via one or more conductive traces of substrate 1560 (e.g. when substrate 1560 comprises one or more single or multiple layer printed circuit boards). Power supply 570 can be positioned (e.g. attached) on a top surface of substrate 1560 as shown, and can be electrically connected to one or more conductive traces of substrate 1560. Housing 510 can comprise a battery door, not shown, such as to allow replacement of power supply 570 (e.g. when power supply 570 is not rechargeable).

External device 500 comprises an external antenna 540 comprising antenna assembly 1550 including antenna 1551 and one or more shields 1552, such as shield 1552a and 1552b shown. In some embodiments, shield 1552a comprises a copper shield and shield 1552b comprises a ferrite shield. Shield 1552a is positioned on top of shield 1552b as shown. Shields 1552a and 1552b are positioned between antenna 1551 and one or more electronic components of external device 500 (e.g. electronic components 1566). In the configuration and layout of antenna assembly 1550 shown in FIG. 33, shields 1552a and 1552b are positioned such that antenna 1551 is shielded from deleterious effects of electronic components 1566 and other electromagnetic field generating elements positioned above the top side of either shields 1552a and 1552b, as described herein. Alternatively or additionally, this orientation improves transmissions (e.g. power and/or data transmissions) of antenna 1551 to implantable device 200, also as described herein.

Antenna assembly 1550 can be electrically connected to substrate 1560 (e.g. electrically connected to one or more electronic components 1566 of substrate 1560) via an electrical connector, connector 1567, a compressible connector positioned between substrate 1560 and antenna 1551. In alternative embodiments, connector 1567 comprises a flexible cable operably attached to antenna assembly 1550 and substrate 1560) and/or a clip connector connected to the sides of antenna 1551 and substrate 1560. In some embodiments, shields 1552*a* and 1552*b* can comprise a cutout 1557, such as cutouts 1557*a* and 1557*b*, and connector 1567 can pass through cutouts 1557*a* and 1557*b*.

In some embodiments, antenna assembly 1550 comprises electronic components 1556, such as one or more electronic components configured as a matching network for antenna 1551. In these embodiments, shield 1552 can comprise cutout 1557 shown, into which components 1556 can extend (e.g. to create clearance for components 1556 to allow shield 1552 to be positioned closer to antenna 1551) Additionally or alternatively, antenna 1551 can include one or more openings, openings 1558, constructed and arranged to slidingly receive one or more charging contacts 573 of external device 500.

As described herein, antenna 540 can be constructed on a PCB with a controlled spacing between the antenna 540 traces and a shielding layer. The spacing can be set by the thickness of the PCB itself. The shielding layer can be comprised of a ferrite with desirable properties at the frequency of interest. The shielding layer can also include a conductive layer, such as second layer comprising copper, such as to protect the other electronics of external device 500 from undesirable interference from antenna 540. External device 500 can additionally include shielding above the electronics to further protect sensitive circuits from interference (including magnetic components, such as inductors) and to mitigate EMI emitted from the electronics itself. This conductive shielding layer can be constructed on a thin flexible PCB that folds over the top of the electronics to create a shielding layer above and below the electronics.

Figure 19A:
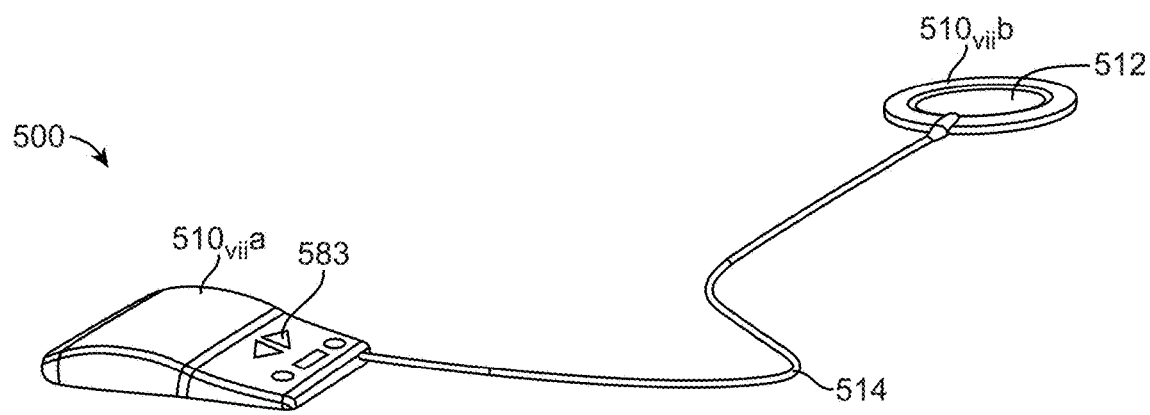
FIG. 19A is a perspective view of an embodiment of an external device, consistent with the present inventive concepts.
Figure 19B:
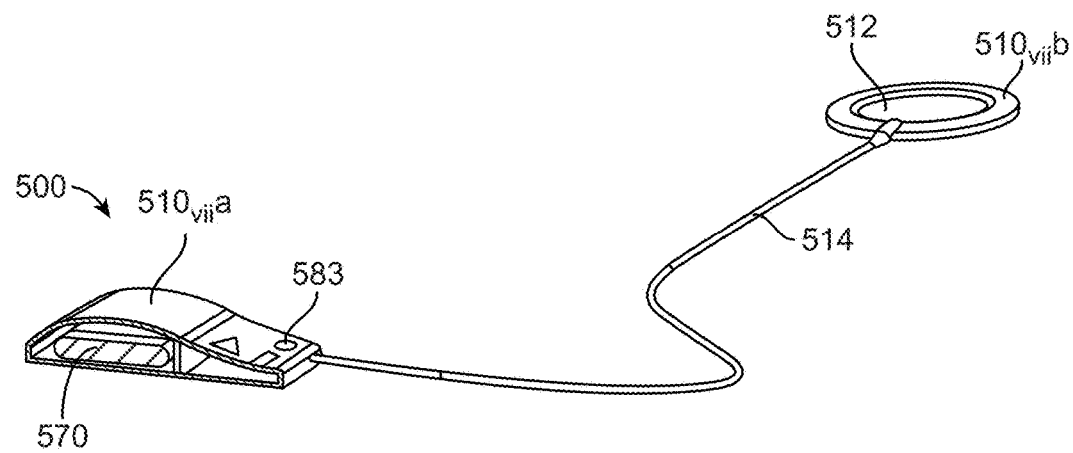
FIG. 19B is a sectional view of an embodiment of an external device, consistent with the present inventive concepts.

Referring to FIGS. 19A and 19B, a perspective view and a sectional view, respectively, of a configuration of an external device are illustrated, consistent with the present inventive concepts. External device 500 comprises a two-piece housing 510 that includes a first portion, housing 510$_{vii}$a, and a discrete second portion, housing 510$_{vii}$b. Housing 510$_{vii}$a at least partially surrounds a power supply, power supply 570, and housing 510$_{vii}$b at least partially surrounds one or more antennas, antenna 540, not shown. In some embodiments, external device 500 includes one or more user interface components, such as one or more buttons, buttons 583. Buttons 583 can be positioned on a surface (e.g. a top surface) of housing 510$_{vii}$a. In some embodiments, housing 510$_{vii}$a (e.g. one or more components within housing 510$_{vii}$a) is electrically connected to housing 510$_{vii}$b (e.g. electrically connected to one or more components within housing 510$_{vii}$b) via a conduit, conduit 514 (e.g. a conduit comprising one or more wires and/or other energy carrying filaments). In some embodiments, housing 510$_{vii}$b includes an opening, opening 512 as shown, wherein the diameter of opening 512 is proportional to the diameter of opening 542 of antenna 540.

Figure 20A:
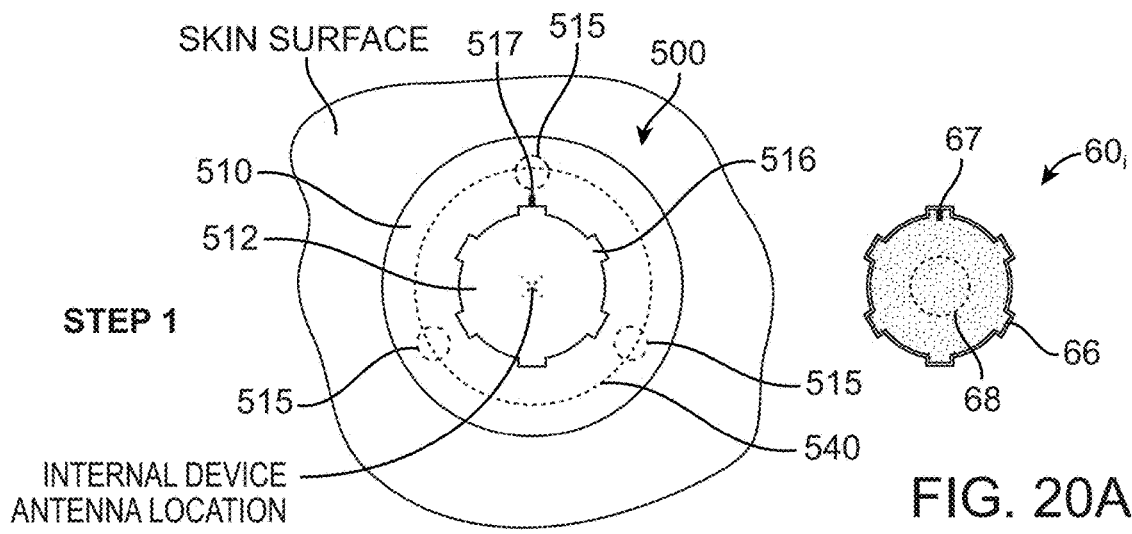
Figure 20B:
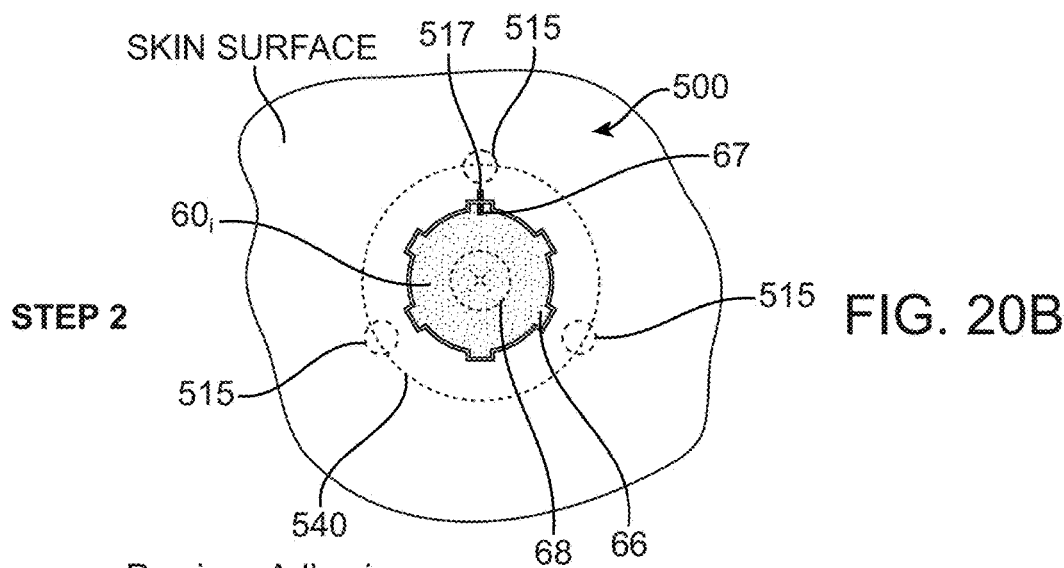
Figure 20C:
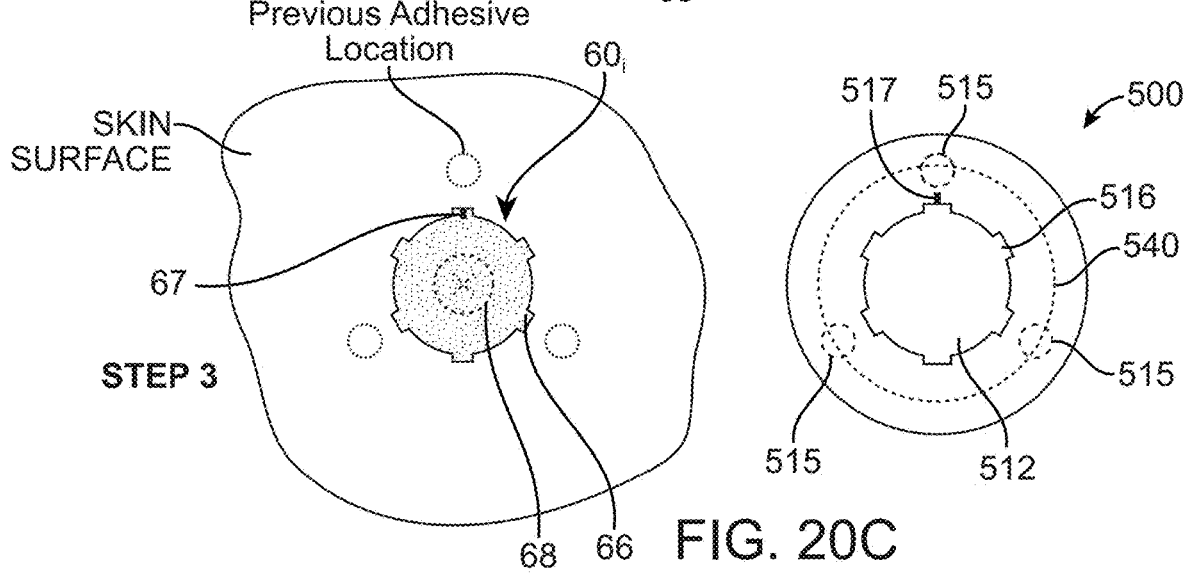

Referring to FIGS. 20A-E, a method for repositioning an external device on a patient's skin using a tool is illustrated, consistent with the present inventive concepts. Each external device 500 comprises a housing 510, an opening 512, and one or more adhesive patches 515. Each external device 500 further comprises one or more antennas, antenna 540, such as a loop antenna. In some embodiments, each external device 500 includes one or more registration cut-outs, cut-outs 516, and a registration marking 517. A tool 60$_i$ is included to aid in the placement of one or more external devices 500 (e.g. a subsequent placement of a new or recharged external device 500) at a location proximate an implanted implantable device 200. Tool 60$_i$ includes one or more registration projections, projections 66, and a registration marking, marking 67. Tool 60$_i$ can further include an adhesive patch, patch 68, for maintaining tool 60$_i$ on the patient's skin during an external device 500 replacement and/or recharging procedure as described herebelow. Referring now to FIG. 20A, Step 1 comprises positioning a first external device 500 antenna 540 in relation to an antenna 240 location of an implanted implantable device 200 ("X" mark as shown in FIGS. 20A-E), such that opening 512 (which geometrically correlates to the position of antenna 540) is positioned above (e.g. and surrounds) antenna 240, as shown. The first external device 500 is adhered to the patient's skin via the one or more patches 515. After placement of the first external device 500, a stimulation period (e.g. a trialing period and/or a period of therapy in which stimulation energy is delivered) can be initiated including implantable device 200 delivering stimulation to tissue based on energy received from the external device 500. After a time period of use (e.g. hours, days or weeks or other time period in which first external device 500 has a depleted power level or otherwise needs user attention), it may be desirable and/or necessary to reposition the first external device 500 (e.g. after a recharging procedure is performed) and/or replace first external device 500 (e.g. with a second external device 500 that is in a charged state). In those instances, Step 2 of FIG. 20B can be performed. Step 2 comprises positioning tool 60, within opening 512 such that marking 67 aligns with marking 517. Alignment of markings 67 and 517 further aligns projections 66 with cut-outs 516, such that projections 66 mate with cut-outs 516. Tool 60$_i$ is adhesively attached to the patient's skin via patch 68. Step 3 of FIG. 20C is then performed in which external device 500 is removed from the patient's skin while tool 60$_i$ remains on the patient's skin (e.g. due to patch 68). After removal from the patient's skin, the first external device 500 can be cleaned, and patches 515 can be cleaned and/or replaced. In Step 4 of FIG. 20D, the first external device 500 (e.g. after a recharging step comprising replacing and/or recharging power supply 570), or an already recharged second external device 500, is reattached to the patient's skin. In some embodiments, the external device 500 is aligned in a different orientation (e.g. using the alignment markings provided by tool 60$_i$) such that new locations on skin are contacted by patches 515 (e.g. to reduce skin irritation from prolonged use of adhesive), however antenna 540 of the replaced external device 500 is positioned to be in sufficient alignment (e.g. concentrically aligned) and proximity to antenna 240 of implantable device 200. After placement of the external device 500 in Step 4, Step 5 of FIG. 20E is performed in which tool 60$_i$ is removed from external device 500, and a stimulation period can be re-initiated including implantable device 200 delivering stimulation to tissue based on energy received from the external device 500.

Steps 2 through 5 can be repeated (e.g. each time an external device 500 is determined to be replaced), such as to routinely change the location of patches 515 on the patient's skin, while maintaining sufficient alignment and proximity between antenna 540 of external device 500 and antenna 240 of implantable device 200.

In some embodiments, one or more components of external device 500 (e.g. housing 510, adhesive patches 515) and/or one or more components of patient attachment device 70 can be configured to prevent adversely affecting portions of the skin contacted by an external device 500 and/or patient attachment device 70. Alternatively or additionally, these or other components of external device 500 can be configured to clean and/or to promote healing of one or more skin-contacting portions. For example, housing 510, adhesive patches 515, and/or another component of external device 500 (e.g. a patient attachment device as described herein) can include an agent (e.g. a coating or other included agent) selected from the group consisting of: a bactericidal agent; an anti-fungal agent; and combinations thereof.

Figure 21:
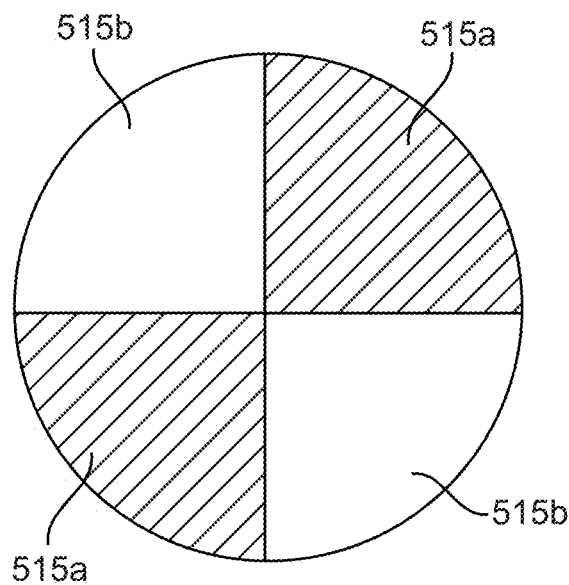
FIG. 21 is a bottom view of an adhesive patch arrangement for an external device, consistent with the present inventive concepts.

Referring to FIG. 21, a bottom view of an adhesive patch arrangement for an external device is illustrated, consistent with the present inventive concepts. Housing 510 of external device 500 can comprise one or more adhesive patches, 515. Patches 515 can be configured to be removed from housing 510 (e.g. after use). In some embodiments, a single patch 515 is positioned on the bottom of a circular housing 510 (such as circular housing $510_v$ shown in FIG. 18F). Patch 515 can comprise at least two adhesive areas, areas 515a and 515b, and each area can include one or more removable liners (not shown) such as to prevent areas 515a and/or 515b (e.g. at least area 515b) from drying out prior to attachment of external device 500 to the patient's skin, and/or while one area 515a,b is attached to the patient's skin while the other area 515a,b is not. In some embodiments, a user (e.g. the patient) removes the removable liner from area 515a to expose the adhesive for attachment of external device 500 to the patient's skin. When the user later detaches external device 500 (e.g. to clean the device or the underlying skin), the user can remove the removable liner from area 515b to expose the adhesive underneath, such that external device 500 can then be reattached to the patient's skin using new adhesive locations (e.g. to reduce skin irritation from prolonged use of adhesive in the same area). In some embodiments, a first patch 515 is replaced with a new, second patch 515 (e.g. by removing first patch 515 from housing 510) after both areas 515a,b are utilized for adhesive attachment of external device 500 to the patient's skin.

Figure 22:
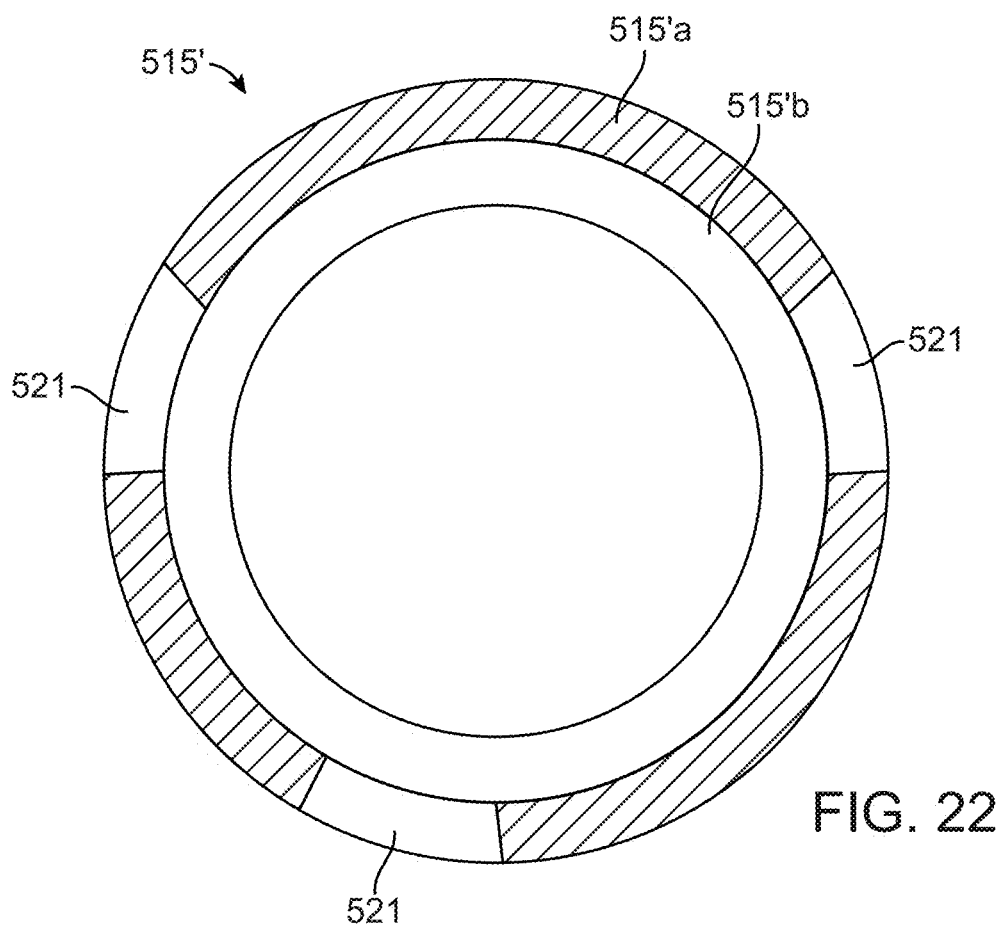
FIG. 22 is a bottom view of a repositioning tool for an external device, consistent with the present inventive concepts.

Referring to FIG. 22, a bottom view of a repositioning tool for an external device is illustrated, consistent with the present inventive concepts. Housing 510 of external device 500 can comprise one or more adhesive patches, 515', in the form of rings as shown. Patches 515' can be configured to be removed from housing 510 (e.g. after use). In some embodiments, a single patch 515' is positioned on the bottom of a circular housing 510 (such as circular housing 510 shown in FIG. 18F). Patch 515' can comprise at least two adhesive ring-shaped areas, areas 515'a and 515'b, and each area can include one or more removable liners (not shown) such as to prevent areas 515'a,b from drying out prior to attachment of external device 500 to the patient's skin, and/or while one area 515'a,b is attached to the patient's skin while the other area 515'a,b is not. In some embodiments, a user (e.g. the patient) removes the removable liner from area 515'a to expose the adhesive for attachment of external device 500 to the patient's skin. When the user later detaches external device 500 (e.g. to clean the device or the underlying skin), the user can remove the removable liner from area 515'b to expose the adhesive underneath, such that external device 500 can then be reattached to the patient's skin using new adhesive locations (e.g. to reduce skin irritation from prolonged use of adhesive in the same area). In some embodiments, a first patch 515' is replaced with a new, second patch 515' (e.g. by removing first patch 515 from housing 510) after both areas 515'a,b are utilized for adhesive attachment of external device 500 to the patient's skin. In some embodiments, housing 510 includes a single ring, patch 515'a, which is used to attach external device 500 to the patient's skin for a first time period. After the first time period has elapsed, a second ring, patch 515'b is attached to patch 515'a and/or housing 510, via attachment elements 521 shown (e.g. adhesive), such that patch 515'b circumferentially surrounds patch 515'a. In these embodiments, second attaching patch 515' can be added without removing external device 500 from the patient's skin, thus avoiding having to realign external device 500 with the associated implanted implantable device 200.

Figure 23:
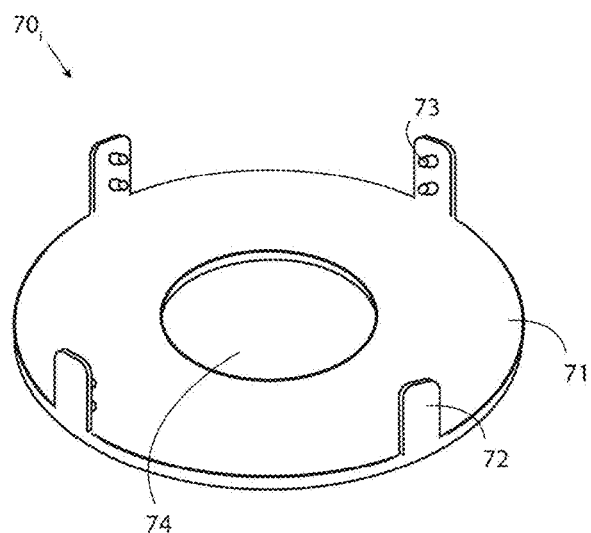
FIG. 23 is a perspective view of an embodiment of a patient attachment device for attaching an external device to a patient, consistent with the present inventive concepts.

Referring to FIG. 23, a perspective view of a patient attachment device for attaching an external device to a patient is illustrated, consistent with the present inventive concepts. Patient attachment device $70_i$ can be configured to removably attach to external device 500, such as to removably position external device 500 on or near the patient's skin at a location proximate the implanted location of an implantable device 200. Patient attachment device $70_i$ comprises a housing 71 that can include one or more projections, projections 72. Projections 72 can be configured to frictionally engage external device 500. In some embodiments, patient attachment device $70_i$ includes one or more engagement elements 73. Engagement elements 73 can be fixedly attached to projections 72, such as to increase friction between external device 500 and projections 72. Housing 71 can comprise a shape that approximates the shape of at least a portion of an external device 500. For example, a contour of housing 71 can approximate a contour of a mating surface of external device 500 (e.g. a surface of a portion of housing 510 of external device 500). Additionally or alternatively, the "footprint" of attachment device $70_i$ (i.e. perimeter shape) can match and/or approximate the "footprint" of housing 510 of external device 500 (e.g. a circle). Housing 71 can include opening 74 that can be positioned near the center of patient attachment device $70_i$, such as to aid the user in positioning patient attachment device $70_i$ over implantable device 200. For example, the user can palpate through opening 74 to locate implantable device 200 beneath the tissue and position patient attachment device $70_i$ accordingly. Patient attachment device $70_i$ can include an attachment element comprising an adhesive patch. In some embodiments, patient attachment device $70_i$ includes an attachment element as described hereabove in reference to patient attachment device 70 of FIG. 1. In some embodiments, a securing filament is included, not shown, but such as lanyard 79 described herebelow in reference to FIG. 24.

Figure 24:
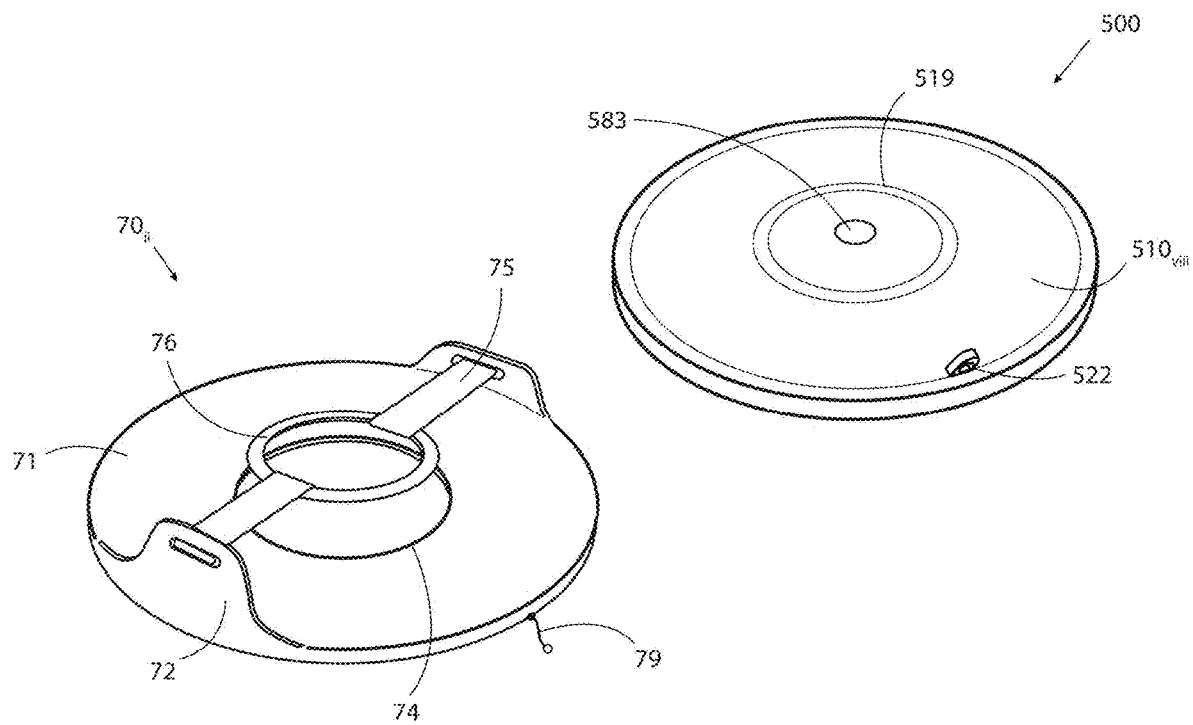
FIG. 24 are perspective views of an embodiment of a patient attachment device for attaching an external device to a patient and the external device, consistent with the present inventive concepts.

Referring to FIG. 24, a perspective view of a patient attachment device for attaching an external device to a patient and the external device is illustrated, consistent with the present inventive concepts. Patient attachment device $70_{ii}$ can be configured to removably attach to external device 500. Patient attachment device $70_{ii}$ comprises a housing 71 that can include one or more projections, projections 72, and a retention element, strap 75. Strap 75 (e.g. an elastic or Velcro band) can be constructed and arranged to be tightened by a user and/or comprise an elastic material. In some embodiments, one or more portions of strap 75 are removably attached to a portion of housing 71, such as with a connector. In the embodiment shown, strap 75 attaches to housing 71 at projections 72. Alternatively, strap 75 attaches to another portion of housing 71. Strap 75 may comprise two or more fixation points, such as a strap with three portions configured to attach to three fixation points of housing 71. Strap 75 can further include an alignment element 76, such as a ring as shown. In some embodiments, housing 510 is configured as housing $510_{viii}$ shown, which includes a recessed portion, groove 519.

Alignment element 76 can be constructed and arranged to approximate the shape of groove 519, such that groove 519 aligns external device 500 with alignment element 76 by slidingly receiving alignment element 76. In some embodiments, one or more buttons 583 are positioned within the perimeter of groove 519, such as a single power button shown. Housing 71 can include opening 74 that can be positioned near the center of patient attachment device $70_{ii}$, such as to aid the user in positioning (e.g. via palpation) patient attachment device $70_{ii}$ over implantable device 200, as described hereabove in reference to FIG. 23. Patient attachment device 70i can include an attachment element comprising an adhesive patch. In some embodiments, patient attachment device 70i can include an attachment element as described hereabove in reference to patient attachment device 70 of FIG. 1. In some embodiments, a securing filament, lanyard 79 shown, provides a connection between external device 500 and patient attachment device 70i, such that if external device 500 accidentally is removed from or falls out of patient attachment device 70i, travel of external device 500 is limited by the length of lanyard 79 (e.g. such that external device 500 isn't lost and/or doesn't hit the ground).

Figure 25B:
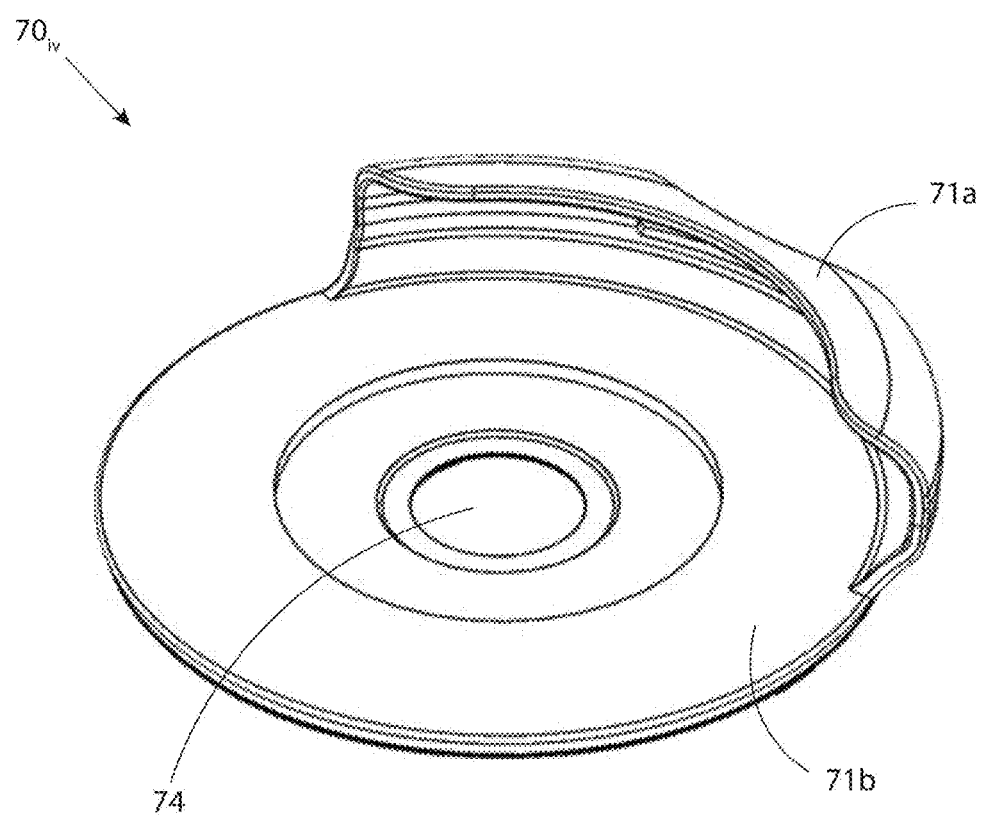
FIG. 25B is a perspective view of an embodiment of a patient attachment device for attaching an external device to a patient and the external device, consistent with the present inventive concepts.

Referring to FIG. 25, a perspective view of a patient attachment device for attaching an external device to a patient is illustrated, consistent with the present inventive concepts. Referring additionally to FIG. 25A, a sectional view of the patient attachment device of FIG. 25 is illustrated. Patient attachment device $70_{iii}$ can be configured to removably attach to external device 500. Patient attachment device $70_{iii}$ comprises a housing 71 that can include at least two portions, portions 71a and 71b, such that portions 71a,b form a "clip-like" structure as shown. Housing 71 can slidingly receive external device 500. In some embodiments, housing 510 is configured as housing $510_{ix}$ shown, which includes a projection, projection 518. Portion 71a can include an opening 77 constructed and arranged to approximate the shape of projection 518, such that projection 518 aligns external device 500 with opening 77 by slidingly receiving opening 77. In some embodiments, portion 71a does not extend (or minimally extends) over the top of external device 500, such that portion 71a is shorter than the width of external device 500, such as is described hereabove in reference to FIG. 25B. Portion 71b can include opening 74 that can be positioned near the center of patient attachment device $70_{iii}$, such as to aid the user in positioning patient attachment device $70_{iii}$ over implantable device 200, such as is described hereabove in reference to FIG. 23. Patient attachment device $70_{iii}$ can include an attachment element comprising an adhesive patch. In some embodiments, patient attachment device $70_{iii}$ can include an attachment element as described hereabove in reference to patient attachment device 70 of FIG. 1. In some embodiments, a securing filament is included, not shown, but such as lanyard 79 described herebelow in reference to FIG. 24.

Referring now to FIG. 25B, a perspective view of a patient attachment device for attaching an external device to a patient is illustrated, consistent with the present inventive concepts. Patient attachment device $70_{iv}$ can be configured to removably attach to external device 500. Patient attachment device $70_{iv}$ can be of similar construction and arrangement to patient attachment device $70_{iii}$. Portion 71a extends minimally over external device 500, such as when portion 71a covers over less than 10% of the top surface area of external device 500. In some embodiments, the transition between portions 71a,b conforms to, and cradles, external device 500.

Referring to FIG. 26, a perspective view of a patient attachment device for an external device is illustrated, consistent with the present inventive concepts. Referring additionally to FIG. 26A, a sectional view of the patient attachment device of FIG. 26 is illustrated. Patient attachment device 70N can be configured to removably attach to external device 500. Patient attachment device 70N comprises a housing 71 that can include one or more clips, clip 78, such as four clips as shown. Clips 78 can be integral to housing 71. In some embodiments, clips 78 are configured such that external device 500 is pressed (e.g. pressed by the patient or other user) against housing $71_{ii}$, causing clips 78 to transition from a first position, $P_1$, to a second position, $P_2$, such as to frictionally engage to external device 500. Housing 716, can include opening 74 that can be positioned near the center of patient attachment device 70N, such as to aid the user in positioning patient attachment device $70_{iv}$ over implantable device 200, as described hereabove in reference to FIG. 23. Patient attachment device 70i can include an attachment element comprising an adhesive patch. In some embodiments, patient attachment device 70i can include an attachment element as described hereabove in reference to patient attachment device 70 of FIG. 1. In some embodiments, a securing filament is included, not shown, but such as lanyard 79 described herebelow in reference to FIG. 24.

Referring to FIG. 27, a perspective view of a lead anchor is illustrated, consistent with the present inventive concepts. Lead anchor $710_i$ comprises a housing 711, conduits 715a and 715b, and a tortuous element 716, which define a tortuous path TP. Housing 711 can include one or more anchor points 712a and 712b, as shown, such that lead anchor $710_i$ can be sutured to the patient's tissue. Lead anchor $710_i$ is constructed and arranged to slidingly receive a lead 265 via the tortuous path TP, such as when lead 265 is inserted into conduit 715a, through tortuous element 716, and out conduit 715b. In some embodiments, housing $711_i$ is configured to flex or otherwise resiliently deform to align tortuous element 716 with conduits 715a,b to ease insertion of lead 265. After the insertion of lead 265, lead anchor $710_i$ takes the shape shown in FIG. 27, and captures (e.g. frictionally engages) lead 265.

Referring to FIGS. 28A and 28B, a transparent perspective and perspective views, respectively, of a lead anchor is illustrated, consistent with the present inventive concepts. Lead anchor $710_{ii}$ comprises a housing 711, a lumen 717, and a covering 719. Housing 711 can further include one or more securing elements configured to frictionally engage an inserted lead 265, projections 718, as shown in FIG. 28B in which covering 719 has been removed for illustrative clarity. Housing 711 can comprise a material selected from the group consisting of: thermoplastic, such as thermoplastic elastomer, thermoplastic urethane; thermoset (silicone); metal, such as stamped, formed, or machined metal and combinations thereof. Covering 719 can comprise a material with a soft durometer and/or include a material selected from the group consisting of: thermoplastic elastomer; thermoplastic urethane; thermoset (silicone); and combinations thereof. In some embodiments, covering 719 comprises a tapered end, as shown. Housing 711 can be resiliently compressed to increase the opening within housing 711 (e.g. a compressing force F as shown that causes projections 718 to separate) such that lead 265 can pass through lumen 717. After the insertion of lead 265, housing 711 can be released (no longer under compression) to allow projections 718 to frictionally engage lead 265 and prevent translation of lead 265. Anchor $710_{ii}$ can be affixed to the patient's tissue via sutures wrapped around and/or through the external surface housing 711 and/or covering 719 (e.g. when housing 711 and/or covering 719 includes grooves, bumps, eyelets, and/or other features for suture retention).

Figure 29:
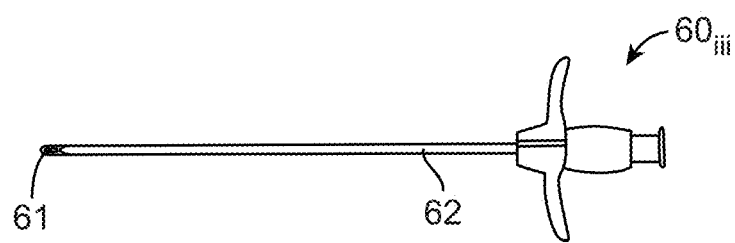
FIG. 29 is a perspective view of an embodiment of an insertion tool for an implantable lead of an implantable device, consistent with the present inventive concepts.

Referring to FIG. 29, an insertion tool for a lead of an implantable device is illustrated, consistent with the present inventive concepts. Insertion tool $60_{iii}$ comprises needle 61 that includes a removable sheath, sheath 62. Sheath 62 can be configured to be separated (e.g. peeled) from needle 61. Needle 61 creates access to the epidural space of the patient, and includes a female luer fitting at its proximal end to allow for attachment to a syringe (e.g. for confirming epidural access has been obtained). Needle 61 can then be removed, leaving the sheath 62 in place (providing access to the epidural space). A lead 265 can then be passed through sheath 62 to the desired location within the epidural space. Sheath 62 is then split and peeled away from the lead 265 allowing for placement of an integrated device, such as shown in FIG. 2D.

Figure 30:
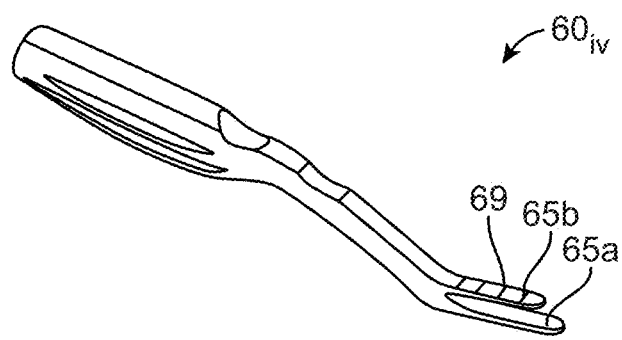
FIG. 30 is a perspective view of an embodiment of an insertion tool for an implantable device, consistent with the present inventive concepts.

Referring to FIG. 30, an insertion tool for an implantable device is illustrated, consistent with the present inventive concepts. Insertion tool $60_{iv}$ is constructed and arranged to insert a portion of an implantable device 200 into a portion of a patient's tissue. Insertion tool $60_{iv}$ includes a bottom member 65a that is utilized for blunt tissue dissection in order to make space (e.g. create a tunnel in tissue) and leave a subcutaneous pocket for the implantable device 200. Insertion tool $60_{iv}$ includes a top member 65b that is maintained on top of the skin and serves as a means for controlling the depth of the tunnel and pocket. Markings, lines 69, on the top member can be spaced at a known interval so that a measure of the length of the created tunnel can be performed. The length of the bottom member 65a is slightly longer than the top member 65b so that bottom member 65a can be introduced perpendicular to the skin, and then turned parallel for tunneling. The two notches on a handle portion of insertion tool 60N allow for various hand positions for better gripping and/or fine adjustment. In some embodiments, bottom member 65a can include a variety of shapes, depending on the size and shape of implantable device 200 and/or its method of insertion into the tissue. For example, the tip of tool $60_{iv}$ can be matched to, undersized or oversized to the implantable device 200 size, such as to vary the interference fit between the implant and the tissue (e.g. the tip of tool $60_{iv}$ can be undersized to potentially avoid need for implantable device 200 anchoring).

Figure 34A:
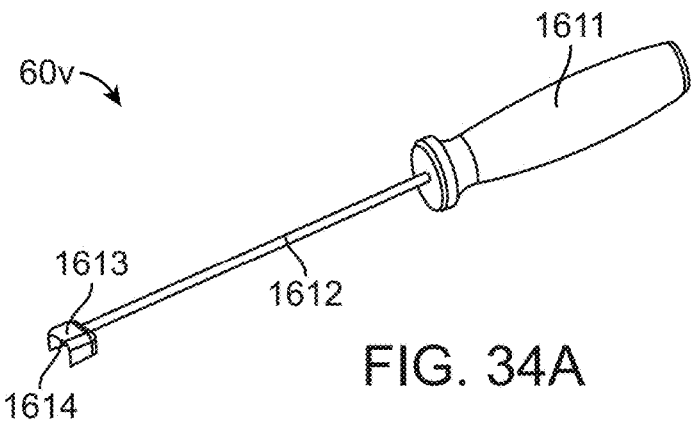
FIGS. 34A-34B are perspective views of an embodiment of an insertion tool for an implantable device, consistent with the present inventive concepts.
Figure 34B:
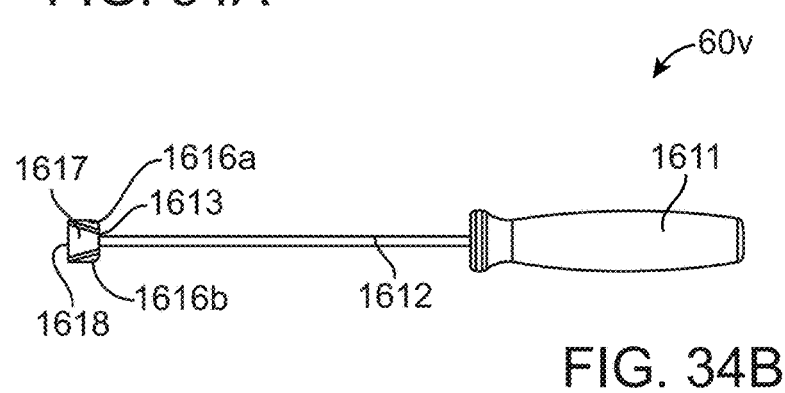

Referring to FIGS. 34A-D, an insertion tool for an implantable device illustrated, consistent with the present inventive concepts. Insertion tool $60_v$ is constructed and arranged to insert all or a portion of an implantable device 200 into patient's tissue. Referring now to FIGS. 34A and 34B, insertion tool $60_v$, that includes a handle 1611, a shaft 1612, and a distal end 1613. Distal end 1613 can comprise a housing 1614 that has at least two projections 1616, such as projections 1616a and 1616b shown. In some embodiments, projections 1616a and 1616b extend towards a median line of tool $60_v$. Projections 1616a and 1616b can be constructed and arranged to form channel 1617 with a distal end opening 1618. Channel 1617 can be configured, via opening 1618, to slidingly receive a portion of housing 210 of implantable device 200, such that projections 1616 engage opposite edges of housing 210.

Figure 34C:
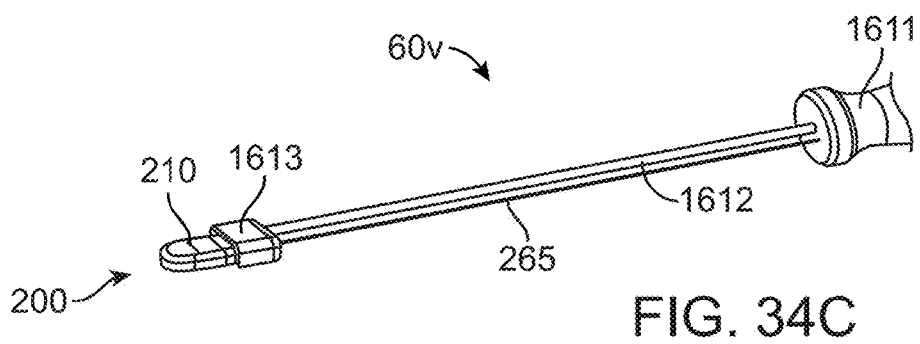
FIG. 34C is a perspective view of distal portion of an embodiment of an insertion tool for an implantable device, consistent with the present inventive concepts.
Figure 34D:
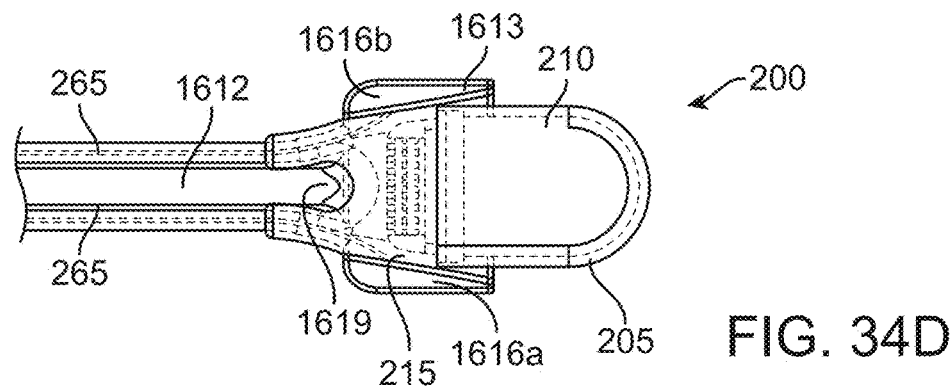
FIG. 34D is a perspective view of a distal end of an embodiment of an insertion tool for an implantable device, consistent with the present inventive concepts.

Referring now to FIGS. 34C and 34D, housing 1614 can further include a proximal end with a proximal end opening 1619 that can be configured to slidingly receive a portion of housing 210 including one or more pre-attached leads 265, such that the one or more leads 265 extend beyond the proximal end of housing 1614 and along shaft 1612. Alternatively, one or more leads 265 can be attachable to housing 210, as described herein. Tool $60_v$ can be constructed and arrange to engage sealing element 205, such as to apply a force without imparting significant stress between connector 215 and connected components internal to housing 210.

Figure 35A:
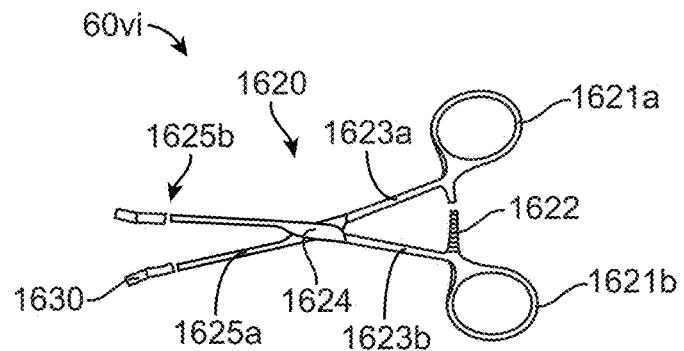
FIG. 35A is a perspective view of an embodiment of an insertion tool for an implantable device, consistent with the present inventive concepts.
Figure 35B:
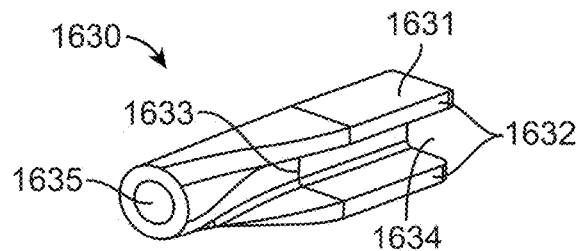
FIG. 35B is a perspective view of an adaptor of an insertion tool for an implantable device, consistent with the present inventive concepts.
Figure 35C:
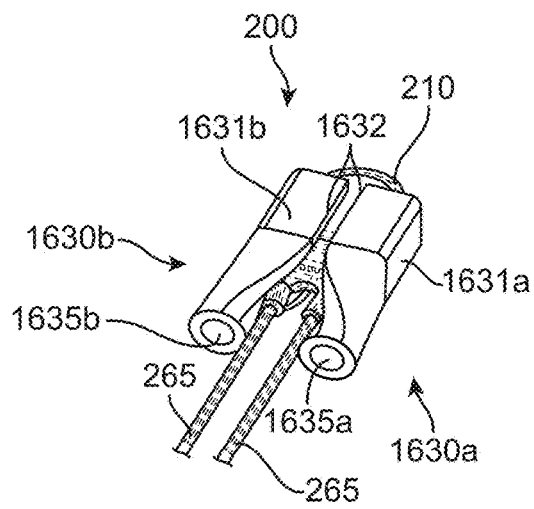
FIGS. 35C and 35D are perspective views of an adaptor slidingly receiving a portion of an implantable device comprising an implantable lead, consistent with the present inventive concepts.

Referring to FIGS. 35A-C, an insertion tool for an implantable device is illustrated, consistent with the present inventive concepts. Insertion tool $60_{vi}$ is constructed and arranged to insert all or a portion of an implantable device 200 into patient's tissue. Referring now to FIG. 35A, insertion tool $60_{vi}$ comprises a clamp 1620 (such as a clamp similar to a DeBakey vascular clamp) and at least one adaptor 1630. Clamp 1620 includes finger receiving rings 1621a and 1621b, latching mechanism 1622, arms 1623a and 1623b, hinge 1624, and jaws 1625a and 1625b, all as shown. Referring now to FIG. 35B, adaptor 1630 comprises a housing 1631 that includes at least two projections 1632 that are positioned parallel to the other. Projections 1632 create a channel 1633 with a distal end opening 1634. Channel 1633 can be configured to slidingly receive a portion of housing 210 of implantable device 200 via opening 1634, such that projections 1632 engage opposite edges of housing 210.

Housing 1631 can further include a proximal end with a hole 1635 that can be configured to slidingly receive either jaw 1625a or 1625b of clamp 1620. In some embodiments, insertion tool $60_{vi}$ includes at least two adaptors 1630, adaptor 1630a and 1630b shown, such that adaptor 1630a slidingly receives jaw 1625a and adaptor 1630b slidingly receives jaw 1625b.

Figure 35D:
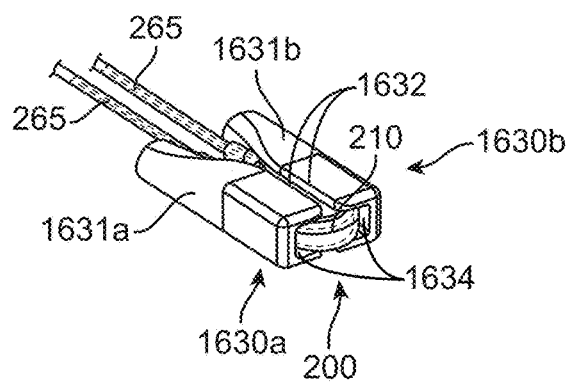

Referring now to FIGS. 35C and 35D, adaptor 1630a slidingly receives jaw 1625a and adaptor 1630b slidingly receives jaw 1625b. Adaptors 1630a and 1630b are positioned such that channel 1633 of each adaptor 1630 faces the other (e.g. adaptors 1630a and 1630b are rotated such that channel 1633 of each adaptor is facing a median line of clamp 1620). Channels 1633 slidingly receive a portion of housing 210, such that one or more attached leads 265 of implantable device 200 extend beyond the proximal ends of adaptors 1630a and 1630b.

Figure 36A:
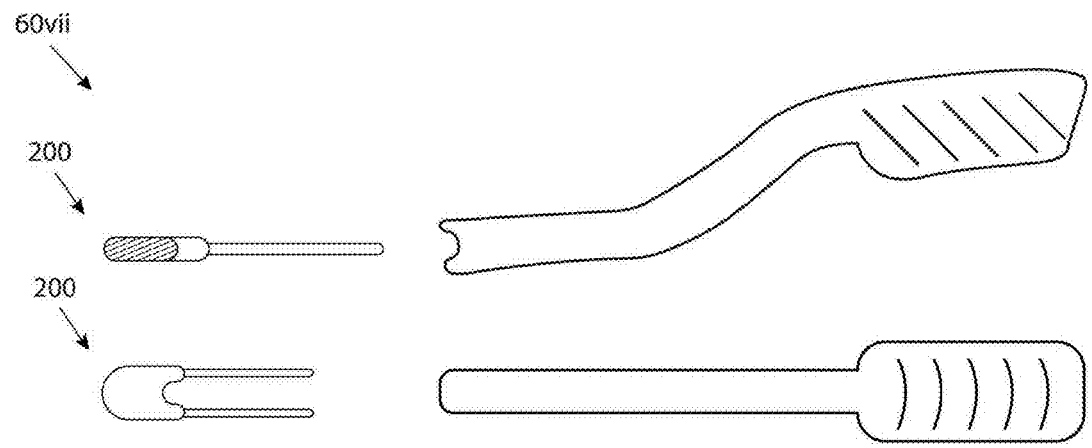
FIGS. 36A and 36B are side and perspective views of an embodiment of an insertion tool for an implantable device, consistent with the present inventive concepts.
Figure 36B:
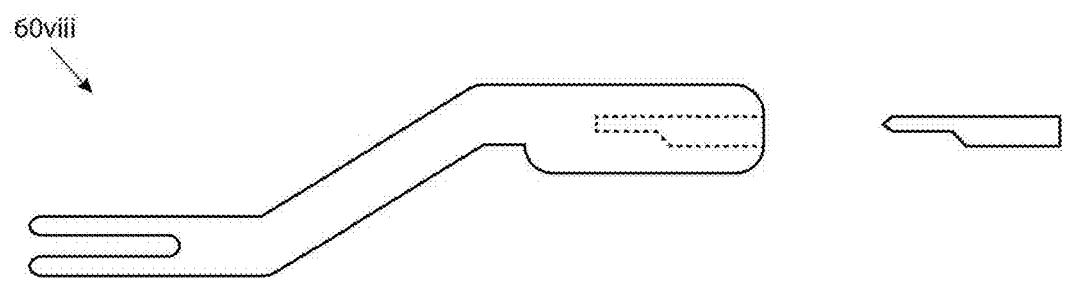

Referring to FIG. 36A, an insertion tool for an implantable device is illustrated, consistent with the present inventive concepts. Insertion tool $60_{vii}$ is constructed and arranged to insert all or a portion of an implantable device 200 into patient's tissue. Tool $60_{vii}$ features a tip geometry that contours to the front area of implantable device 200 and can be used to guide implantable device 200 down the length of a (previously created) tunnel in tissue of the patient. The tip geometry can be C-shaped, and can surround implantable device 200 so as to avoid damaging one or more portions of implantable device 200 (e.g. connector 215 and/or sealing element 205 described herein, such as to avoid damage to connecting wires within housing 210). Referring now to FIG. 36B, tool $60_{vii}$ is configured two provide two functions: to tunnel subcutaneously a pocket in tissue for later implant placement; and to insert implantable device 200 into the subcutaneous pocket, such as with a tool portion, as shown, included in the handle of tool $60_{vii}$. The nested tool can have a similar tip geometry to tool $60_{vii}$ described hereabove in reference to FIG. 36A. The compact nature of the dual function tool $60_{viii}$ is desirable for minimizing the overall volume necessary for implantable device 200 and/or tool $60_{viii}$ transport and packaging.

Figure 31:
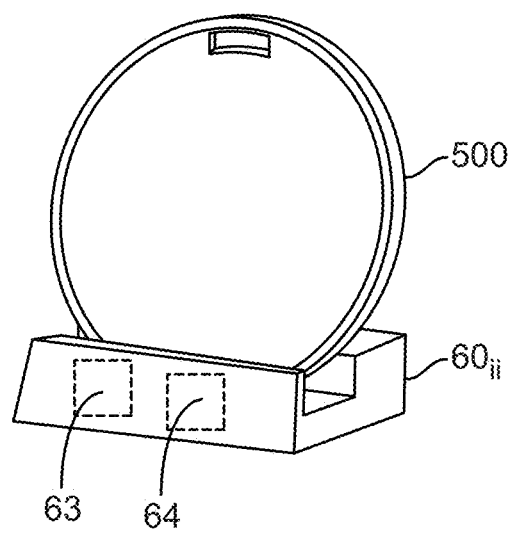
FIG. 31 is a perspective view of an external charger for an external device, consistent with the present inventive concepts.

Referring to FIG. 31, an external charger for an external device is illustrated, consistent with the present inventive concepts. One or more external devices 500 can comprise an integrated power supply 570 comprising one or more rechargeable elements, such as a rechargeable battery. Each external device 500 can be configured to engage a charging device, tool $60_{ii}$, such that power supply 570 can be recharged. In some embodiments, tool $60_{ii}$ comprises a cradle-configuration as shown in FIG. 31, such that charging contacts (e.g. contacts 573 described hereabove in reference to FIG. 16) of external device 500 are aligned with mating charging contacts of tool $60_{ii}$. The charging contacts of tool $60_{ii}$ can comprise a standard micro or mini USB port. Tool $60_{ii}$ can be configured to attach to standard wall AC power, and/or it can include an integral battery (e.g. a replaceable or rechargeable battery).

In some embodiments, tool 6011 comprises a memory module 63 which includes electronic memory and circuitry configured to record and process information related to charge and/or discharge cycles of one or more external devices 500, as well as record other characteristics, each of which can be used to predict power supply 570 condition, expected longevity and the like, which can be presented to a user or manufacturer of external device 500 (e.g. via a user interface of tool $60_{ii}$, not shown, or other user interface of apparatus 10.

In some embodiments, tool $60_{ii}$ comprises an interface module 64 which is configured to interface with a communication network via a wired or wireless communication, such as a communication network selected from the group consisting of: cellular service; the Internet; LAN; WAN; computer network; and combinations thereof. In these embodiments, communication with an external device 500 attached to tool $60_{ii}$ can be performed remotely, such as by a clinician of the patient or a manufacturer of external device 500. The communication can include downloading of apparatus 10 use information, and/or programming of external device 500 or other apparatus 10 component.

Figure 53A:
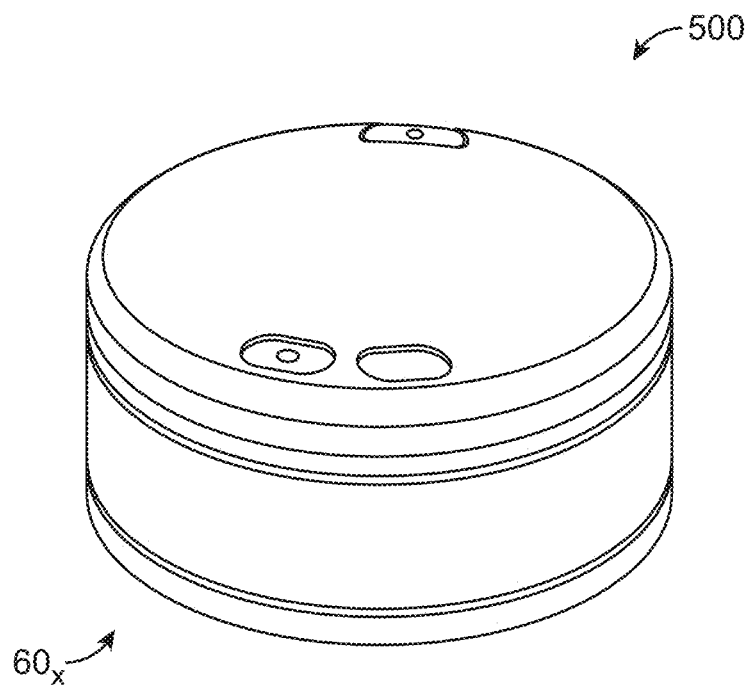
FIGS. 53A and 53B are perspective and cross-sectional views of an embodiment of an external charger for an external device, consistent with the present inventive concepts.
Figure 53B:
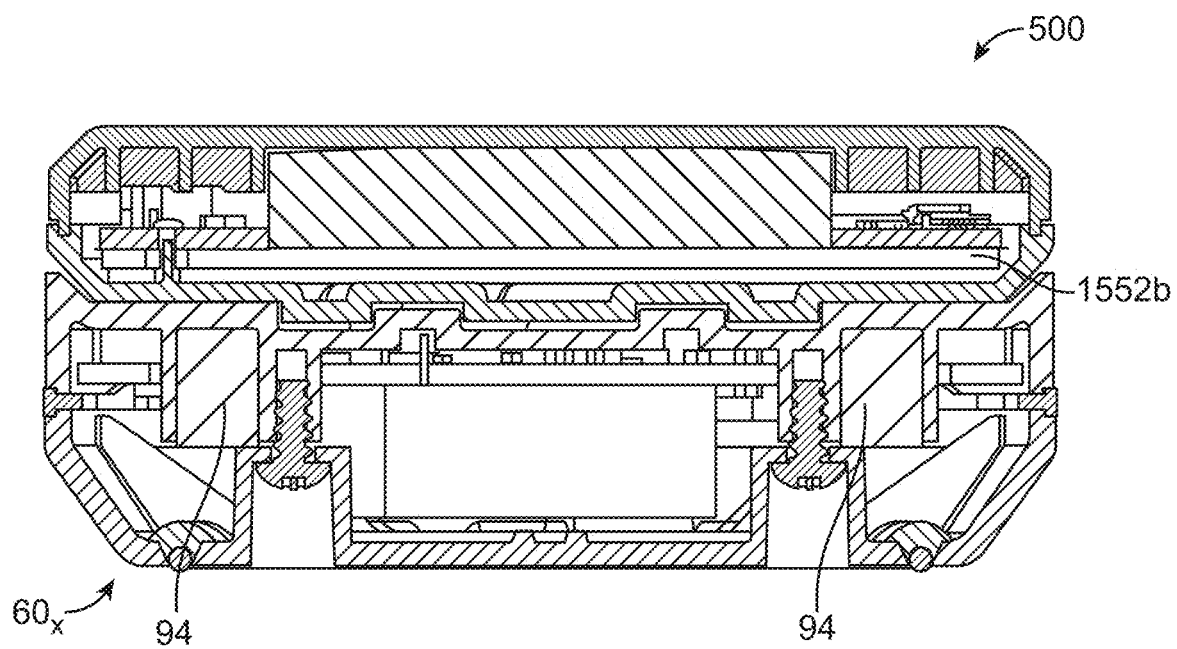

Referring to FIGS. 53A and 53B, a perspective view and cross-sectional view of an external charger for an external device is illustrated, respectively, consistent with the present inventive concepts. One or more external devices 500 can comprise an integrated power supply 570 comprising one or more rechargeable elements, such as a rechargeable battery. Each external device 500 can be configured to engage a charging device, tool $60_x$, such that power supply 570 can be recharged. Tool $60_x$ can comprise one or more components similar to tool $60_{ii}$ as described hereabove in reference to FIG. 31.

Tool $60_x$ can comprise a cylindrical geometry such that the upper face of tool $60_x$ receives the bottom portion of external device 500 as shown in FIG. 53A. Tool $60_x$ can include one or more magnets 94 configured to attract a ferrite component within external device 500 (e.g. ferrite shield 1552b as described herebelow in reference to FIG. 33 or other ferrite component of external device 500). Magnets 94 can be positioned to ensure proper alignment and stability between tool $60_x$ and external device 500 as shown in FIG. 53B.

Figure 32:
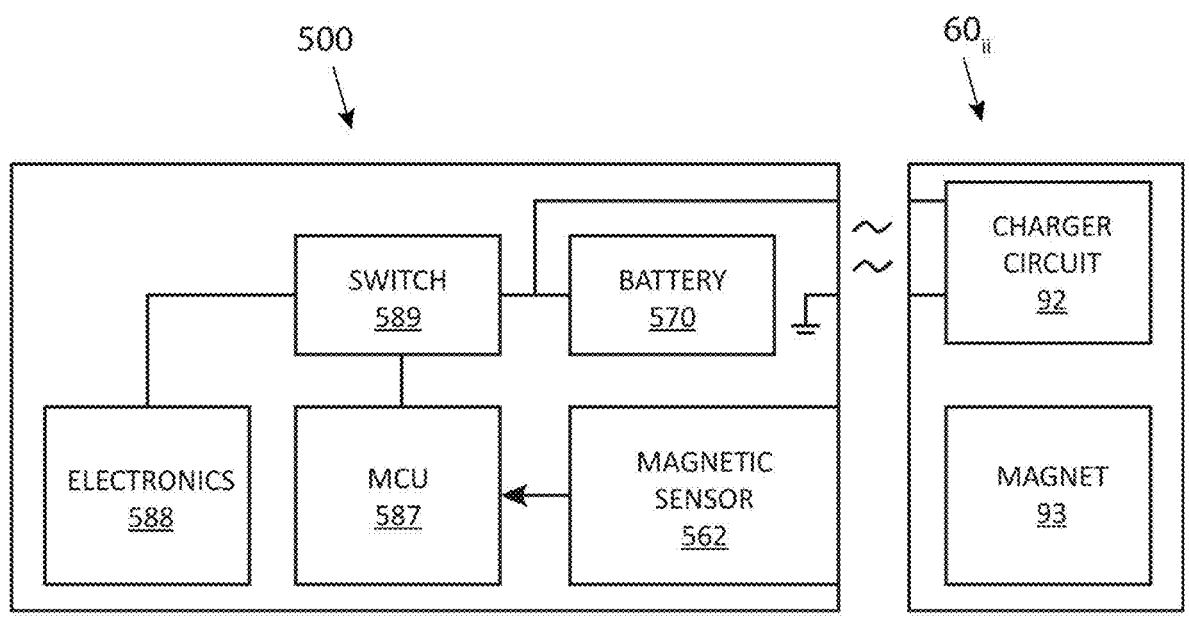
FIG. 32 is a schematic view of an external device and charging tool including automatic disconnection componentry, consistent with the present inventive concepts.

Referring to FIG. 32, a schematic view of an external device and charger are illustrated, consistent with the present inventive concepts. When external device 500 is operably attached (e.g. at least electrically attached via a wired or wireless connection, such as an inductive coupling wireless connection) to a charging device, such as tool $60_{ii}$ shown, a charging circuit 92 of tool $60_{ii}$ can become electrically attached to power supply 570 (e.g. a rechargeable battery) as well as other electrical loads (e.g. resistive loads) of external device 500, such as MCU 587 and electronic assembly 588 shown. Attachment to these non-storage components may be undesirable, and switches, circuitry, and/or other componentry can be included in external device 500 to disconnect these loads during charging. In some embodiments, external device 500 comprises a sensor, such as magnetic sensor 562 shown, and tool $60_{ii}$ includes a magnet, such as magnet 93 shown, such as a permanent magnet or electromagnet. Magnetic sensor 562 and magnet 93 can be positioned such that when external device 500 is operably positioned relative to tool 60ii, charging circuit 92 electrically attaches to power supply 570, and magnet 93 activates magnetic sensor 562. Magnetic sensor 562 can be configured to provide a signal (e.g. a signal provided to MCU 587 as shown) that is used by external device 500 to disconnect one or more loads of external device 500 from charging circuit 92, such as by disconnecting charging circuit 92 from these load components via the opening of electrical contacts of a switch of external device 500, such as switch 589 shown. In some embodiments, magnetic sensor 562 includes switch 589, such as when magnetic sensor 562 comprises a reed switch or other magnetically activated switch, directly disconnecting the switch without the need for external device 500 separately controlling the switch based on a signal provided by magnetic sensor 562. In some embodiments, tool $60_{ii}$ includes BLE functionality that communicates with external device 500. In some embodiments, tool $60_{ii}$ determines the end of a charging cycle has been reached. In some embodiments, tool $60_{ii}$ moves or disables magnet 93 (e.g. when magnet 93 comprises an electromagnet), such as to change the connection status of switch 589 (e.g. change from open circuit to closed). In some embodiments, tool $60_{ii}$ transmits data (e.g. data from tool $60_{ii}$ and/or data collected from external device 500) to a "cloud-based" repository (e.g. over a wifi or cellular connection). Alternatively or additionally, tool $60_{ii}$ can store the data locally (e.g. on a removable storage element such as an SD card). The stored data can be transferred or otherwise shared with another device of apparatus 10, such as programmer 600.

Figure 38A:
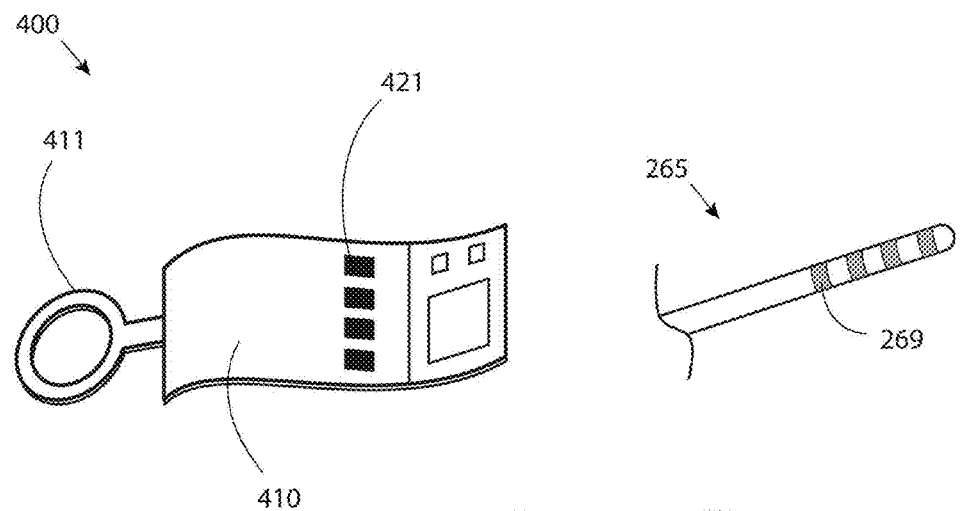
FIGS. 38A-38C are perspective views of the steps of a method for assembling an implantable assembly for attaching to an implantable lead, consistent with the present inventive concepts.
Figure 38B:
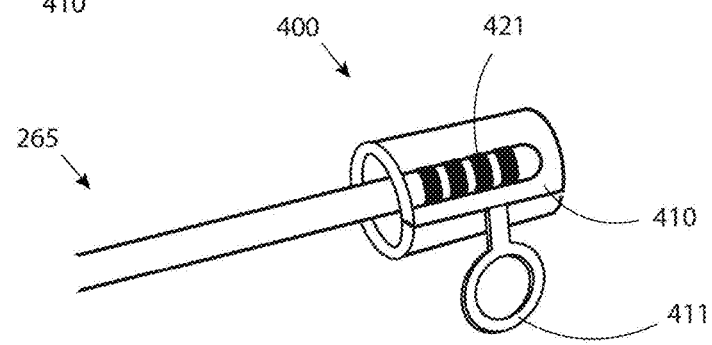
Figure 38C:
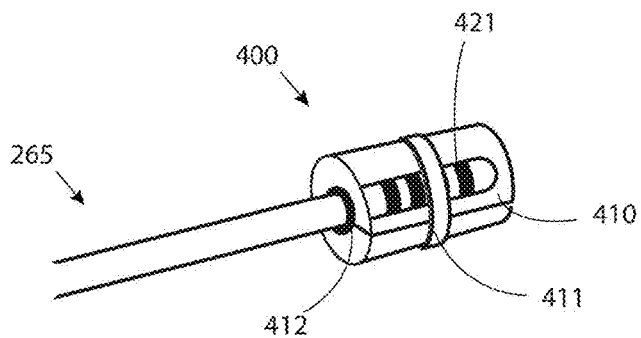
Figure 39:
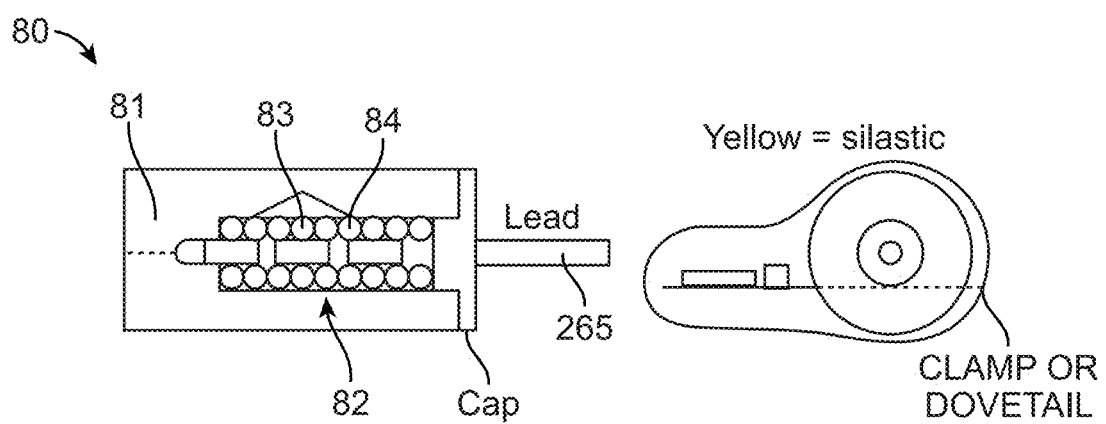
FIG. 39 is a perspective view of a trialing interface comprising an O-ring connector, consistent with the present inventive concepts.
Figure 40A:
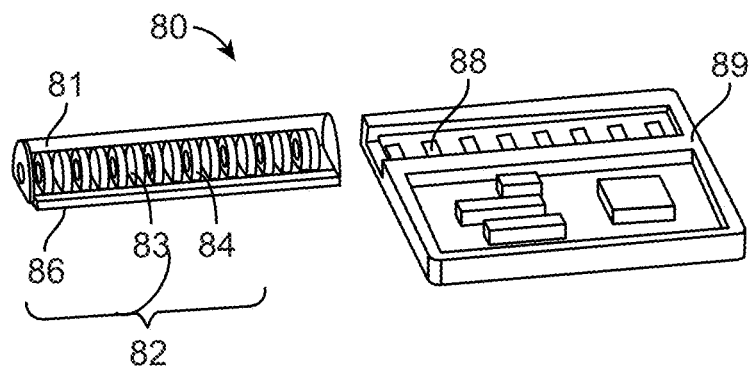
FIGS. 40A-40C are sectional views of a trialing interface comprising an O-ring connector and a housing assembly, consistent with the present inventive concepts.
Figure 40B:
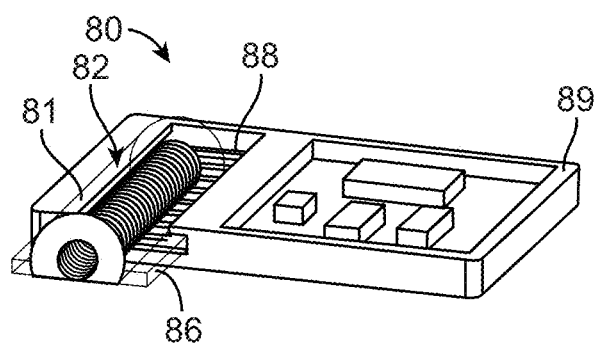
Figure 40C:
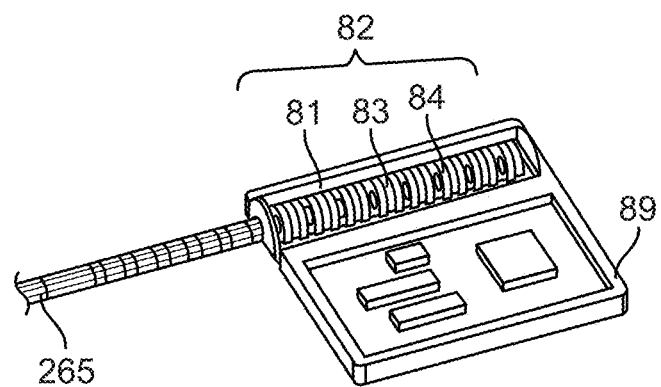

Referring to FIGS. 38A-C, a series of perspective views of an implantable assembly for attaching to an implantable lead are illustrated. consistent with the present inventive concepts. Implantable device 400 includes a flexible housing 410, into and/or onto which one or more electronic or other components are included, such as contacts 421. Contacts 421 and aligned with corresponding contacts 269 on the proximal portion of lead 265. Housing 410 is configured to be rolled around the proximal portion of lead 265, as shown in FIG. 38B, such that an electrical connection is made between contacts 259 and contacts 421. In a subsequent step, a ring 411 is positioned about the rolled-up housing 410, securing housing 410 in the cylindrical shape shown in FIG. 38C. In some embodiments, ring 411 comprises a flexible ring (e.g. an elastomeric ring). In some embodiments, ring 411 is attached to housing 410 as shown in FIG. 38A. In some embodiments, a sealing element 412 is included, such as an adhesive or gasket configured to provide a seal between one or more edges of housing 410, and/or between housing 410 and lead 265.

In some embodiments, implantable device 400 is of similar construction and arrangement to implantable device 200, trialing interface 80 (e.g. an implantable stimulator configured as a trialing interface), and/or connector 285, each as described herein.

Figure 41:
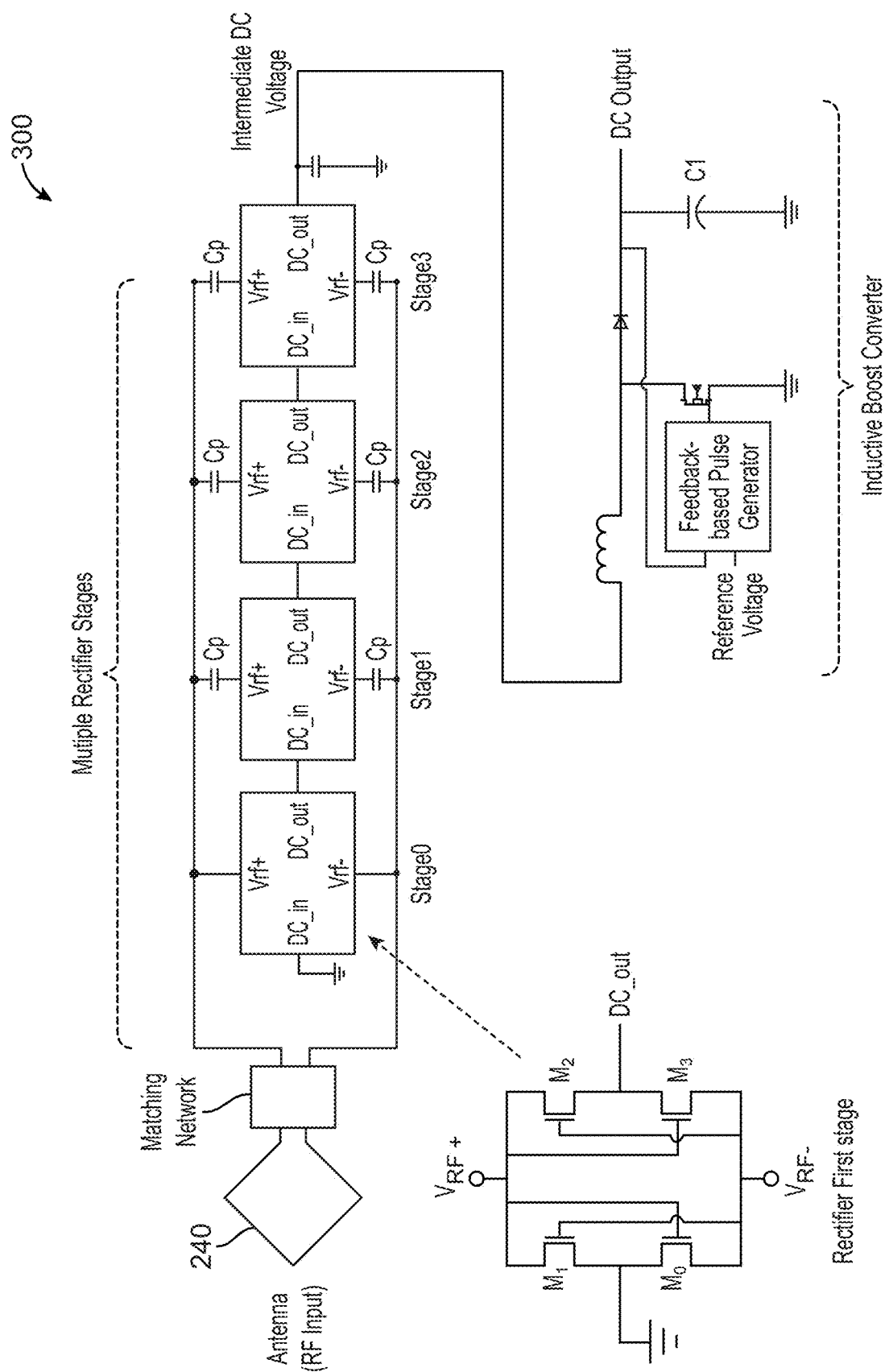
FIG. 41 is a schematic of an antenna and electronics assembly of an implantable device, consistent with the present inventive concepts.

Referring to FIG. 41, a schematic of an antenna and electronics assembly of an implantable device are illustrated, consistent with the present inventive concepts. An implantable antenna 240 is electrically attached to a matching network of electronics assembly 300. Electronics assembly 300 includes a convertor that combines multiple self-driven synchronous rectifier (SDSR) stages with an additional DC-DC conversion stage, such as an inductive boost convertor. The SDSR stages rectify the RF power from antenna 240 (e.g. as received from an antenna 540 of an external device 500), and by using the capacitive input coupling to all but the first stage, a voltage multiplication is achieved. For example, using four SDSR stages, an intermediate DC voltage in the 2V-4V range can be achieved with only 0.5V-2V RF amplitudes being received at the antenna input under various loading conditions. This intermediate DC voltage is the input to an inductive boost convertor, and is at a high enough voltage for the boost convertor to operate efficiently. The inductive boost convertor performs further voltage multiplication, providing, for example, a 2V to 17V output range from the 2V-4V input range. The boost convertor also provides line and load regulation, and the ability to adjust the output voltage. If the output voltage commanded by the boost converter is lower than the input voltage, the boost converter simply passes the input directly to the output without regulation.

In alternate embodiments (e.g. at the cost of some design complexity and additional switching losses), a buck-boost converter is used instead of the boost converter, such as to allow regulation of an output voltage either above or below the input voltage. All components in the implantable device 200, with the possible exception of the inductor and the two capacitors on the intermediate output voltage nodes, can be implemented in a single CMOS integrated circuit yielding small implant size.

In yet another embodiment, the DC-to-DC regulator is replaced with additional SDSR stages that generate the final DC output required for stimulation. The control required to maintain the DC output voltage is then be mediated by the RF transmissions of external device 500, in one instance by feedback through RF telemetry back to the external device 500 for adjusting the RF power dynamically, or in another instance by feedforward control using characterized load data to predict the required RF power.

In some embodiments, electronics assembly 300 efficiently converts the RF signal received from external device 500 to a DC signal via the matching at the antenna 240, which is load dependent, and via the efficiency provided by the rectifier and boost converter. The rectifier efficiency is a function of the input and output power, input and output voltage, and the load it is driving. The steady-state load of the rectifier is set by the intended operation of the implantable device 200. In stimulation applications, there are typically high instantaneous loads (e.g. stimulation energy being delivered) followed by long periods without loading, resulting in much lower average loads. By incorporating an intermediate stage with an energy storage element (e.g. a capacitor such as capacitor C1 shown), the rectifier loading can be kept relatively constant as power is drawn intermittently, allowing it to be controlled more precisely and operate more efficiently. The power flow can also be adjusted to control the input and output voltage at a given loading condition. This adjustability allows the rectifier efficiency to be further optimized based on its voltage characteristics. Higher output voltages from the rectifier can improve the efficiency of the boost converter because the multiplication factor is reduced. The intermediate capacitive stage in combination with the rectifier characteristic allows for an adaptive loading mechanism on the antenna 240. The load on the rectifier is approximately determined by its output current, which changes as the energy storage element charges. At lower voltages, the energy storage element requires more current and presents a larger load. As the voltage increases, the current draw reduces and it presents a lighter load.

Figure 42:
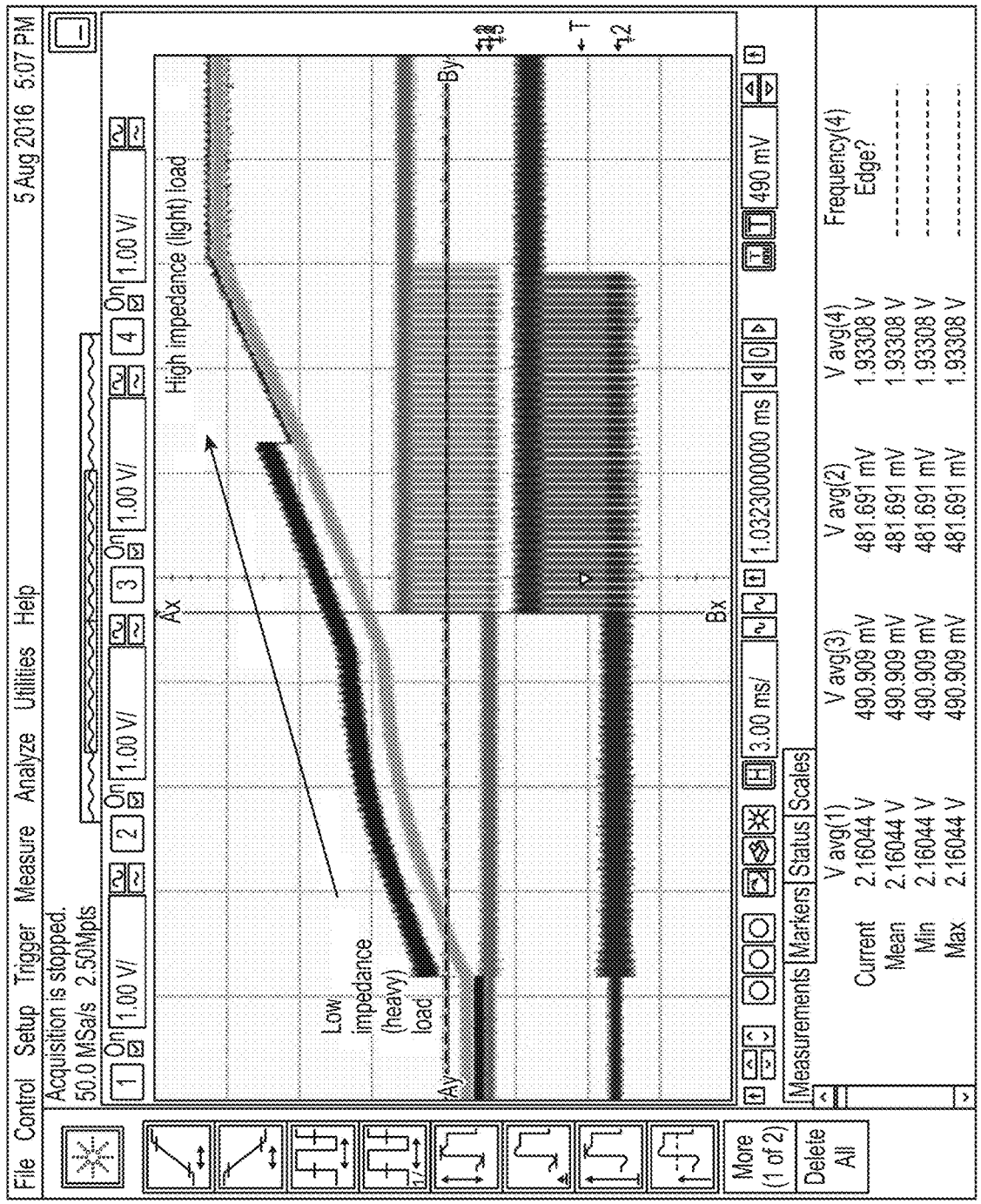
FIG. 42 is a graph of a startup transient of an implantable device, consistent with the present inventive concepts.

Referring to FIG. 42, a graph of a startup transient of implantable device 200 is illustrated, consistent with the present inventive concepts. As shown in the graph, an intermediate storage capacitor is charging up, measured on Ch1 (Yellow=Rectifier Output) and Ch4 (Red=Capacitor Voltage) (e.g. channels which are separated by a PFET switch, which if not on presents a diode drop of ~0.5V from Ch1 to Ch4). To first order, the rectifier behaves like a constant current source which linearly ramps up the voltage on the storage capacitor. Hence the equivalent load resistance presented to the rectifier is simply the capacitor voltage divided by a constant current, and directly proportional to the capacitor voltage.

The direct relationship between equivalent load resistance and capacitor voltage can be used to ensure the antenna 240 is well-matched during power transfer and communications. For example, in the same waveform above, Ch2 (Green) and Ch3 (Blue) show RF communication packets arriving which contain a command to close the switch between Ch1 and Ch4. At a certain loading condition near the top of the curve (~2.5V on Ch4), it can be observed that the antenna 240 becomes well matched to receive the communication packets as shown by the switch closing to eliminate the diode drop and make Ch1=Ch4.

As described hereabove, the amount of power can be controlled by adjusting power levels, and/or by performing different forms of power cycling over time. These configurations ensure that an optimal efficiency point can be attained in which the transmitter (e.g. external device 500), antennas (e.g. antennas 540 and/or 240), rectifier, and boost converter are all performing efficiently for a desired steady-state load.

Figure 43:
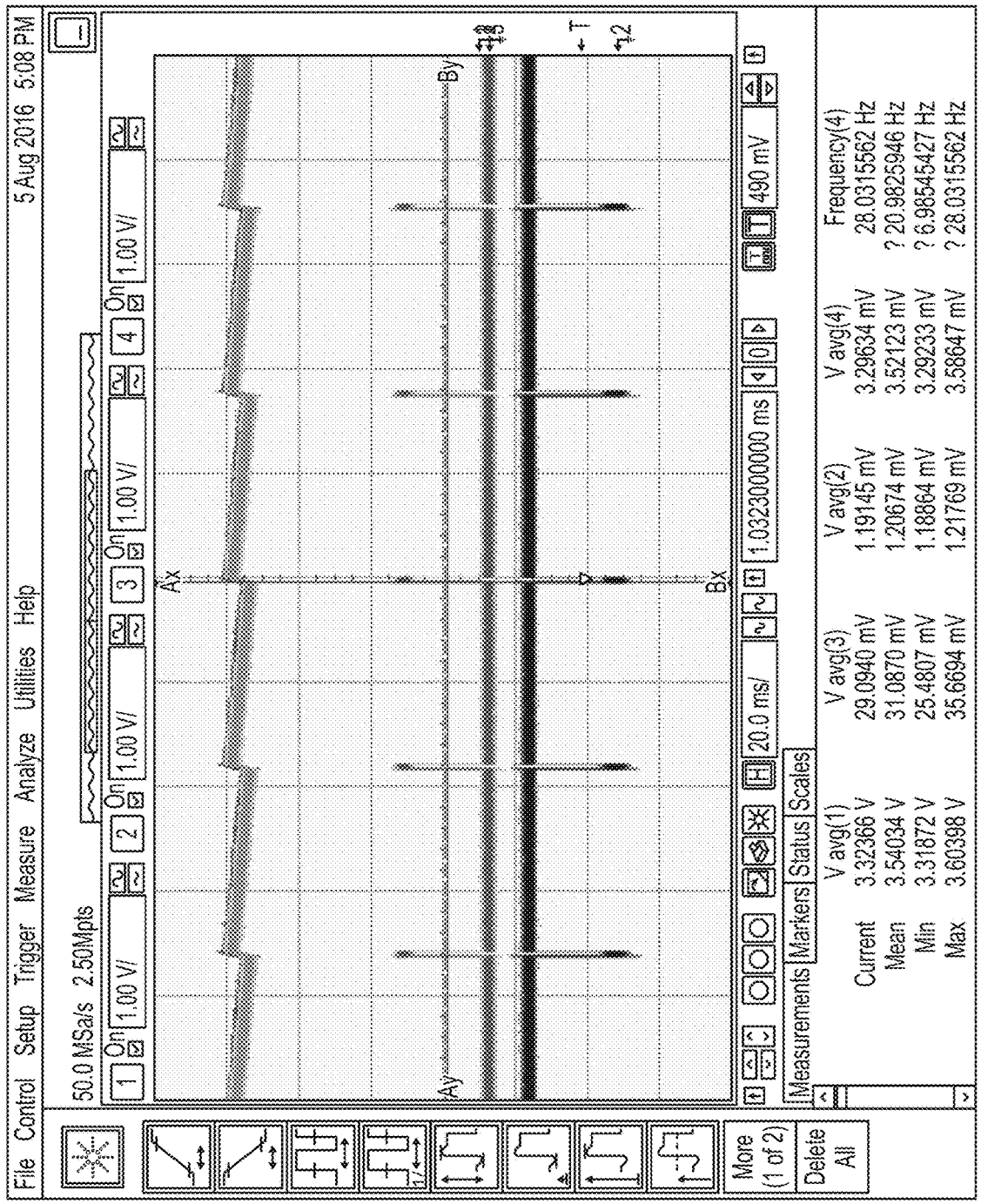
FIG. 43 is a graph of a steady state behavior with power cycling, consistent with the present inventive concepts.

Referring to FIG. 43, a graph of steady state behavior with power cycling is illustrated, consistent with the present inventive concepts. As shown in the graph, power and communications are sent at a very low duty cycle (~3% every 35 ms), which is enough to maintain the voltage on the storage capacitor (shown as Ch1=Ch4) hovering between 3.3V-3.6V as indicated by the measurements tab at the bottom of the figure. The duty cycle can be very low when the electronic assembly 300 is idle, as in this example. However, when the implantable device 200 requires more power (e.g. when stimulating), both duty cycle and frequency of charging can be increased accordingly to maintain the capacitor voltage at a given level; the charging ramp can thereby start and end at about the same points to maintain an efficient, near-optimal loading condition for the implantable device 200.

Performing RF-to-DC conversion by generation of an intermediate DC voltage enables the following advantages in this system: a high-efficiency SDSR cascade is exploited as the first RF-to-DC rectifier stage, which is easily integrated "on chip" using small, low-voltage devices; the subsequent DC-to-DC boost or buck-boost converter then maintains high efficiency by a lower voltage multiplication factor to transform the intermediate DC voltage into the final DC output voltage; the DC-to-DC converter uses internal feedback to maintain a constant DC output voltage, and desensitizes the DC output from changes in the intermediate DC voltage, and hence the external (RF) environment; the antenna 240 matching impedance can be controlled by maintaining the intermediate DC voltage in steady-state using RF power cycling. The load impedance is set to first order by the DC voltage divided by a constant charging current. Hence an optimal antenna 240 match can be chosen to achieve maximum RF efficiency (and reliable RF communications) simply by powering the implantable device 200 at a level required to maintain a certain intermediate DC voltage; and this optimal operating point can be achieved independent of other loads in the system, as long as the storage capacitor dominates the rectifier load impedance. Due to the large value capacitance, it will be the dominant (lowest) impedance as long as the system is not given an over-supply of RF power causing the capacitor voltage to saturate. That latter condition can be guaranteed by RF power cycling. Additionally, this flexibility in power and loading control allows the transmitter to operate as efficiently as possible while still operating near the optimal point in the receiver.

Figure 44:
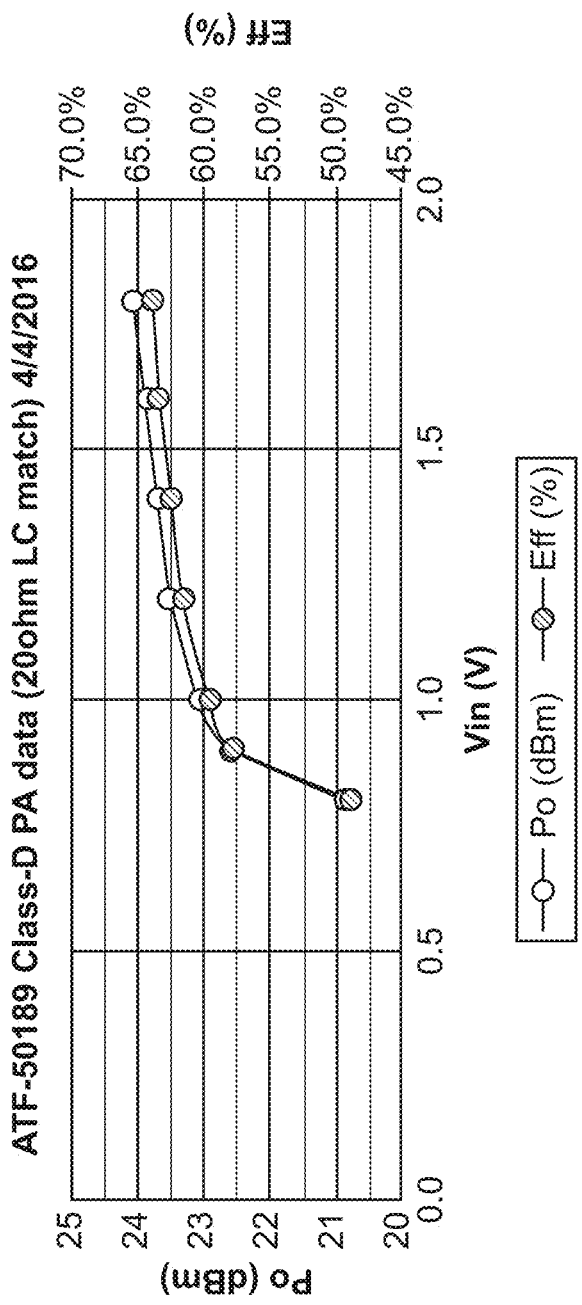
FIG. 44 is a graph of an output-power and efficient curve for a saturated class-D power amplified, consistent with the present inventive concepts.

Referring to FIG. 44, a graph of an output-power and efficiency curve for a saturated class-D power amplifier is illustrated, consistent with the present inventive concepts. Power amplifiers (PA's) have competing tradeoffs in their design, and one notable tradeoff is between linearity and efficiency. For applications in which data is modulated on a carrier, high linearity is usually a requirement in order to effectively transfer information. By using modulation that doesn't require linearity, such as amplitude modulation with data encoded in the pulse width, the non-linearity of the modulation doesn't degrade performance of the data transfer. As long as a change in amplitude can be detected, the information can be recovered from pulse widths (i.e. the data is encoded in the pulse duration). This configuration allows for highly efficient amplifier architectures to be used while maintaining effective data transfer.

Note in FIG. 44 that high efficiency is achieved only when the input amplitude Vin (gate drive) exceeds 1V, which also causes the power output to saturate. Linearity of the PA is sacrificed to operate in this high efficiency (or saturated) regime. However, fine control over AM depth can still be achieved in this regime because output power is insensitive to Vin but not completely flat, and this property can be leveraged to maintain high power efficiency, even during modulation. Alternatively or additionally, the power supply of the amplifier can be modulated to produce a variable modulation depth at the output, which will also have non-linear behavior. This approach can incur power losses associated with modulating the supply voltage of the amplifier, which can reduce efficiency. However, it also increases complexity of the design, in that the modulator and the power supply are not independent.

Additionally, since only a change in amplitude is required, in some embodiments the modulation depth itself is set to operate in an optimized range of the amplifier, in order to minimize efficiency losses during data transfer. In applications in which the carrier sent by external device 500 also provides wireless power to the implantable device 200, minimizing the change in amplitude helps keep power transfer relatively constant. Additionally, it minimizes bandwidth usage and unwanted frequency content in the frequency spectrum, reducing unwanted electromagnetic interference. Several highly efficient power amplifier architectures can be utilized, such as switching architectures (class D) or classes that make use of small conduction angles, such as class C (and its subsets), class AB, or class B. In a class D architecture, the input waveform can be modulated to produce modulation in the output, and although it is non-linear, the data transfer performance is not affected.

Another benefit of a flexible amplifier architecture, such as a class D amplifier architecture, is that it can be designed to efficiently be power cycled by turning the input on and off. This type of power cycling can be used to control power transfer for remotely powered devices. Power cycling can also have adjustable amplitudes, so that it is never turned fully off but delivers different power levels at different times. The adjustments to power cycling pulses or power transfer amplitude can be based on the overall apparatus 10 operation or apparatus 10 efficiencies, including both efficiencies in the transmitter (e.g. external device 500) and the receiver (e.g. implantable device 200). The transmitter efficiency will vary with output power, and the power harvesting efficiency of the receiver will vary with received power, DC-DC conversion, and/or loading.

Figure 45:
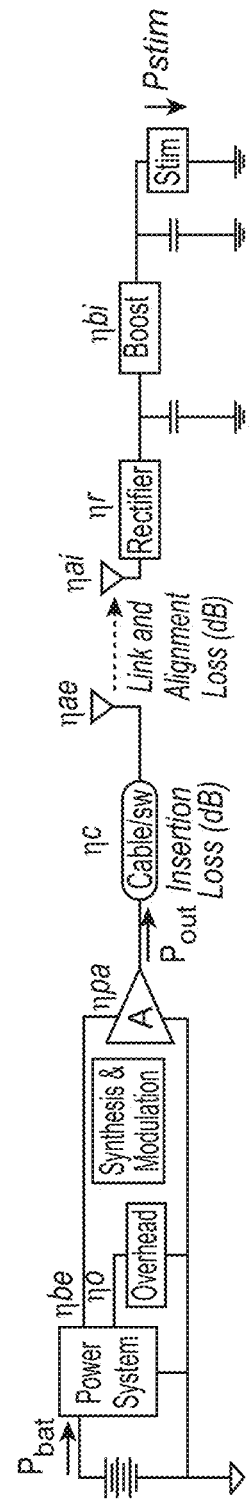
FIG. 45 is a schematic of an electronics assembly of a stimulation apparatus, consistent with the present inventive concepts.

Referring to FIG. 45, a schematic of an electronics assembly of a stimulation apparatus is illustrated, consistent with the present inventive concepts. Different efficiencies ($\eta$) in apparatus 10 are shown. The loading condition is determined by $P_{stim}$, which directly affects both DC-DC conversion efficiency ($\eta_{bi}$) and rectifier efficiency ($\eta_r$). To maintain a given $P_{stim}$, PA output power ($P_{out}$) is adjusted as the efficiencies downstream vary, which then affects both PA efficiency ($\eta_{pa}$) and power supply efficiency ($\eta_{be}$) at the transmitter (e.g. external device 500).

Power requirements for the intended use of apparatus 10 may also change over time. Apparatus 10 efficiencies can be monitored and information can be exchanged over the communication link between external device 500 and implantable device 200, and adjustments to power transfer properties can be made in real-time and/or at desired intervals. External device 500 and implantable device 200 can require different power levels depending on their current operating mode, such as operating modes selected from the group consisting of: power transfer; power transfer with one-way data transfer; power transfer with two-way data transfer; data transfer without power transfer; and combinations of one or more of these. In each of these modes, the external device 500 can be adjusted to optimize power efficiency.

External device 500 architecture can also be designed to have parameters that are sensitive to changes in impedance, for example the output power can be a function of the impedance it's driving. This impedance can be the impedance of the transmitting antenna 540, which can change based on the relative position of the external device 500 and implantable device 200. The change in output power can then be sensed, such as by sensing the voltage level of the output, such as a Received Signal Strength Indication (RSSI) or other signal strength indicator. The sensed parameter can be used to estimate relative position, implantation depth, and/or the link gain to the receiving antenna 240. This information can be used to adjust operating parameters of the external device 500 such as power output, power cycling, data rate, and/or modulation depth itself, or to inform higher level changes such as informing the patient or doctor. The patient or doctor could then make necessary adjustments, such as repositioning the antenna 540 of external device 500.

A saturated PA design is leveraged to achieve both high power efficiency and finely controlled AM depth for communication without the typical requirement of linearity in the PA. Data doesn't require different levels of AM depth (which are non-linear), but is instead encoded in the length of time that the amplitude is changed (which is easily controlled).

The minimum AM depth that is required for robust communication can thereby be chosen easily, by selecting the Vin level used for modulation. This choice maximizes efficiency, maintains constant power transfer and simultaneously achieves minimum EMI impact. The AM depth could also be set by modulating the power supply of the amplifier. This method could also produce a controllable depth at the output, which would likely also exhibit non-linear behavior with respect to the output waveform, though the data transfer is insensitive to this non-linearity.

A fast-switching class-D amplifier enables an easy method of power cycling by digital gating of its input. This configuration enables quick adaptation to the power requirements of apparatus 10 that may change over time.

Using feedback from data-transfer and/or RSSI sensing of transmitter impedance, precise information about power transfer, communications, and antenna position at precise times at which power is delivered can be determined and used to maximize the apparatus 10 efficiency and robustness of communications by adjusting operating parameters, such as power cycling and power output.

Figure 46:
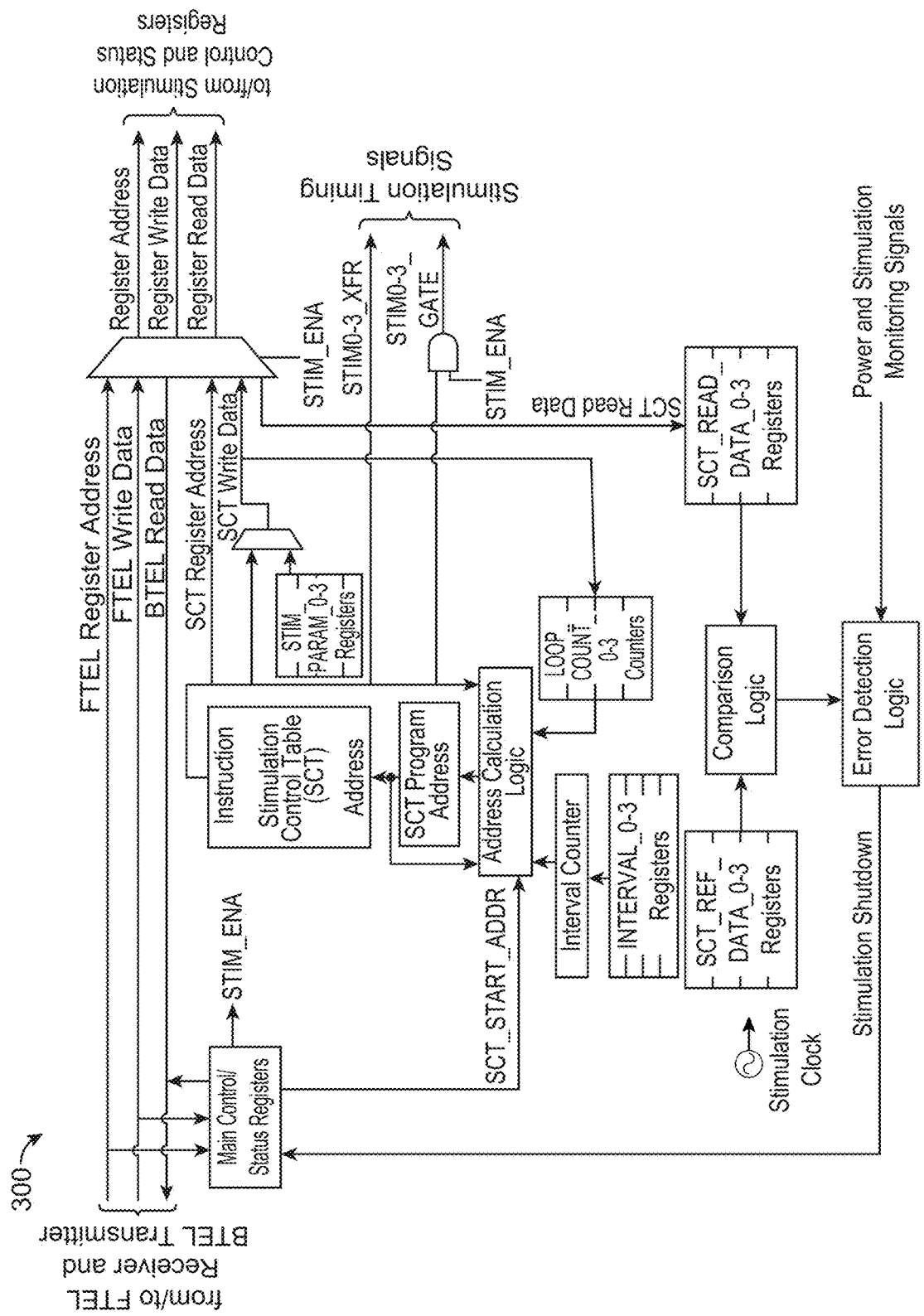
FIG. 46 is a schematic of an electronics assembly of an implantable device, consistent with the present inventive concepts.

Referring to FIG. 46, a schematic of an electronic assembly of an implantable device is illustrated consistent with the present inventive concepts. Electronic assembly 300 includes various components configured to safely and effectively deliver stimulation energy to tissue. Electronics assembly 300 includes address-mapped registers that can be written directly from external device 500 via a forward-telemetry (FTEL) link, but bandwidth constraints of that link could limit the rate at which stimulation delivered by implantable device 200 can occur. To overcome this limitation, a digital control structure known as the Stimulation Control Table (SCT) is used. Electronics assembly 300 of implantable device 200 includes a configurable state machine (Stimulation Control Table—SCT) that can execute autonomously (e.g. within pre-determined limits) to generate stimulation pulses and maintain fine grained (e.g. precision) stimulation control of timing and amplitude. Being a state machine (as opposed to a microcontroller) the SCT cannot perform computations or make decisions, and therefore its behavior is deterministic and highly predictable. Specifically, the following types of parameters can be encoded in the registers and parameters that drive the state table: pulse width; inter phase gap; and/or inter pulse interval. The SCT can also specify the amplitude of stimulation from a register. Alternatively, the amplitude (and timing) can be specific directly in the sequence or it can be provided dynamically.

Layered above a pulse or series of pulses, a "loop" can be used to play a sequence repeatedly (e.g. the SCT includes 4 nested loop levels). The loops also allow for long sequences of pulses to be played without involvement from external device 500 (thereby reducing telemetry traffic, such as to improve EMI and/or power efficiency). With a local clock source, the SCT can execute commands without any external involvement for significant periods of time (depending on the stability and accuracy of the clocks of external device 500 and implantable device 200). Loops can also be used to implement trains of stimulation pulses and/or bursts of stimulation pulses.

The SCT can include the ability to implement a 1-level sub-routine. The sub-routine minimizes the usage of program memory (allowing the electronic circuitry to be smaller). Additionally or alternatively, the sub-routine can allow for complex and arbitrary waveforms to be implemented.

The stimulation amplitude, loop counters and intervals (which can be used for pulse width, inter-pulse interval, etc.) can be modified by the external device 500 at run time and are used by the SCT when a subsequent start command is received. In this manner, significant change can be made to the stimulation patterns with minimal telemetry information needing to be transmitted from external device 500 to implantable device 200. The SCT can trigger measurements. The SCT can check status registers (whose contents can be set from comparisons between registers and/or measured quantities) and relay results to the external device and/or autonomously take action as a result of the checking. The SCT can halt stimulation if errors are detected.

Figure 47:
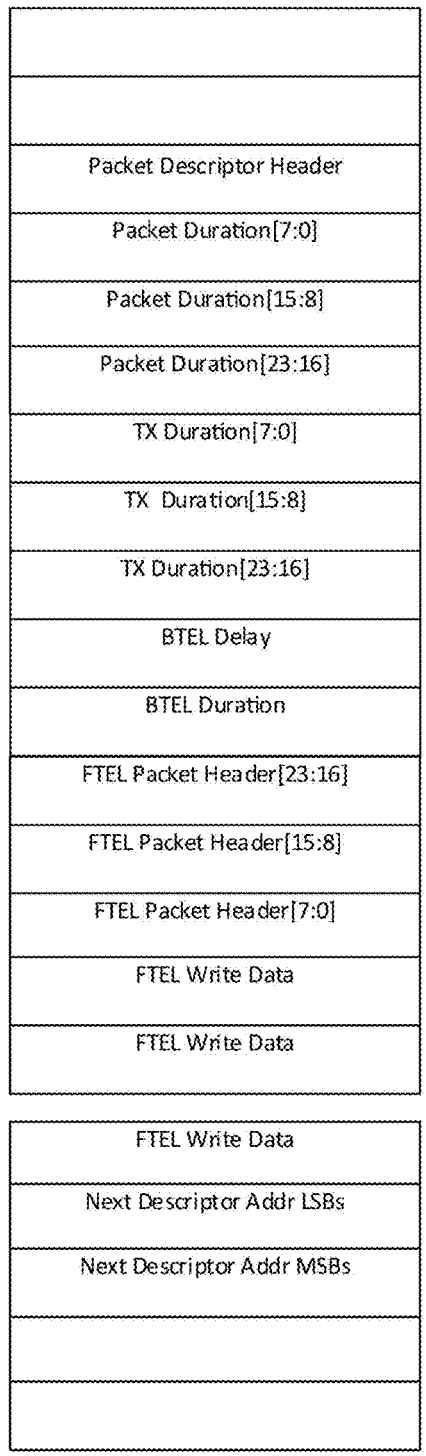
FIG. 47 is a representation of a TTAP packet description format, consistent with the present inventive concepts.

Referring to FIG. 47, a representation of a TAP packet description format is illustrated, consistent with the present inventive concepts. External device 500 includes a digital control structure called the Telemetry Timing Aware Peripheral (TTAP). The TAP works with the SCT described hereabove to ensure reliable and efficient operation of apparatus 10. The TTAP starts the sequence of stored in the SCT program table, where the SCT executes the sequence once and waits for further TAP start commands.

In this manner, the autonomous execution time can be controlled while starting a new sequence with minimal telemetry. The TAP can turn the external device 500 on and off to coincide with the stimulation pulses delivered by implantable device 200, within a sequence, to ensure optimal and sufficient power delivery. The TTAP uses a crystal-controlled clock source, and is the master time base for apparatus 10. The rate at which the TTAP issues start commands to the SCT can determine the overall stimulation rate.

Figure 48:
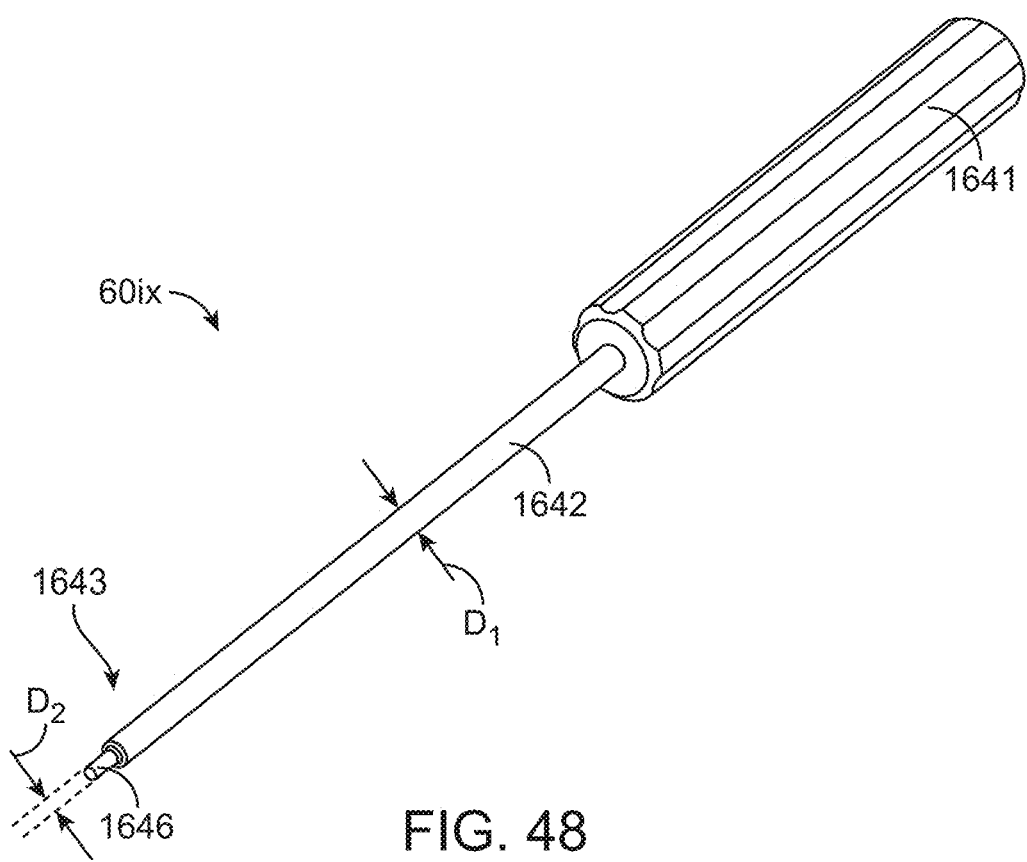
FIG. 48 is a perspective view of an embodiment of an insertion tool for an implantable device, consistent with the present inventive concepts.

Referring to FIG. 48, an insertion tool for an implantable device is illustrated, consistent with the present inventive concepts. Insertion tool $60_{ix}$ can be used to insert all or a portion of an implantable device 200 into and through patient's tissue. As shown in FIG. 48, insertion tool $60_{ix}$ includes a handle 1641, a shaft 1642, and a distal portion 1643. Distal portion 1643 can comprise an elongate extension, projection 1646, that extends axially from shaft 1642, and is sized and oriented to be positioned in a mating opening of implantable device 200, as described herebelow. In some embodiments, shaft 1642 comprises a diameter D1 that is larger than a diameter D2 of projection 1646, as shown.

Figure 48A:
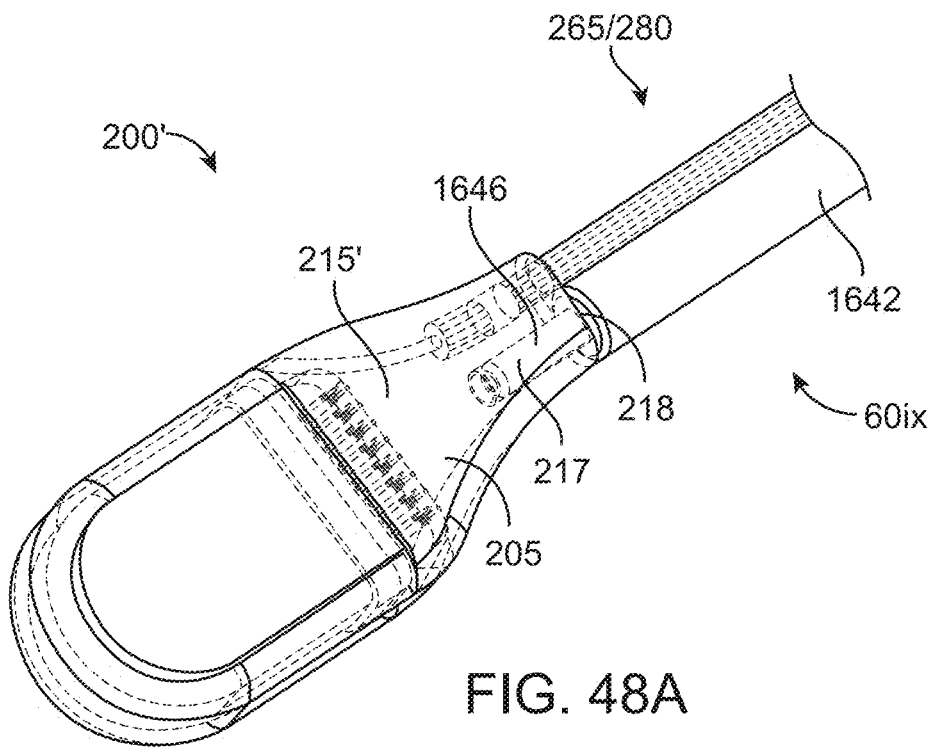
FIGS. 48A and 48B are perspective views of an insertion tool inserted into an implantable device, consistent with the present inventive concepts.
Figure 48B:
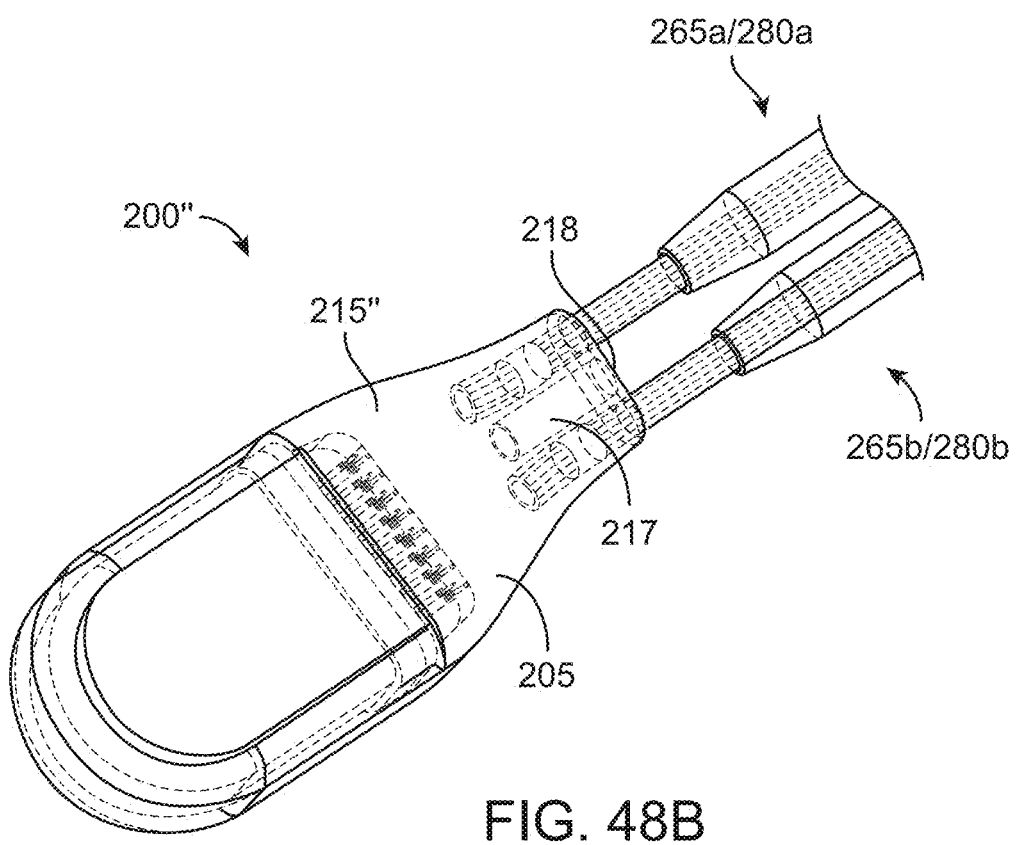

Referring additionally to FIGS. 48A-B, projection 1646 of tool $60_{ix}$ can be inserted into an elongate depression, cavity 217, of connector 215' of implantable device 200' of FIG. 48A and/or connector 215" of implantable device 200" of FIG. 48B. Implantable device 200' comprises a single lead 265 and is shown attached to tool $60_{ix}$. Implantable device 200" comprises two leads 265a and 265b, and can also be attached to a tool $60_{ix}$ (e.g. between the two leads 265a,b, with tool $60_{ix}$ not shown for illustrative clarity). The distal portions of connectors 215' and/or 215" comprise cavity 217 with an opening 218 that is sized and oriented to receive projection 1646. Projection 1646 can engage cavity 217 via opening 218, such as via sliding engagement to create a frictional fit between projection 1646 and cavity 217. Alternatively or additionally, insertion tool $60_{ix}$ can interface with implantable device 200 using one or more of the following: a mechanical interlock; mating threads; adhesive such as a temporary adhesive; and/or a magnetic coupling.

Cavity 217 comprises an axis that is relatively parallel to the neighboring portion of an attached lead 265, such that tool $60_{ix}$, when attached to implant 200, is relatively parallel to lead 265 to support advancement of each through a tissue tunnel.

While implants 200 of FIGS. 48, 48A-B are shown with an attached or attachable lead 265, a lead connection assembly 280 can be attached or attachable to implant 200, such that a lead 265 can be attached to the other end of the lead extension connection 280.

After attachment of an implantable device 200 to insertion tool $60_{ix}$, implantable device 200 (with or without an attached lead 265 or lead connection assembly 280) can be tunneled through tissue to an implantation site (e.g. with tool $60_{ix}$ and one or more attached leads 265 or lead connection assemblies 280 positioned in a parallel arrangement). Subsequently, tool $60_{ix}$ can be detached from the implantable device. Detachment of tool $60_{ix}$ can be accomplished by applying a pulling force to tool $60_{ix}$ (e.g. when projection 1646 is frictionally engaged with cavity 217) and/or by rotating tool $60_{ix}$ (e.g. when projection 1646 and cavity 217 comprise mating threads). In some embodiments, a clinician may apply pressure to the skin above the implanted implantable device 200, such as to provide a fixation force during the detachment of tool $60_{ix}$ from the attached implantable device 200.

Figure 49A:
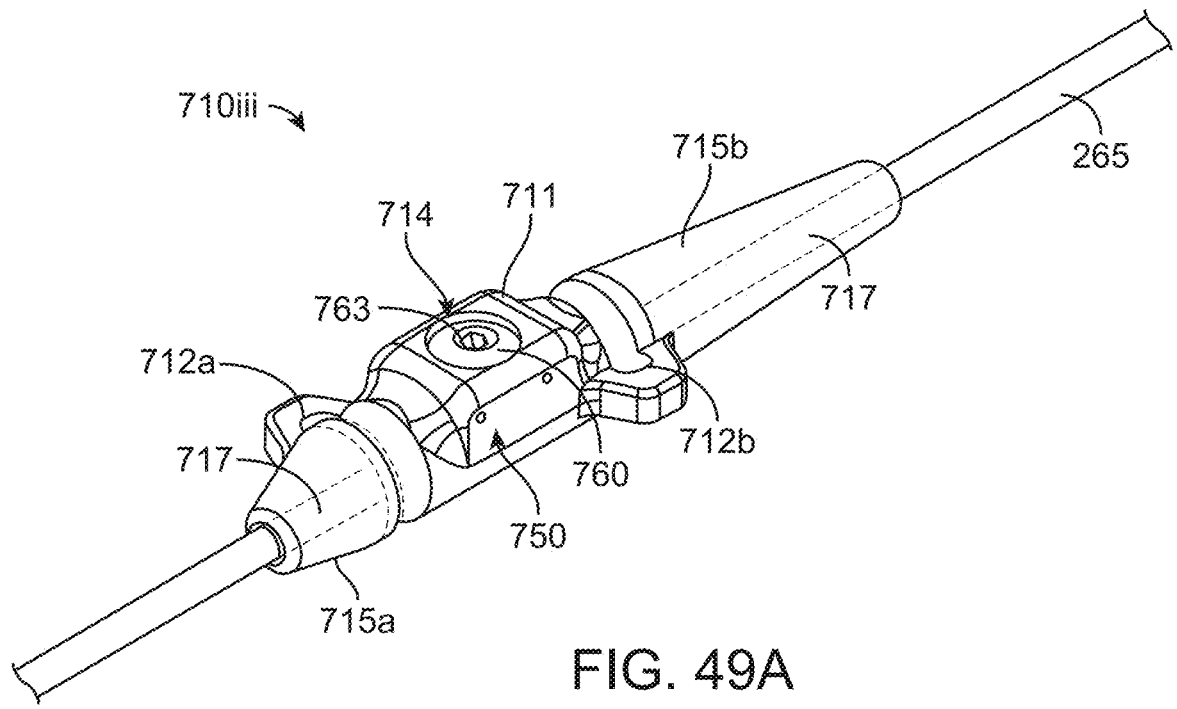
FIGS. 49A and 49B are perspective and transparent views of an embodiment of a lead anchor for an implantable lead, consistent with the present inventive concepts.
Figure 49B:
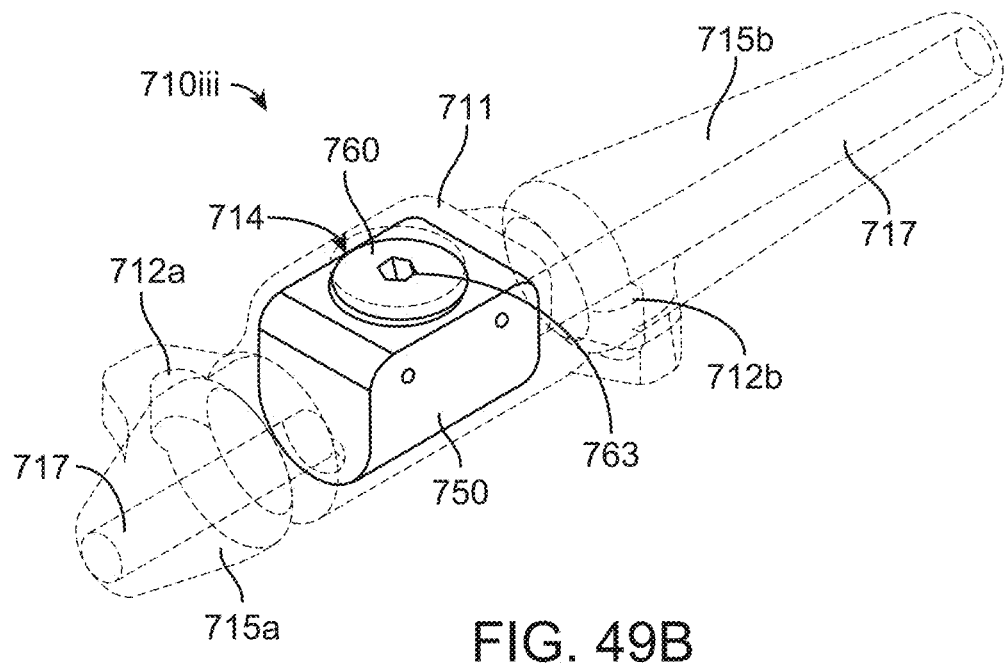

Referring to FIGS. 49A-B, a perspective view and a perspective transparent view, respectively, of a lead anchor comprising a clamping assembly are illustrated, consistent with the present inventive concepts. Lead anchor $710_{iii}$ can be used to anchor one or more leads 265 to tissue (e.g. to prevent migration of lead 265), and can include clamping assembly 750 which allows an implanting clinician to attach lead anchor $710_{iii}$ to one or more leads 265. As shown in FIG. 49A, lead anchor $710_{iii}$ comprises a housing 711, projections 715a and 715b, and a lumen 717 extending therethrough. One or more portions of housing 711 can comprise an overmold, such as a silicone overmold. Housing 711 can surround clamping assembly 750, and can include an opening 714. Opening 714 provides access to a rotatable actuator, actuator 760 of clamping assembly 750, such as to provide access to an engagement portion (e.g. a tool engagement portion), recess 763 of actuator 760. In some embodiments, housing 711 can include one or more anchor points 712a and 712b, such that lead anchor $710_{iii}$ can be sutured to the patient's tissue. Anchor points 712a,b can each comprise a groove configured to receive a suture. Anchor points 712a,b can circumferentially surround one or more portions of lead anchor $710_{iii}$ (e.g. circumferentially surround projections 715a,b and/or housing 711). As shown in FIG. 49B, lumen 717 can extend through projections 715a, through clamping assembly 750 (e.g. through housing 711), and through conduit 715b. Lead anchor $710_{iii}$ can slidingly receive a lead 265, via lumen 717, such as when lead 265 is inserted into conduit 715a, through clamping assembly 750, and out projection 715b.

Figure 50A:
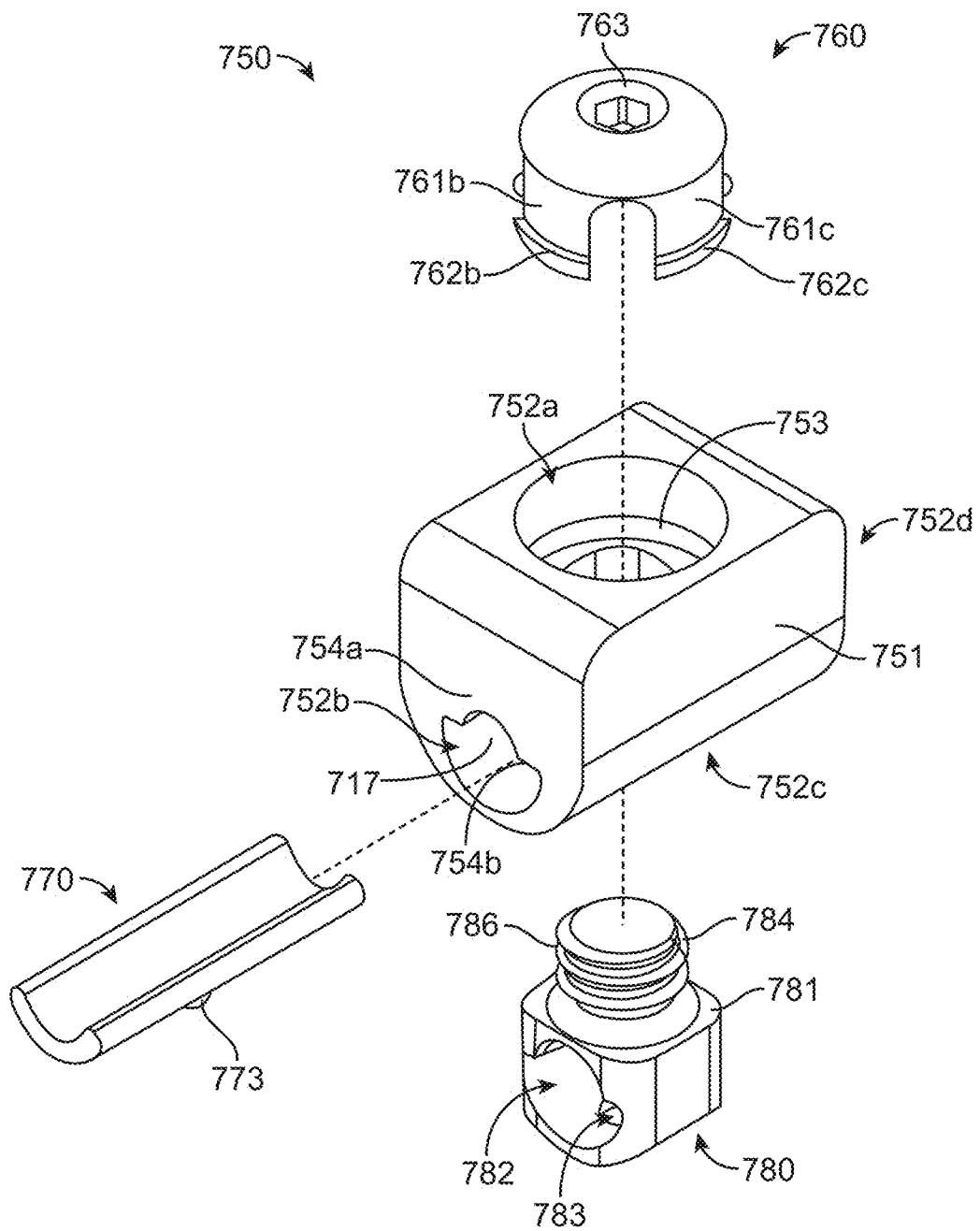
FIGS. 50A-E are exploded, perspective, and cross-sectional views of an embodiment of a clamping assembly for a lead anchor, consistent with the present inventive concepts.
Figure 50B:
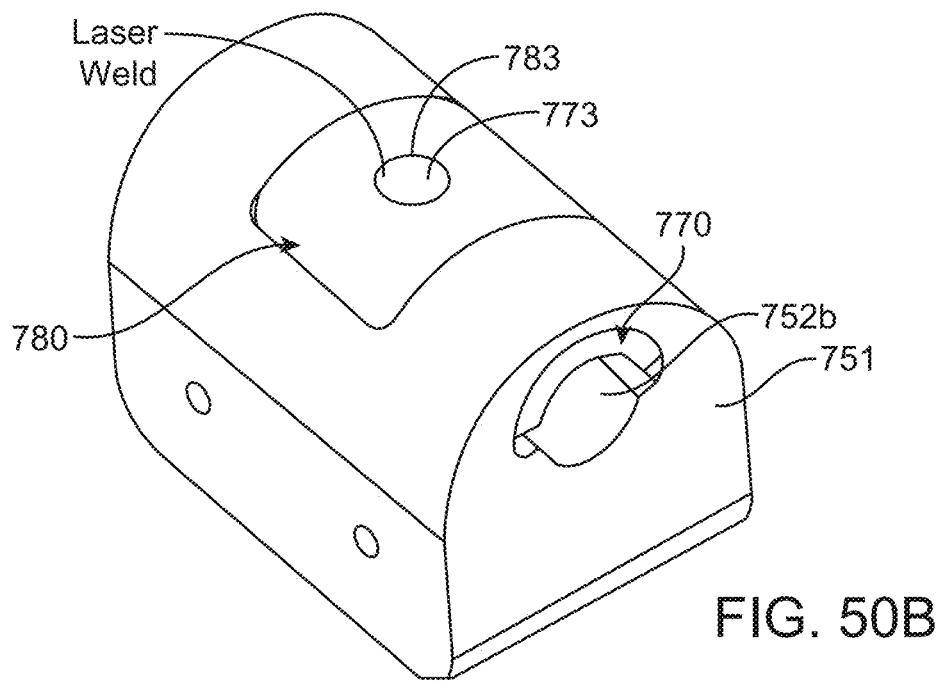
Figure 50C:
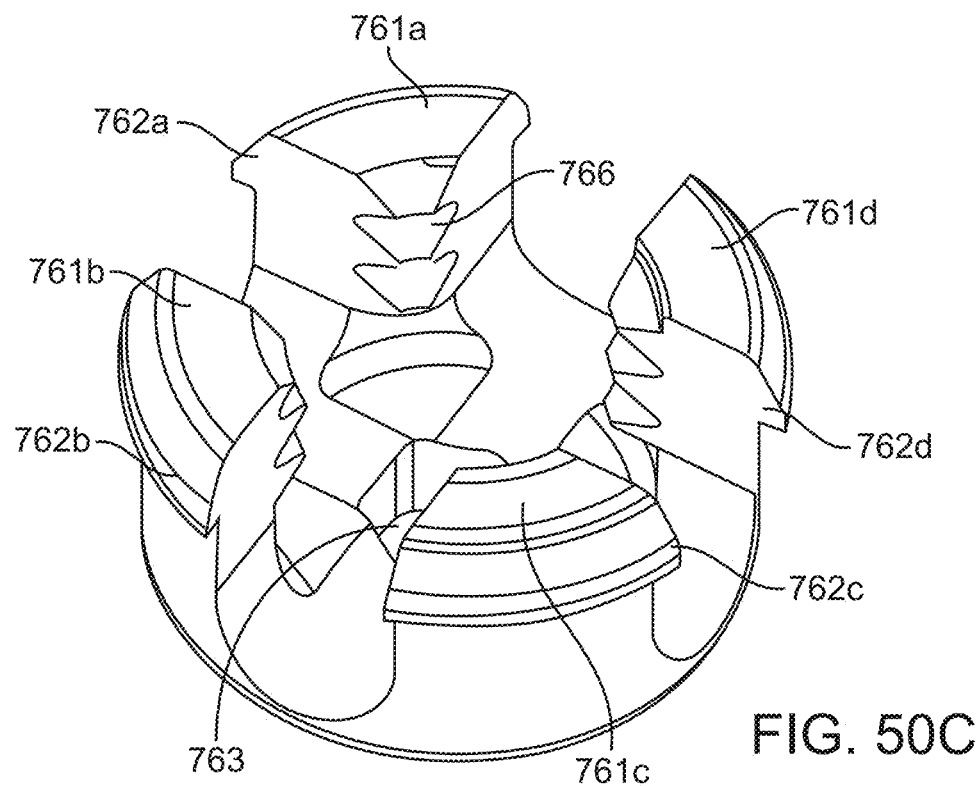
Figure 50D:
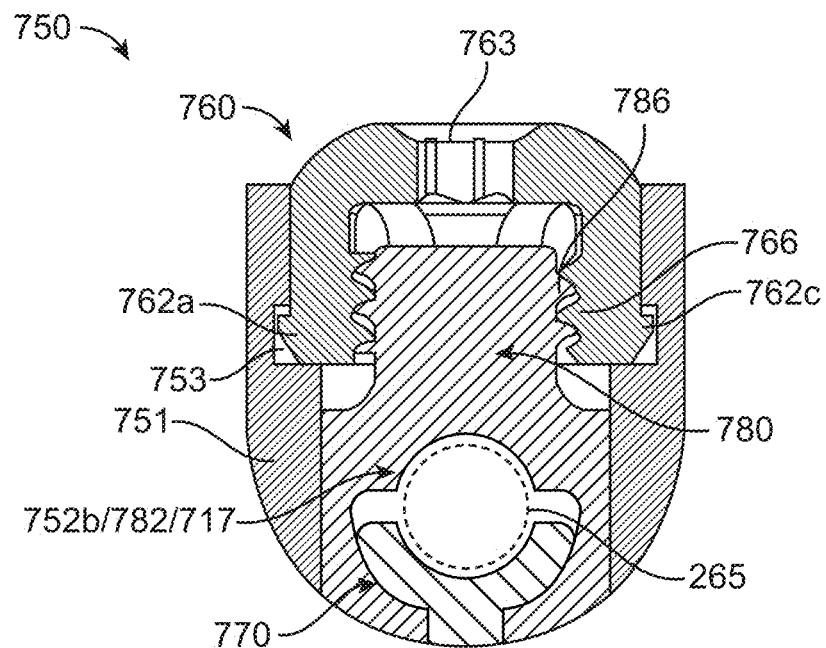
Figure 50E:
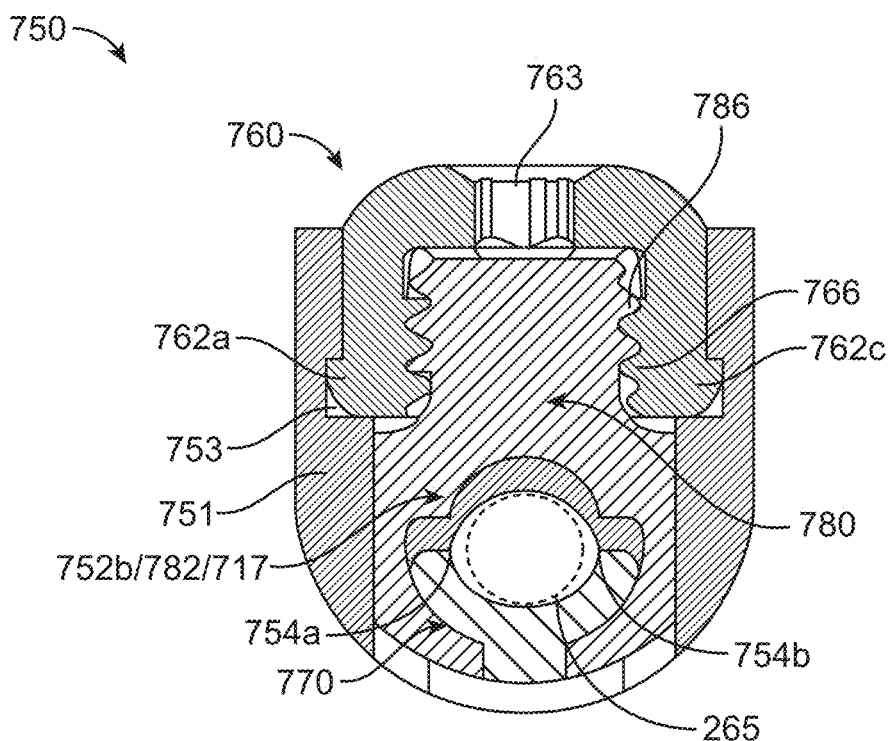
Figure 51A:
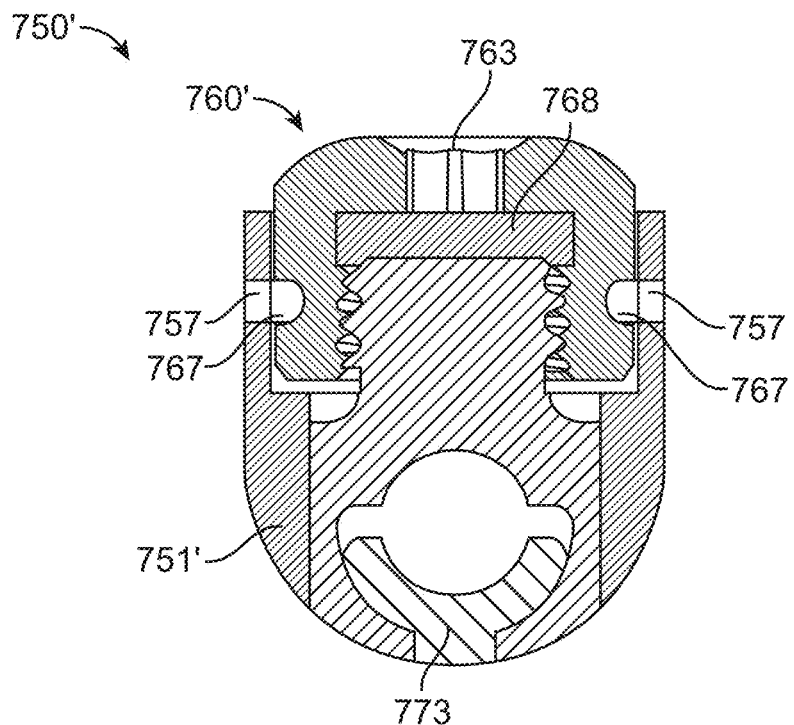
FIGS. 51A and 51B are sectional and transparent views of another embodiment of a clamping assembly for a lead anchor, consistent with the present inventive concepts.
Figure 51B:
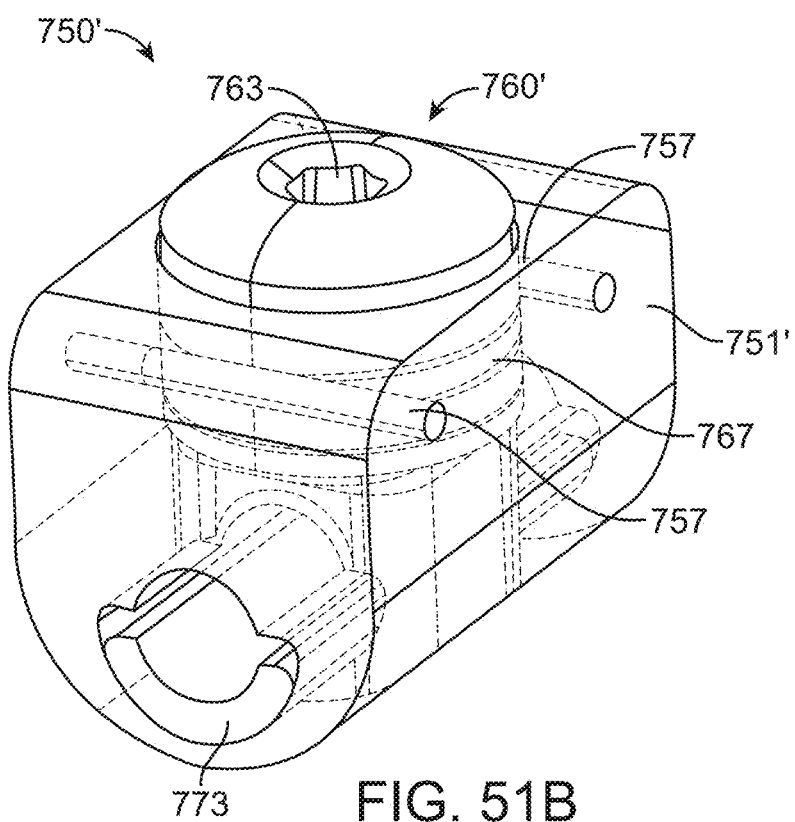

Lead anchor $710_{iii}$ of FIGS. 49A-B can include a clamping assembly of similar construction and arrangement to clamping assembly 750 described herebelow in reference to FIGS. 50A-E and/or clamping assembly 750' described herebelow in reference to FIGS. 51A-B.

Referring to FIGS. 50A-E, an exploded view, perspective views, and cross-sectional views of a clamping assembly for a lead anchor are illustrated, also consistent with the present inventive concepts. Clamping assembly 750 of FIGS. 50A-E can be integrated into a lead anchor of the present inventive concepts, such as lead anchor $710_{iii}$ described hereabove in reference to FIGS. 49A-B. Clamping assembly 750 can operably engage (e.g. frictionally or otherwise engage) a portion of lead 265 and/or a portion of lead connection assembly 280 (lead 265 and/or lead connection assembly 280 referred to as lead 265 herein), such as to temporarily and/or permanently affix lead 265 to a lead anchor. Clamping assembly 750 can comprise a clamping mechanism, as described herebelow, which can be compressed onto a lead 265 to operably engage it, such that the lead anchor including clamping assembly 750 can be secured to tissue of the patient. As shown in FIG. 50A, a clamping assembly 750 comprises a housing 751 with openings 752a-d (752c,d hidden behind housing 741 but indicated on figure via arrows shown). In some embodiments, opening 752a is positioned on the top face of housing 751, opening 752b is positioned on a side face (e.g. the proximal or distal face) of housing 751, opening 752c is positioned on the bottom face of housing 751, and opening 752d is positioned on the side face opposite opening 752b, as shown. Housing 751 can include projections 754a,b that border openings 752b,d as shown. Openings 752b,d each comprise an upper portion and a lower portion. The upper portion can comprise a width that is less than the width of the lower portion. Projections 754a,b are positioned between the upper and lower portions.

As described herebelow, clamping assembly 750 further includes actuator 760, a sleeve 770, and a clamp 780. Opening 752a can slidingly receive actuator 760, openings 752b,d can slidingly receive sleeve 770, and opening 752c can slidingly receive clamp 780.

Actuator 760 can comprise one or more engagement elements, such as four extensions 761a-d (extensions 761a and 761d hidden), that each include a retention element, flanges 762a-d, respectively, and internal (female) threads, threads 766 (as shown in FIG. 50C). Flanges 762a-d can be constructed and arranged to temporarily deflect and then expand into a receiving element within housing 751, such as groove 753 (shown in FIGS. 50D-E). Groove 753 can comprise an undercut recess in housing 751. In some embodiments, as actuator 760 is inserted into housing 751, via opening 752a, extensions 761a-d radially compress. As flanges 762a-d reach the groove 753, extensions 761a-d expand and flanges 762a-d engage groove 753. The engagement between flanges 762a-d and groove 753 can prevent actuator 760 from migrating out of housing 751. Actuator 760 can further include a recess 763 that is constructed and arranged to receive a tool, such as a hex wrench, screwdriver, or other tool configured to engage and rotate actuator 760 within housing 751.

Sleeve 770 can comprise a semicircular geometry that slidingly receives a portion of lead 265. Sleeve 770 can include a projection 773 that extends from the bottom face of sleeve 770. In some embodiments, sleeve 770 can circumferentially surround a portion of lead 265 such as to form a protective barrier between lead 265 and clamp 780.

Clamp 780 can comprise a housing 781, with a lumen 782 therethrough, lumen 782 sized to slidingly receive sleeve 770 and lead 265. In some embodiments, housing 781 includes an opening 783 that slidingly receives projection 773 of sleeve 770. Clamp 780 can further include a projection 784 extending from the top face of housing 781. Projection 784 can comprise external (male) threads, threads 786. Threads 786 can be configured to rotatably engage threads 766 of actuator 760 as described hereabove.

In some embodiments, clamp 780 is inserted into housing 751 via opening 752c and subsequently sleeve 770 is inserted into clamp 780 via opening 752b through lumen 782. As shown in FIG. 50B, opening 783 of clamp 780 can slidingly receive projection 773 of sleeve 770. Sleeve 770 can be fixedly attached to clamp 780, such as via a laser weld formed around opening 783.

As shown in FIGS. 50D-E, actuator 760, sleeve 770, and clamp 780 are inserted into housing 751 via openings 752a-c, respectively. Flanges 762a-d engage groove 753 and threads 766 rotatably receive threads 786. In an unclamped state, as shown in FIG. 50D, clamping assembly 750 is constructed and arranged to slidingly receive a lead 265 (shown dashed for illustrative clarity) via opening 752b, through lumens 717 and 782, and out opening 752d. Once lead 265 has been slidingly received, clamping assembly 750 can transition to a clamped state, as shown in FIG. 50E, operably attached to lead 265. Rotation (e.g. clockwise rotation) of actuator 760 via recess 763 causes the threaded interface between threads 766 and 786 to pull clamp 780 towards the top face of housing 751 (e.g. actuator 760 rotates and clamp 780 cannot rotate and is therefore pulled upward). As clamp 780 is pulled towards the top face of housing 711, the space of lumen 782 is reduced and a compression force is exerted on lead 265. Sufficient compression of lead 265 can be achieved when the edges of sleeve 770 engage projections 754a,b of openings 752b,d. Alternatively, a reverse rotation (e.g. counter-clockwise) of actuator 760 via recess 763 causes the threaded interface between threads 766 and 786 to push clamp 780 towards the bottom face of housing 751 (e.g. actuator 760 rotates and clamp 780 cannot rotate and is therefore pushed downward). As clamp 780 is pushed towards the bottom face of housing 751, the space of lumens 717 and 782 are increased and the compression force on lead 265 is reduced to allow for the translation of lead 265 within clamping assembly 750 (e.g. within lead anchor $710_{iii}$). The amount of compression force can be modulated either by the physical limit of the edges of sleeve 770 interfering with the projections 754a,b of openings 752b,d or by a torque limiting element of the tool utilized to rotate actuator 760 (e.g. torque wrench).

Referring to FIGS. 51A-B, a sectional view and a transparent perspective view of another embodiment of a clamping assembly for a lead anchor are illustrated, respectively, consistent with the present inventive concepts. Clamping assembly 750' of FIGS. 51A-B can be integrated into a lead anchor of the present inventive concepts, such as lead anchor $710_{iii}$ described hereabove in reference to FIGS. 49A-B. Clamping assembly 750' can comprise housing 751' and actuator 760'. As shown in FIG. 51A, actuator 760' can comprise a cavity 768, that includes internal (female) threads, threads 766. In some embodiments, actuator 760' comprise an outer surface depression (e.g. a circumferential depression), recess 767. Housing 751' can comprise one or more retention elements, projections 757. As shown in FIG. 51B, projections 757 can comprise rods that extend from one side of housing 751 to the opposite side of housing 751. Projections 757 can slidingly engage recess 767. The engagement of projections 757 with recess 767 can prevent actuator 760' from migrating out of housing 751'. Actuator 760' can further include a recess 763 that is constructed and arranged similar to recess 763 of actuator 760 described hereabove. Clamping assembly 750' can operably engage lead 265 similar to clamping assembly 750 as described in reference to FIGS. 50D and 50E hereabove, such that the lead 265 can be secured to tissue via the lead anchor comprising clamping assembly 750.

Referring to FIGS. 52A-H, sequential suppression waveforms as applied to a pulse train to achieve a therapeutic benefit are illustrated, consistent the present inventive concepts. In some embodiments, a stimulation apparatus of the present inventive concepts, such as apparatus 10 described hereabove, is configured to apply one or more suppression waveforms to a pulse train to create a stimulation waveform. The application of the suppression waveforms can be performed by an external device 500 and/or by an implantable device 200. Referring now to FIGS. 52A-D, a series of pulse trains are illustrated. Each pulse train can comprise a series of pulses. Each pulse can comprise a pulse shape selected from the list consisting of: a square pulse; a negatively sloping exponential pulse; a positively sloping exponential pulse; a negatively sloping logarithmic pulse; a positively sloping logarithmic pulse; a negatively sloping ramped pulse; a positively sloping ramped pulse; and combinations thereof.

Figure 52A:
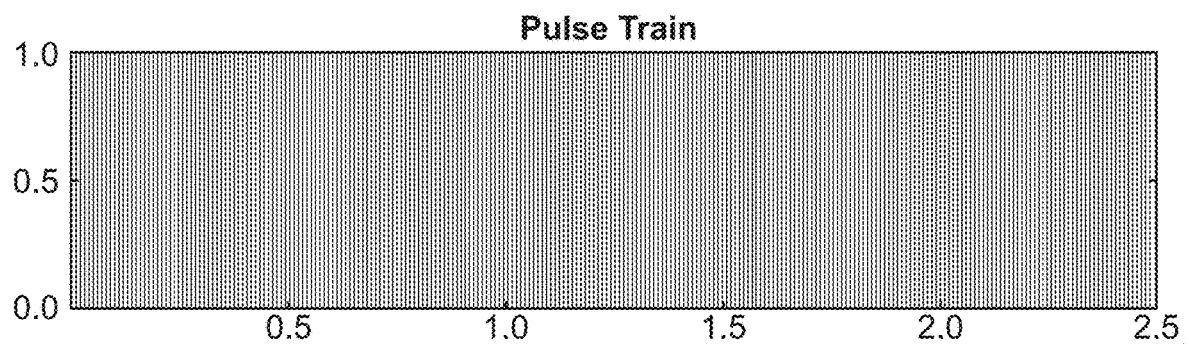
FIGS. 52A-H are sequential suppression waveforms as applied to a pulse train to achieve a stimulation waveform that provides a therapeutic benefit, consistent with the present inventive concepts.
Figure 52B:
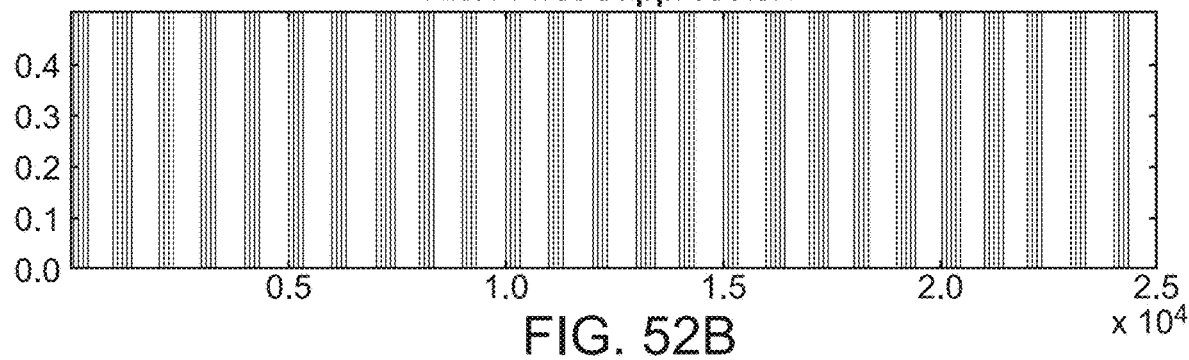
Figure 52C:
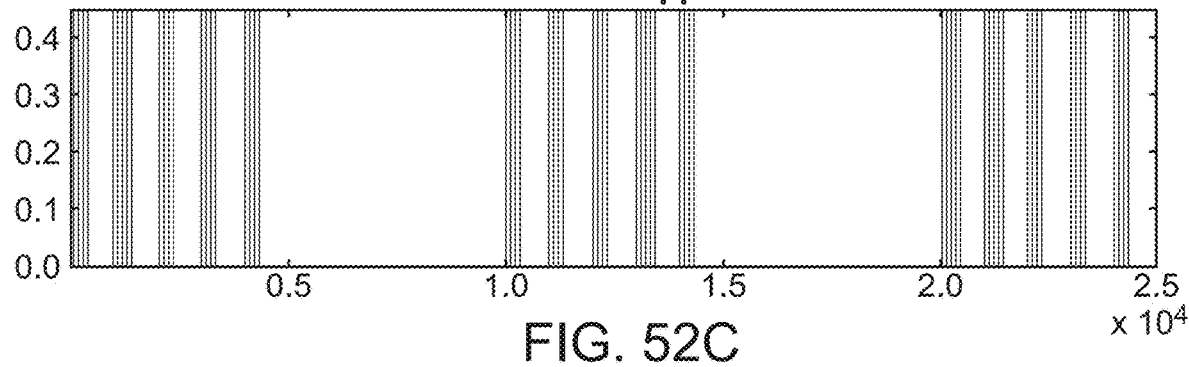
Figure 52D:
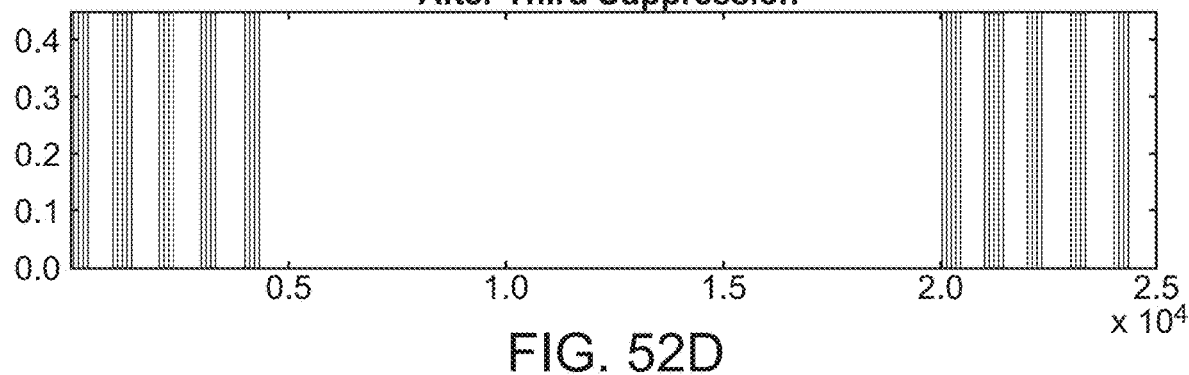
Figure 52E:
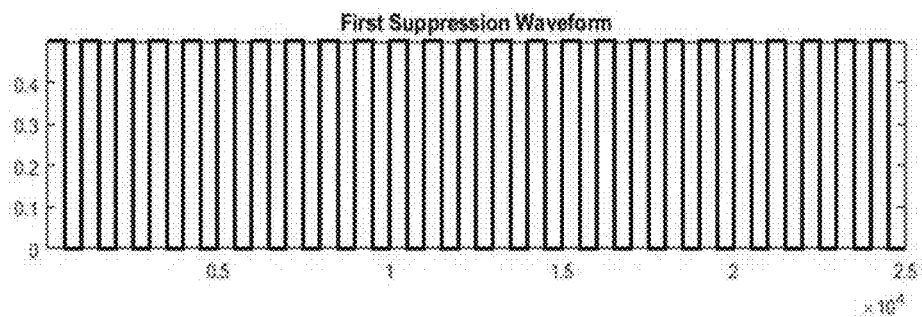
Figure 52F:
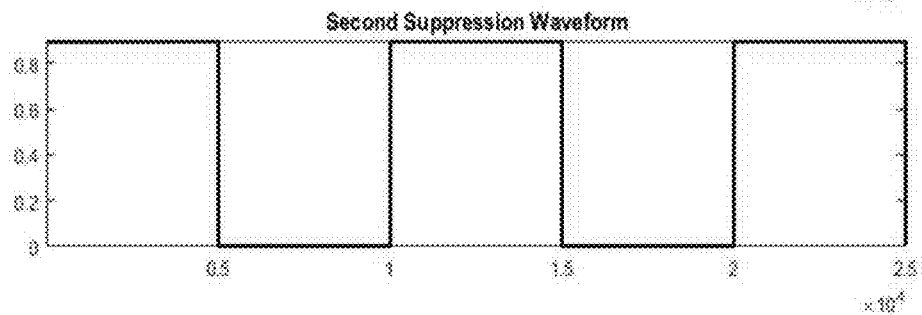
Figure 52G:
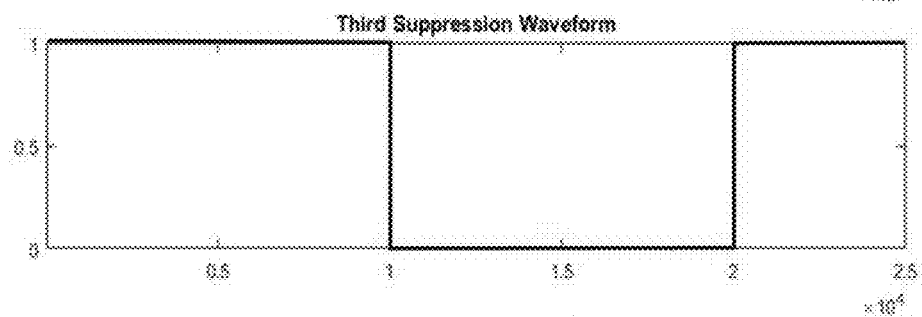
Figure 52H:
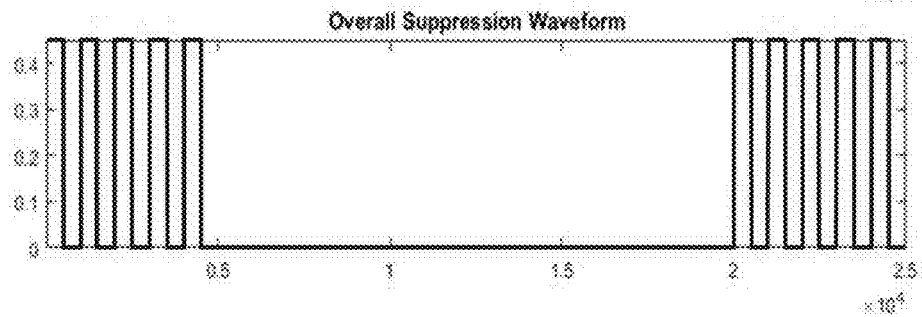

Referring now to FIGS. 52F-H, a series of suppression waveforms are illustrated. The suppression waveforms can comprise a series of "on" and "off" time periods, such that the "on" time periods permit (i.e. do not suppress) stimulation pulses and the "off" time periods suppress stimulation pulses. Suppression waveforms can comprise a comparable percentage of "on" time and "off" time (as shown in FIG. 52E-G). In some embodiments, suppression waveforms comprise a greater percentage of "on" time than "off" time, such as two times greater, such as three times greater, such as four times greater, and such as five times greater. In other embodiments, suppression waveforms comprise a greater percentage of "off" time than "on" time (as shown in FIG. 52H), such as two times greater, three times greater, four times greater, or five times greater.

A first suppression waveform (e.g. the first suppression waveform of FIG. 52E), can be applied to a pulse train (e.g. the pulse train of FIG. 52A comprising a series of equally spaced square wave pulses), such that any pulses of the pulse train that align with the "off" time periods of the first suppression waveform are suppressed, resulting in a first modified pulse train (e.g. the pulse train of FIG. 52B). A second suppression waveform (e.g. the suppression waveform of FIG. 52F) can be applied to the first modified pulse train (e.g. the modified pulse train of FIG. 52B), such that any of the remaining pulses of the first modified pulse train that align with the "off" time periods of the second suppression waveform are suppressed, resulting in a second modified pulse train (e.g. the modified pulse train of FIG. 52C). A third suppression waveform (e.g. the suppression waveform of FIG. 52G), can be applied to the second modified pulse train (e.g. the modified pulse train of FIG. 52C), such that any of the remaining pulses of the second modified pulse train that align with the "off" time periods of the third suppression waveform are suppressed, resulting in a third modified pulse train (e.g. the modified pulse train of FIG. 52D). An aggregate of two or more suppression waveforms, such as the three suppression waveforms shown in FIGS. 52E-G can be configured as an overall suppression waveform, such as is shown in FIG. 52H. In some embodiments, the suppression waveforms as shown in FIGS. 52E-G can be applied sequentially (i.e. temporally discrete) such that a patient receiving the various stimulation waveforms has an opportunity to confirm whether a therapeutic benefit is achieved via each modified pulse train (e.g. before the application of a subsequent suppression waveform).

While the configuration of creating a stimulation waveform described hereabove in reference to FIGS. 52A-H has been described in terms of applying one or more suppression waveforms to remove pulses from a pulse train, it is within the spirit and scope of the present application that one or more of the suppression waveforms (perhaps better described in this configuration as "addition waveforms")

could be applied to a pulse train to add pulses (e.g. add pulses during an "on" period, and do nothing during an "off period", or vice versa. Multiple addition waveforms could be applied simultaneously or sequentially to add pulses, such as in a similar manner that is described hereabove in reference to removal of pulses. In some embodiments, a pulse train includes minimal pulses, even as few as a single pulse, and pulses are added via one or more addition waveforms that are applied to increase the number of pulses to provide a stimulation waveform that results in an enhanced therapy. In some embodiments, a stimulation waveform comprises a series of pulses derived from two or more functions in a convoluted arrangement.

Figure 54A:
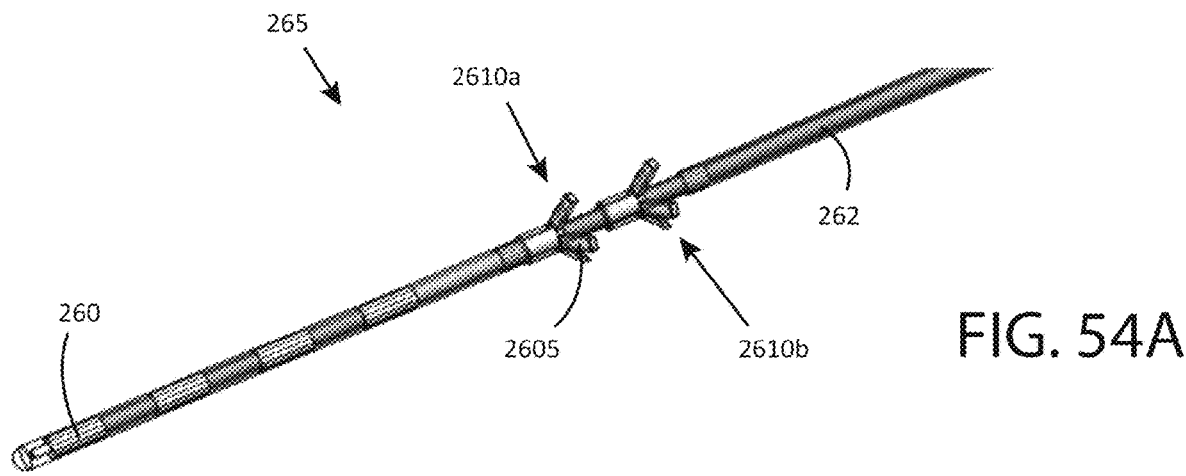
FIGS. 54A and 54B are perspective views of a distal portion of an implantable lead comprising unidirectional tissue engagement elements and bidirectional tissue engagement elements, respectively, consistent with the present inventive concepts.
Figure 54B:
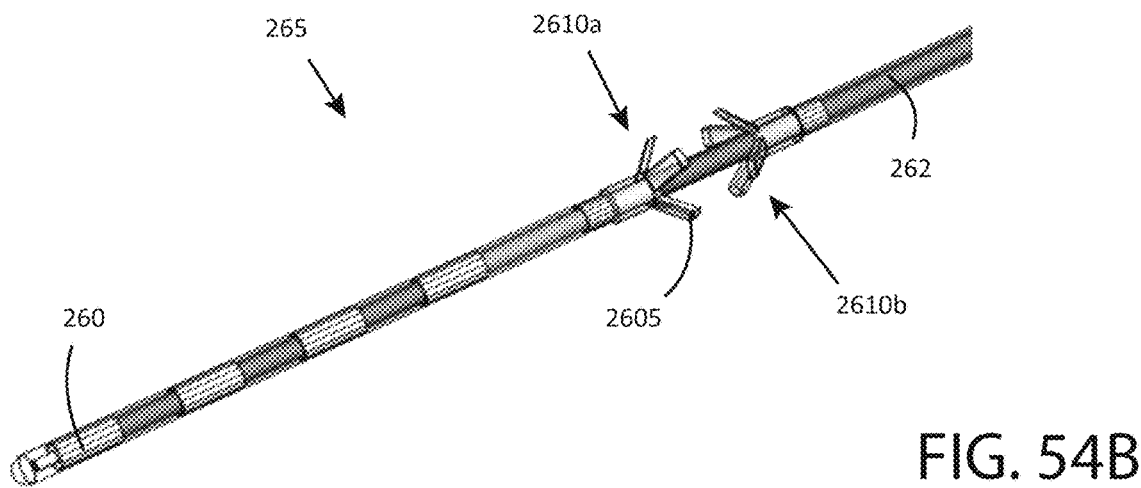

Referring to FIGS. 54A and 54B, perspective views of a distal portion of an implantable lead comprising unidirectional tissue engagement elements and bidirectional tissue engagement elements are illustrated, respectively, consistent with the present inventive concepts. Lead 265 comprises conduit 262 (e.g. a flexible conduit comprising one or more wires or other energy carrying filaments) and one or more stimulation elements 260 positioned on a distal portion of lead 265. Lead 265 can comprise one more tissue engagement elements, projections 2605. Projections 2605 engage surrounding patient tissue to resist migration of lead 265. Projections 2605 can be positioned proximate stimulation elements 260. Projections 2605 can comprise a circumferential arrangement (e.g. are evenly spaced about lead 265). Lead 265 can comprise one or more arrangements 2610 of projections 2605, such as arrangements 2610a,b shown.

As shown in FIG. 54A, arrangements 2610a,b comprise a unidirectional orientation to resist migration of lead 265 in an opposite direction relative to the insertion path of lead 265 (e.g. projections 2605 of arrangements 2610a,b are oriented in the same direction). In some embodiments, projections 2605 of arrangements 2610a,b are both oriented toward the proximal end of lead 265. As shown in FIG. 54B, arrangements 2610a,b comprise a bidirectional orientation to resist migration of lead 265 in either direction relative to the insertion path of lead 265 (e.g. projections 2605 of arrangement 2610a are oriented opposite the projections 2605 of arrangement 2610b). In some embodiments, projections 2605 of arrangement 2610a are oriented towards the proximal end of lead 265 and projections 2605 of arrangement 2610b are oriented towards the distal end of lead 265.

Figure 55A:
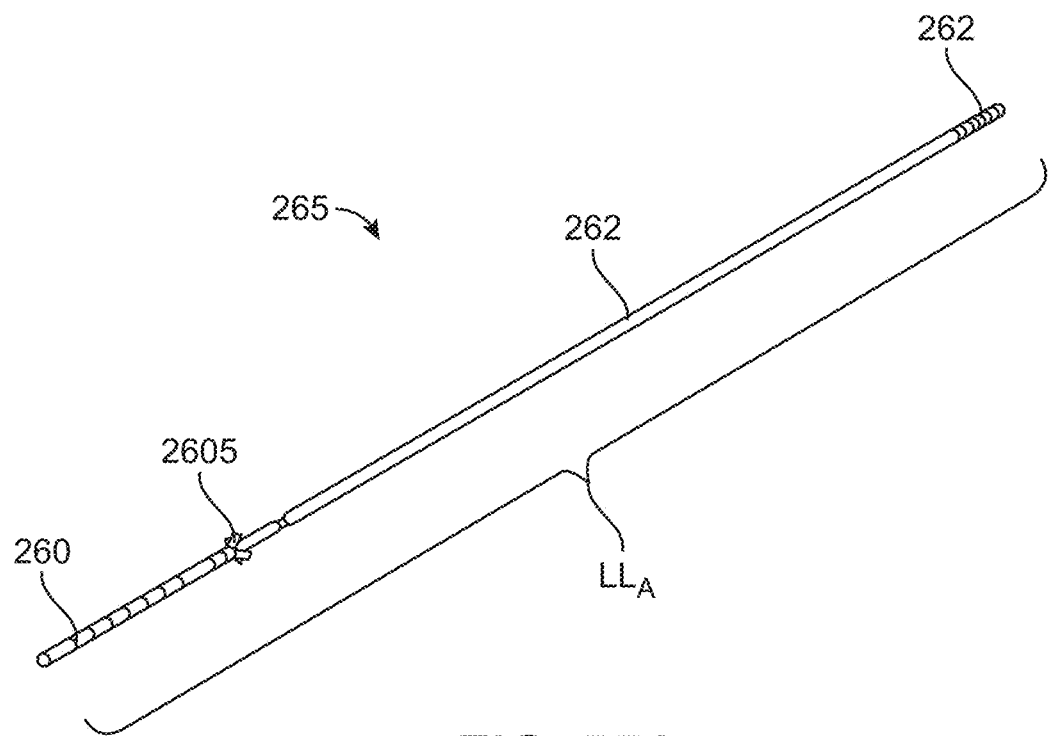
FIGS. 55A and 55B are perspective views of an implantable lead and an implantable device connected to the implantable lead, respectively, consistent with the present inventive concepts.
Figure 55B:
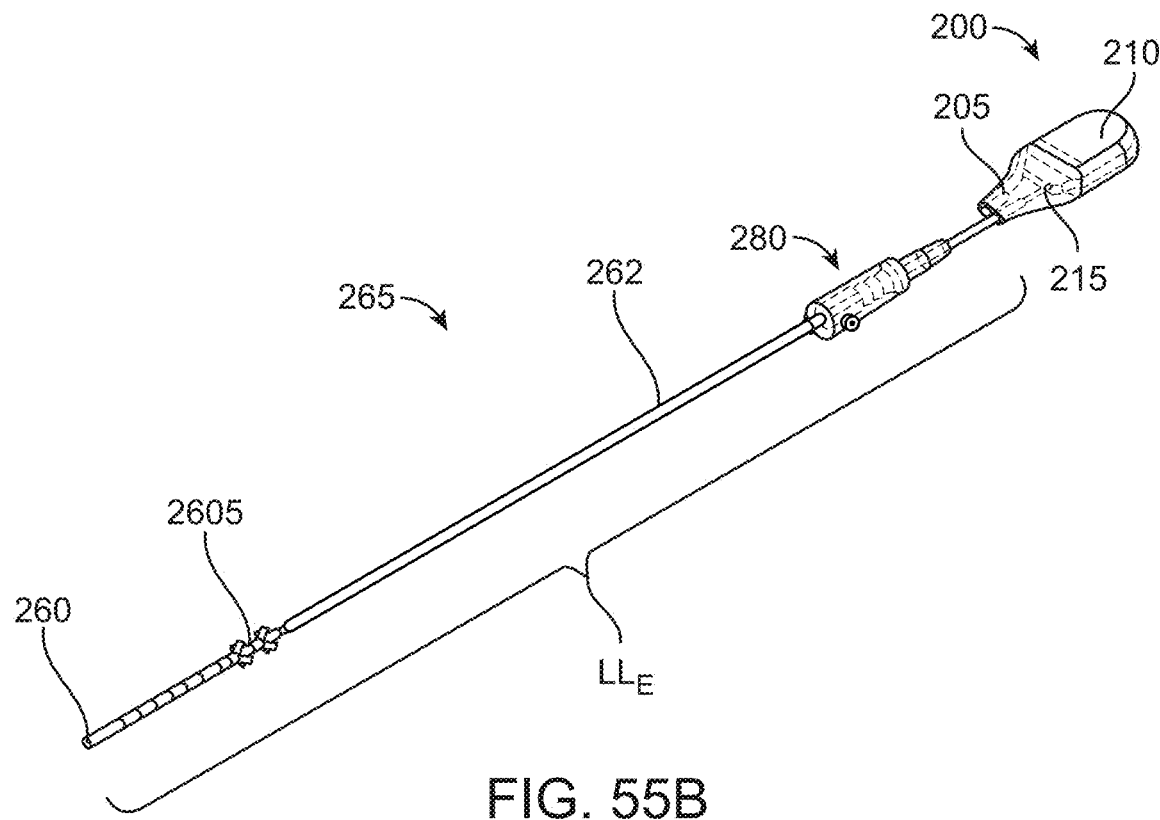

Referring to FIGS. 55A and 55B, perspective views of an implantable lead and an implantable device connected to the implantable lead are illustrated, respectively, consistent with the present inventive concepts. Lead 265 comprises conduit 262 (e.g. a flexible conduit comprising one or more wires or other energy carrying filaments). The distal portion of lead 265 can comprise one or more stimulation elements 260. The proximal portion of lead 265 can comprise multiple contacts 269 operably connected (e.g. electrically connected) to corresponding stimulation elements 260 (e.g. via a set of wires). In some embodiments, lead 265 can comprise one more projections 2605 positioned proximate stimulation elements 260, as described hereabove in reference to FIGS. 54A,B. Implantable device 200 comprises a housing 210 and a connector 215 constructed and arranged as described hereabove in reference to any of FIGS. 1, 2A-D, 3, 3A-D, 4A-B, 5C and/or 8. In some embodiments, connector 215 passes through an opening in housing 210, in a feed-through arrangement. In some embodiments, a sealing element 205 provides a seal about connector 215, the opening in housing 210 and/or the interface between connector 215 and housing 210.

Lead 265 can comprise an actual lead length LLA comprising the distance from the proximal end of lead 265 to the distal end of lead 265, as shown in FIG. 55A. Lead 265 can comprise an actual lead length LLA of between 8 cm and 60 cm such as between 15.85 cm and 17.85 cm. Lead 265 can comprise an effective lead length LLE comprising the distance from the distal end of sealing element 205 of a connected implantable device 200 to the distal end of lead 265, as shown in FIG. 55B. Lead 265 can comprise an effective lead length of between 10 cm and 70 cm such as between 18 cm and 20 cm. The effective lead length LLE provides sufficient exposure of contacts 269 and stimulation elements 265 to allow for test stimulation during an implantation procedure with an introducer device present (e.g. a Tuohy needle or tear-away lead introducer) prior to deploying projections 2605 to secure the position of lead 265 relative to the patient tissue. In some embodiments, the effective lead length LLE comprises approximately 20 cm for use with a 6 inch Tuohy needle. In some embodiments, the effective lead length LLE comprises approximately 18 cm for use with a tear-away lead introducer, such as insertion tool $60_{iii}$ as described hereabove in reference to FIG. 29.

Referring to FIGS. 56A-C, a series of steps for manipulating a user interface to select a stimulation element configuration is illustrated, consistent with the present inventive concepts. Programmer 600 includes user interface 680 comprising touchscreen 682, such as is described hereabove in reference to FIG. 17. Touchscreen 682 can display stimulation and/or other apparatus 10 information, and/or allow user control (e.g. adjustment) of one or more components of external device 500 and/or implantable device 200. Touchscreen 682 can include a stimulating electrode configuration interface, electrode interface 686, configured to allow a user (e.g. clinician) to change the configuration of one or more stimulating electrodes, such as stimulation elements 260 of lead 265. A change in the stimulating electrode configuration can achieve customized stimulation across a targeted range, or area, of patient tissue. Electrode interface 686 can visually represent at least one electrode array 6801 with two or more electrodes 6803, such as electrodes 6803a-f shown, wherein at least a first electrode 6803 is assigned an anode polarity and at least a second electrode 6803 is assigned a cathode polarity. An anode polarity can be visually represented as a plus-sign icon (+) and a cathode polarity can be visually represented as a minus-sign icon (−). A user can reassign the anode and/or cathode polarities to a different electrode 6803 by dragging cursor 6805 (e.g. a touch-activated cursor, mouse-activated cursor, keyboard-activated cursor, and/or other controllable cursor), or otherwise repositioning the respective polarity icon to a different electrode 6803 within array 6801 (as shown in FIGS. 56B and 56C). Any electrode 6803 that is not assigned as either the anode or cathode polarity can be identified as "inactive" by apparatus 10 (e.g. the "inactive" electrodes do not provide stimulation energy).

For example, electrode 6803a can comprise the anode polarity, electrode 6803c can comprise the cathode polarity, and the user can reassign the cathode polarity to electrode 6803d by dragging, or otherwise repositioning, the cathode polarity icon from electrode 6803c to electrode 6803d, as shown. In this example, stimulation energy will be delivered to patient tissue proximate the area between electrodes 6803a and 6803d. In some embodiments, the user reassigns both the anode and cathode polarities to a different electrode 6803. In some embodiments, similar techniques can be used to assign one or more electrodes for delivering stimulation energy (e.g. energy delivered in a bipolar and/or monopolar mode).

Figure 57A:
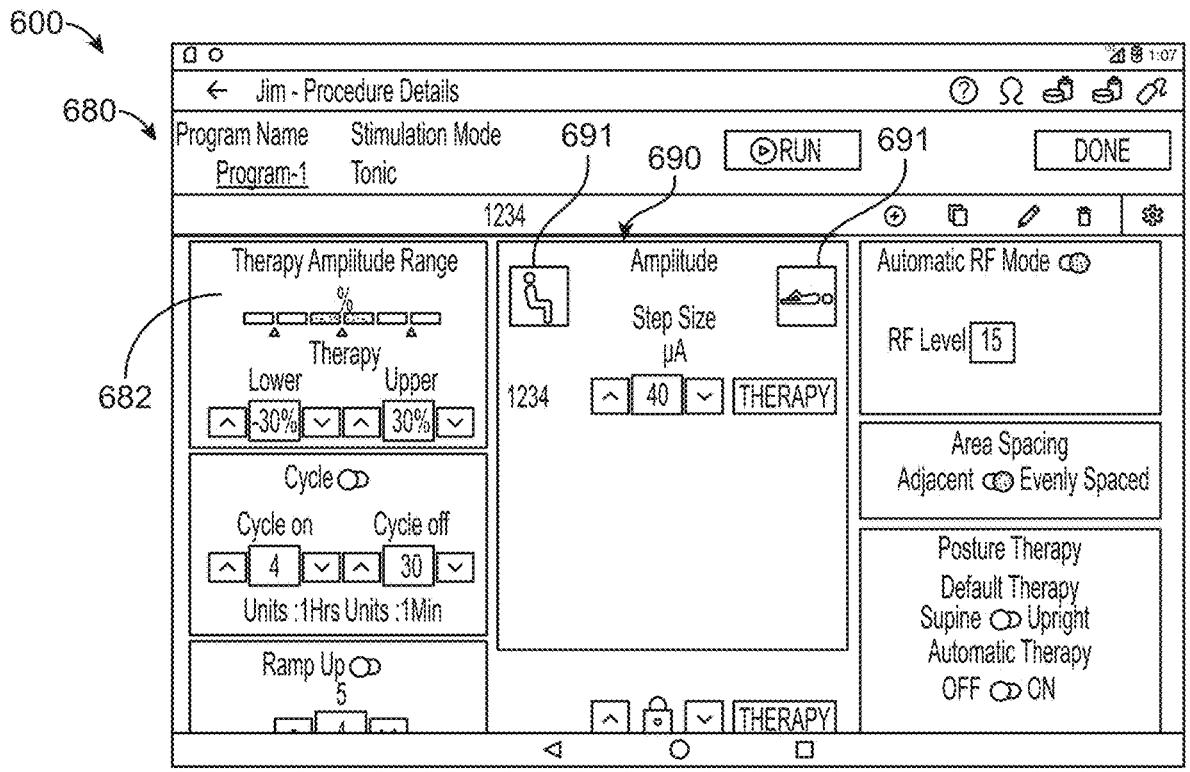
FIGS. 57A and 57B illustrates alternative user interfaces of a programmer for the configuration of stimulation parameters associated with patient posture, consistent with the present inventive concepts.
Figure 57B:
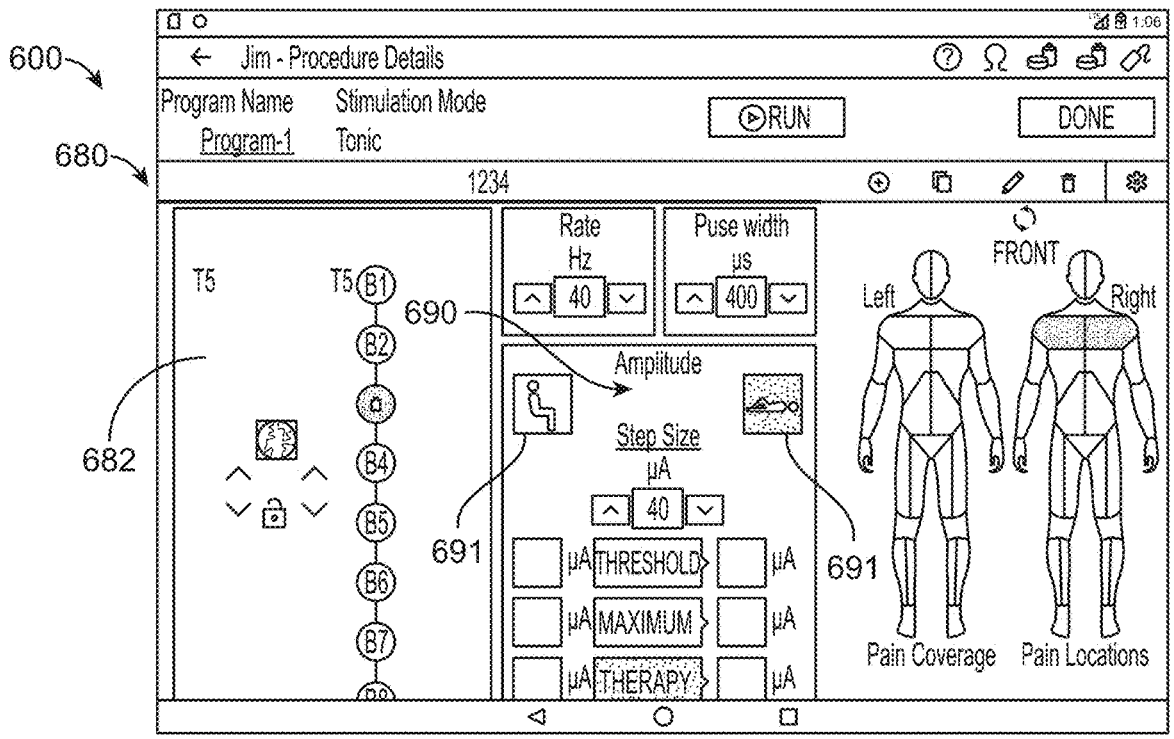

Referring to FIGS. 57A and 57B, two alternative user interfaces of a programmer for the configuration of stimulation parameters associated with patient posture are illustrated, consistent with the present inventive concepts. Programmer 600 includes user interface 680 comprising touchscreen 682, such as is described hereabove in reference to FIG. 17. Touchscreen 682 can display stimulation and/or other apparatus 10 information, and/or allow user control (e.g. adjust) one or more components of external device 500 and/or implantable device 200. External device 500 can comprise an accelerometer (e.g. accelerometer 561 described herein) configured to provide a signal based on the position of the patient (e.g. an upright or supine position). Apparatus 10 can be configured to adjust the stimulation energy delivered to the patient based on the patient position. Touchscreen 682 can include a patient position interface, position interface 690, configured to allow a user (e.g. clinician) to configure one or more stimulation programs based on patient position. Position interface 690 can comprise one or more user input components, buttons 691. Buttons 691 can enable a user to indicate whether the patient is in an upright or supine position and configure the stimulation program parameters (e.g. the stimulation rate, stimulation pulse width, stimulation amplitude, etc.) to be associated with that position. External device 500 can be configured to stimulate patient tissue using the stimulation programs associated with the respective patient position. In some embodiments, a user manually inputs the patient position to cause external device 500 to stimulate patient tissue using the respective stimulation programs. For example, a user can indicate a supine patient position and external device 500 can stimulate patient tissue using the one or more stimulation programs configured for the supine position. In some embodiments, the external device 500 is configured to automatically detect patient position (e.g. via accelerometer 561 and/or other accelerometer) and subsequently stimulate patient tissue using the associated stimulation programs.

Additionally, touchscreen 682 can display and/or allow the adjustment of at least one of the following: stimulation parameters; anatomic representation of target tissue; pulse width; stimulation rate; amplitude; on/off controls; select and/or add target tissue areas; duty cycle parameter; RF mode and/or level; stimulation mode (e.g. waveform); and combinations thereof.

Figure 58C:
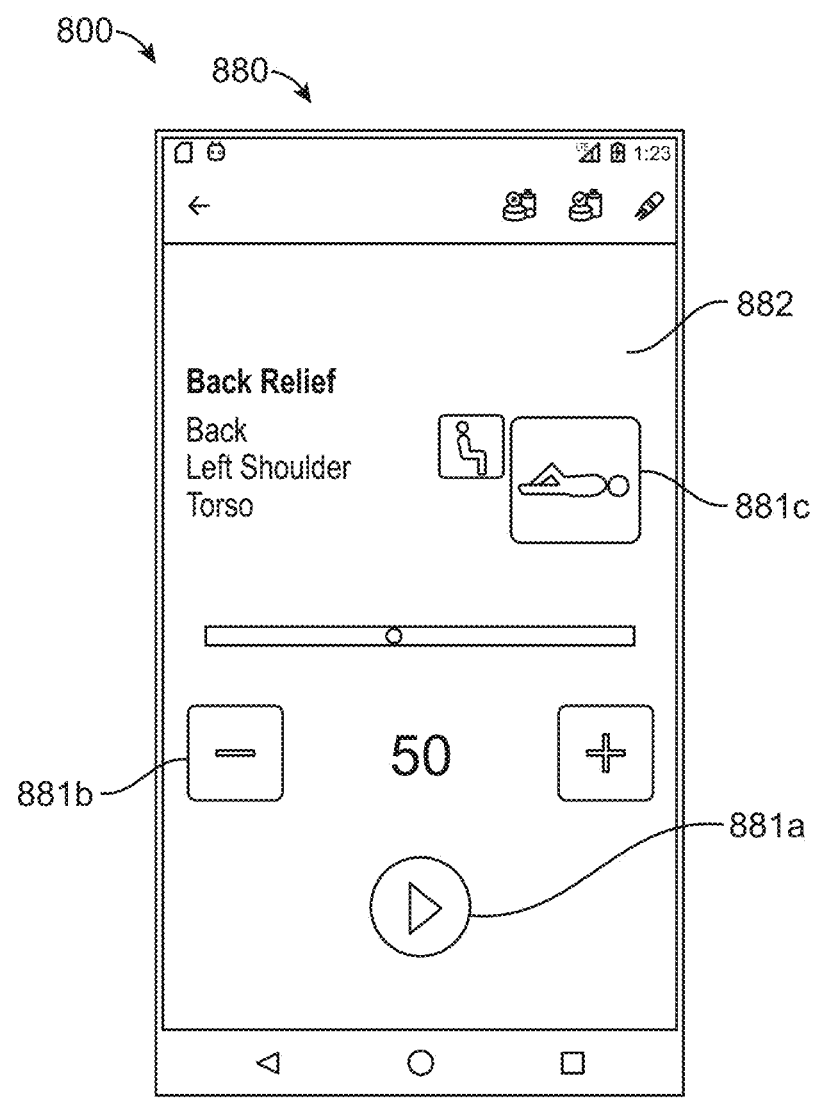

Referring to FIGS. 58A-C, a user interface of a programmer for a stimulation apparatus are illustrated, consistent with the present inventive concepts. Portable programmer 800 can comprise a portable computer, such as a laptop, cell phone, or tablet. Programmer 800 includes user interface 880 comprising one or more user interface components, such as one or more buttons 881 and a touchscreen 882. Programmer 800 can be configured to communicate (e.g. via Bluetooth or other wireless and/or wired communication) with one or more components of apparatus 10, such as external device 500 and/or implantable device 200. In some embodiments, programmer 800 is constructed and arranged similar to programmer 600 as described hereabove in reference to FIGS. 17, 57A, and/or 57B.

User interface 880 can comprise a "default view" that displays a listing of the one or more stimulation programs of apparatus 10, as shown in FIG. 58A. With each stimulation program, user interface 880 can include one or more buttons 881a configured to allow a user to activate and deactivate a stimulation program (e.g. a blue and white arrow for activation, and a red and white square for deactivation). In some embodiments, the default view displays stimulation programs for the relief of back pain, leg pain, and shoulder pain, as shown.

In the default view, a user can select one of the stimulation programs to further access a "program view" that displays one or more parameters of the respective stimulation program, as shown in FIGS. 58B and 58C. The program view can include one or more buttons 881a to activate and deactivate the stimulation program (e.g. a blue and white arrow for activation, and a red and white square for deactivation). The program view can include one or more buttons 881b configured to allow a user to adjust the amplitude of the stimulation program (e.g. along a sliding scale). Additionally, the program view can include one or more buttons 881c configured to allow a user to indicate patient position (e.g. an upright or supine position). In some embodiments, external device 550 automatically detects patient position (e.g. via an accelerometer) and communicates the patient position to programmer 800. An automatic detection of patient position can be indicated by an "auto" icon, as shown in FIG. 58B. A user can manually identify patient position, as shown in FIG. 58C (e.g. when the automatic detection of patient position provided by external device 500 is incorrect). External device 500 can be configured to recalibrate its posture vectors in response to a manual change of patient posture.

Figure 59:
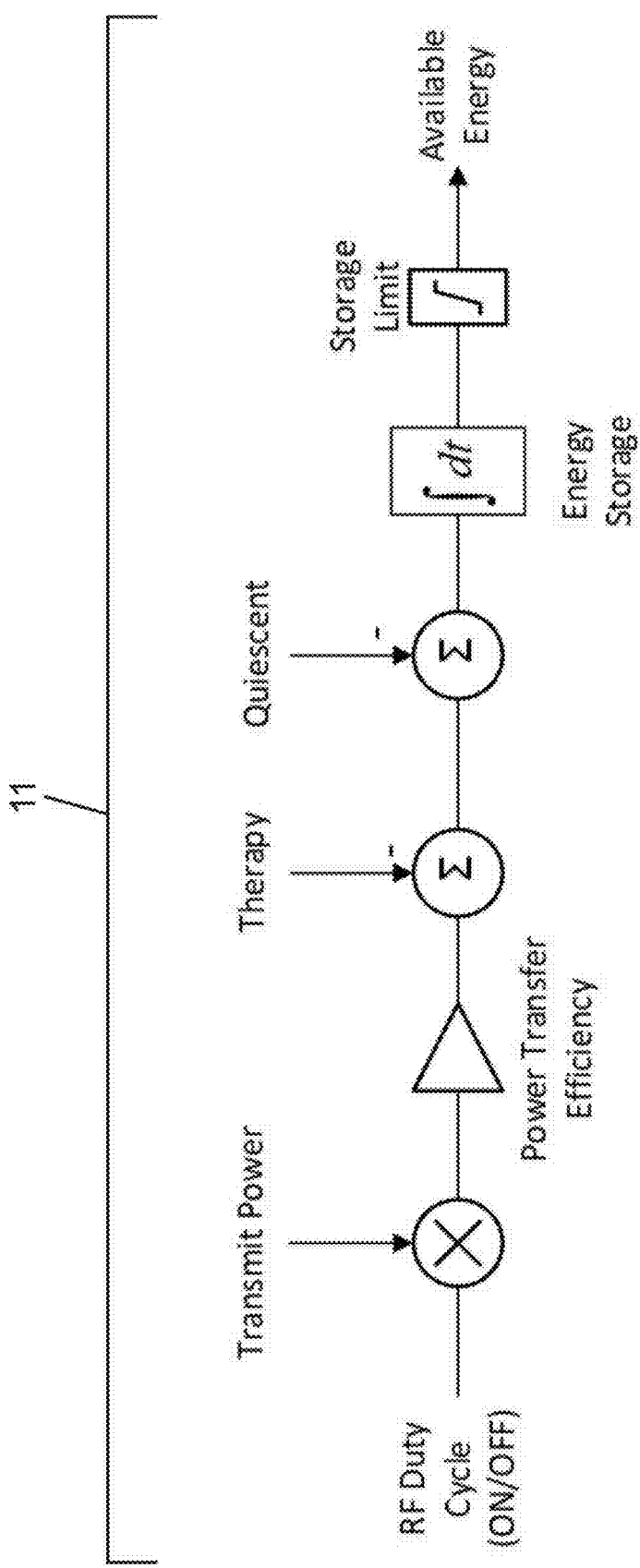
FIG. 59 is a schematic view of a power delivery and consumption arrangement of a stimulation apparatus, consistent with the present inventive concepts.

Referring now to FIG. 59, a schematic view of a power delivery and consumption arrangement of a stimulation apparatus is illustrated, consistent with the present inventive concepts. Apparatus 10 of the present inventive concepts, can include arrangement 11 which can be configured to enhance reliability of apparatus 10 (e.g. enhance reliability of therapy delivery and/or other functionality). Arrangement 11 can be performed by and/or can include one or more components positioned within external device 500, implantable device 200, and/or another component of apparatus 10. In some embodiments, arrangement 11 can be configured to reduce power consumption (e.g. enhance battery or other power supply life of an external device 500). In some embodiments, an implantable device 200 receives wireless power from an external device 500, and arrangement 11 is configured to both enhance reliability (e.g. enhance reliability of therapy delivery by the implantable device 200) and reduce power consumption (e.g. enhance battery life of the external device 500). For example, arrangement 11 can be configured to avoid time periods in which insufficient power is received by an implantable device 200. Simultaneously, arrangement 11 includes one or more algorithms (e.g. one or more "optimization" algorithms) which routinely (e.g. continuously) and intelligently adapt to the physical environment of one or more components of apparatus 10, while external device 500 provides power above a minimum threshold required for reliable operation (e.g. reliable stimulation of implantable device 200). These algorithms can also adapt to diverse therapy configurations (e.g. diverse amounts of stimulation energy being delivered) and/or adapt to various implantable device 200 state conditions, and manage transitions in these configurations and conditions.

Each implantable device 200 is desired to be relatively small, and therefore can have limited energy storage capacity (e.g. limited energy storage capacity of energy storage assembly 270). When there is a change in power transfer (e.g. a sudden change that can occur with patient motion) and/or there is a change in power consumption (e.g. due to a change in delivery of stimulation energy), arrangement 11 can be configured to rapidly adapt so that power delivery from an external device 500 to the implantable device 200 remains sufficient for safe and reliable operation.

Apparatus 10 can include multiple mechanisms for adjusting power delivery between an external device 500 and an implantable device 200. For example, a first mechanism can adjust the amplitude of power transmitted by external device 500 to change the output power of the transmission signal (e.g. an RF signal). Alternatively or additionally, a second mechanism can turn the power transmitted by external device 500 on and off, such as via a duty cycle that is set and/or adjusted by an algorithm (e.g. an optimization algorithm of arrangement 11, such as an algorithm of external device 500). Power is wasted if energy stored on implantable device 200 reaches a maximum value (e.g. further charging can't occur) and external device 200 continues to deliver power. This energy storage maximum can be limited by an acceptable input voltage of a rectifier (e.g. rectifier 232) of implantable device 200, the rectifier operating as a charge pump, providing a voltage multiplication of an input voltage of an antenna (e.g. antenna 240) of implantable device 200. Implantable device 200 can include other electronic componentry that limits a maximum voltage for energy storage (e.g. the circuitry includes a voltage clamp that prevents an excessive voltage from damaging an electronic component).

Arrangement 11 can be configured to perform duty cycle modulation of power transferred by an external device 500 based on an amplifier of external device 500 being more efficient when charging at particular power levels (e.g. high-power levels) that do not saturate circuitry of implantable device 200 and/or do not cause reduced efficiency by exceeding an optimal input voltage of a rectifier of implantable device 200. As described hereabove, power can be delivered in bursts via duty cycle modulation which can deliver power before and after stimulation pulses (e.g. in a symmetric pattern). Power delivery before stimulation can prevent a significant voltage drop (e.g. of energy storage assembly 270) when implantable device 200 transitions from operating at a quiescent current to delivering stimulation energy to tissue. If sufficient energy is available, boosting circuitry of implantable device 200 can operate with a minimum conversion ratio, which increases efficiency and maximizes the instantaneous power implantable device 200 can deliver (e.g. stimulation energy delivered to tissue). Power delivery after stimulation can replenish energy used during stimulation, and can reduce impact of disturbances in power transfer. Duty cycle modulation can be applicable to idle (e.g. no stimulation) modes and/or lower frequency stimulation modes (e.g. stimulation below approximately 1.5 kHz or below 1 kHz). When varying power transfer with duty cycle, an optimization algorithm of arrangement 11 can measure stored energy in implant 200 (e.g. stored in energy storage assembly 270) once every stimulation period (e.g. a period of time in which one or more forms of stimulation energy is delivered), and adjust the duty cycle based on an analysis of energy requirements for that stimulation period. Energy measurements (e.g. voltage measurements) can be taken (immediately) prior to a first stimulation pulse in the stimulation period, a point in which the stored energy can be high. To measure a target energy level effectively, a target voltage of energy storage assembly 270 can be set slightly below the maximum allowed value. An optimization algorithm can determine a target (maximum) value of energy storage by increasing (or maximizing) the duty cycle for a (short) time period, and subsequently measuring the energy level. Alternatively or additionally, the energy level can be occasionally increased over time until a constant error is observed (e.g. a maximum has been achieved), which also indicates a limit has been reached. The target energy level for the algorithm can then be adjusted slightly below the maximum thereby allowing optimized energy storage with the described control loop (also referred to as "tracking loop" or "feedback loop" herein). During optimization, the duty cycle at each stimulation cycle can be fed to a lowpass digital filter with a time constant that is much slower than the stimulation rate, and the output of this filter can be sampled after several time constants. The filtered value is the average duty cycle during the sampling period. If the average duty cycle is too high, then the output power of the transmitter of external device 500 can be increased. If the average duty cycle is too low, then the output power of the transmitter can be decreased. Controlling the average duty cycle can allow the power transmitter of external device 500 to operate at an optimized point, and it can allow a feedback loop of arrangement 11 to quickly raise duty cycle in response to a disturbance in power.

Arrangement 11 can utilize duty cycle modulation when there are multiple stimulation pulses delivered in a stimulation period. The power transferred from external device 500 to implantable device 200 can be allocated based on energy of stimulation pulses, as well as when the pulses occur in the stimulation period. With multiple stimulation pulses, the periodic measurement of available energy in implantable device 200 can be performed immediately prior to the stimulation pulse delivering the greatest energy. In other words, if a stimulation period consists of multiple pulses, a timing of a stimulation period can be defined such that the largest energy pulse is the first pulse.

Arrangement 11 of FIG. 59 demonstrates the available energy over time, as power is transmitted and used by the device. As described above, power transmission is represented by two parameters, the amplitude of the transmission signal, and the duty cycle of transmission. Power consumption by each implantable device 200 comprises: energy delivered during stimulation; energy delivered performing other functions (e.g. sensing functions, data transmission function, and/or other functions); and/or quiescent energy required by implantable device during minimal operation. Integrating the sum of power used over time determines energy to be stored in implantable device 200, which can have one or more limits as described hereabove. If energy storage element 270 is a capacitor or battery, this limit will be reflected as a limit in the voltage as described hereabove. Circuitry of implantable device 200 can also have a maximum operating voltage that limits the energy that can be stored, also as described hereabove.

The power transfer efficiency between an external device 500 and an implantable device 200 represents the ability of external device 500 to provide energy to the implantable device 200 and represents the quality of the wireless link between two devices. This efficiency can vary over time (such as with patient motion and/or changes in environment), and can be tracked by arrangement 11 such that the implantable device 200 neither loses power (causing an interruption in stimulation delivery and/or other implantable device 200 operation), nor is excessively charged (wasting power).

When apparatus 10 reaches a steady state, the duty cycle of power transmission can be stable. For example, over a (repeated) period of time of a control loop (a control loop managed by an optimization algorithm of arrangement 11), the energy transmitted from external device 500 to implantable device 200 can be approximately equal to the sum of: the energy for therapy (e.g. stimulation energy delivered), the energy required for other functions of implantable device 200; and quiescent energy requirements of implantable device 200. As a result, the available energy of implantable device 200 will rise and fall the same amount during each time period. Furthermore, the maximum energy will be maintained at a value slightly lower than a limit (e.g. a maximum voltage).

Figure 60:
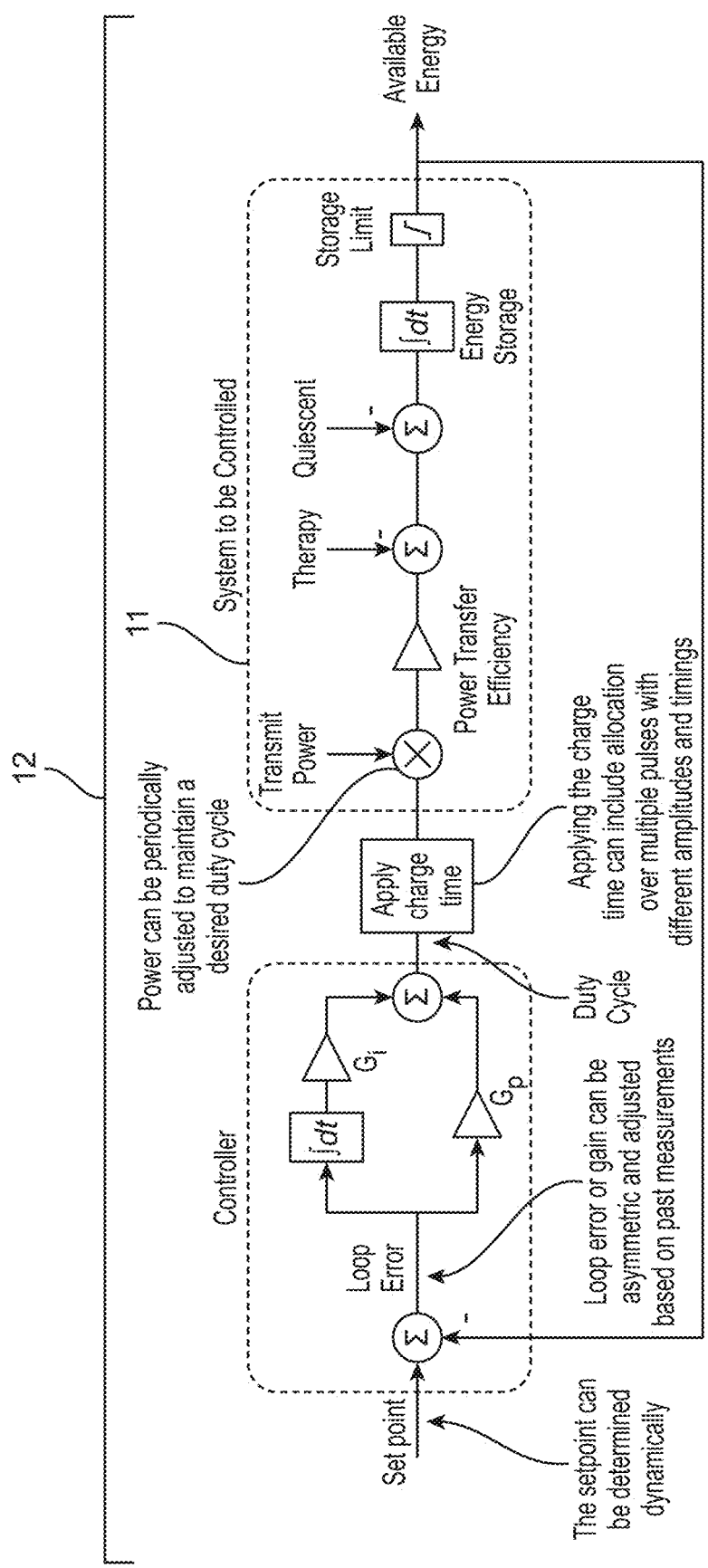
FIG. 60 is a schematic view of a power delivery and consumption arrangement of a stimulation apparatus, consistent with the present inventive concepts.

Referring now to FIG. 60, a schematic view of a power delivery and consumption arrangement of a stimulation apparatus is illustrated, consistent with the present inventive concepts. Apparatus 10 of the present inventive concepts, can include arrangement 12 which can be configured to enhance reliability of apparatus 10 (e.g. enhance reliability of therapy delivery and/or other functionality). Arrangement 12 can control duty cycle of power transfer between an external device 500 and an implantable device 200. Arrangement 12 can be performed by and/or can include one or more components positioned within external device 500, implantable device 200, and/or another component of apparatus 10. Arrangement 12 includes arrangement 11 as shown, such as arrangement 11 described hereabove in reference to FIG. 59. Arrangement 12 comprises a block to calculate an error (also referred to as a "loop error") between a setpoint energy level and a measured energy level. The calculated error is provided to a Proportional Integrator (PI) controller (e.g. a PI controller that includes a derivate control) which determines a power transmission duty cycle based on the calculated error. A high proportional path gain allows the control loop of arrangement 12 to respond quickly to disturbances (e.g. power transfer disturbances), thereby providing reliability in implantable device 200 function (e.g. uninterrupted delivery of stimulation energy). Periodically updating the amplitude of power transfer to keep the average duty cycle low provides a large dynamic range in the duty cycle, such that the proportional path has the required dynamic range to quickly respond to disturbances. The integral path drives the steady state error to zero, thereby providing the optimized resilience to disturbance and optimized efficiency.

The setpoint can be determined dynamically. The error and/or gain can be asymmetric, and can be adjusted based on previous measurements. Applying the charge time can include allocation over multiple stimulation pulses, each with different amplitudes and/or timings (e.g. timings such as pulse width timing and/or burst duration timing). Power transfer from external device 500 to implantable device 200 can be periodically adjusted to maintain a duty cycle with the desired dynamic range.

Arrangement 12 manages significant disturbances by maintaining an energy setpoint that is close to the energy storage limit of energy storage assembly 270. The setpoint can be determined by periodically determining the energy storage limit itself, such as by increasing the duty cycle limit to the maximum for a short period (e.g. as described hereabove in reference to FIG. 59). The energy storage limit can be measured, and the energy setpoint can be set to a value slightly below the measured maximum. If apparatus 10 is in a steady-state mode and power transfer efficiency suddenly increases, the available energy can rise and reach the limit. The measured error will therefore be limited to a value slightly above the setpoint, and, response could be slow causing power to be wasted. This undesired performance can be mitigated by raising the loop gain in response to consecutive negative errors, or with asymmetric gain based on the direction of the error. If power transfer is high and the therapy at a low level (e.g. a low energy delivery level), the minimum duty cycle required for the energy storage measurement can be greater than necessary, and power could be wasted. Conversely, if power transfer is too low, then the average duty cycle can be large, and apparatus 10 may not have the dynamic range to respond to a disturbance. Therefore, it can be desirable to keep the duty cycle within a controlled range, such as a range between approximately 20% and 40%, or between 25% and 33%. This range can be maintained by lowpass filtering the duty cycle with a first order digital filter, and sampling the output every several time-constants, such as every 4 time-constants. The time constant of the digital filter can be approximately the same as the stimulation period or longer than the stimulation period in order to behave as a lowpass filter. If the duty cycle is out of this range, power transfer amplitude can be adjusted accordingly.

Figure 61:
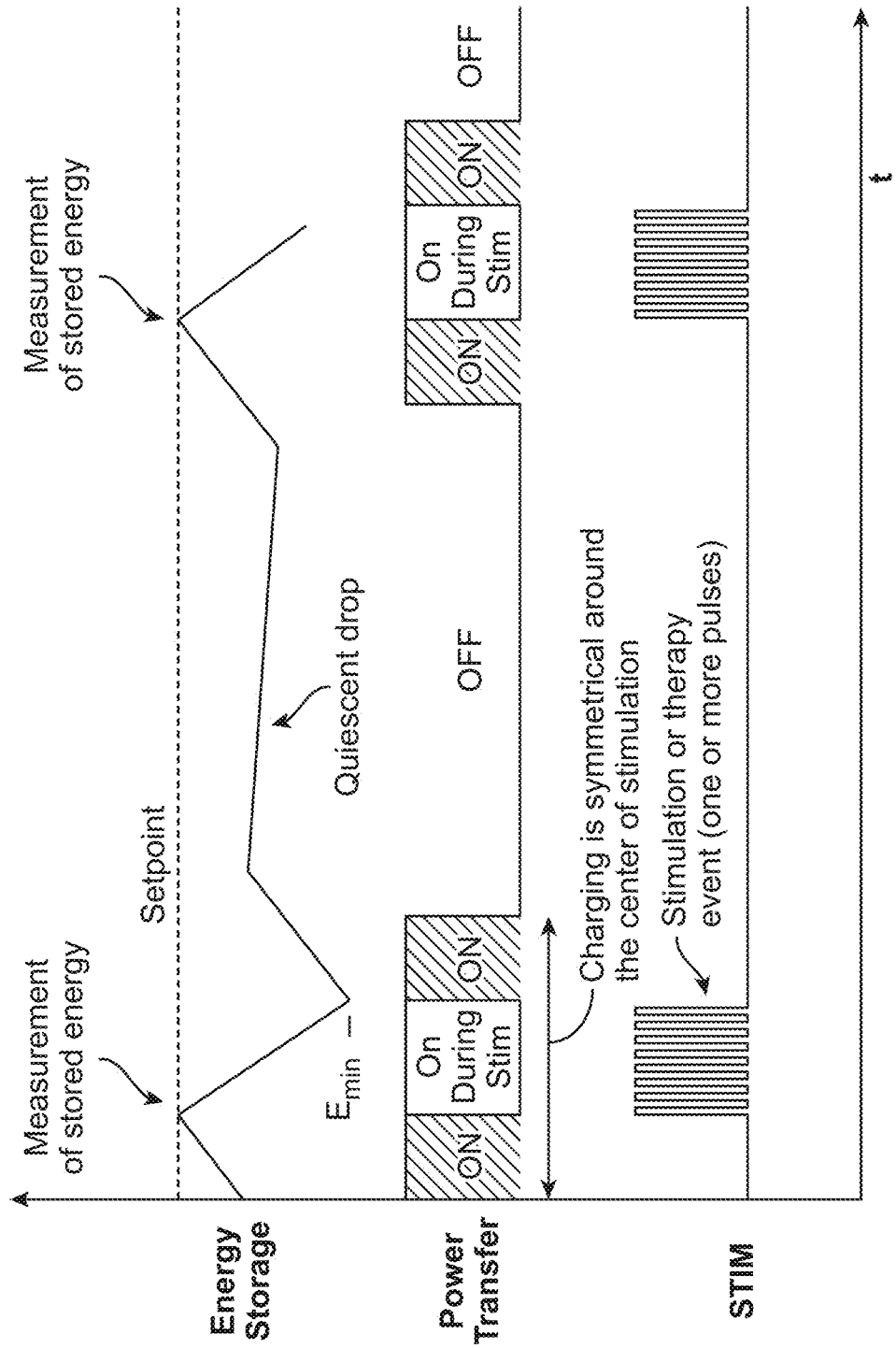
FIG. 61 is a graphical representation of a duty cycle of a power control arrangement, consistent with the present inventive concept.

Referring now to FIG. 61, a graph of a duty cycle of a power control arrangement is illustrated, consistent with the present inventive concepts. The graph of FIG. 61 depicts normal operation when apparatus 10 is operating in a duty cycle mode. The trace marked STIM shows the stimulation pulse which can be a single pulse or a group of closely-spaced pulses. The pulse represents energy transferred from an implantable device 200 to the patient. When the power in the stimulation pulse exceeds the energy stored in energy storage assembly 270, a power transfer from external device 500 can be performed (e.g. during stimulation). Power can be delivered at times positioned symmetrically about the center of the time of pulse delivery, thereby insuring that the energy storage assembly (e.g. including a capacitor) is fully charged prior to stimulation delivery, and then replenished immediately after. Typically, the stimulation power will exceed the power transferred, and so energy storage assembly 270 will deplete during stimulation. When charging stops, the energy stored can slowly decay, due to the quiescent power consumption of implantable device 200. Charging via power transfer can begin prior to stimulation delivery, such that the energy stored equals the control loop setpoint when the energy measurement is made.

Figure 62:
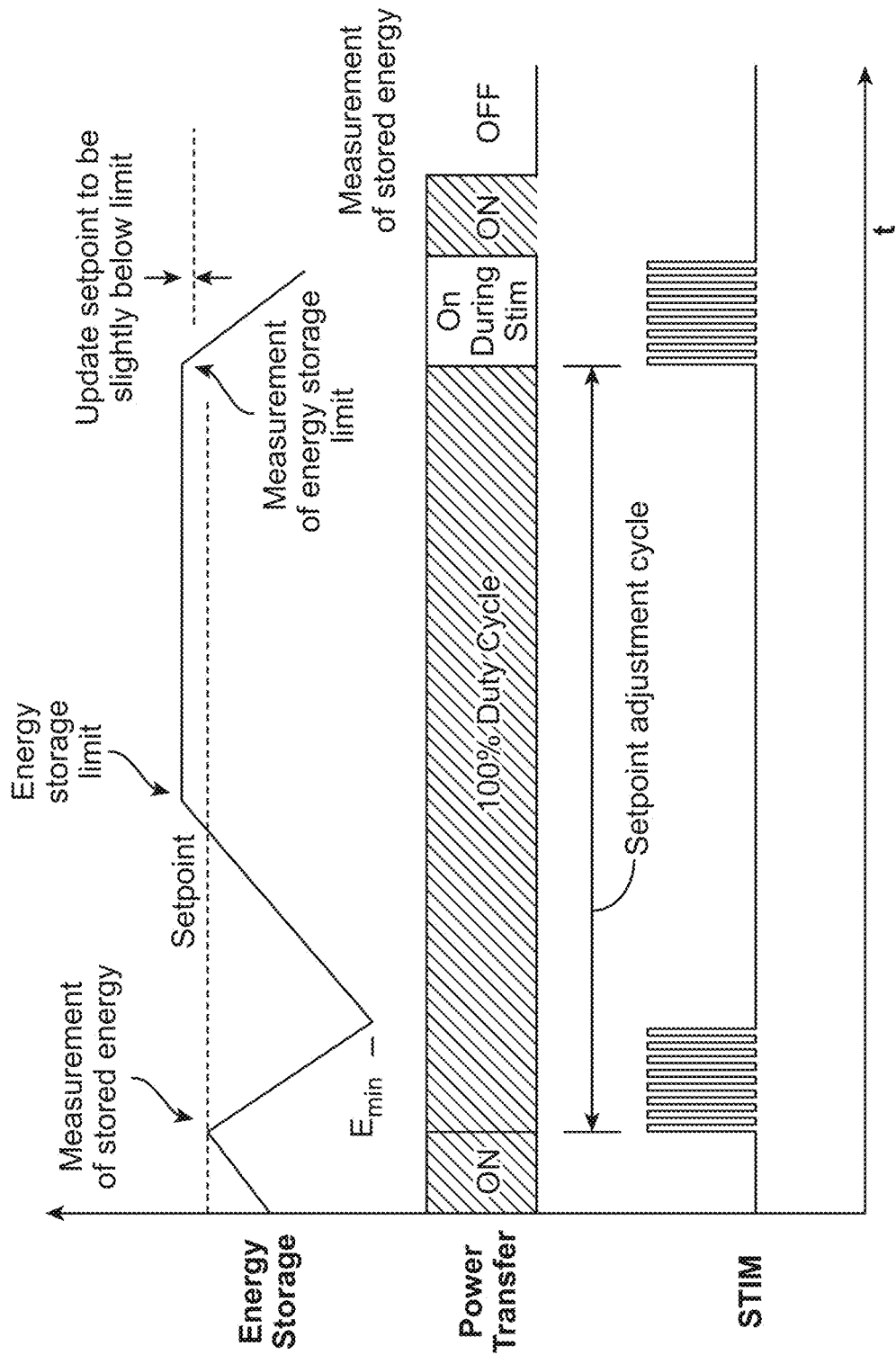
FIG. 62 is a graphical representation of an energy setpoint update cycle of a power control arrangement, consistent with the present inventive concept.

Referring now to FIG. 62, a graph of an energy setpoint update cycle of a power control arrangement is illustrated, consistent with the present inventive concepts. The setpoint adjustment cycle of FIG. 62 can occur periodically, such as at a much slower rate than the operation of the control loop. The power transmission amplitude of external device 500 can be adjusted, after low pass filtering, to reach a target duty cycle. The setpoint adjustment can be used to determine the maximum energy that can be stored under a current set of conditions. In some embodiments, an adjustment is made approximately every 4 time constants, after low pass filtering. The function of the setpoint adjustment cycle is to measure the limit of energy storage assembly 270 under the current operating conditions. The limit of energy storage may change with the relative position of the antennas, rectifier behavior, or other circuit behavior (such as protective voltage clamping circuitry). By measuring the limit of the energy storage system, the control loop can operate near the maximum level without wasting energy, and it can be adaptive to changes in environmental conditions or the applied therapy. This measurement is performed by applying more power than required, such as power applied during the entire duration of the stimulation cycle, which can cause energy storage assembly 270 to remain saturated until the next measurement is made.

Figure 63:
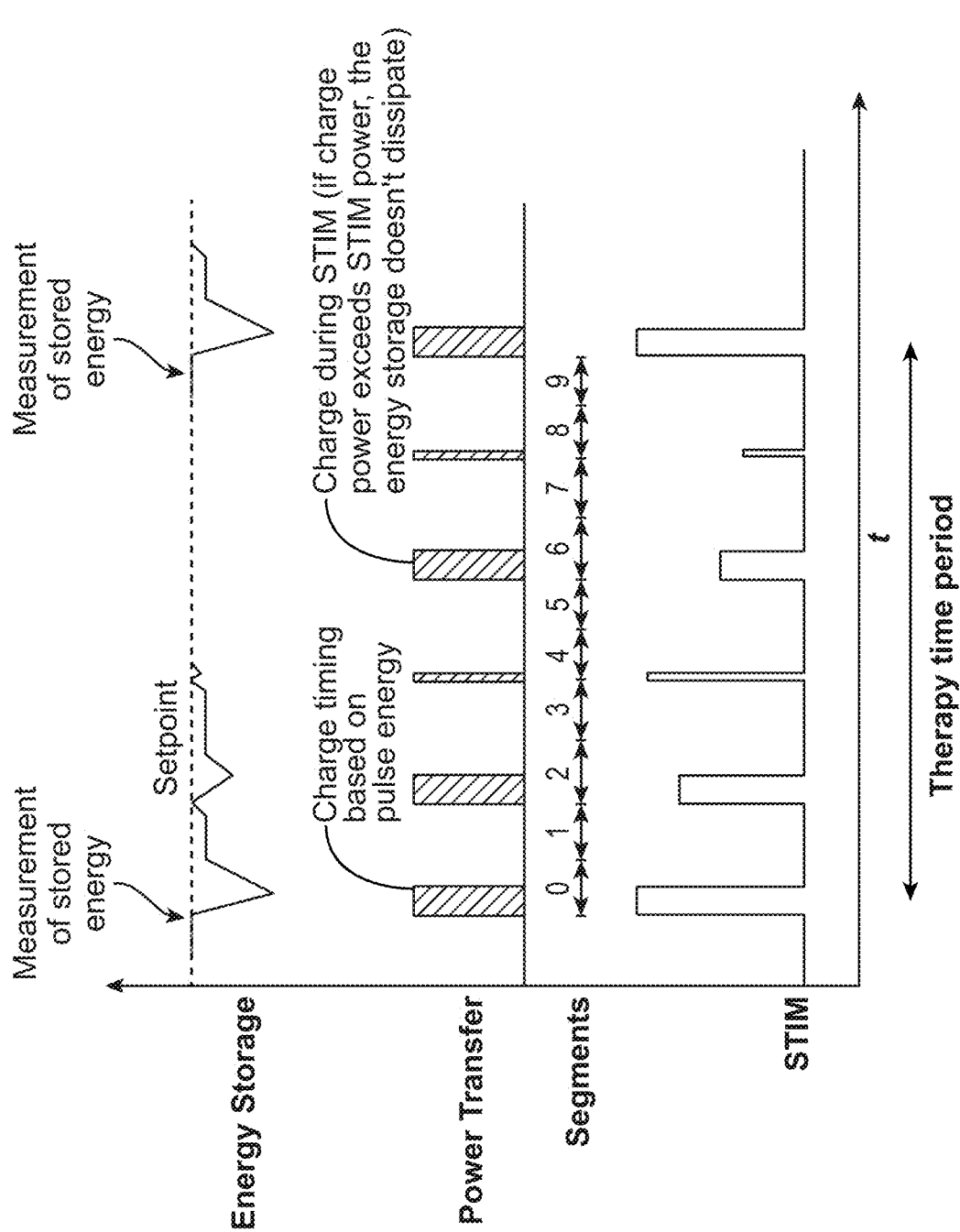
FIG. 63 is a graphical representation of a stimulation therapy including five pulses per a stimulation cycle delivered by an implantable device, consistent with the present inventive concepts.

FIGS. 61 and 62 show a single pulse per stimulation period. In some embodiments, apparatus 10 can provide therapies with multiple pulses per stimulation period, and each pulse can include different pulse energy and/or can occur at arbitrary times within the stimulation period. For example, as shown in FIG. 63, a therapy is performed by apparatus 10 in which five pulses per stimulation cycle are delivered by an implantable device 200. As described above in reference to FIGS. 59 and 60, an energy measurement can be made once per stimulation cycle, and a control loop can be included (e.g. in arrangement 11 and/or 12) that calculates the total amount of charging time that will occur during the next cycle. This time can then be allocated such that charging is applied symmetrically about the stimulation pulses, and the charge time for each pulse is proportional to its relative energy. If the charge time exceeds the time between pulses, this time can be carried over and charging delivered (i.e. energy received by implantable device 200 via power delivered by external device 500) after subsequent pulses. If the charge time exceeds the total time, the amplitude of power transfer can be adjusted.

Energy can be allocated among the pulses according to an algorithm (e.g. an optimization algorithm of arrangement 11 and/or 12). An input to the algorithm can be the total amount of charge time for all the stimulation pulses (e.g. computed by a controller), that must be applied during the next stimulation period. The output of the algorithm is the amount of charge time to be applied around each stimulation pulse during the next stimulation cycle. The algorithm uses information about the therapy (e.g. stimulation levels and delivery times) which can be computed and/or stored when the stimulation therapy is determined (e.g. entered by the patient or other user).

For example, if a therapy includes N pulses, the stimulation can be divided into 2·N segments. Segment zero begins at the beginning of the first stimulation pulse in a stimulation period, and ends at the midpoint between the beginning of the first pulse and the beginning of the second pulse. Segment 1 follows Segment 0 and ends at the beginning of the second pulse. Additional segments can be defined similarly. If an "overhead time" associated with a stimulation pulse exceeds the segment time, the boundary between segments can be shifted so the segment time exceeds the overhead time. The overhead time can include the time to recover the measurement of the energy storage system, the time to give commands to or receive information from implantable device 200, the stimulation pulse width, and/or other periods when power is not adjusted during a stimulation period. FIG. 63 shows 10 segments for five pulses. Segment durations can be stored as integer numbers of clock cycles (ticks) in array TSEG which contains 2 N elements.

Each segment can have a fixed amount of ticks where charging always occurs. The overhead ticks for each segment can be stored in an array which contains 2 N elements. For example, if power is received from external device 500 during stimulation delivery, the even numbered segments will have overhead equal to their associated stimulation duration. Also, the last segment in the stimulation period will have overhead equal to the time required for the energy storage measurement.

The next array contains the relative energy in each pulse, which is stored in array ERSEG which contains 2·N elements. Each element contains an integer representing the number of charging intervals for the segment, where a charging interval represents $\frac{1}{2}^n$ times the stimulation period. This configuration enables fast real-time integer computations when the algorithm is running. The relative energy for each pulse can be calculated using the following equation:

$$E_R[\text{Pulse}] = \left(\frac{E[\text{Pulse}]}{\Sigma E}\right) \cdot 2^n$$

Energy is proportional to the product of the booster voltage, VSTIM, the specified stimulation current, and the pulse width. Since energy appears in both the numerator and denominator of the above equation, any convenient normalization method can be used. After computing the relative energy of each pulse, half can be allocated to the segment before the pulse, and half can be allocated to the segment after.

An optimization algorithm can be performed once per stimulation period, and can accept the total charge time, computed by a controller, for the next cycle. The algorithm can compute the desired charge time for each segment, then performs the following for each segment: (1) if the desired charge time of the previous segment exceeded the previous segment's duration, add the remainder to the charge time for this segment; (2) if the charge time of this segment plus the remainder for the last segment exceeds this segment's charge time, set this segment's charge time equal to the segment length and compute the remainder. The output of the algorithm is an array containing the charge time for each segment for the next stimulation cycle.

In some instances, power received by implantable device 200 can exceed the power used in therapy (e.g. stimulation energy delivery), as shown in FIG. 63. In these instances, power can still be provided symmetrically around the pulse, resulting in some inefficiency. Alternatively, power transfer by external device 500 could be delayed, giving the energy storage assembly 270 time to discharge before power transfer is initiated. This delay would cause the transferred power to store energy in addition to providing energy for stimulation pulses, resulting in higher efficiency of apparatus 10. The amplitude of stimulation pulses at which this higher efficiency occurs can be estimated from information about the power transfer efficiency, and the control loop can make adjustments accordingly.

In some embodiments, apparatus 10 (e.g. arrangements 11 and/or 12) can utilize amplitude modulation, such as to avoid interruptions in therapy (e.g. interruptions in stimulation energy delivery performed by an implantable device 200) while optimizing energy utilization efficiency of external devices providing wireless power to the therapy delivering device (e.g. extending battery or other power supply life of an external device 500). In an amplitude modulation mode, power transmission componentry of external device 500 can be continuously enabled, and a control loop can be used to adjust the amplitude of transmitted power to control the energy received by an implantable device (e.g. implantable device 200). This mode can be used when the stimulation rate is high (e.g. high energy delivered over time) and individual stimulation pulses have low energy. For example, stimulation can be delivered at 500 Hz, stimulation pulses can be delivered at less than 5 mA, stimulation pulses can be less than 100 µs per phase, and/or stimulation pulses can drive loads up to 1 kOhm. Under these conditions, individual stimulation pulses do not cause large energy depletions, and the power delivery and consumption is approximately constant.

Stimulation including a high stimulation pulse rate can make it impractical and/or inefficient to turn power transmissions from external device 500 on and off. As described hereabove, an optimization algorithm of apparatus 10 can be iterated at a rate that is lower than the stimulation rate. The algorithm can control the amplitude of power transmitted to track a targeted voltage at the energy storage system that is based on a measurement that occurs at the iterated rate. The algorithm can occasionally track a charging maximum (e.g. a maximum voltage) using a gradient tracking loop. Once the maximum is determined, the control loop can use that information to set a tracking point slightly below the maximum. In some embodiments, it may be necessary or at least desired to track at power levels higher than the charging maximum because with amplitude control this maximum may represent the bare minimum power required for operation. Amplitude modulation control can include a second energy measurement to determine the slope of charging and more accurately estimate when energy storage assembly 270 is fully charged. Alternatively or additionally, the control loop can set the tracking point to fixed voltage deemed appropriate for the current operating conditions. The fixed tracking point can be pre-determined by a measurement of the energy storage system or based on the power consumption of the applied therapy and system behavior (e.g. rectifier, voltage booster, stimulation circuitry).

Referring collectively to FIGS. 59 through 63, a method and design for efficiently and reliably tracking and controlling the available energy in implantable device 200 is described. Power is provided to implantable device 200 by external device 500 over a wireless link. The wireless link can also transfer data between external device 500 and implantable device 200, providing not only therapy configuration information (e.g. stimulation energy delivery information), but also information about available energy at a given moment in time. While implantable device 200 is functioning (e.g. delivering energy, monitoring sensors, transmitting data, and/or operating in a quiescent, "wait" state), its energy consumption and the quality of the wireless link can vary significantly.

Power transfer from external device 500 can be adjusted by controlling the duty cycle of power delivery. The timing of power delivery can be centered around a period of high power consumption of implantable device 200, such as a time in which stimulation energy is delivered. This timing of power delivery can effectively charge energy storage assembly 270 before delivery of stimulation energy, it can provide increased power delivery during the event, and/or it can partially recharge energy storage assembly 270 after the stimulation. The energy available in energy storage assembly 270 can be tracked and controlled using a measurement that occurs immediately before stimulation, and adjusting the duty cycle of power delivery from external device 500 to minimize the error with respect to a desired (target) available energy. The timing of the measurement can be altered to increase reliability and/or to improve the dynamics of the tracking system.

The desired available energy of implantable device 200 (the "setpoint" of the tracking loop as described hereabove) can be dynamically determined through a periodic measurement of the energy storage limit of energy storage assembly 270. This energy storage limit can change with the performance of the circuitry and/or the wireless link, and periodically updating the measurement can ensure the tracking loop operates efficiently. Once the energy storage limit is determined, the setpoint can be set slightly below the determined limit, such as to allow the tracking loop to operate (tracking error will be present with too much or too little power).

The control loop adjustments can include asymmetric gain settings, gain settings that are altered over time based on previous measurements, and/or operation specific gain settings. Gain settings can be based on the integral of the error, they can be proportional to the error, and/or they can be based on the derivative of the error. If the setpoint is near the energy storage limit of implantable storage assembly 270, there will be a small error when the system receives too much power. To improve performance, the adjustment for this small error can be increased, such as when it is increased if the error remains constant over several stimulation periods (the energy limit has been reached). If implantable device 200 is determined to be rapidly losing power, the power transfer from external device 500 can be rapidly increased, such as with a very large adjustment, to prevent an undesired event (e.g. interruption in stimulation energy delivery), even if this results in temporary inefficiency (e.g. one or more algorithms are biased to prioritize prevention of interrupted therapy over improvement in battery life of external device 500).

Multiple stimulation periods can be controlled via a single measurement of available energy by allocating power transfer from external device 500 according to the energy requirements of the stimulation pulses to be delivered by implantable device 200. If apparatus 10 (e.g. arrangements 11 and/or 12) is using duty cycle control of power transfer, and there is insufficient time between stimulation pulses, the remaining required energy can be appended to subsequent pulses to ensure the proper total energy is delivered by external device 500 over the overall stimulation period. The ability to accommodate multiple stimulation pulses with a single measurement reduces data transfer requirements and can improve efficiency (e.g. since transfer efficiency can be degraded during data transfer).

Additionally or alternatively, power transmitted by external device 500 can be adjusted by controlling the amplitude of power delivery. The amplitude can be adjusted to achieve a desired steady-state duty cycle, which can give duty cycle control more dynamic range for increasing the amount of power transferred. For stimulation periods including rapid stimulation pulses, it can become impractical to control the duty cycle, so power can instead be controlled additionally and/or solely through adjustments of the amplitude.

When an optimizing control loop of apparatus 10 isn't tracking or otherwise doesn't have information about how much power is needed (such as during operating state transitions, or therapy changes), the control loop can intentionally provide more power than necessary. This configuration allows the control loop to reach a tracking point by reducing the transmitted power to implantable device 200. For example, a control loop can be reset, after which maximum power is provided to implantable device 200 (e.g. more power than needed), after which that power can be safely reduced. While the control loop determines a desired operating point, implantable device 200 will have sufficient power to operate. This configuration also ensures that implantable device 200 doesn't unintentionally power cycle (e.g. reset as described hereabove). If a major change occurs rapidly in the control loop, and the control loop is unable to respond quickly enough, the control loop can reset to a state in which it provides a large amount of power (such as maximum power) to avoid power cycling implantable device 200. A major change can be detected as a measured voltage below a threshold value in the energy storage system, which can then override the behavior of the loop and reset it so it can recover.

Power delivered by external device 500 can be controlled at a varied rate, such as when controlled at a repetition rate of the therapy (e.g. a repetition rate of stimulation energy delivery), and/or at a fixed rate, such as when power is controlled independent of the timing of the therapy (e.g. for very high stimulation rates) or when there is no therapy occurring (e.g. no stimulation energy is being delivered). The majority of stored energy can be used during delivery of therapy (e.g. delivery of stimulation energy), and control of transmitted power can be synchronized to the therapy, regardless of its periodicity (such as with aperiodic therapies). Transmitted power can also be controlled based on anticipated energy loss, rather than based on a periodic rate. For example, the control loop can be updated after a specific amount of energy depletion has occurred in energy storage assembly 270 (e.g. a specific amount of energy has been consumed by therapeutic energy delivery).

Apparatus 10 can include a power delivery control loop that can monitor one or more states of external device 500 and/or implantable device 200, and adjust power delivery accordingly. Initially, external device 500 can establish a connection with implantable device 200, which can be accomplished by transmitting more power to implantable device 200 than is likely to be necessary. Power transmissions can be adjusted during this phase if an implantable device 200 isn't discovered (e.g. no confirming transmissions are received from an implantable device 200). Once a connection is established, implantable device 200 can enter an idle state. In the idle state, the power transmission control can have a periodic update rate. Once therapy begins (e.g. implantable device 200 is delivering stimulation energy to the patient), the control loop can be reset and a proper energy tracking point re-determined. Apparatus 10 can cause a similar reset when therapy changes occur (e.g. changes to delivered stimulation energy are programmed and/or occur). The control loop can be insensitive to missing one more update periods because of the chosen rate of updating and/or the resilience of steady-state operation. The control loop can be manually overridden when necessary, which may be desirable during device programming.

Figure 64:
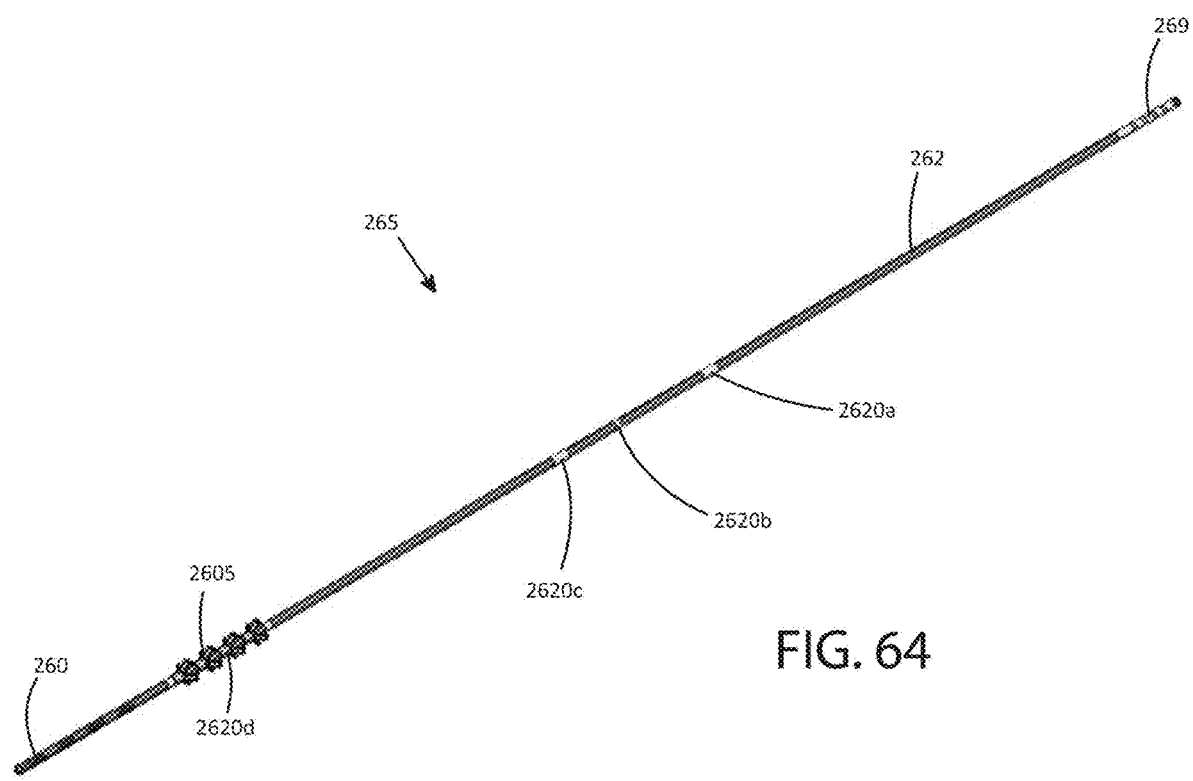
FIG. 64 is a perspective view of an implantable lead, consistent with the present inventive concepts.

Referring to FIG. 64, a perspective view of an implantable lead is illustrated, consistent with the present inventive concepts. Lead 265 can be of similar construction and arrangement to lead 265 as described hereabove in reference to FIGS. 54A-B, 55A-B, and/or as otherwise described herein. Lead 265 can comprise one or more stimulation elements 260 (e.g. electrodes) such as for delivering stimulation energy to tissue, and one or more contacts 269, such as for electrically connecting to internal electronics of implantable device 200. Lead 265 can be mechanically fixed (e.g. attached in manufacturing) or attachable (e.g. attached during a clinical procedure) to implantable device 200 (e.g. to connector 215 of implantable device 200). Lead 265 can comprise one or more markers 2620 positioned along the length of lead 265 (e.g. along the length of conduit 262). During an implantation procedure, markers 2620 can be configured to indicate a position of lead 265 relative to an insertion tool, such as insertion tool $60_{xi}$, as described herebelow in reference FIGS. 65 and 65A-C. Lead 265 can comprise a proximal marker 2620a, a medial marker 2620b, and/or a distal marker 2620c, as shown. In some embodiments, lead 265 comprises only one marker 2620 (e.g. medial marker 2620b), such as is described herebelow in reference to FIGS. 65 and 65A-C. Medial marker 2620b can be positioned approximately mid-way between proximal marker 2620a and distal marker 2620c. In some embodiments, proximal marker 2620a and distal marker 2620c are wider than medial marker 2620b.

Lead 265 can further include one or more markers 2620d positioned to indicate a position of projections 2605 relative to an anatomical structure. In some embodiments, marker 2620d is positioned on and/or proximate projection 2605. In some embodiments, marker 2620d comprises a marker (e.g. a radiopaque and/or ultrasonically reflective marker) configured to be visible during an implantation and/or trialing procedure (e.g. when viewed via an X-ray imaging device and/or ultrasound imaging device, respectively).

Referring to FIGS. 65 and 65A-C, a perspective view and close-up views of an implantable lead and an insertion tool for the implantable lead are illustrated, respectively, consistent with the present inventive concepts. Lead 265 can be of similar construction and arrangement to lead 265 as described hereabove in reference to FIGS. 54A-B, 55A-B, 64, and/or as otherwise described herein. Lead 265 can be mechanically fixed (e.g. attached in manufacturing) or attachable (e.g. attached during a clinical procedure) to implantable device 200. Insertion tool $60_{xi}$ can comprise a sheath 2662 extending distally from a hub 2665. Insertion tool $60_{xi}$ can be of similar construction and arrangement to insertion tool $60_{iii}$ as described hereabove in reference to FIG. 29 and/or as otherwise described herein. Sheath 2662 can slidingly receive a distal portion of lead 265 via an opening 2667 of hub 2665. In some embodiments, sheath 2662 is configured to surround (e.g. depress) the one or more projections 2605 of lead 265 during a test stimulation and/or implantation procedure, as described herebelow.

Figure 65:
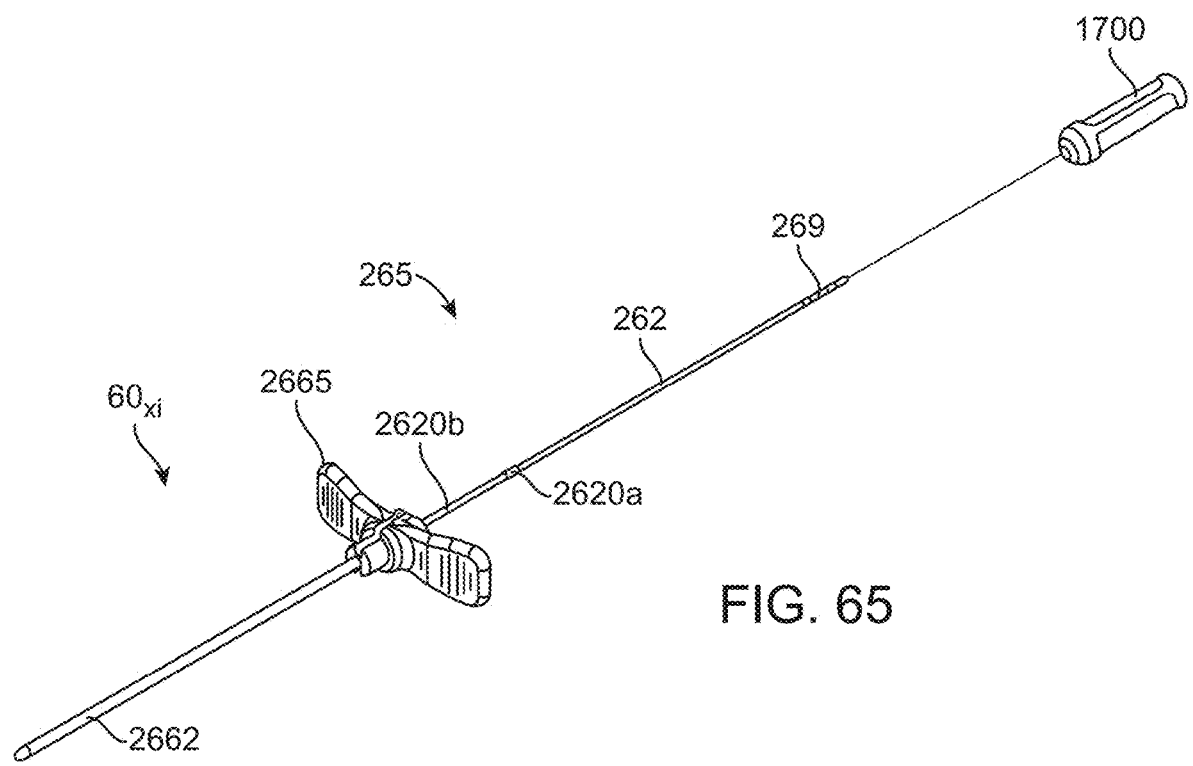
FIG. 65 is a perspective view of an implantable lead and an insertion tool for the implantable lead, consistent with the present inventive concepts.
Figure 65A:
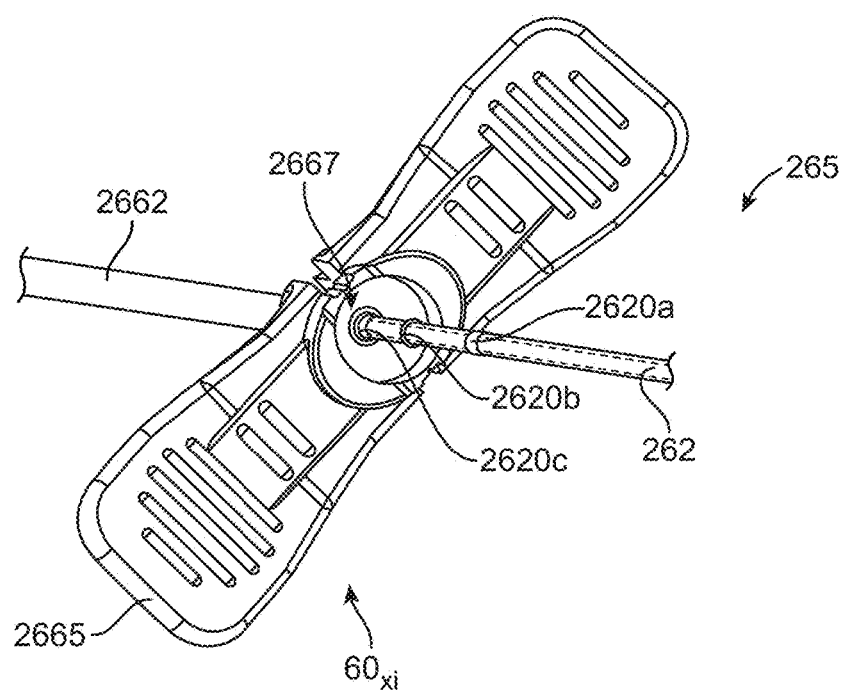
FIGS. 65A-C are close-up views of an implantable lead and an insertion tool for the implantable lead, consistent with the present inventive concepts.
Figure 65B:
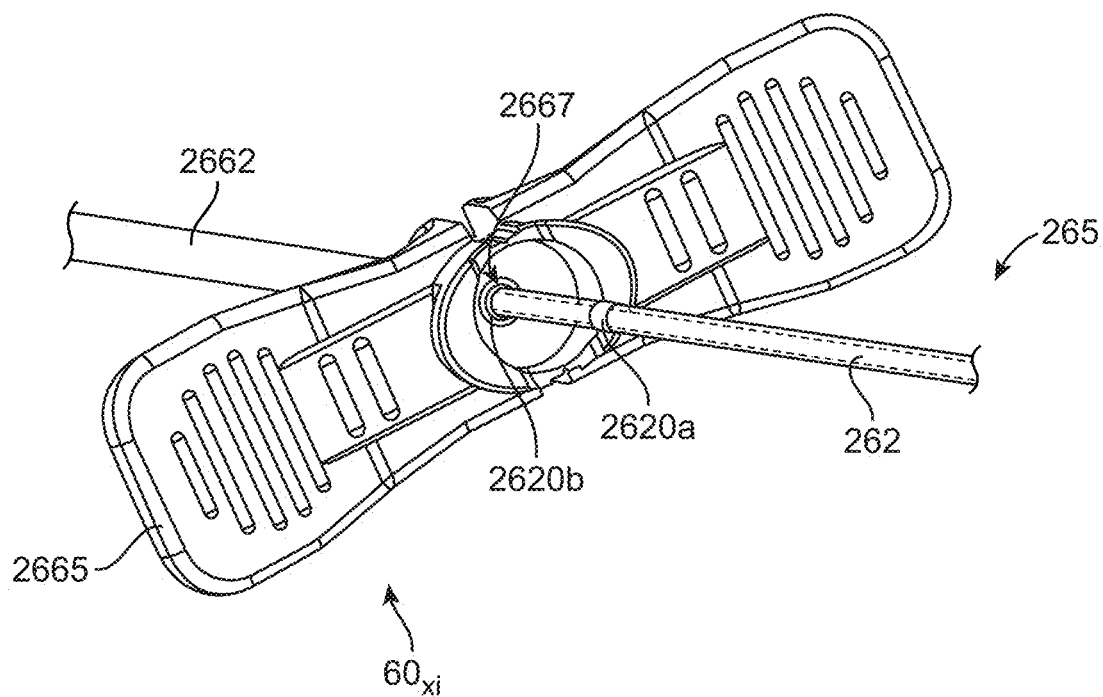
Figure 65C:
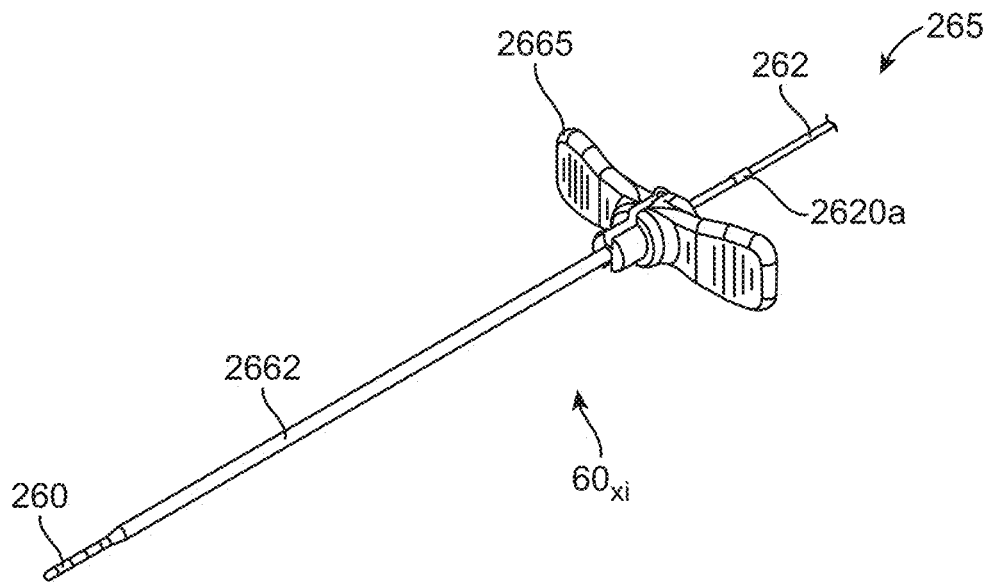

During a test stimulation and/or implantation procedure, lead 265 can be advanced into insertion tool $60_{xi}$ (e.g. inserted into opening 2667 and/or sheath 2662) until distal marker 2620c is aligned with opening 2667, as shown in FIG. 65A. Lead 265 can be advanced into insertion tool $60_{xi}$ via stylet 1700. When aligned with opening 2667, distal marker 2620c can be configured to indicate the distal end of lead 265 is aligned with the distal end of sheath 2662 (e.g. the most distal lead contact 262 does not extend beyond the distal end of sheath 2662), as shown in FIG. 65. Lead 265 can be further advanced into insertion tool $60_{xi}$ until medial marker 2620b is aligned with opening 2667, as shown in FIG. 65B. When aligned with opening 2667, medial marker 2620b can be configured to indicate approximately one-half, at least one-half, and/or at least one but less than all of lead contacts 262 have been exposed to patient tissue (e.g. one-half of lead contacts 262 extend beyond the distal end of sheath 2662), as shown in FIG. 65C. In some embodiments, when aligned with opening 2667, medial marker 2620 can be configured to indicate at least two lead contacts 262 have been exposed. In some embodiments, a test stimulation is performed when medial marker 2620b is aligned with opening 2667, such as to minimize the risk of prematurely retracting insertion tool $60_{xi}$ and/or deploying one or more projections 2605. Lead 265 can be further advanced into insertion tool $60_{xi}$ until proximal marker 2620a is aligned with opening 2667. When aligned with opening 2667, proximal marker 2620a can be configured to indicate more than one-half of lead contacts 262 and/or one or more projections 2605 have been exposed or are about to be exposed to patient tissue (e.g. more than one-half of lead contacts 262 and/or one or more projections 2605 extend or are about to extend beyond the distal end of sheath 2662). In some embodiments, insertion tool $60_{xi}$ (e.g. sheath 2662) is retracted, or otherwise removed, when proximal marker 2620a is aligned with opening 2667.

In some embodiments, lead 265 comprises a single marker 2620 configured to indicate approximately one-half, at least one-half, and/or at least one but less than all of lead contacts 262 have been exposed to patient tissue (e.g. one-half of lead contacts 262 extend beyond the distal end of sheath 2662). Lead 265 can comprise a single marker 2620 configured to indicate two lead contacts 262 have been exposed to patient tissue.

Figure 66B:
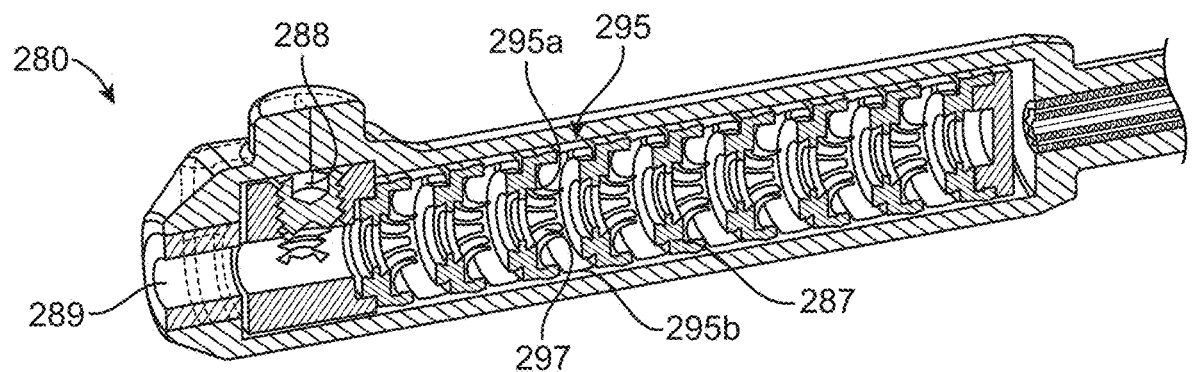
FIG. 66B is a sectional view a lead connection assembly comprising radially contacting conductors, consistent with the present inventive concepts.
Figure 66C:
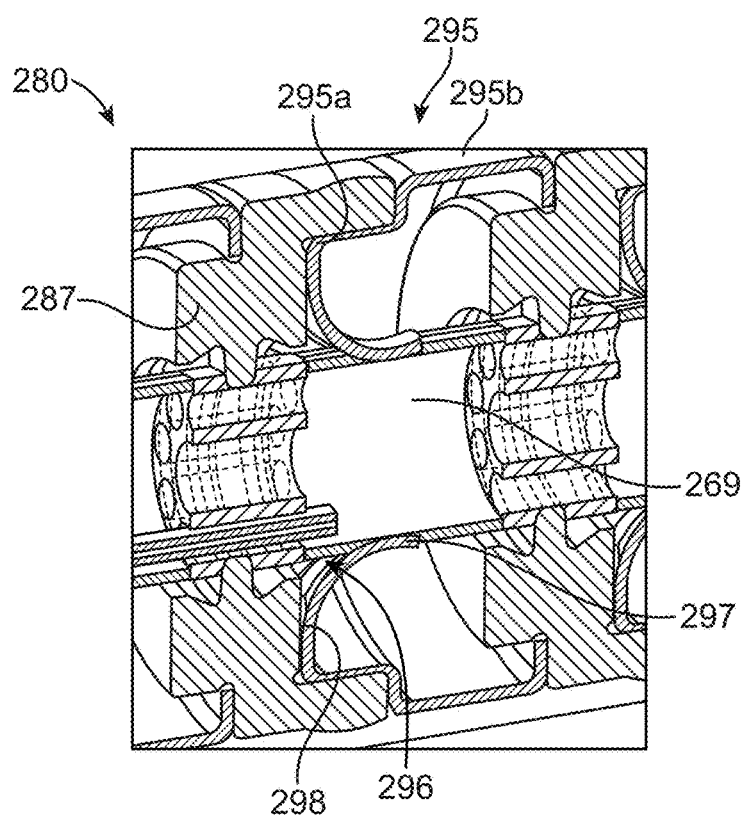
FIG. 66C is a close-up sectional view a lead connection assembly comprising radially contacting conductors, consistent with the present inventive concepts.

Referring now to FIG. 66A, front and back views of a radially contacting conductor of a lead connection assembly are illustrated, consistent with the present inventive concepts. Referring additionally to FIGS. 66B and 66C, a sectional view and a close-up sectional view of a lead connection assembly comprising the radially contacting conductors of FIG. 66A are illustrated, respectively. Lead connection assembly 280 can be of similar construction and arrangement to lead connection assembly 280 as described hereabove in reference to FIGS. 6 and 6A. Lead connection assembly 280 can comprise one or more radially contacting conductors, conductor 295. Conductor 295 can comprise a first portion 295a and a second portion 295b, with an opening 296 therethrough. First portion 295a can comprise an outer diameter that is less than the outer diameter of second portion 295b. First portion 295a can comprise a plurality of curved projections 297 that are constructed and arranged to descend into opening 296. In some embodiments, conductor 295 is stamped and formed from a single sheet of material, such a gold or silver plated stainless steel (e.g. 302 SS, 304 SS), or a gold or silver plated nickel alloy (e.g. MP35N, 35NLT). In some embodiments, conductor 295 comprises a polymeric biodegradable conductor configured to facilitate short-term use (e.g. for short-term implantation and/or trialing procedures).

Conductors 295 can be positioned proximate set screw 288 of lead connection assembly, as shown in FIG. 66B. Each conductor 295 can engage spacer 287 to form a barrier 298 between the electrical connection and patient bodily fluids (e.g. prevent a short circuiting of adjacent conductors 295), as shown in FIG. 66C. During an implantation and/or trialing procedure, a proximal portion of lead 265 (e.g. contacts 269) can be inserted into lead connection assembly 280 via opening 289, as described hereabove in reference to FIGS. 6 and 6A-B. Lead 265 can be further advanced through opening 296 of conductors 295. Projections 297 can be configured to deflect as lead 265 is advanced through conductors 295. The deflection of projections 297 can exert a pressure on an outer surface of contacts 269, such that projections 297 can maintain electrical continuity with contacts 269, as shown in FIG. 66C. In some embodiments, the distal ends of projections 297 are curved outwards, such that lead 265 can be removed and/or reinserted into lead connection assembly 280 without interference with projections 297.

Refering now to FIGS. 67A-D, perspective and side sectional views of an expanded and collapsed distal portion of an implantable lead comprising unidirectional tissue engagement elements are illustrated, consistent with the present inventive concepts. Lead 265 can be of similar construction and arrangement to lead 265 as described hereabove in reference to FIGS. 54A-B, 55A-B, 64, and/or as otherwise described herein. Lead 265 can be mechanically fixed (e.g. attached in manufacturing) or attachable (e.g. attached during a clinical procedure) to implantable device 200 (e.g. to connector 215 of implantable device 200). Lead 265 can comprise one or more arrangements 2610 of projections 2605. Projections 2605 can engage surrounding patient tissue to resist migration of lead 265. Projections 2605 can comprise a material selected from the group consisting of: silicone; polyurethane; nylon; polyethylene; and combinations of these. Arrangements 2610 can comprise a hub 2607 comprising a first portion 2607a and a second portion 2607b. First portion 2607a can comprise an outer diameter $OD_1$ that is less than the outer diameter $OD_2$ of second portion 2607b. Second portion 2607b can comprise projections 2605. Projections 2605 can comprise a proximal portion 2606 with a recessed inner surface, such that projections 2605 taper in thickness proximally.

Proximal portion 2606 and first portion 2607a can each comprise an equivalent, or otherwise comparable, wall thickness $WT_1$. In some embodiments, $WT_2$ comprises a thickness that is at least twice the thickness of $WT_1$. In some embodiments, the collective wall thickness $WT_C$ of proximal portion 2606 and first portion 2607a comprise an equivalent, or otherwise comparable, wall thickness $WT_2$ of second portion 2607b. Alternatively or additionally, projections 2605 and first portion 2607a can comprise a collective outer diameter $OD_C$ that can be equivalent, or comparable, to outer diameter $OD_2$ of second portion 2607b.

Figure 67A:
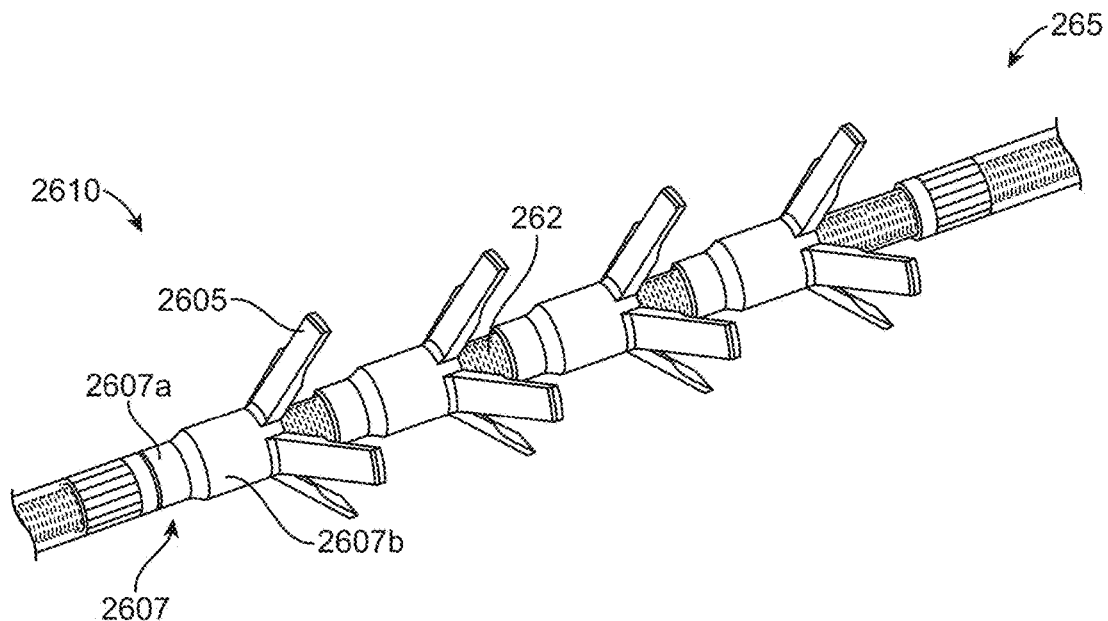
FIGS. 67A-D are perspective and side sectional views of an expanded and collapsed distal portion of an implantable lead comprising unidirectional tissue engagement elements, consistent with the present inventive concepts.
Figure 67B:
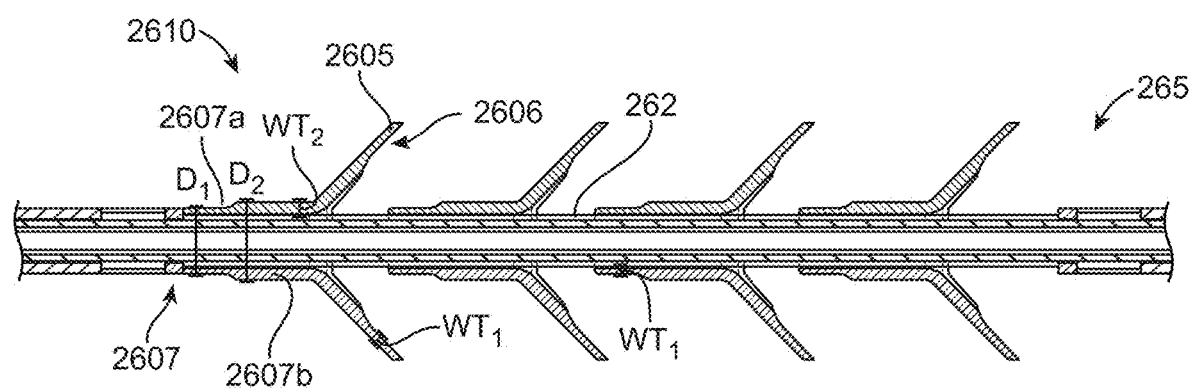
Figure 67C:
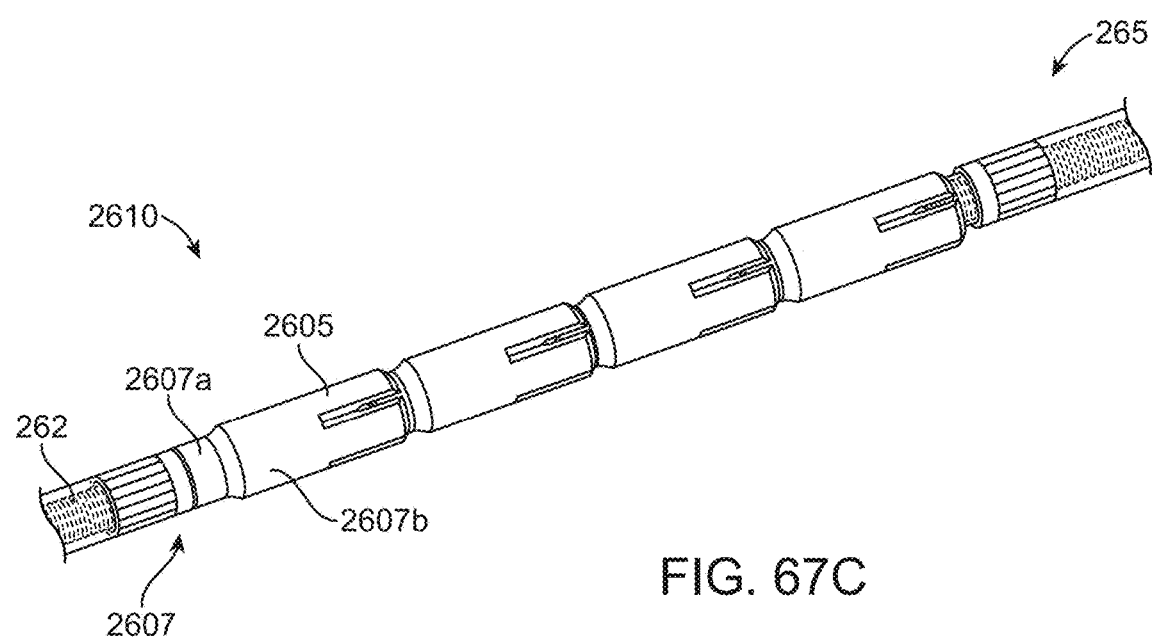
Figure 67D:
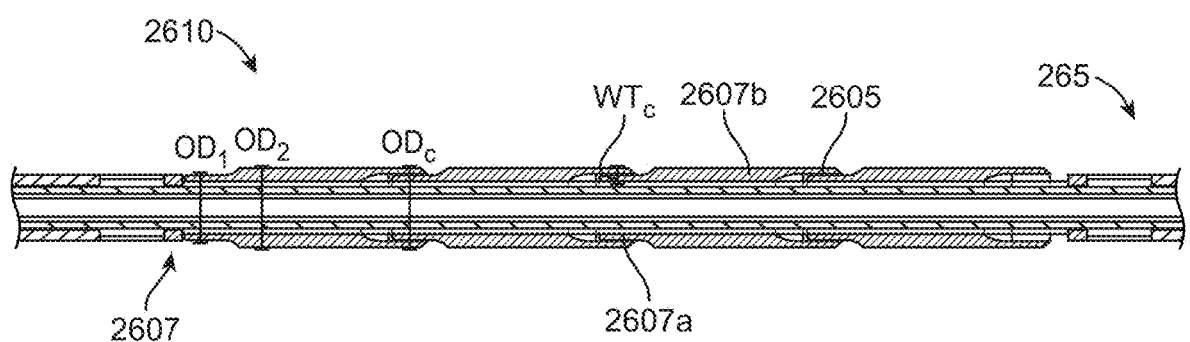

Projections 2605 can be configured to transition between a collapsed state and an expanded state. In some embodiments, projections 2605 are reliantly biased in the expanded state, such that they can be compressed for placement in an introducer and/or other insertion tool, as described herein, and radially expand into tissue as the insertion tool is removed. In an expanded state, as shown in FIGS. 67A and B, projections 2605 can radially extend from second portion 2607b. In a collapsed state, as shown in FIGS. 67C and D, projections 2605 can laterally extend from second portion 2607b and overlap first portion 2607a of an adjacent arrangement 2610. Overlapping projections 2605 can provide numerous advantages, including but not limited to: more projections 2605 per unit length of arrangement 2610; longer length of projections 2605; relatively continuous diameter of lead 265, especially along arrangement 2610; and combinations of these.

As described hereabove, in the collapsed state (e.g. when surrounded by an insertion tool), the collective outer diameter $OD_C$ of projections 2605 and first portion 2607a can be equivalent, or comparable, to outer diameter $OD_2$ of second portion 2607b. During an implantation and/or trialing procedure, lead 265 can be inserted into patient tissue in a collapsed state (e.g. when inserted into an insertion tool), such as to avoid inadvertent tissue engagement. Lead 265 can be transitioned from a collapsed state to an expanded state at a patient location where tissue engagement is desired. Lead 265 can be transitioned from an expanded state to a collapsed state when removal and/or replacement of lead 265 is desired.

While the preferred embodiments of the devices and methods have been described in reference to the environment in which they were developed, they are merely illustrative of the principles of the present inventive concepts. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A medical apparatus for a patient, comprising:
   an implantable device comprising:
      at least one stimulation element configured to deliver stimulation energy to the patient; and
      control structure configured to control the at least one stimulation element;
   a first external device comprising a user interface including a patient posture interface configured to receive user input to change a stimulation program based on the patient position; and a second external device communicably coupled to the first external device via a first communication link and to the implantable device via a second, different communication link, wherein the second external device is configured to transmit data to the implantable device via the second communication link to change the stimulation program based on the user input, the data comprising a command to deliver the stimulation energy based on the changed stimulation program, and wherein the first external device is further configured to monitor, via the first communication link, the second communication link between the second external device and the implantable device.

2. The apparatus according to claim 1, wherein the patient posture interface comprises one or more user input components configured to enable the user to manually indicate when the patient is in an upright or a supine position.

3. The apparatus according to claim 1, wherein the second external device comprises:
an antenna configured to transmit the data to the implantable device via the second communication link
a transmitter configured to drive the at least one antenna;
a power supply configured to provide power to at least the transmitter; and
a controller configured to control the transmitter.

4. The apparatus according to claim 3, wherein the second external device is configured to automatically detect when the patient is in an upright or a supine position.

5. The apparatus according to claim 4, wherein the user interface comprises an icon configured to indicate when the patient position is automatically detected by the second external device.

6. The apparatus according to claim 4, wherein a user can manually change the patient position when the patient position detected by the second external device is incorrect.

7. The apparatus according to claim 6, wherein the second external device is configured to recalibrate one or more posture vectors in response to a manual change of the patient position by the user.

8. The apparatus according to claim 3, wherein the implantable device further comprises an antenna configured to receive the transmission signal from the second external device via the second communication link, and the apparatus further comprises a positioning tool for one or more of positioning and repositioning the second external device on the patient's skin, wherein the tool includes alignment markings corresponding to multiple positions of placement of the second external device in the positioning tool, each of the positions resulting in sufficient alignment between the antenna of the second external device and the antenna of the implantable device.

9. The apparatus according to claim 8, wherein the positioning tool comprises at least one replaceable skin attachment patch.

10. The apparatus according to claim 3, wherein the implantable device-further comprises:
an antenna configured to receive the transmission signal from the second external device via the second communication link; and
a receiver configured to receive the transmission signal from the antenna.

11. The apparatus according to claim 3, wherein the second external device comprises a sensor configured to provide a signal based on the patient position.

12. The apparatus according to claim 11, wherein the sensor comprises an accelerometer.

13. The apparatus according to claim 8, wherein the apparatus is configured to debounce the signal provided by the sensor.

14. The apparatus according to claim 1, wherein the first external device comprises a portable computer, a laptop, a cell phone, or a tablet.

15. The apparatus according to claim 1, wherein the second external device is configured to be removably positioned on or near the patient's skin.

16. The apparatus according to claim 1, further comprising a positioning tool for attaching the second external device to the patient.

17. The apparatus according to claim 1, wherein the user input to change the stimulation program comprises an indication that the patient has moved from an upright position to a supine position or from the supine position to the upright position.

18. The apparatus according to claim 1, wherein the user input to change the stimulation program comprises a modification of one or more stimulation program parameters.

19. The apparatus according to claim 18, wherein the one or more stimulation program parameters is one or more of a stimulation rate, a stimulation pulse width, and a stimulation amplitude.

20. The apparatus according to claim 1, wherein the control structure comprises a state machine configured to generate stimulation pulses.

21. The apparatus according to claim 1, wherein the first communication link comprises a near field communication (NFC) network, and RFID network, or a Bluetooth low energy (BLE) network.

22. The apparatus according to claim 1, wherein the second communication link comprises an RFID network.

23. The apparatus according to claim 22 further comprising a charging device configured to communicate with the second external device via a Bluetooth Low Energy (BLE) network to charge a power supply of the second external device.

24. The apparatus according to claim 1, wherein the second external device is further configured to transmit power to the implantable device.

25. The apparatus according to claim 1 further comprising a third external device communicably coupled to the second external device via a third communication link.

26. The apparatus according to claim 25, wherein the user interface is a first user interface and the patient posture interface is a first patient posture interface, and wherein the third external device comprises a second user interface including a second patient posture interface configured to receive user input to change the stimulation program.

27. The apparatus according to claim 25, wherein the first external device is a clinician programmer and the third external device is a patient programmer.

* * * * *